US012715907B2

(12) United States Patent
Sok et al.

(10) Patent No.: US 12,715,907 B2
(45) **Date of Patent: *Aug. 25, 2026**

(54) RAPID ELICITATION OF BROADLY NEUTRALIZING BOVINE ANTIBODIES TO HIV Env

(71) Applicants: International AIDS Vaccine Initiative, New York, NY (US); The Scripps Research Institute, La Jolla, CA (US); The Texas A&M University System, College Station, TX (US)

(72) Inventors: Devin Sok, New York, NY (US); Dennis R. Burton, La Jolla, CA (US); Vaughn V. Smider, La Jolla, CA (US); Ian Wilson, La Jolla, CA (US); Michael Criscitiello, College Station, TX (US); Waithaka Mwangi, College Station, TX (US)

(73) Assignees: International AIDS Vaccine Initiative, New York, NY (US); The Scripps Research Institute, La Jolla, CA (US); The Texas A&M University System, College Station, TX (US)

( * ) Notice: Subject to any disclaimer, the term of this patent is extended or adjusted under 35 U.S.C. 154(b) by 68 days.

This patent is subject to a terminal disclaimer.

(21) Appl. No.: 18/470,044

(22) Filed: Sep. 19, 2023

(65) Prior Publication Data

US 2024/0109956 A1 Apr. 4, 2024

Related U.S. Application Data

(63) Continuation of application No. 16/630,768, filed as application No. PCT/US2018/041729 on Jul. 12, 2018, now Pat. No. 11,795,211.

(60) Provisional application No. 62/534,501, filed on Jul. 19, 2017, provisional application No. 62/532,766, filed on Jul. 14, 2017.

(51) Int. Cl.

| | |
|---|---|
| ***C07K 16/114*** | (2026.01) |
| ***C07K 14/16*** | (2006.01) |
| *A61K 38/00* | (2006.01) |

(52) U.S. Cl.

CPC ........ *C07K 16/1145* (2026.01); *C07K 14/162* (2013.01); *A61K 38/00* (2013.01); *C07K 2317/10* (2013.01); *C07K 2317/24* (2013.01); *C07K 2317/31* (2013.01); *C07K 2317/33* (2013.01); *C07K 2317/565* (2013.01); *C07K 2317/76* (2013.01); *C07K 2319/02* (2013.01); *C07K 2319/31* (2013.01)

(58) Field of Classification Search

None

See application file for complete search history.

(56) References Cited

U.S. PATENT DOCUMENTS

| | | | | |
|---|---|---|---|---|
| 11,795,211 B2 * | 10/2023 | Sok | ...................... | C07K 14/162 |
| 2020/0165324 A1 | 5/2020 | Sok et al. | | |

OTHER PUBLICATIONS

Winkler et al., J Immunol. Oct. 15, 2000;165(8):4505-14. doi: 10.4049/jimmunol.165.8.4505. PMID: 11035090.*

Written Opinion of the International Searching Authority for corresponding application No. PCT/US2018/041729, mailed Nov. 26, 2018.

International Search Report for corresponding application No. PCT/US2018/041729, mailed Nov. 26, 2018.

Cheeseman, HM, el al., “Broadly Neutralizing Antibodies Display Potential for Prevention of HIV-1 Infection of Mucosal Tissue Superior to That of Nonneutralizing Antibodies,”. J Virology, vol. 91, No. 1, Jan. 2017.

Sanders, R.W. et al. “A Next-Generation Cleaved, Soluble HIV-1 Env Trimer, BG505 SOSIP.664 gp140, Expresses Multiple Epitopes for Broadly Neutralizing but Not Non-Neutralizing Antibodies,” PLOS Pathogens, vol. 9, No. 9, Sep. 19, 2013.

Guenaga, J, et al., “Well-Ordered Trimeric HIV-1 Subtype Band C Soluble Spike Mimetics Generated by Negative Selection Display Native-like Properties,” PLOS Pathogens, vol. 11, No. 1, Jan. 8, 2015.

Heydarchi, B., et al., “Repeated Vaccination of Cows with HIV Env gp140 during Subsequent Pregnancies Elicits and Sustains an Enduring Strong Env-Binding and Neutralising Antibody Response”, PLOS ONE, vol. 11, No. 6, Jun. 14, 2016.

Heydarchi, B., et al., Broad Neutralizing Antibodies to HIV Env and Other Complex Viral Antigens from Vaccinated Cows. Journal of Vaccines & Vaccination, vol. 7, No. 6, Dec. 2, 2016.

Sok, D., et al., “A Prominent Site of Antibody Vulnerability on HIV Envelope Incorporates a Motif Associated with CCR5 Binding and Its Camouflaging Glycans,” Immunity, vol. 45; pp. 31-45, Jul. 19, 2016.

Sok, D., et al., “Rapid Elicitation of Broadly Neutralizing Antibodies to HIV by Immunization in Cows,” Nature, vol. 548, No. 7665, pp. 108-111, Jul. 20, 2017.

(Continued)

*Primary Examiner* — Michael Szperka

(74) *Attorney, Agent, or Firm* — Nixon & Vanderhye, PC

(57) ABSTRACT

The present disclosure relates to methods for generating broadly neutralizing bovine anti-HIV Env antibodies, compositions comprising the broadly neutralizing bovine antibodies, and methods of treatment or prevention of HIV using the broadly neutralizing bovine antibodies. In certain embodiments, a broadly neutralizing bovine antibody comprises a polyclonal F(ab) or F(ab')2 fragment. In certain embodiments, a broadly neutralizing bovine antibody comprises a humanized bovine monoclonal antibody.

18 Claims, 24 Drawing Sheets

Specification includes a Sequence Listing.

(56) References Cited

OTHER PUBLICATIONS

Yacoob et al., Cell Rep. Nov. 1, 2016 ;17(6):1560-1570. doi: 10.1016/j.celrep.2016.10.017. PMID: 27806295 PMCID: PMC5207042.
Janeway et al., Immunobiology, 3rd edition, Garland Publishing Inc., 1997, pp. 3:1-3:11.
Rudikoff et al., Proc Natl Acad Sci USA. Mar. 1982; 79(6):1979-83.
Edwards et al.,J Mol Biol. Nov. 14, 2003; 334(1): 103-18.
Goel et al., J Immunol. Dec. 15, 2004; 173(12):7358-67.
Llyod et al., Protein Eng Des Sel. Mar. 2009;22(3):159-68. doi: 10.1093/protein/gzn058. Epub Oct. 29, 2008.
Kanyavuz et al., Nat Rev Immunol. Jun. 2019;19(6):355-368. doi: 10.1038/S41577-019-0126-7.
Lescar, et al. Journal of Biological Chemistry 270.30 (1995): 18067-18076.
Stryer, L., Biochemistry, 4th edition, W. H. Freeman and Company, 1995, pp. 18-23.
Johnson MC., AIDS Res Hum Retroviruses. Mar. 2011;27(3):239-47. doi: 10.1089/AID.2010.0350. Epub Feb. 22, 2011. PMID: 21247353.
Heydarchi et al., MAbs. Apr. 2017;9(3):550-566. doi: 10.1080/19420862.2016.1270491. Epub Dec. 20, 2016. PMID: 27996375.

* cited by examiner

Experiment 1: JRFL gp120 + BG505 SOSIP
Experiment 2: BG505 SOSIP
Test neutralization
prime
boost
boost
prime
boost
boost
boost
boost
boost
0
14
21
28
35
42
50
56
63
70
77
84
91
98
105
133
148
168
175
182
217
224
231
238
360
367
374
381
bleed (days)

Cow 148
Cow 3441
Cow 26
Cow 27
Neutralization Titers (1/dilution)
$10^0$
$10^1$
$10^2$
$10^3$
$10^4$
$10^5$
398F1, A
X2278, B
TRO.11, B
25710, C
CE0217, C
CE1176, C
X1632, G
246F3, AC
CNE8, AE
CNE55, AE
CH119, BC
BJOX2000, BC
MLV

Fig. 2B.

| | | Percent Breadth | | | | Median ID50 | | | |
|---|---|---|---|---|---|---|---|---|---|
| Clade | n | d42 | d77 | d238 | d381 | d42 | d77 | d238 | d381 |
| A | 10 | 60% | 90% | 100% | 100% | 265 | 389 | 5796 | 5635 |
| B | 23 | | 70% | 100% | 100% | | 47 | 192 | 233 |
| C | 30 | 13% | 93% | 97% | 97% | 63 | 148 | 791 | 600 |
| D | 2 | | 100% | 100% | 100% | | 32 | 162 | 263 |
| G | 7 | 14% | 43% | 71% | 86% | 38 | 25 | 1144 | 342 |
| AC | 5 | 80% | 100% | 100% | 100% | 44 | 163 | 1539 | 1742 |
| AE | 16 | 6% | 44% | 75% | 88% | 116 | 68 | 897 | 469 |
| AG | 7 | 43% | 86% | 86% | 86% | 25 | 94 | 942 | 1004 |
| BC | 10 | 20% | 100% | 100% | 100% | 114 | 261 | 993 | 1101 |
| CD | 5 | 20% | 80% | 80% | 100% | 25 | 112 | 504 | 253 |
| ACD | 2 | 50% | 100% | 100% | 100% | 25 | 88 | 9873 | 12181 |
| | 117 | 20% | 79% | 92% | 96% | 62 | 108 | 671 | 595 |

Fig. 3.

| COW 26 | 398F1 | 25710 | CNE8 | TRO.11 | X2278 | BJOX2000 | X1632 | Ce1176 | 246F3 | CH119 | Ce0217 | CNE55 |
|---|---|---|---|---|---|---|---|---|---|---|---|---|
| D0 | < 25 | < 25 | < 25 | < 25 | < 25 | < 25 | < 25 | < 25 | < 25 | < 25 | < 25 | < 25 |
| D14 | < 25 | < 25 | < 25 | < 25 | < 25 | < 25 | < 25 | < 25 | < 25 | < 25 | < 25 | < 25 |
| D21 | < 25 | < 25 | < 25 | < 25 | < 25 | < 25 | < 25 | < 25 | < 25 | < 25 | < 25 | < 25 |
| D28 | < 25 | < 25 | < 25 | < 25 | < 25 | < 25 | < 25 | < 25 | < 25 | < 25 | < 25 | < 25 |
| D35 | < 25 | < 25 | < 25 | < 25 | < 25 | < 25 | < 25 | < 25 | < 25 | < 25 | < 25 | < 25 |
| D42 | 221 | < 25 | < 25 | < 25 | < 25 | < 25 | < 25 | < 25 | < 25 | < 25 | < 25 | < 25 |
| D50 | 887 | 67 | < 25 | < 25 | < 25 | < 25 | < 25 | < 25 | 172 | < 25 | < 25 | < 25 |
| D56 | 292 | 60 | < 25 | < 25 | < 25 | < 25 | < 25 | < 25 | 132 | < 25 | < 25 | < 25 |
| D63 | 388 | 60 | < 25 | < 25 | < 25 | < 25 | < 25 | < 25 | 37 | < 25 | < 25 | < 25 |
| D70 | 2196 | 398 | < 25 | 31 | < 25 | 182 | 73 | 58 | 286 | 215 | 31 | < 25 |
| D77 | 2656 | 398 | < 25 | 126 | < 25 | 948 | 70 | 38 | 583 | 472 | 77 | < 25 |
| D84 | 2002 | 450 | < 25 | 43 | < 25 | 286 | 29 | 40 | 284 | 217 | 32 | < 25 |
| D91 | 621 | 202 | < 25 | < 25 | < 25 | 96 | < 25 | 31 | 58 | 185 | < 25 | < 25 |
| D98 | 871 | 248 | < 25 | < 25 | < 25 | 182 | < 25 | 25 | 93 | 424 | < 25 | < 25 |
| D105 | 1525 | 311 | < 25 | 39 | < 25 | 270 | 65 | 25 | 121 | 795 | 50 | < 25 |
| D133 | 298 | 112 | < 25 | < 25 | < 25 | 62 | 27 | < 25 | 30 | 120 | 25 | < 25 |
| D148 | 453 | 43 | < 25 | < 25 | < 25 | < 25 | < 25 | < 25 | 49 | 30 | < 25 | < 25 |
| D168 | 10233 | 717 | < 25 | 86 | < 25 | 1940 | 289 | 168 | 270 | 858 | 416 | 420 |
| D175 | 4931 | 275 | < 25 | 55 | < 25 | 2525 | 285 | 317 | 452 | 1052 | 362 | 802 |
| D182 | 5337 | 420 | < 25 | 57 | < 25 | 536 | 171 | 249 | 286 | 199 | 366 | 74 |
| D217 | 14845 | 1555 | 1351 | 363 | 1015 | 1397 | 470 | 457 | 1107 | 544 | 3228 | 1901 |
| D224 | 61312 | 4582 | 1021 | 7199 | 7244 | 24385 | 1727 | 4160 | 2395 | 3171 | 7018 | 6310 |
| D231 | 30004 | 5788 | 397 | 9326 | 7244 | 18413 | 1435 | 3651 | 2618 | 1319 | 7018 | 2735 |
| D238 | 8385 | 2403 | < 25 | 922 | 5372 | 1996 | 569 | 1696 | 1539 | 578 | 1876 | 1164 |
| D360 | 980 | 197 | < 25 | < 25 | < 25 | 44 | < 25 | 43 | 176 | 39 | 88 | 28 |
| D367 | 44855 | 8347 | 1050 | 21324 | 2442 | 37456 | 575 | 1780 | 2501 | 1379 | 7593 | 1712 |
| D374 | 71955 | 9970 | 787 | 13647 | 7275 | 30598 | 1676 | 3907 | 5411 | 2576 | 12473 | 3422 |
| D381 | 29580 | 4097 | 1380 | 1514 | 9003 | 3009 | 788 | 2163 | 1864 | 940 | 2234 | 1171 |

Fig. 3. cont.

| COW 27 | 398F1 | 25710 | CNE8 | TRO.11 | X2278 | BJOX2000 | X1632 | Ce1176 | 246F3 | CH119 | Ce0217 | CNE55 |
|---|---|---|---|---|---|---|---|---|---|---|---|---|
| D0 | < 25 | < 25 | < 25 | < 25 | < 25 | < 25 | < 25 | < 25 | < 25 | < 25 | < 25 | < 25 |
| D14 | < 25 | < 25 | < 25 | < 25 | < 25 | < 25 | < 25 | < 25 | < 25 | < 25 | < 25 | < 25 |
| D21 | < 25 | < 25 | < 25 | < 25 | < 25 | < 25 | < 25 | < 25 | < 25 | < 25 | < 25 | < 25 |
| D28 | < 25 | < 25 | < 25 | < 25 | < 25 | < 25 | < 25 | < 25 | < 25 | < 25 | < 25 | < 25 |
| D35 | < 25 | < 25 | < 25 | < 25 | < 25 | < 25 | < 25 | < 25 | < 25 | < 25 | < 25 | < 25 |
| D42 | < 25 | < 25 | < 25 | < 25 | < 25 | < 25 | < 25 | < 25 | < 25 | < 25 | < 25 | < 25 |
| D50 | 350 | < 25 | < 25 | < 25 | < 25 | < 25 | < 25 | < 25 | < 25 | < 25 | < 25 | < 25 |
| D56 | 193 | < 25 | < 25 | < 25 | < 25 | < 25 | < 25 | < 25 | < 25 | < 25 | < 25 | < 25 |
| D63 | 123 | < 25 | < 25 | < 25 | < 25 | < 25 | 25 | < 25 | < 25 | < 25 | < 25 | < 25 |
| D77 | 821 | < 25 | < 25 | < 25 | < 25 | < 25 | 25 | < 25 | < 25 | < 25 | < 25 | < 25 |
| D84 | 688 | < 25 | < 25 | < 25 | < 25 | < 25 | 76 | < 25 | < 25 | < 25 | < 25 | < 25 |
| D91 | 385 | < 25 | < 25 | < 25 | < 25 | < 25 | 612 | < 25 | < 25 | < 25 | < 25 | < 25 |
| D98 | 878 | < 25 | < 25 | < 25 | 25 | 66 | 612 | < 25 | 58 | < 25 | < 25 | < 25 |
| D105 | 1354 | 25 | < 25 | < 25 | 139 | < 25 | 413 | < 25 | 53 | < 25 | < 25 | < 25 |
| D133 | 675 | 59 | < 25 | < 25 | < 25 | < 25 | 316 | < 25 | 31 | < 25 | < 25 | < 25 |
| D148 | 2561 | 54 | < 25 | 30 | 25 | 533 | 2458 | < 25 | 77 | < 25 | < 25 | < 25 |
| D168 | 2846 | 97 | < 25 | < 25 | 25 | 2184 | 3319 | < 25 | 89 | < 25 | < 25 | < 25 |
| D175 | 555 | 76 | < 25 | < 25 | 358 | 61 | 771 | < 25 | 37 | < 25 | < 25 | < 25 |
| D182 | 1068 | 31 | 50 | 36 | 64 | 336 | 766 | < 25 | 140 | < 25 | < 25 | 25 |
| D217 | 6845 | 58 | 287 | 244 | 117 | 7288 | 7288 | < 25 | 662 | < 25 | 100 | 83 |
| D224 | 5493 | 172 | 398 | 75 | 631 | 1585 | 3584 | < 25 | 409 | < 25 | 100 | 67 |
| D231 | 1462 | 134 | 36 | < 25 | 1243 | 470 | 634 | < 25 | 196 | < 25 | 100 | < 25 |
| D238 | 210 | 105 | < 25 | < 25 | 385 | 75 | 74 | < 25 | 65 | < 25 | 25 | < 25 |
| D360 | 10275 | < 25 | 1008 | 588 | 95 | 25 | 51 | < 25 | 9697 | 109 | 25 | 97 |
| D367 | 24629 | 1458 | 1344 | 418 | 3115 | 4835 | 3369 | < 25 | 13407 | 84 | 454 | 236 |
| D374 | 5615 | 1689 | 94 | 38 | 8495 | 6645 | 6112 | < 25 | 2350 | 28 | 318 | 73 |
| D381 | 12144 | 310 | 71 | 25 | 781 | 1368 | 1515 | < 25 | 1864 | 25 | 129 | 1171 |

Fig. 5A.

| Virus | Clade | d42 | d77 | d238 | d381 | NC-Cow1 |
|---|---|---|---|---|---|---|
| 94UG103 | A | < 25 | 25 | 649 | 474 | 0.043 |
| 398F1 | A | 221 | 2656 | 8385 | 29580 | 0.015 |
| BG505 | A | 448 | 15931 | 69935 | 198743 | 0.010 |
| MS208 | A | 9498 | 21263 | 8451 | 8357 | 0.036 |
| Q23.17 | A | 133 | 1657 | 10880 | 9847 | 0.023 |
| Q461.e2 | A | < 25 | 270 | 3207 | 2913 | 0.071 |
| Q769.d22 | A | < 25 | 120 | 2564 | 2556 | 0.012 |
| 0330.v4.c3 | A | 46 | 389 | 12248 | 11394 | 0.008 |
| 0260.v5.c36 | A | 308 | 184 | 2243 | 2530 | 0.020 |
| 191084_B7-19 | A (T/F) | < 25 | < 25 | 371 | 918 | 0.022 |
| 92BR020 | B | < 25 | 49 | 685 | 780 | 0.025 |
| JR-CSF | B | < 25 | < 25 | 25 | 101 | 2.51 |
| 6535.3 | B | < 25 | 57 | 25 | 33 | 3.96 |
| QH0692.42 | B | < 25 | 83 | 113 | 130 | 1.27 |
| SC422661.8 | B | < 25 | < 25 | 25 | 119 | > 50 |
| PVO.4 | B | < 25 | 28 | 286 | 303 | 0.151 |
| TRO.11 | B | < 25 | 25 | 193 | 234 | 0.035 |
| AC10.0.29 | B | < 25 | 74 | 192 | 228 | > 50 |
| RHPA4259.7 | B | < 25 | 36 | 217 | 233 | 1.71 |
| REJO4541.67 | B | < 25 | < 25 | 50 | 87 | > 50 |
| TRJO4551.58 | B | < 25 | 25 | 33 | 172 | 0.197 |
| WITO4160.33 | B | < 25 | 401 | 1663 | 1783 | 0.033 |
| CAAN5342.A2 | B | < 25 | 25 | 77 | 110 | 0.021 |
| X2278 | B | < 25 | < 25 | 5372 | 9003 | 0.004 |
| WEAU_d15_410_5017 | B (T/F) | < 25 | 25 | 248 | 319 | 0.396 |
| 1006_11_C3_1601 | B (T/F) | < 25 | < 25 | 483 | 528 | 0.037 |
| 1054_07_TC4_1499 | B (T/F) | < 25 | < 25 | 25 | 47 | 1.20 |
| 1056_10_TA11_1826 | B (T/F) | < 25 | 155 | 257 | 401 | 0.805 |

Fig. 5B.

| Virus | Clade | d42 | d77 | d238 | d381 | NC-Cow1 |
|---|---|---|---|---|---|---|
| 1012_11_TC21_3257 | B (T/F) | < 25 | < 25 | 101 | 185 | 0.029 |
| 6240_08_TA5_4622 | B (T/F) | < 25 | 44 | 149 | 153 | 0.162 |
| 6244_13_B5_4576 | B (T/F) | < 25 | 68 | 704 | 749 | 0.056 |
| 62357_14_D3_4589 | B (T/F) | < 25 | 25 | 161 | 330 | 0.090 |
| SC05_8C11_2344 | B (T/F) | < 25 | 248 | 659 | 455 | > 50 |
| IAVI C22 | C | < 25 | 1584 | 6310 | 3897 | 0.006 |
| 25710 | C | < 25 | 398 | 2403 | 4097 | 0.006 |
| Du156.12 | C | < 25 | 513 | 1820 | 890 | > 50 |
| Du172.17 | C | < 25 | 103 | 684 | 425 | 0.119 |
| Du422.1 | C | < 25 | 188 | 1157 | 1579 | 0.020 |
| ZM197M.PB7 | C | < 25 | 317 | 244 | 350 | 0.733 |
| ZM214M.PL15 | C | < 25 | 254 | 1304 | 1969 | 0.004 |
| ZM233M.PB6 | C | < 25 | 43 | 579 | 385 | > 50 |
| ZM249M.PL1 | C | < 25 | 258 | 1313 | 1074 | 0.566 |
| ZM53M.PB12 | C | < 25 | 428 | 1759 | 2184 | 0.010 |
| ZM109F.PB4 | C | < 25 | 53 | 81 | 144 | > 50 |
| ZM135M.PL10a | C | < 25 | < 25 | < 25 | < 25 | > 50 |
| CAP45 | C | < 25 | 100 | 606 | 313 | 0.792 |
| CAP210.2.00.E8 | C | < 25 | 94 | 223 | 232 | > 50 |
| HIV-001428-2.42 | C | < 25 | 87 | 426 | 590 | 0.023 |
| HIV-16055-2.3 | C | < 25 | 89 | 430 | 600 | 0.021 |
| HIV-16845-2.22 | C | < 25 | 624 | 791 | 334 | > 50 |
| Ce0217 | C | < 25 | 77 | 1876 | 2234 | 0.007 |
| Ce704809221_1B3 | C | < 25 | 100 | 2246 | 1539 | 0.022 |
| Ce0393_C3 | C (T/F) | 309 | 1618 | 14830 | 5577 | 0.002 |
| Ce1176_A3 | C (T/F) | < 25 | 25 | 481 | 561 | 0.013 |
| Ce2010_F5 | C (T/F) | < 25 | 260 | 4032 | 2818 | > 50 |
| Ce1172_H1 | C (T/F) | < 25 | 107 | 334 | 289 | 0.866 |
| Ce703010054_2A2 | C (T/F) | < 25 | 25 | 113 | 113 | > 50 |
| BF1266.431a | C (T/F) | < 25 | 524 | 1202 | 461 | > 50 |
| 246F_C1G | C (T/F) | 25 | 46 | 136 | 444 | 0.120 |
| 249M_B10 | C (T/F) | 25 | 50 | 7048 | 1417 | > 50 |
| ZM247v1(Rev-) | C (T/F) | < 25 | 294 | 545 | 644 | 0.060 |
| 7030102001E5(Rev-) | C (T/F) | < 25 | < 25 | 109 | 120 | 0.043 |
| 1394C9G1(Rev-) | C (T/F) | 100 | 723 | 2616 | 1212 | 0.008 |
| A07412M1.vrc12 | D | < 25 | 38 | 298 | 444 | 0.007 |
| 231965.c01 | D | < 25 | 25 | 26 | 81 | > 50 |
| X1193_c1 | G | < 25 | < 25 | 1144 | 314 | 0.031 |
| P0402_c2_11 | G | 38 | 214 | 2674 | 2337 | 0.013 |
| X1254_c3 | G | < 25 | < 25 | < 25 | < 25 | > 50 |
| X2088_c9 | G | < 25 | < 25 | < 25 | 43 | > 50 |
| P1981_C5_3 | G | < 25 | < 25 | 53 | 42 | > 50 |
| X1632_S2_B10 | G | < 25 | 25 | 1313 | 1081 | 0.022 |
| 3016.v5.c45 | G | < 25 | 25 | 138 | 370 | 0.017 |
| 3301.v1.c24 | AC | 25 | 77 | 196 | 205 | > 50 |
| 6041.v3.c23 | AC | 165 | 1364 | 11062 | 10202 | 0.006 |

Fig. 5C.

| Virus | Clade | d42 | d77 | d238 | d381 | NC-Cow1 |
|---|---|---|---|---|---|---|
| 6540.v4.c1 | AC | 62 | 163 | 1747 | 1742 | > 50 |
| 6545.v4.c1 | AC | 25 | 79 | 984 | 989 | > 50 |
| 246F3 | AC | < 25 | 583 | 1539 | 1864 | 0.147 |
| 92TH021 | CRF01_AE | < 25 | 25 | 2667 | 2516 | 0.005 |
| 620345.c01 | CRF01_AE | < 25 | 167 | 25 | 817 | 0.009 |
| C1080.c03 | CRF01_AE | 116 | 259 | 574 | 544 | 0.030 |
| R2184.c04 | CRF01_AE | < 25 | 25 | 519 | 393 | > 50 |
| R1166.c01 | CRF01_AE | < 25 | 40 | 1814 | 2253 | 0.009 |
| R3265.c06 | CRF01_AE | < 25 | < 25 | 1242 | 335 | 0.251 |
| C3347.c11 | CRF01_AE | < 25 | < 25 | 1109 | 855 | 0.006 |
| C4118.c09 | CRF01_AE | < 25 | 68 | 1119 | 1667 | 0.009 |
| CNE8 | CRF01_AE | < 25 | < 25 | < 25 | 77 | 2.81 |
| CNE55 | CRF01_AE | < 25 | < 25 | < 25 | < 25 | 0.001 |
| CNE5 | CRF01_AE | < 25 | < 25 | 40 | 187 | 0.092 |
| BJOX009000.02.4 | CRF01_AE | < 25 | 249 | 1438 | 354 | > 50 |
| BJOX015000.11.5 | CRF01_AE (T/F) | < 25 | < 25 | < 25 | < 25 | > 50 |
| BJOX010000.06.2 | CRF01_AE (T/F) | < 25 | < 25 | 685 | 668 | > 50 |
| BJOX025000.01.1 | CRF01_AE (T/F) | < 25 | < 25 | 465 | 369 | 0.009 |
| BJOX028000.10.3 | CRF01_AE (T/F) | < 25 | < 25 | < 25 | 80 | 0.354 |
| T257-31 | CRF02_AG | < 25 | 110 | 841 | 783 | 0.015 |
| 928-28 | CRF02_AG | < 25 | 25 | 251 | 284 | > 50 |
| 263-8 | CRF02_AG | 724 | 822 | 6818 | 6372 | 0.005 |
| T250-4 | CRF02_AG | 25 | 78 | 1043 | 1225 | > 50 |
| T251-18 | CRF02_AG | < 25 | 25 | 150 | 139 | 0.141 |
| T278-50 | CRF02_AG | < 25 | < 25 | < 25 | < 25 | > 50 |
| 235-47 | CRF02_AG | 25 | 1136 | 5000 | 3365 | > 50 |
| CNE19 | BC | 55 | 250 | 1351 | 1262 | 0.007 |
| CNE20 | BC | < 25 | 471 | 542 | 739 | > 50 |
| CNE21 | BC | < 25 | 55 | 634 | 617 | 3.38 |
| CNE17 | BC | < 25 | 139 | 304 | 318 | > 50 |
| CNE30 | BC | < 25 | 25 | 329 | 656 | 0.027 |
| CNE52 | BC | < 25 | 141 | 1888 | 2531 | 0.005 |
| CNE53 | BC | 173 | 3523 | 10880 | 7604 | 0.011 |
| CNE58 | BC | < 25 | 271 | 1917 | 1604 | 0.007 |
| CH119 | BC | < 25 | 472 | 578 | 940 | 0.032 |
| BJOX2000 | BC | < 25 | 948 | 1996 | 3009 | 2.14 |
| 3817.v2.c59 | CD | < 25 | 179 | 753 | 658 | 0.253 |
| 6480.v4.c25 | CD | < 25 | 44 | 143 | 253 | > 50 |
| 6952.v1.c20 | CD | < 25 | < 25 | < 25 | 25 | 2.05 |
| 6811.v7.c18 | CD | < 25 | 397 | 314 | 139 | > 50 |
| 89-F1_2_25 | CD | 25 | 44 | 694 | 761 | 0.034 |
| 0815.v3.c3 | ACD | 25 | 151 | 19422 | 24128 | 0.010 |
| 3103.v3.c10 | ACD | < 25 | 25 | 324 | 233 | 0.103 |

| | 3441, d35 | 148, d35 |
|---|---|---|
| 398F1, A | 1398 | 100 |
| X2278, B | <25 | <25 |
| TR0.11 , B | <25 | <25 |
| 25710, C | 225 | <25 |
| CE0217, C | 182 | <25 |
| CE1176, C | 26 | <25 |
| X1632, G | <25 | <25 |
| 246F3, AC | 248 | 25 |
| CNE8, AE | <25 | <25 |
| CNE55, AE | <25 | <25 |
| CH119, BC | 25 | 25 |
| BJOX2000, BC | 150 | <25 |
| MLV | <25 | <25 |

Fig. 9A.

| | V | N | D | J | L | # Cys |
| --- | --- | --- | --- | --- | --- | --- |
| germline | CTTVHQ | | SCPDGYSYGYGCGYGYGCSGYDCYGYGGYGGYGGYGYSSYSYSYTYEY | YVDAWGQGLLVTVSS | | |
| NC-Cow1 | CITAHQ | KTNKK | ECPEDYTYNPRCPQQYGWSDCDCMGDRFGGYCRQDGCSNYIHRSTYEW | YVSAWGQGLLVTVSS | 60 | 6 |
| NC-Cow2 | CGTVHQ | KTQRKP | ICPDGYSDDSTLRYYSRCSDRDCWRCTGTTYYDTCQCGTYTWIDTHEL | HVDAWGQGLLVTVSS | 61 | 6 |
| NC-Cow3 | CGTVHQ | RTHRKQ | NCPGGYSDDNALRYRSRCDDRDCWRCTGTTYYDTCQCASYFYTDTYEF | YVDAWGQGLLVTVSS | 61 | 6 |
| NC-Cow4 | CGTVHQ | RTQPKQ | TCPNGYSDDSALRYYSRCSDRDCWRCTGTTYYDTCQCSSYTYIHTYEL | YVDAWGQGLLVTVSS | 61 | 6 |
| NC-Cow5 | CGTVHQ | RTQPKQ | TCPNGYSDDSALRYYSRCSDRDCWRCTGTTYYDTCQCSSYTYIHTYEL | YVDAWGQGLLVTVSS | 61 | 6 |
| NC-Cow6 | CGTVHQ | RTQPKQ | TCPNGYSDDSALRYYSRCSDRDCWRCTGTTYYDTCQCSSYTYIHTYEL | YVDAWGQGLLVTVSS | 61 | 6 |
| NC-Cow7 | CTTVHQ | KAYKK | VCPDDYSSNPDCVRLYGWSHCDCMRDSFGGWCRADGCSSTVEIGPYEW | YVNAWGQGLLVTVSS | 60 | 6 |
| NC-Cow8 | CTTVYQ | KTTKK | DCPEYYTYNPDCARRYGWSDCECMADKFGGYCRHDGCATNTVRSTYEW | HLDAWGQGLLVTVSS | 60 | 6 |
| NC-Cow9 | CTTVYQ | KTTKK | DCPEYYTYNPDCARRYGWSDCECMADKFGGYCRHDGCATNTVRSTYEW | HLDAWGQGLLVTVSS | 60 | 6 |
| NC-Cow10 | CTTVHQ | KTNEK | DCPEYYSYNPDCPRRYGWSNCDCMADKFGGWCRHDGCSDYADMTTDEW | YVDAWGQGLLVTVSS | 60 | 6 |
| * | | 100 | B2 | 101 | | |

Fig. 9B.

NC-Cow1

| Clade | n | % Breadth | Median IC50 |
| --- | --- | --- | --- |
| A | 10 | 100% | 0.021 |
| B | 23 | 83% | 0.151 |
| C | 30 | 67% | 0.021 |
| D | 2 | 50% | 0.007 |
| G | 7 | 57% | 0.019 |
| AC | 5 | 40% | 0.077 |
| AE | 16 | 75% | 0.009 |
| AG | 7 | 43% | 0.015 |
| BC | 10 | 80% | 0.019 |
| CD | 5 | 60% | 0.253 |
| ACD | 2 | 100% | 0.057 |
| | 117 | 72% | 0.028 |

Fig. 9C.

| | | VRC01-class | | | CD4bs | | V3-glycan | | V2-apex | | Interface | |
|---|---|---|---|---|---|---|---|---|---|---|---|---|
| | Self | VRC01 | 12A12 | 3BNC117 | b12 | CH103 | PGT121 | PGT128 | PGDM1400 | PG9 | PGT151 | 35022 |
| NC-Cow1 | 93 | 73 | 88 | 79 | 14 | 8 | -5 | 31 | 10 | 10 | 6 | -5 |
| NC-Cow2 | 91 | 93 | 94 | 93 | 0 | 11 | 27 | 57 | 18 | 4 | 11 | 11 |
| NC-Cow3 | 80 | 94 | 95 | 95 | 4 | 24 | 19 | 50 | -2 | 6 | 2 | 1 |
| NC-Cow4 | 84 | 94 | 95 | 95 | 29 | 13 | -11 | 35 | 22 | 7 | 20 | 18 |
| NC-Cow5 | 37 | 95 | 95 | 94 | 23 | 38 | 21 | 71 | 3 | 21 | 2 | 14 |
| NC-Cow6 | 90 | 95 | 95 | 95 | 0 | 12 | 17 | 27 | -13 | 6 | 3 | -5 |
| NC-Cow7 | 90 | 87 | 92 | 90 | 9 | 35 | 23 | 31 | 12 | 8 | 20 | 5 |
| NC-Cow8 | 89 | 87 | 92 | 89 | 15 | 28 | 24 | 15 | -2 | 4 | 0 | 5 |
| NC-Cow9 | 91 | 83 | 92 | 91 | 2 | 30 | 22 | 28 | 0 | -1 | -5 | 11 |
| NC-Cow10 | 93 | 82 | 91 | 89 | 27 | 16 | 0 | 28 | 10 | 13 | 11 | 2 |

Fig. 10A.

```
            1        10        20        30        40        50        60        70        80        90
Consensus   MGWSCIILFLVATATGVHSKVQLQESGPSLVKPSQTLSLTCTVSGFSLSDKAVGWVRQAPGKALEWLGTIDTSGNTNYNPGLKSRLSITKDNSK
NC-Cow1     ...................Q...R......M..............S..N..S............Q...SV......D.................
NC-Cow7     .................................FE.......G.........A..........P....S...G...G......Y..........
NC-Cow8     .......................R..........................V...................Y......V..............A.
NC-Cow9     ...................Q..............................V...................Y......V..............A.
NC-Cow10    ........................................................................NR....H...............

                100       110       120       130       140       150       160       170       180    187
Consensus   SQVSLSVTSMTTEDSATYYCTTVHQKTXKKDCPEYYTYNPDCXRRYGWSDCDCMADKFGGYCRHDGCSTXTVRSTYEWYVDAWGQGLLVTVSS
NC-Cow1     .RI..T..G...........I.A....N..E...D.....R.PQQ.........G.R......Q....NYIH........S............
NC-Cow7     ......S...S...............AY..V..DD.SS....V.L....H....R.S...W..A....STVEIGP.....N............
NC-Cow8     ........L..D...........Y...T..............A........E...............A.N........HL.............
NC-Cow9     ........L..D...........Y...T..............A........E...............A.N........HL.............
NC-Cow10    .R....ST...................NE.......S.....P......N..........W.......DYADMT.D.................
```

Fig. 10B.

```
            1        10        20        30        40        50        60        70        80        90
Consensus   MGWSCIILFLVATATGVHSQVQLRESGPSLVKPSQTLSLTCMVSGFSLNDKAVGWVRQAPGKALEWLGSIDAGGSTGYNPGLKSRLSISKDNSK
NC-Cow2     ...................K.........................S..S...................I.S...NR...S..R...T.......
NC-Cow3     ......................................................................GT..NK...............S..
NC-Cow4     ...................K..............................E...........................................
NC-Cow5     .......................Q......................................................................
NC-Cow6     ..............................................................................................

                100       110       120       130       140       150       160       170       180    188
Consensus   NQVSLSVSSVTTEDSATYYCGTVHQRTQPKQTCPNGYSDDSALRYYSRCSDRDCWRCTGTTYYDTCQCSSYTYIHTYELYVDAWGQGLLVTVSS
NC-Cow2     .E...R.R..........F......K..R.PI..D......T..........................GT..W.D.H..H..............
NC-Cow3     ......M....................HR..N..G.....N....R...D..................A..F.TD...F...............
NC-Cow4     ..............................................................................................
NC-Cow5     ..............................................................................................
NC-Cow6     ..............................................................................................
```

Fig. 10D.

| PBMC timepoint: | | d238 | d238 | d238 | d70 | d70 | d70 | d381 | d381 | d381 | d381 |
|---|---|---|---|---|---|---|---|---|---|---|---|
| | CLADE | NC-Cow1 | NC-Cow2* | NC-Cow3* | NC-Cow4 | NC-Cow5 | NC-Cow6 | NC-Cow7 | NC-Cow8 | NC-Cow9 | NC-Cow10 |
| BG505.N332 | A | 0.010 | 0.440 | 1.69 | 0.027 | 10.1 | 0.134 | 0.001 | 0.001 | 0.007 | 0.003 |
| MG505.A2 | A | 0.011 | 1.72 | 1.53 | 0.023 | 4.48 | 0.057 | 0.002 | 0.003 | 0.011 | 0.020 |
| 398F1 | A | 0.015 | > 50 | > 50 | > 50 | > 50 | > 50 | 5.80 | 4.87 | 7.94 | 0.317 |
| 25710 | C | 0.006 | > 50 | > 50 | > 50 | > 50 | > 50 | 2.14 | 0.251 | 0.211 | 0.002 |
| CNE8 | CRF01_AE | 2.81 | > 50 | > 50 | > 50 | > 50 | > 50 | > 50 | > 50 | > 50 | > 50 |
| TRO.11 | B | 0.035 | > 50 | > 50 | > 50 | > 50 | > 50 | > 50 | > 50 | > 50 | > 50 |
| X2278 | B | 0.019 | > 50 | > 50 | > 50 | > 50 | > 50 | > 50 | 10.7 | 21.5 | > 50 |
| BJOX2000 | CRF07_BC | 2.14 | > 50 | > 50 | > 50 | > 50 | > 50 | 2.25 | > 50 | > 50 | > 50 |
| X1632 | G | 0.022 | > 50 | > 50 | > 50 | > 50 | > 50 | 1.26 | 0.051 | 0.165 | 0.034 |
| Ce1176 | C | 0.013 | > 50 | > 50 | > 50 | > 50 | > 50 | 25.6 | 0.247 | 2.300 | 0.079 |
| 246F3 | AC | 0.147 | > 50 | > 50 | > 50 | > 50 | > 50 | > 50 | > 50 | > 50 | 20.5 |
| CH119 | CRF07_BC | 0.032 | > 50 | > 50 | > 50 | > 50 | > 50 | 21.0 | > 50 | > 50 | 1.88 |
| Ce0217 | C | 0.007 | > 50 | > 50 | > 50 | > 50 | > 50 | 1.87 | 0.211 | 0.913 | 0.004 |
| CNE55 | CRF01_AE | 0.001 | > 50 | > 50 | > 50 | > 50 | > 50 | > 50 | 0.27 | 1.86 | 0.48 |
| MS208.A1 | A | 0.036 | > 50 | > 50 | > 50 | > 50 | > 50 | 4.30 | 6.67 | 13.4 | 4.15 |
| Q23.17 | A | 0.023 | > 50 | > 50 | > 50 | > 50 | > 50 | 0.002 | 0.021 | 0.160 | 0.009 |
| Q461.e2 | A | 0.071 | 1.64 | > 50 | 2.46 | > 50 | 2.02 | 0.01 | 0.01 | 0.03 | 0.02 |
| Q769.d22 | A | 0.012 | 0.566 | 35.3 | 0.543 | > 50 | 0.858 | 0.000 | 0.003 | 0.059 | 0.003 |
| Q259.d2.17 | A | 3.983 | > 50 | > 50 | > 50 | > 50 | > 50 | > 50 | > 50 | > 50 | > 50 |
| Q842.d12 | A | 0.010 | 0.896 | 5.50 | 0.085 | 13.9 | 0.150 | 0.003 | 0.088 | 0.128 | 0.042 |
| 0260.v5.c36 | A | 0.020 | > 50 | > 50 | > 50 | > 50 | > 50 | 0.003 | 0.006 | 0.118 | 0.006 |
| 191955_A11 | A | > 50 | > 50 | > 50 | > 50 | > 50 | > 50 | 0.008 | > 50 | > 50 | > 50 |
| 191084 B7-19 | A | 0.008 | > 50 | > 50 | > 50 | > 50 | > 50 | 1.40 | 0.668 | 3.86 | 0.035 |
| SIVmac239 | NA | > 50 | > 50 | > 50 | > 50 | > 50 | > 50 | > 50 | > 50 | > 50 | > 50 |
| M-MLV | NA | > 50 | > 50 | > 50 | > 50 | > 50 | > 50 | > 50 | > 50 | > 50 | > 50 |

* = paired with universal cow light chain

ELISA DATA

| | PGT121 | VRC01 | NC-Cow1 |
|---|---|---|---|
| BG505 | 1.20 | 0.200 | 0.040 |
| K121A | 1.00 | 0.700 | 0.040 |
| L179A | 0.500 | 0.600 | 0.050 |
| N197A | 1.30 | 0.400 | 0.040 |
| N279A | 4.90 | 25.4 | 0.110 |
| K282A | 1.30 | 0.600 | 1.18 |
| N283A | 3.40 | 1.00 | 0.100 |
| N332T | 0.700 | 0.200 | 0.050 |
| N363A | 2.30 | 0.900 | 0.090 |
| S364A | 1.10 | 0.400 | 0.140 |
| S365A | 2.20 | 1.40 | 0.070 |
| G366A | 0.900 | 0.700 | 0.130 |
| G367A | 4.00 | 9.40 | 1.34 |
| L369A | 2.20 | 1.60 | 0.240 |
| E370A | 2.20 | 1.10 | 0.110 |
| V371A | 1.40 | 1.30 | 0.240 |
| T372A | 1.60 | 0.400 | 0.070 |
| T373A | 1.10 | 0.500 | 0.120 |
| G471A | 2.50 | 0.300 | 0.050 |
| G472A | 1.40 | 0.900 | 0.370 |
| M475A | 1.20 | 0.300 | 0.080 |
| R476A | 1.00 | 0.500 | 0.070 |

| | PGT121 | VRC01 | NC-Cow1 |
|---|---|---|---|
| JR-CSF | 1.33 | 0.720 | 0.075 |
| T198A | 0.604 | 0.400 | 0.045 |
| S199A | 1.91 | 0.455 | 0.058 |
| K207A | 0.437 | 0.317 | 0.052 |
| N276A | 1.25 | 0.070 | 0.029 |
| N279A | 0.535 | 8.19 | 0.036 |
| N262A | 0.947 | 0.641 | 5.64 |
| N283A | 0.615 | 0.348 | 0.133 |
| N362A | 0.747 | 0.327 | 0.038 |
| S365A | 0.935 | 0.153 | 0.028 |
| G366A | 0.489 | 0.572 | 0.027 |
| D368A | 0.942 | 2.58 | 2.09 |
| E370A | 0.933 | 2.09 | 1.16 |
| V371A | 0.810 | 1.62 | 1.36 |
| T373A | 0.643 | 0.456 | 0.067 |
| T372A | 0.698 | 0.494 | 0.209 |
| G471A | 0.619 | 0.207 | 0.148 |
| G472A | 0.664 | 0.333 | 11.2 |
| G473A | 0.460 | 0.428 | 6.83 |
| R476A | 0.984 | 0.454 | 0.281 |

NEUTRALIZATION DATA

| | PGT121 | 12A12 | NC-Cow1 |
|---|---|---|---|
| BG505 | 0.012 | 0.020 | 0.006 |
| K121A | 0.026 | 0.053 | 0.029 |
| L179A | 0.032 | 0.056 | 0.018 |
| N262A | 0.011 | 0.017 | 0.014 |
| N276A | 0.016 | 0.003 | 0.011 |
| N279A | 0.020 | 0.058 | 0.012 |
| K282A | 0.009 | 0.040 | 0.020 |
| N332T | 0.019 | 0.031 | 0.018 |
| N363A | 0.026 | 0.038 | 0.013 |
| S364A | 0.018 | 0.032 | 0.014 |
| S365A | 0.022 | 0.057 | 0.015 |
| L369A | 0.021 | 0.030 | 0.015 |
| T372A | 0.019 | 0.037 | 0.028 |
| T373A | 0.017 | 0.039 | 0.016 |
| G471A | 0.014 | 0.029 | 0.013 |
| D474A | 0.023 | 0.020 | 0.009 |
| R476A | 0.020 | 0.026 | 0.012 |

| | PGT121 | 12A12 | NC-Cow1 |
|---|---|---|---|
| JR-CSF | 0.028 | 0.219 | 0.821 |
| T198A | 0.046 | 0.622 | 2.98 |
| S199A | 0.030 | 0.032 | 0.404 |
| K207A | 0.032 | 0.383 | 1.80 |
| N276A | 0.033 | 2.72 | 1.76 |
| D279A | 0.029 | > 50 | 1.02 |
| K282A | 0.049 | 2.33 | > 50 |
| N283A | 0.017 | 0.219 | 6.94 |
| N362A | 0.026 | 0.110 | 0.496 |
| S365A | 0.026 | 0.180 | 0.129 |
| P369A | 0.032 | 0.205 | 1.24 |
| V372A | 0.018 | 0.214 | > 50 |
| M373A | 0.022 | 0.134 | 2.52 |
| G471A | 0.015 | 0.114 | 50.0 |
| D474A | 0.015 | 0.075 | 0.744 |
| R476A | 0.014 | 0.082 | > 50 |

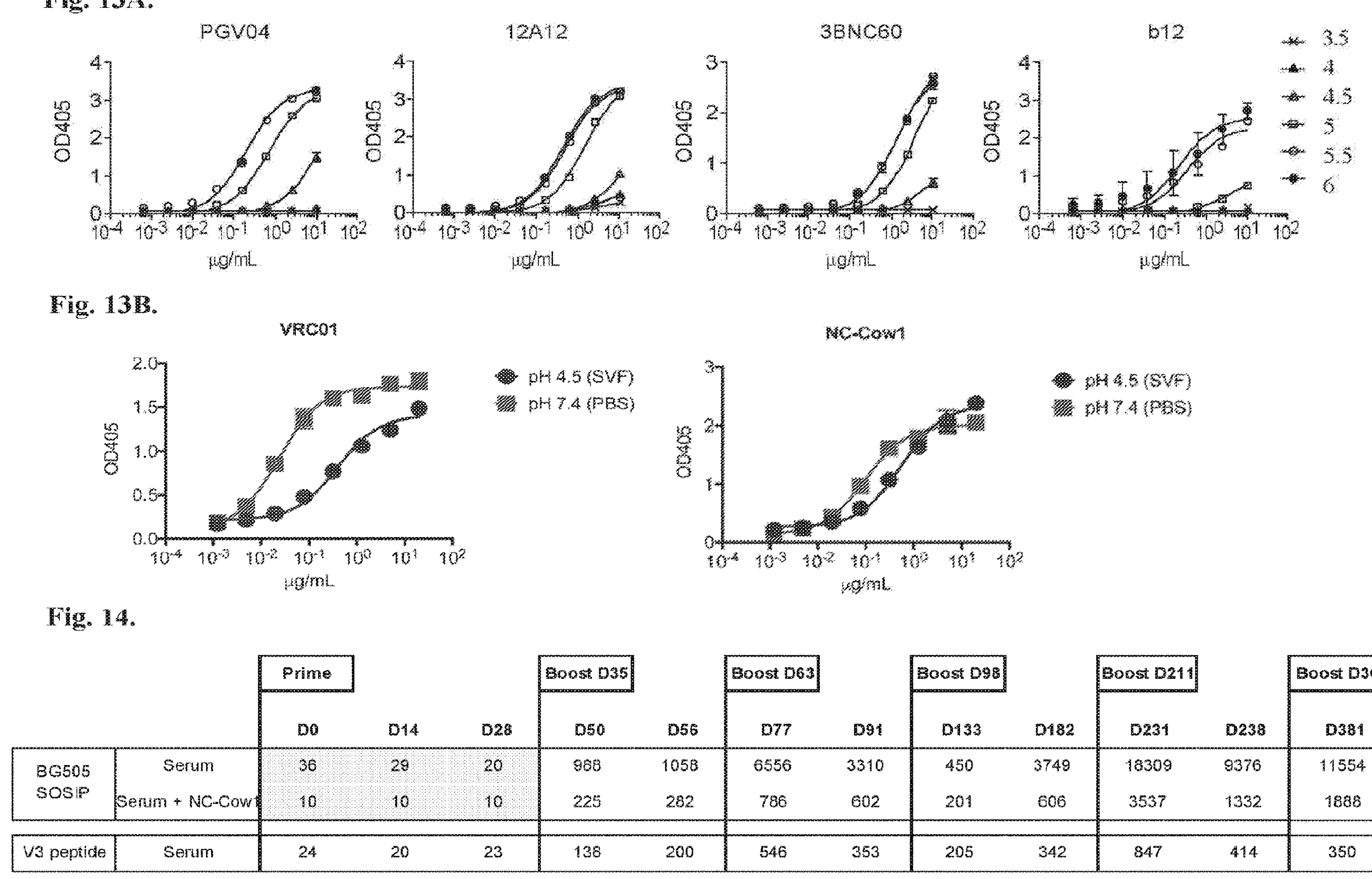
| | | Prime | | | Boost D35 | | Boost D63 | | Boost D98 | | Boost D211 | | Boost D360 |
|---|---|---|---|---|---|---|---|---|---|---|---|---|---|
| | | D0 | D14 | D28 | D50 | D56 | D77 | D91 | D133 | D182 | D231 | D238 | D381 |
| BG505 SOSIP | Serum | 36 | 29 | 20 | 968 | 1058 | 6556 | 3310 | 450 | 3749 | 18309 | 9376 | 11554 |
| | Serum + NC-Cow1 | 10 | 10 | 10 | 225 | 282 | 786 | 602 | 201 | 606 | 3537 | 1332 | 1888 |
| V3 peptide | Serum | 24 | 20 | 23 | 138 | 200 | 546 | 353 | 205 | 342 | 847 | 414 | 350 |

Fig. 15B.

```
IGHV1-7    CTTVHQ
IGHD8-2                      SCPDGYSYGYGCGYGYGCSGYDCYGYGGYGGYGGYGYSSYSYSYTYEY
IGHJ10                                                                            YVDAW
NC-Cow1    CITAHQ  KTNKKE  CPEDYTYNPRCPQQYGWSDCDCMGDRFGGYCRQDGCSNYIHRSTYEW   YVSAW
NC-Cow7    CTTVHQ  KAYKKV  CPDDYSSNPDCVRLYGWSHCDCMRDSFGGWCRADGCSSTVEIGPYEW   YVNAW
NC-Cow8    CTTVYQ  KTTKKD  CPEYYTYNPDCARRYGWSDCECMADKFGGYCRHDGCATNTVRSTYEW   HLDAW
NC-Cow9    CTTVYQ  KTTKKD  CPEYYTYNPDCARRYGWSDCECMADKFGGYCRHDGCATNTVRSTYEW   HLDAW
NC-Cow10   CTTVHQ  KTNEKD  CPEYYSYNPDCPRRYGWSNCDCMADKFGGWCRHDGCSDYADMTTDEW   YVDAW
NC-Cow11   CTTVYQ  KTTKKD  CPEYYTYNPDCARRYGWSDCDCMADKFGGSCRLDGCATNTVRSTYEW   HLDAW
NC-Cow12   CTTVYQ  KTTKKD  CPEYYTYNRDCERRYGWSDCECRADNVGGHCRHEGCATNTVRSTYEW   HLDAW
NC-Cow13   CTTVYL  KTTKQD  CPEYYTYNPDCARRYGWSDCECMADKFGGYCRHDGCATNTVRSTDEW   HLDAW
NC-Cow14   CTTVYL  KTTKQD  CPEYYTYNPDCARRYGWRDCECLADKVGGYCRHVGCANNTVRSTDEW   HLDAW
NC-Cow15   CTTVYL  KTTKQD  CPEYYTYNPDCARRYGWSDCECMADKVGGECRHDGCATNTVRSNDEW   HLDAW
NC-Cow16   CTTVYQ  KTTKKD  CPEYYTYNPDCARRSGWSDCECMADKFGGYCRHDGCATNTVRSTYEW   HLDAW
NC-Cow17   CTTVYL  KTTKQD  CPEYYTYNPDCARRYGWSDCECMADKFGGYCRHDGCATNPVRSTDEW   HLDAW
NC-Cow18   CTTVYL  KTTKQD  CPEYYTYNPDCARRYGWSDCECMADKFGGYCRHDGCATNTVRSTDGF   HLDAW
NC-Cow19   CTTVYQ  KTTKQD  CPEYYTYNPDCARRYGWSDCECMADKFGGYCRHDGCATNTVRSTYEW   HLDAW
NC-Cow20   CTTVYL  KTTKQD  CPEYYTYNPDRARRSGWSDCECMADKFGGYCRHDGCATNTVRSTDEW   HLDAW
NC-Cow21   CTTVYQ  KTTKQD  CPEYYTYNPDCARRYGWSDCECMADKFGGYCRHEGFATHTVRSPYEW   HLHAW
NC-Cow22   CTTVYQ  KTTKKD  CPEYYTYNPDCAMRYGWSYCECMAGKFWGYWCHESCATNTVRSTYEG   PRDAW

Posi.      h92     h100    d2      d10       d20        d30        d40     d48  h101

           |   Stalk A   |              Knob                 |     Stalk B     |
```

RAPID ELICITATION OF BROADLY NEUTRALIZING BOVINE ANTIBODIES TO HIV Env

CROSS-REFERENCE TO RELATED APPLICATIONS

This application is a continuation of U.S. patent application Ser. No. 16/630,768, 371 (c) date Jan. 13, 2020, which is a U.S. National Phase of PCT Application No. PCT/US2018/041729, filed Jul. 12, 2018, which claims the benefit of Provisional Patent Application Nos. 62/532,766 and 62/534,501, filed Jul. 14, 2017, and Jul. 19, 2017, respectively, each of which is incorporated herein by reference in its entirety.

GOVERNMENT INTEREST

The invention was made with government support under Grant Nos. R21 AI120791 and R01 GM105826 awarded by the NIH, Grant No. UM1AI100663 awarded by the Center for HIV/AIDS Vaccine Immunology and Immunogen Discovery Grant, Grant No. IOS 1257829 awarded by the National Science Foundation, and Grant No. CSREES 2008-35204 awarded by the USDA-NIFA. The U.S. government has certain rights in the invention.

REFERENCE TO SEQUENCE LISTING SUBMITTED ELECTRONICALLY

The content of the electronically submitted sequence listing (Name: 6765_0110_Sequence_Listing.xml; Size: 355,546 bytes; and Date of Creation: Sep. 18, 2023) filed with the application is incorporated herein by reference in its entirety.

FIELD OF THE INVENTION

The field of the invention generally relates to the generation of broadly neutralizing antibodies to HIV Env, and their use in the treatment or prevention of HIV.

BACKGROUND

In 2015, there were approximately 2.1 million new human immunodeficiency virus (HIV) infections, over 36.7 million people living with HIV, and 1.1 million acquired immune deficiency syndrome (AIDS) related deaths. unaids.org/en/resources/fact-sheet (accessed on Jun. 29, 2017) While great progress has been made in the treatment of HIV/AIDS, all individuals living with HIV will have to be treated with anti-retroviral therapy (ART) for the rest of their lives since drug therapy is unable to clear latent viral reservoirs that exist in resting CD4+ T cells at a frequency of about $1/10^6$ cells. See, Eriksson, S. 2013. *PLoS Pathog* 9:e1003174.

HIV isolates can be classified into different groups and clades based on genotype and geographic location. For example, the population episensus (i.e., epitope based consensus sequence) antigen is central to the B clade epidemic in the United States while the population episensus antigen is central to the HIV C clade epidemic in South Africa. Because of the diversity between HIV clades, many treatments involving antibodies has focused on treating infections by only one clade.

Broadly neutralizing anti-Env antibodies can neutralize more than one HIV isolate. To date, however, no immunogen has been able to reliably elicit the rapid development of broadly neutralizing antibodies (bnAbs) to HIV by vaccination. The difficulty in eliciting bnAbs has been attributed to the enormous antigenic diversity of the envelope glycoprotein among HIV isolates and to the dense N-linked glycan coat that covers Env (the 'glycan shield'). BnAbs isolated from chronically infected subjects have a number of unusual features, including much longer than average VH CDR3 loops, that have been selected to cope with the glycan shield. See Walker, L. M. et al. *Nature* 477, 466-470 (2011); Doria-Rose, N. A. et al. *Nature* 509, 55-62 (2014); Bonsignori, M. et al. *J. Virol.* 85, 9998-10009 (2011).

VH CDR3s in most vertebrates have restricted lengths that predominantly encode loops of 12-16 amino acids upon VDJ recombination. See Wang, F. et al. *Cell* 153, 1379-1393 (2013); Shi, B. et al. *Theor Biol Med Model* 11, 30 (2014); Lee, E.-C. et al. *Nat. Biotechnol.* 32, 356-363 (2014); Kodangattil, S. et al. *MAbs* 6, 628-636 (2014). Therefore, in many species, relatively few antibody precursors can be affinity-matured to HIV bnAbs. Bovine antibodies, however, comprise VH CDR3s that average ~26 amino acids in length with an ultralong subset (10-15% of the repertoire) that can be over 70 amino acids in length. See, e.g., Berens, S. J., Wylie, D. E. & Lopez, O. *J. Int. Immunol.* 9, 189-199 (1997). Previous work has shown that repeated immunization of cows over multiple years with an uncleaved AD8 gp140 trimer may lead to some neutralization breadth in the immunoglobulin-rich colostrum, but with very low potency. See Heydarchi, B. et al. *PLOS ONE* 11, e0157353 (2016); Kramski, M. et al. *Antimicrob. Agents Chemother.* 56, 4310-4319 (2012). While some monoclonal antibodies isolated from these cows inhibited soluble CD4 binding to gp140 Env, they did not have neutralizing activity against HIV infection. Heydarchi, B. et al. *MAbs* 9, 0-00 (2016);

Broad serum neutralization and subsequent isolation of bnAbs has been achieved in llamas, when 7 immunizations with an Env trimer (not well-ordered) over 4 months resulted in poor serum neutralization breadth and potency. The subsequent screening of >2,800 unique camelid-specific variable region (VHH) fragments identified only one with broad and potent neutralizing activity. McCoy, L. E. et al. *PLOS Pathog.* 10, e1004552 (2014); see also McCoy, L. E. et al. *J. Exp. Med.* 209, 1091-1103 (2012).

Thus, there remains an unmet need for more effective methods for generating broadly neutralizing antibodies that can be used in the treatment and prevention of HIV.

BRIEF SUMMARY OF THE INVENTION

In one embodiment, provided herein are methods of producing a broadly neutralizing anti-Env antibody, comprising: (a) immunizing a bovine by administering at least one dose of an antigenic composition comprising an HIV specific antigen to produce a broadly neutralizing anti-Env antibody, wherein the HIV specific antigen comprises a well-ordered Env trimer polypeptide or a polynucleotide encoding a well-ordered Env trimer polypeptide. In one embodiment, a virus, pseudovirus, or virus-like particle comprises the well-ordered Env trimer polypeptide. In one embodiment, the well-ordered Env trimer polypeptide is an isolated polypeptide. In one embodiment, the well-ordered Env trimer polypeptide comprises a SOSIP trimer. In one embodiment, the SOSIP trimer comprises BG505 SOSIP. In one embodiment, the antigenic composition further comprises an adjuvant.

In one embodiment, the immunizing comprises administering a priming dose and at least one booster dose of the antigenic composition. In one embodiment, the method comprises administering more than one booster dose of the antigenic composition. In one embodiment, the priming dose and at least one booster dose comprise the same antigenic composition. In one embodiment, the more than one booster doses comprise the same antigenic composition. In one embodiment, the HIV specific antigen is derived from a single HIV isolate. In one embodiment, the HIV specific antigen is derived from a BG505 HIV isolate.

In one embodiment, the methods further comprise (b) isolating from the bovine a biological sample comprising the broadly neutralizing anti-Env antibody.

In one embodiment, the methods further comprise (b) isolating from the bovine a biological sample comprising the broadly neutralizing anti-Env antibody; (c) purifying the broadly neutralizing anti-Env antibody; (d) processing the broadly neutralizing anti-Env antibody to prepare an F(ab) or F(ab')2 fragment; and (e) recovering the F(ab) or F(ab')2 fragment. In one embodiment, the biological sample is milk, blood, serum, colostrum, or peripheral blood mononuclear cells.

In one embodiment, the methods further comprise purifying the broadly neutralizing anti-Env antibody.

In one embodiment, the methods further comprise (b) isolating a peripheral blood mononuclear cell (PMBC) from the bovine, and (c) cloning a polynucleotide from the PBMC that encodes a broadly neutralizing anti-Env antibody. In one embodiment, the cloning of the polynucleotide comprises performing single-cell RT-PCR amplification. In one embodiment, the methods further comprise (d) expressing the polynucleotide that encodes the broadly neutralizing anti-Env antibody in a host cell. In one embodiment, the methods further comprise (d) expressing the polynucleotide that encodes the broadly neutralizing anti-Env antibody in a cell-free expression system.

In one embodiment, the bovine is a domestic cattle, bison, African buffalo, water buffalo, or yak. In one embodiment, the bovine is a domestic cattle. In one embodiment, the bovine is pregnant.

In one embodiment, the immunizing step elicits production of polyclonal serum capable of neutralizing at least about 50%, 60%, 70%, 80%, 90%, or 100% of cross-clade HIV isolates in the 6-member indicator virus panel. In one embodiment, the immunizing elicits production of polyclonal serum capable of neutralizing at least about 50%, 60%, 70%, 80%, 90%, or 100% of cross-clade HIV isolates in the 12-member indicator virus panel. In one embodiment, the immunizing elicits production of polyclonal serum capable of neutralizing at least about 50%, 60%, 70%, 80%, 90%, or 100% of cross-clade HIV isolates in the 117-member indicator virus panel. In one embodiment, the polyclonal serum comprises an antibody capable of neutralizing the cross-clade HIV isolates with a median $IC_{50}$ equal to or less than about 0.1 microg/ml, 0.05 microg/ml, 0.025 microg/ml, 0.01 microg/ml, or 0.005 microg/ml. In one embodiment, the polyclonal serum is capable of neutralizing the cross-clade HIV isolates with a median $ID_{50}$ of at least about 50, 100, 500, 1000, 5000, or 10000.

In one embodiment, the immunizing elicits production of polyclonal serum capable of neutralizing at least about 10%, 15%, 20%, 25% or 30% of cross-clade HIV isolates in the 117-member indicator virus panel with a median $ID_{50}$ of at least about 1000 within less than about 3 month after administering the first dose of the antigenic composition. In one embodiment, the immunizing elicits production of polyclonal serum capable of neutralizing at least about 50%, 60%, 70%, 80%, or 90% of cross-clade HIV isolates in the 117-member indicator virus panel with a median $ID_{50}$ of at least about 1000 within less than about 6 months, 9 months, or 12 months after administering the first dose of the antigenic composition. In one embodiment, the immunizing elicits production of polyclonal serum capable of neutralizing at least about 70%, 80%, 90%, 95%, 97%, 98%, 99% or 100% of cross-clade HIV isolates in the 12-member indicator virus panel with a median $ID_{50}$ of at least about 1000 less within than about 3 months, 6 months, 9 months, or 12 months after administering the first dose of the antigenic composition.

In one embodiment, the broadly neutralizing anti-Env antibody is polyclonal. In one embodiment, the broadly neutralizing anti-Env antibody is monoclonal. In one embodiment, the broadly neutralizing anti-Env antibody is an F(ab) fragment. In one embodiment, wherein the broadly neutralizing anti-Env antibody is an F(ab')2 fragment.

In one embodiment, provided herein is a broadly neutralizing antibody that specifically binds to Env, wherein the broadly neutralizing antibody is produced by a method described herein. In one embodiment, the antibody is polyclonal. In one embodiment, the antibody is monoclonal. In one embodiment, the antibody is an F(ab) fragment. In one embodiment, the antibody is an F(ab')2 fragment.

In one embodiment, provided herein is a composition comprising bovine serum, colostrum, or milk, wherein the serum, colostrum, or milk is produced according to the methods disclosed herein. In one embodiment, the composition is a lyophilized composition.

In one embodiment, provided herein is a bovine antibody that specifically binds to Env and is capable of neutralizing at least two cross-clade isolates of HIV. In one embodiment, the bovine antibody is capable of neutralizing at least about 50%, 60%, 70%, 80%, 90%, or 100% of cross-clade HIV isolates in the 6-member indicator virus panel. In one embodiment, the bovine antibody is capable of neutralizing at least about 50%, 60%, 70%, 80%, 90%, or 100% of cross-clade HIV isolates in the 12-member indicator virus panel. In one embodiment, the bovine antibody is capable of neutralizing at least about 50%, 60%, 70%, 80%, 90%, or 100% of cross-clade HIV isolates in the 117-member indicator virus panel. In one embodiment, the bovine antibody is capable of neutralizing the cross-clade HIV isolates with a median $IC_{50}$ equal to or less than about 0.1 microg/ml, 0.05 microg/ml, 0.025 microg/ml, 0.01 microg/ml, or 0.005 microg/ml. In one embodiment, the bovine antibody is capable of neutralizing the cross-clade HIV isolates with a median $ID_{50}$ of at least about 50, 100, 500, 1000, 5000, or 10000. In one embodiment, the bovine of the bovine antibody is a domestic cattle, bison, African buffalo, water buffalo, or yak. In one embodiment, the bovine is a domestic cattle. In one embodiment, the antibody is an F(ab) fragment. In one embodiment, the antibody is an F(ab')2 fragment. In one embodiment, the antibody is produced by a method disclosed herein. In one embodiment, the antibody is a polyclonal antibody. In one embodiment, the antibody is a monoclonal antibody. In one embodiment, antibody is a recombinant antibody, a chimeric antibody, a humanized antibody, an antibody fragment, a bispecific antibody, or a trispecific antibody.

In one embodiment, provided herein is a composition comprising a bovine antibody disclosed herein. In one embodiment, the composition is a lyophilized composition. In one embodiment, the composition is a pharmaceutical composition further comprising a pharmaceutical excipient.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3, 13, 23, 33, 43, 53, 63, 73, 83, or 93. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 227-238.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3 or SEQ ID NO: 121 (CITAHQKTNKKECPEDYTYN-PRCPQQYGWSDCDCMGDRFG-GYCRQDGCSNYIHRSTYEWYVS AW). In one embodiment, also provided herein is an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10 comprising 0, 1, 2, 3, 4, or 5 substitutions, insertions, or deletions.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow7, NC-Cow8, NC-Cow9, or NC-Cow10 comprising 0, 1, 2, 3, 4, or 5 substitutions, insertions, or deletions. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3, 13, 23, 33, 43, 53, 63, 73, 83, or 93 comprising 0, 1, 2, 3, 4, or 5 substitutions, insertions, or deletions. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 227-238 comprising 0, 1, 2, 3, 4, or 5 substitutions, insertions, or deletions. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1 comprising 0, 1, 2, 3, 4, or 5 substitutions, insertions, or deletions. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3 or SEQ ID NO: 121 comprising 0, 1, 2, 3, 4, or 5 substitutions, insertions, or deletions.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 101. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 102. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 122. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 268. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 269.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133. In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 or 253-260.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 140.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 141.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 142.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133 comprising 0, 1, 2, 3, 4, or 5 substitutions, insertions, or deletions.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 or 253-260 comprising 0, 1, 2, 3, 4, or 5 substitutions, insertions, or deletions.

In one embodiment, provided herein is an isolated monoclonal antibody that specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein a) the stalk A comprises a Stalk A amino acid sequence listed in Table 4, the knob comprises a knob amino acid sequence listed in Table 4, and the stalk B comprises a stalk B amino acid sequence listed in Table 4;
b) the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4;
c) the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4;
d) the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions;
e) the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions;
f) the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions;
g) the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions;
h) the stalk A comprises an amino acid sequence of SEQ ID NO: 131; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 151;
i) the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150;
j) the stalk A comprises an amino acid sequence of SEQ ID NO: 131; the knob comprises an amino acid sequence with at least about 80% 90%, 95%, or 100% identity to any one of SEQ ID NO:133-139 or 253-260, and the stalk B comprises an amino acid sequence of SEQ ID NO: 151;
k) the stalk A comprises an amino acid sequence of SEQ ID NO: 130; the knob comprises an amino acid sequence with at least about 80% 90%, 95%, or 100% identity to any one of SEQ ID NO:133-139 or 253-260, and the stalk B comprises an amino acid sequence of SEQ ID NO: 150;
l) the stalk A comprises an amino acid sequence of SEQ ID NO: 131; the knob comprises an amino acid sequence of SEQ ID NO: 141, and the stalk B comprises an amino acid sequence of SEQ ID NO: 151;
m) the stalk A comprises an amino acid sequence of SEQ ID NO: 132; the knob comprises an amino acid sequence of SEQ ID NO: 142, and the stalk B comprises an amino acid sequence of SEQ ID NO: 152; or
n) the stalk A comprises an amino acid sequence of SEQ ID NO: 130-132; the knob comprises an amino acid sequence of SEQ ID NO: 140-142, and the stalk B comprises an amino acid sequence of SEQ ID NO: 150-152.

In one embodiment, the VH CDR3 of the isolated monoclonal antibody is derived from a first donor antibody and the VH CDR1, VH CDR2, VL CDR1, VL CDR2, and VL CDR3 are derived from a second donor antibody. In one embodiment, the second donor antibody is an anti-Env antibody. In one embodiment, the second donor antibody is a broadly neutralizing anti-Env antibody. In one embodiment, the second donor antibody is a human antibody. In one embodiment, the second donor antibody is PG9. In one embodiment, the second donor antibody is a germline reverted variant of PG9. In one embodiment, the second donor antibody is a bovine anti-Env antibody. In one embodiment, the second donor antibody is a broadly neutralizing bovine anti-Env antibody. In one embodiment, the second donor antibody is a bovine anti-Env antibody produced by a method disclosed herein. In one embodiment, the second donor antibody is NC-Cow1, NC-Cow2, NC-Cow3, NC-Cow4, NC-Cow5, NC-Cow6, NC-Cow7, NC-Cow8, NC-Cow9, or NC-Cow10. In one embodiment, the second donor antibody is NC-Cow1, NC-Cow7, NC-Cow8, NC-Cow 9, or NC-Cow10. In one embodiment, the second donor antibody is NC-Cow2, NC-Cow3, NC-Cow4, NC-Cow5, or NC-Cow6. In one embodiment, the second donor antibody is NC-Cow1.

In one embodiment, the VL CDR1, VL CDR2, and VL CDR3 of the isolated monoclonal antibody herein are derived from a bovine germline encoded light chain variable region (VL). In one embodiment, the bovine germline encoded VL is V30. In one embodiment, the bovine germline encoded VL comprises the amino acid sequence of SEQ ID NO: 103.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10; (b) the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and (c) the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10; (b) the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and (c) the VH CDR3 comprises the VH CDR3 of NC-Cow11, NC-Cow12, NC-Cow13, NC-Cow14, NC-Cow15, NC-Cow16, NC-Cow17, NC-Cow18, NC-Cow19, NC-Cow20, NC-Cow21 or NC-Cow22.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the VH CDR1 of NC-Cow1, NC-Cow7, NC-Cow8, NC-Cow9, or NC-Cow10; (b) the VH CDR2 comprises the VH CDR2 of NC-Cow1, NC-Cow7, NC-Cow8, NC-Cow9, or NC-Cow10; and (c) the VH CDR3 comprises the VH CDR3 of NC-Cow1, NC-Cow7, NC-Cow8, NC-Cow9, or NC-Cow10.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1, 11, 21, 31, 41, 51, 61, 71, 81, or 91; (b) the VH CDR2 comprises the amino acid sequence of SEQ ID NO: 2, 12, 22, 32, 42, 52, 62, 72, 82, or 92; and (c) the VH CDR3 comprises the amino acid sequence of SEQ ID NO: 3, 13, 23, 33, 43, 53, 63, 73, 83, 93, or 121.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein (a) the VH CDR1 comprises the amino acid sequence of SEQ ID NO: 1, 11, 21, 31, 41, 51, 61, 71, 81, or 91; (b) the VH CDR2 comprises the amino acid sequence of SEQ ID NO: 2, 12, 22, 32, 42, 52, 62, 72, 82, or 92; and (c) the VH CDR3 comprises the amino acid sequence of SEQ ID NO: 227-238.

In one embodiment, the isolated monoclonal antibody of the disclosure comprises (a) the VL CDR1 comprises the VL CDR1 of NC-Cow1, NC-Cow2, NC-Cow3, NC-Cow4, NC-Cow5, NC-Cow6, NC-Cow7, NC-Cow8, NC-Cow9, or NC-Cow10; (b) the VL CDR2 comprises the VL CDR2 of NC-Cow1, NC-Cow2, NC-Cow3, NC-Cow4, NC-Cow5, NC-Cow6, NC-Cow7, NC-Cow8, NC-Cow9, or NC-Cow10; and (c) the VL CDR3 comprises the VL CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the isolated monoclonal antibody of the disclosure comprises (a) the VL CDR1 comprises the VL CDR1 of NC-Cow1, NC-Cow7, NC-Cow8, NC-Cow9, or NC-Cow10; (b) the VL CDR2 comprises the VL CDR2 of NC-Cow1, NC-Cow7, NC-Cow8, NC-Cow9, or NC-Cow10; and (c) the VL CDR3 comprises the VL CDR3 of NC-Cow1, NC-Cow7, NC-Cow8, NC-Cow9, or NC-Cow10. In one embodiment, the isolated monoclonal antibody of the disclosure comprises (a) the VL CDR1 comprises the amino acid sequence of SEQ ID NO: 4, 14, 24, 34, 44, 54, 64, 74, 84, or 94; (b) the VL CDR2 comprises the amino acid sequence of GDT or GDS; and (c) the VL CDR3 comprises the amino acid sequence of SEQ ID NO: 6, 16, 26, 36, 46, 56, 66, 76, 86, or 96.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR1, VH CDR2, VH CDR3, VL CDR1, VL CDR2, and VL CDR3, respectively.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow7, NC-Cow8, NC-Cow9, or NC-Cow10 VH CDR1, VH CDR2, VH CDR3, VL CDR1, VL CDR2, and VL CDR3, respectively.

In one embodiment, provided herein is an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 1-4, GDT and SEQ ID NO: 6, respectively; (b) SEQ ID NO: 11-14, GDT and SEQ ID NO: 16, respectively; (c) SEQ ID NO: 21-24, GDT and SEQ ID NO: 26, respectively; (d) SEQ ID NO: 31-34, GDT and SEQ ID NO: 36, respectively; (e) SEQ ID NO: 41, GDT and SEQ ID NO: 46, respectively; (f) SEQ ID NO: 51-54, GDT and SEQ ID NO: 56, respectively; (g) SEQ ID NO: 61-64, GDT and SEQ ID NO: 66, respectively; (h) SEQ ID NO: 71-74, GDS and SEQ ID NO: 76, respectively; (i) SEQ ID NO: 81-84, GDS and SEQ ID NO: 86, respectively; or (j) SEQ ID NO: 91-94, GDT and SEQ ID NO: 96, respectively.

In one embodiment, provided herein is an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow2, NC-Cow3, NC-Cow4, NC-Cow5, NC-Cow6, NC-Cow7, NC-Cow8, NC-Cow9, or NC-Cow10. In one embodiment, provided herein is an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow7, NC-Cow8, NC-Cow9, or NC-Cow10. In one embodiment, provided herein is an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 7, 17, 27, 37, 47, 57, 67, 77, 87, 97, 113, 115, 117, or 119. In one embodiment, the VL of the isolated monoclonal antibody comprises an amino acid sequence that is at least about 90%, 95%, 97%, 98%, 99% or 100% identical to the VL of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the VL of the isolated monoclonal antibody comprises an amino acid sequence that is at least about 90%, 95%, 97%, 98%, 99% or 100% identical to the VL of NC-Cow1, NC-Cow7, NC-Cow8, NC-Cow9, or NC-Cow10. In one embodiment, the VL of the isolated monoclonal antibody comprises an amino acid sequence that is at least about 90%, 95%, 97%, 98%, 99% or 100% identical to SEQ ID NO: 8, 18, 28, 38, 48, 58, 68, 87, 88, 98, 114, 116, 118, or 120. In one embodiment, the VL of the isolated monoclonal antibody comprises a bovine germline encoded light chain variable region (VL). In one embodiment, the bovine germline encoded VL is V30. In one embodiment, the bovine germline encoded VL comprises the amino acid sequence of SEQ ID NO: 103. In one embodiment, the VL comprises the NC-Cow1 VL. In one embodiment, the VL comprises the amino acid sequence of SEQ ID NO: 8.

In one embodiment, provided herein is an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow2, NC-Cow3, NC-Cow4, NC-Cow5, NC-Cow6, NC-Cow7, NC-Cow8, NC-Cow9, or NC-Cow10 VH and VL, respectively.

In one embodiment, provided herein is an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow7, NC-Cow8, NC-Cow9, or NC-Cow10 VH and VL, respectively.

In one embodiment, provided herein is an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to (a) SEQ ID NO: 7 and 8, respectively; (b) SEQ ID NO: 17 and 18, respectively (c) SEQ ID NO: 27 and 28, respectively; (d) SEQ ID NO: 37 and 38, respectively; (e) SEQ ID NO: 47 and 48, respectively; (f) SEQ ID NO: 57 and 58, respectively; (g) SEQ ID NO: 67 and 68, respectively; (h) SEQ ID NO: 77 and 78, respectively; (i) SEQ ID NO: 87 and 88, respectively; (j) SEQ ID NO: 97 and 98, respectively; (k) SEQ ID NO: 113 and 114, respectively; (1) SEQ ID NO: 115 and 116, respectively; (m) SEQ ID NO: 117 and 8, respectively; (n) SEQ ID NO: 117 and 118, respectively; or (o) SEQ ID NO: 119 and 120, respectively.

In one embodiment, the isolated antibody is not NC-Cow1, NC-Cow2, NC-Cow3, NC-Cow4, NC-Cow5, NC-Cow6, NC-Cow7, NC-Cow8, NC-Cow9, or NC-Cow10. In one embodiment, the isolated antibody is not NC-Cow1, NC-Cow7, NC-Cow8, NC-Cow9, or NC-Cow10. In one embodiment, the isolated antibody is not NC-Cow11, NC-Cow12, NC-Cow13, NC-Cow14, NC-Cow15, NC-Cow16, NC-Cow17, NC-Cow18, NC-Cow19, NC-Cow20, NC-Cow21 or NC-Cow22.

In one embodiment, the monoclonal antibody disclosed herein further comprises a heavy and/or light chain constant region. In one embodiment, the monoclonal antibody disclosed herein further comprises a human heavy and/or light chain constant region. In one embodiment, the heavy chain constant region is selected from the group consisting of a human immunoglobulin $IgG_1$, $IgG_2$, $IgG_3$, $IgG_4$, $IgA_1$, and $IgA_2$ constant region. In one embodiment, the heavy chain constant region comprises a native amino acid sequence. In one embodiment, the heavy chain constant region comprises a variant amino acid sequence. In one embodiment, the antibody is a recombinant antibody, a chimeric antibody, a humanized antibody, an antibody fragment, a bispecific antibody, or a trispecific antibody. In one embodiment, the antibody fragment comprises a single-chain Fv (scFv), F(ab) fragment, F(ab')2 fragment, or an isolated VH domain.

In one embodiment, provided herein is a fusion polypeptide that specifically binds to Env and comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, provided herein is a fusion polypeptide that specifically binds to Env and comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10. In one embodiment, provided herein is a fusion polypeptide that specifically binds to Env and comprises an amino acid sequence that is at least about 90%, 95%, 97%, 98%, 99% or 100% identical to SEQ ID NO: 3, 13, 23, 33, 43, 53, 63, 73, 83, or 93. In one embodiment, provided herein is a fusion polypeptide that specifically binds to Env and comprises an amino acid sequence that is at least about 90%, 95%, 97%, 98%, 99% or 100% identical to SEQ ID NO: 227-238. In one embodiment, provided herein is a fusion polypeptide that specifically binds to Env and comprises an amino acid sequence that is at least about 90%, 95%, 97%, 98%, 99% or 100% identical to the VH CDR3 of NC-Cow1. In one embodiment, provided herein is a fusion polypeptide that specifically binds to Env and comprises an amino acid sequence that is at least about 90%, 95%, 97%, 98%, 99% or 100% identical to SEQ ID NO: 3 or SEQ ID NO: 121. In one embodiment, the fusion polypeptide comprises an Fc domain.

In one embodiment, provided herein is a fusion polypeptide that specifically binds to Env and comprises the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR3 comprising 0, 1, 2, 3, 4, or 5 substitutions, insertions, or deletions. In one embodiment, provided herein is a fusion polypeptide that specifically binds to Env and comprises the amino acid sequence of the NC-Cow1, NC-Cow7, NC-Cow8, NC-Cow9, or NC-Cow10 VH CDR3 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 3, 13, 23, 33, 43, 53, 63, 73, 83, or 93 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 3, 13, 23, 33, 43, 53, 63, 73, 83, or 93 comprising 0, 1, 2, 3, 4, 5, 6, 7, 8, 9, 10, 11, 12, 13, 14, or 15 substitutions, insertions, or deletions. In one embodiment, provided herein is a fusion polypeptide that specifically binds to Env and comprises the amino acid sequence of SEQ ID NO: 227-238 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 227-238 comprising 0, 1, 2, 3, 4, 5, 6, 7, 8, 9, 10, 11, 12, 13, 14, or 15 substitutions, insertions, or deletions. In one embodiment, provided herein is a fusion polypeptide that specifically binds to Env and comprises the amino acid sequence of the NC-Cow1 VH CDR3 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 3 or SEQ ID NO: 121 comprising 0, 1, 2, 3, 4, or 5 substitutions, insertions, or deletions.

In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 3 or SEQ ID NO: 121. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 101. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 102. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 268. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 269. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 122. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 133. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 134-139 or 253-260. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 140. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 141. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 142. In one embodiment, provided herein is a fusion polypeptide that specifically binds to Env and comprises the amino acid sequence of the NC-Cow1 VH CDR3. In one embodiment, provided herein is a fusion polypeptide that specifically binds to Env and comprises the amino acid sequence of SEQ ID NO: 133 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 134-139 or 253-260 comprising 0, 1, 2, 3, 4, or 5 substitutions, insertions, or deletions. In one embodiment, provided herein is a fusion polypeptide that specifically binds to Env and comprises the amino acid sequence of SEQ ID NO: 133-139 or 253-260 comprising 0, 1, 2, 3, 4, 5, 6, 7, 8, 9, 10, 11, 12, 13, 14, or 15 substitutions, insertions, or deletions. In one embodiment, the fusion polypeptide comprises an Fc domain.

In one embodiment, provided herein is a fusion polypeptide that specifically binds to Env and comprises a domain having the structure, from N to C terminus, of stalk A-knob-stalk B, wherein a) the stalk A comprises a Stalk A amino acid sequence listed in Table 4, the knob comprises a knob amino acid sequence listed in Table 4, and the stalk B comprises a stalk B amino acid sequence listed in Table 4;
b) the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4;
c) the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4;
d) the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions;
e) the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions;
f) the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, 5, 6, 7, 8, 9, 10, 11, 12, 13, 14, or 15 substitutions, and the stalk B comprises a stalk B amino acid sequence listed in Table 4 comprising 0, 1, 2, 3, 4, or 5 substitutions;

g) the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions;

h) the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions;

i) the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, 5, 6, 7, 8, 9, 10, 11, 12, 13, 14, or 15 substitutions, insertions, or deletions, and the stalk B comprises a stalk B amino acid sequence listed in Table 4 comprising 0, 1, 2, 3, 4, or 5 substitutions, insertions, or deletions;

j) the stalk A comprises an amino acid sequence of SEQ ID NO: 131; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 151;

k) the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150;

l) the stalk A comprises an amino acid sequence of SEQ ID NO: 130; the knob comprises a knob amino sequence of SEQ ID NO:133-139 or 253-260 comprising 0, 1, 2, 3, 4, 5, 6, 7, 8, 9, 10, 11, 12, 13, 14, or 15 substitutions, insertions, or deletions, and the stalk B comprises an amino acid sequence of SEQ ID NO: 150;

m) the stalk A comprises an amino acid sequence of SEQ ID NO: 131; the knob comprises an amino acid sequence with at least about 80% 90%, 95%, or 100% identity to any one of SEQ ID NO:133-139 or 253-260, and the stalk B comprises an amino acid sequence of SEQ ID NO: 151;

n) the stalk A comprises an amino acid sequence of SEQ ID NO: 130; the knob comprises an amino acid sequence with at least about 80% 90%, 95%, or 100% identity to any one of SEQ ID NO:133-139 or 253-260, and the stalk B comprises an amino acid sequence of SEQ ID NO: 150;

o) the stalk A comprises an amino acid sequence of SEQ ID NO: 131; the knob comprises an amino acid sequence of SEQ ID NO: 141, and the stalk B comprises an amino acid sequence of SEQ ID NO: 151;

p) the stalk A comprises an amino acid sequence of SEQ ID NO: 132; the knob comprises an amino acid sequence of SEQ ID NO: 142, and the stalk B comprises an amino acid sequence of SEQ ID NO: 152; or q) the stalk A comprises an amino acid sequence of SEQ ID NO: 130-132; the knob comprises an amino acid sequence of SEQ ID NO: 140-142, and the stalk B comprises an amino acid sequence of SEQ ID NO: 150-152.

In one embodiment, the fusion polypeptide comprises an Fc domain.

In one embodiment, the fusion polypeptide comprises a non-immunoglobulin polypeptide or a fragment thereof. In one embodiment, the non-immunoglobulin polypeptide or a fragment thereof comprises human serum albumin, ferritin, or a fragment thereof. In one embodiment, the polypeptide comprises an Fc domain. In one embodiment, the Fc domain is a human $IgG_1$, $IgG_2$, $IgG_3$, $IgG_4$, $IgA_1$, or $IgA_2$Fc domain.

In one embodiment, the antibody or fusion polypeptide disclosed herein is capable of neutralizing at least two cross-clade isolates of HIV. In one embodiment, the antibody or fusion polypeptide is capable of neutralizing at least about 50%, 60%, 70%, 80%, 90%, or 100% of cross-clade HIV isolates in the 6-member indicator virus panel. In one embodiment, the antibody or fusion polypeptide is capable of neutralizing at least about 50%, 60%, 70%, 80%, 90%, or 100% of cross-clade HIV isolates in the 12-member indicator virus panel. In one embodiment, the antibody or fusion polypeptide is capable of neutralizing at least about 50%, 60%, 70%, 80%, 90%, or 100% of cross-clade HIV isolates in the 117-member indicator virus panel. In one embodiment, the antibody or fusion polypeptide is capable of neutralizing the cross-clade HIV isolates with a median $IC_{50}$ equal to or less than about 0.1 microg/ml, 0.05 microg/ml, 0.025 microg/ml, 0.01 microg/ml, or 0.005 microg/ml. In one embodiment, the antibody or fusion polypeptide is capable of neutralizing the cross-clade HIV isolates with a median $ID_{50}$ of at least about 50, 100, 500, 1000, 5000, or 10000.

In one embodiment, provided herein is a pharmaceutical composition comprising a broadly neutralizing antibody disclosed herein, a polyclonal antibody disclosed herein, a monoclonal antibody disclosed herein, or a fusion polypeptide disclosed herein, and a pharmaceutically acceptable excipient. In one embodiment, the pharmaceutical composition is lyophilized. In one embodiment, a pharmaceutical composition disclosed herein is for use in preventing HIV infection, reducing the risk of a subject becoming infected with HIV, passively immunizing a subject, or treating HIV/AIDS.

In one embodiment, provided herein is an isolated polynucleotide encoding the heavy chain variable region or heavy chain of an antibody disclosed herein. In one embodiment, provided herein is an isolated polynucleotide encoding the light chain variable region or light chain of an antibody disclosed herein. In one embodiment, provided herein is an isolated polynucleotide encoding the heavy chain variable region or heavy chain of an antibody disclosed herein and the light chain variable region or light chain of an antibody disclosed herein. In one embodiment, the isolated polynucleotide encodes a heavy chain variable region comprising the amino acid sequence of SEQ ID NOs: 7, 17, 27, 37, 47, 57, 67, 77, 87, or 97. In one embodiment, the isolated polynucleotide encodes a light chain variable region comprising the amino acid sequence of SEQ ID NOs: 8, 18, 28, 38, 48, 58, 68, 87, 88, or 98. In one embodiment, the isolated polynucleotide is an mRNA. In one embodiment, the mRNA comprises a modified nucleotide.

In one embodiment, provided herein is an isolated polynucleotide encoding a fusion polypeptide of the disclosure.

In one embodiment, provided herein is an isolated vector comprising a polynucleotide of the disclosure. In one embodiment, the isolated vector is a viral vector. In one embodiment, provided herein is a recombinant virus comprising a polynucleotide of the disclosure. In one embodiment, the recombinant virus is a recombinant adeno-associated virus (AAV).

In one embodiment, provided herein is a host cell comprising a polynucleotide of the disclosure, a vector of the disclosure, or a first vector comprising the nucleic acid of the disclosure and a second vector comprising the nucleic acid of the disclosure. In one embodiment, the host cell is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture.

In one embodiment, provided herein is a method of producing an antibody or fusion polypeptide that binds to HIV comprising culturing the host cell described herein so that the polynucleotide is expressed and the antibody or fusion polypeptide is produced.

In one embodiment, provided herein is an isolated antibody that specifically binds to Env and is encoded by the isolated polynucleotide of the disclosure.

In one embodiment, provided herein is method of neutralizing an HIV virus comprising contacting the virus with a sufficient amount of an antibody of the disclosure, a composition of the disclosure, the fusion polypeptide of the disclosure, or a pharmaceutical composition of the disclosure.

In one embodiment, provided herein is a method of preventing HIV infection comprising administering to a subject in need thereof a therapeutically sufficient amount of an antibody of the disclosure, a composition of the disclosure, a pharmaceutical composition of the disclosure, an isolated nucleotide of the disclosure, a fusion polypeptide of the disclosure, or the recombinant virus of the disclosure.

In one embodiment, provided herein is a method of reducing the risk of a subject becoming infected with HIV comprising administering to the subject in need thereof an effective amount of an antibody of the disclosure, a composition of the disclosure, a pharmaceutical composition of the disclosure, an isolated nucleotide of the disclosure, a fusion polypeptide of the disclosure, or the recombinant virus of the disclosure.

In one embodiment, provided herein is a method for passively immunizing a subject comprising administering to the subject in need thereof an effective amount of an antibody of the disclosure, a composition of the disclosure, a pharmaceutical composition of the disclosure, an isolated nucleotide of the disclosure, a fusion polypeptide of the disclosure, or the recombinant virus of the disclosure.

In one embodiment, provided herein is a method of treating HIV/AIDS comprising administering to a subject in need thereof a therapeutically sufficient amount of an antibody of the disclosure, a composition of the disclosure, a pharmaceutical composition of the disclosure, an isolated nucleotide of the disclosure, a fusion polypeptide of the disclosure, or a recombinant virus of the disclosure.

In one embodiment, the methods disclosed herein comprise administering to the subject, wherein the administering to the subject is by at least one mode selected from oral, parenteral, subcutaneous, intramuscular, intravenous, vaginal, rectal, buccal, sublingual, and transdermal. In one embodiment, provided herein are methods further comprising administering at least one additional therapeutic agent. In one embodiment, the additional therapeutic agent is an antiretroviral agent or a second antibody. In one embodiment, the additional therapeutic agent is a second broadly neutralizing antibody. In one embodiment, the additional therapeutic agent is a second and third broadly neutralizing antibody.

In one embodiment, provided herein is a method for detecting HIV in a sample comprising contacting the sample with an antibody of the disclosure or a fusion polypeptide of the disclosure. In one embodiment, provided herein is a method of purifying HIV from a sample comprising contacting the sample with an antibody of the disclosure or a fusion polypeptide of the disclosure.

In one embodiment, provided herein is a kit comprising an antibody of the disclosure, a fusion polypeptide of the disclosure, or a pharmaceutical composition o of the disclosure and (a) a detection reagent, (b) an HIV antigen, (c) a notice that reflects approval for use or sale for human administration, or (d) any combination thereof.

In one embodiment, provided herein is an antibody of the disclosure or fusion polypeptide of the disclosure, wherein the antibody or fusion polypeptide specifically binds to BG505 Env. In one embodiment, provided herein is an antibody o of the disclosure or fusion polypeptide of the disclosure, wherein the antibody or fusion polypeptide specifically binds to BG505 SOSIP.

BRIEF DESCRIPTION OF THE DRAWINGS

FIG. 1A. Schematic of SOSIP immunization experiments in cows. FIG. 1B. Neutralization breadth and potency of sera from cows 148, 3441, 26, and 27 were tested for neutralization on a 12-virus "global isolate" panel as an indicator for breadth and potency. Presented values are neutralization $ID_{50}$ titers. Murine Leukemia Virus (MLV) was included as a negative control.

FIGS. 2A-B: Rapid development of neutralization breadth and potency in cows. FIG. 2A Sera collected longitudinally for cow #26 and cow #27 were tested for neutralization on the 12-virus indicator panel. Neutralization $ID_{50}$ titers are presented for each virus by color at each time point. Percent neutralization breadth is indicated by the black line. FIG. 2B. Sera at select time points were tested on a larger cross-clade 117-virus panel. Presented values are neutralization breadth and median neutralization $ID_{50}$ titers grouped by virus clade.

FIG. 3. Serum $ID_{50}$ values. Serum collected at different time points over the course of immunization for cow 26 and cow 27 were evaluated for neutralization breath and potency on the 12-virus global indicator panel. Values represent serum $ID_{50}$ against the indicated virus and colored according to the legend.

FIGS. 5A-5C. Serum samples from cow 26 collected at days 42, 77, 238, and 381 were tested on a 117 cross-clade virus panel. Values are serum neutralization $ID_{50}$. NC-Cow1 monoclonal antibody was also tested on the same panel, values are neutralization $IC_{50}$ in μg/ml.

FIG. 7A. Cow PBMCs were sorted for IgG+ cells that bound to biotinylated BG505 SOSIP-AviTag conjugated on PE and APC fluorophores. FIG. 7B. To isolate epitope-specific antibodies, unliganded BG505 SOSIP (blue) and BG505 SOSIP liganded with NC-Cow1 was used to antigen-sort memory B cells. Epitope-specific B cells are defined as binding unliganded SOSIP and not binding to liganded SOSIP. This sort strategy yielded the broadly neutralizing antibodies NC-Cow7 to NC-Cow10.

FIG. 8A. Amplified heavy chains were paired with universal cow light chain or with NC-Cow1 light chain and tested for expression (anti-Fc ELISA), Ag binding (BG505 SOSIP), autologous neutralization (BG505 pseudovirus), and heterologous neutralization (Q23 pseudovirus). Sequence alignment of recovered heavy chains is listed underneath. FIG. 8B. Alignment of heavy chain sequences of isolated monoclonal antibodies (Consensus SEQ ID NO:180; d70-P1A5_NC-Cow4 SEQ ID NO:181; d70-P2E1_NC-Cow5 SEQ ID NO: 182; d70-P1F7_NC-Cow6 SEQ ID NO:183; d70-P1C4 SEQ ID NO:184; d238-P1B4_NC-Cow1 SEQ ID NO: 185; d238-P1F1_NC-Cow2 SEQ ID NO:186; d238-P3H4_NC-Cow3 SEQ ID NO:187; d238-P1A6 SEQ ID NO:188; d238-P1A8 SEQ ID NO: 189; d238-P1D1 SEQ ID NO: 190; d238-P3C10_SEQ ID NO: 191; d238-P1G4 SEQ ID NO:192; d238-P2C2 SEQ ID NO:193; d238-P1B12 SEQ ID NO: 194; d381-P1G5_NC-Cow7 SEQ ID NO:195; d381-P2A1_NC-Cow8 SEQ ID NO:196; d381-P2A6_NC-Cow9 SEQ ID NO: 197; d381-P3G10_NC-Cow10 SEQ ID NO:198). Kearse, M. et al., *Bioinformatics* 28, 1647-1649 (2012).

FIGS. 9A-9D: Isolation and characterization of a broadly neutralizing cow antibody. FIG. 9A VH CDR3s are shown for antibodies NC-Cow1-10. The sequence for germline IGHV1-7/VHBUL, IGHD8-2, and IGHJ10 regions are shown at the top. VH CDR3 length (L), number of cysteines within VH CDR3 (#Cys), and VH CDR3 numbering are listed. Cysteines within VH CDR3 are highlighted in yellow, with those conserved within the germline underlined, and the cysteine and tryptophan residues defining the VH CDR3 are highlighted cyan. Germline SEQ ID NO:153; NC-Cow1 residues 95 to 168 of SEQ ID NO:7; NC-Cow2 residues 95 to 169 of SEQ ID NO:17; NC-Cow3 residues 95 to 169 of SEQ ID NO:27; NC-Cow4 residues 95 to 169 of SEQ ID NO:37; NC-Cow5 residues 95 to 169 of SEQ ID NO:47; NC-Cow6 residues 95 to 169 of SEQ ID NO:57; NC-Cow7 residues 95 to 168 of SEQ ID NO:67; NC-Cow8 residues 95 to 168 of SEQ ID NO:77; NC-Cow9 residues 95 to 168 of SEQ ID NO:87; and NC-Cow10 residues 95 to 168 of SEQ ID NO:97. FIG. 9B. NC-Cow1 was analyzed for neutralization breadth and potency on a 117-virus panel. FIG. 9C. NC-Cow1-10 antibodies map to the VRC01-class epitope by competition ELISA. FIG. 9D. To determine if the VH CDR3 of NC-Cow1 is effective at neutralization on its own, four chimeras were tested on the 12-virus global isolates indicator panel. An $IC_{50}$ value of 50 μg/ml was used a cut-off for neutralization.

FIGS. 10A-D. Evaluation of purified recombinant antibody for neutralization breadth and potency. FIG. 10A shows the alignment for the VH sequences for NC-Cow1 (SEQ ID NO: 154), NC-Cow7 (SEQ ID NO:155), NC-Cow8 (SEQ ID NO:156), NC-Cow9 (SEQ ID NO:157), and NC-Cow10 (SEQ ID NO: 158). The consensus sequence for NC-Cow1 and 7-10 VHs is SEQ ID NO: 153. FIG. 10B shows the alignment for the VH sequences for NC-Cow2 (SEQ ID NO: 161), NC-Cow3 (SEQ ID NO: 162), NC-Cow4 (SEQ ID NO: 163), NC-Cow5 (SEQ ID NO: 164), and NC-Cow6 (SEQ ID NO: 165). The consensus sequence for NC-Cow2-6 VHs is SEQ ID NO: 160. FIG. 10C shows the VL alignment of NC-Cow1 to NC-Cow10 (SEQ ID NO: 167 to 176, respectively). The consensus sequence for NC-Cow1-10 VLs is SEQ ID NO: 166. FIG. 10D. Evaluation of purified recombinant antibody for neutralization breadth and potency. Antibodies were expressed and purified and tested on the 12-virus global indicator panel as well as clade A viruses. Values are neutralization $IC_{50}$ in μg/ml. The time point from which the antibodies were isolated is indicated at the top and antibodies paired with universal light chain are indicated with an asterisk-all other antibodies were produced using native heavy and light chain pairs.

FIG. 11A. NC-Cow1 was tested for antigen reactivity in a HEp2 assay compared to the known polyreactive antibody 4E10, and negative and positive control sera supplied by the manufacturer. FIG. 11B. NC-Cow1 was also tested for reactivity with a range of typical human autoantigens by ELISA as well as for binding to solubilized membrane (SMP) and cytosolic preparations (SCP) from CHO cells. Values are optical density values (OD405) at a 100 μg/ml dose. Black line indicates cut-off values as indicated by the manufacturer.

FIG. 12A. Representative 2D class averages of cow Fabs NC-Cow1 and NC-Cow2 bound to BG505 SOSIP trimers to demonstrate CD4bs site specificity. FIG. 12B. Top and side views of 3D reconstruction of NC-Cow1 bound to BG505 SOSIP trimer with previously published Env trimer structure (green, PDB 5CEZ) and cow Fab (orange, PDB 5IJV) docked in. FIG. 12C-D. NC-Cow 1 was tested for binding by ELISA to BG505 or JRCSF gp120 captured from lysed virions with PGT121 (V3-glycan epitope) and VRC01 (CD4bs epitope) included for comparison. Values are $EC_{50}$ in μg/ml. NC-Cow1 was also tested on BG505 or JR-CSF pseudoviruses and corresponding alanine mutants with PGT121 (V3-glycan epitope) and 12A12 (CD4bs epitope) included for comparison. Values are $IC_{50}$ in μg/ml. FIG. 12E. NC-Cow1 was tested for binding to WT and D368R protein. Antibodies VRC01 (CD4bs) and 14e (V3) were included for comparison.

FIGS. 13A-B. Effects of pH on binding of NC-Cow1 and CD4bs antibodies to gp120. FIG. 13A. CD4bs antibodies PGV04, 12A12, 3BNC60, and b12 were tested for binding to gp120 (isolate 92BR020) by ELISA in buffers at different pHs (3.5, 4.0, 4.5, 5.0, 5.5, and 6.0). FIG. 13B. NC-Cow1 and VRC01 were tested for binding to BG505 gp120 in PBS buffer (pH 7.4) compared to simulated vaginal fluid (SVF), pH 4.5.

FIG. 14. Mapping epitope specificity over time. Serum samples from cow 26 were tested for competition by NC-Cow1. Values present serum dilution $EC_{50}$ titers for BG505 SOSIP and for BG505 V3 peptide.

FIG. 15A-B. Alanine scanning of NC-Cow1 VH CDR3. FIG. 15A. Neutralization of BGN505 by variant antibodies comprising a single alanine substitution. For comparison to an unmodified antibody, a purified IgG control of NC-Cow1 (WT IgG) and unpurified transfected supernatants of NC-Cow1 at two concentrations (1.2 μg/ml and 10 μg/ml) were included. FIG. 15B. Sequence alignment of NC-Cow1 VH CDR3 region scanned by alanine substitution. Residues whose replacement with alanine results in loss or reduction of neutralization are bolded and underlined. Sequences shown are IGHV1-7 SEQ ID NO: 177; IGHD8-2 SEQ ID NO: 178, IGHJ10 SEQ ID NO: 179; NC-Cow1 residues 95 to 158 of SEQ ID NO:7; NC-Cow7 residues 95 to 158 of SEQ ID NO:67; NC-Cow8 residues 95 to 158 of SEQ ID NO:77; NC-Cow9 residues 95 to 158 of SEQ ID NO:87; NC-Cow10 residues 95 to 158 of SEQ ID NO:97; NC-Cow11-22 SEQ ID NO:227-250.

DETAILED DESCRIPTION OF THE INVENTION

Figures 1A, 1B:
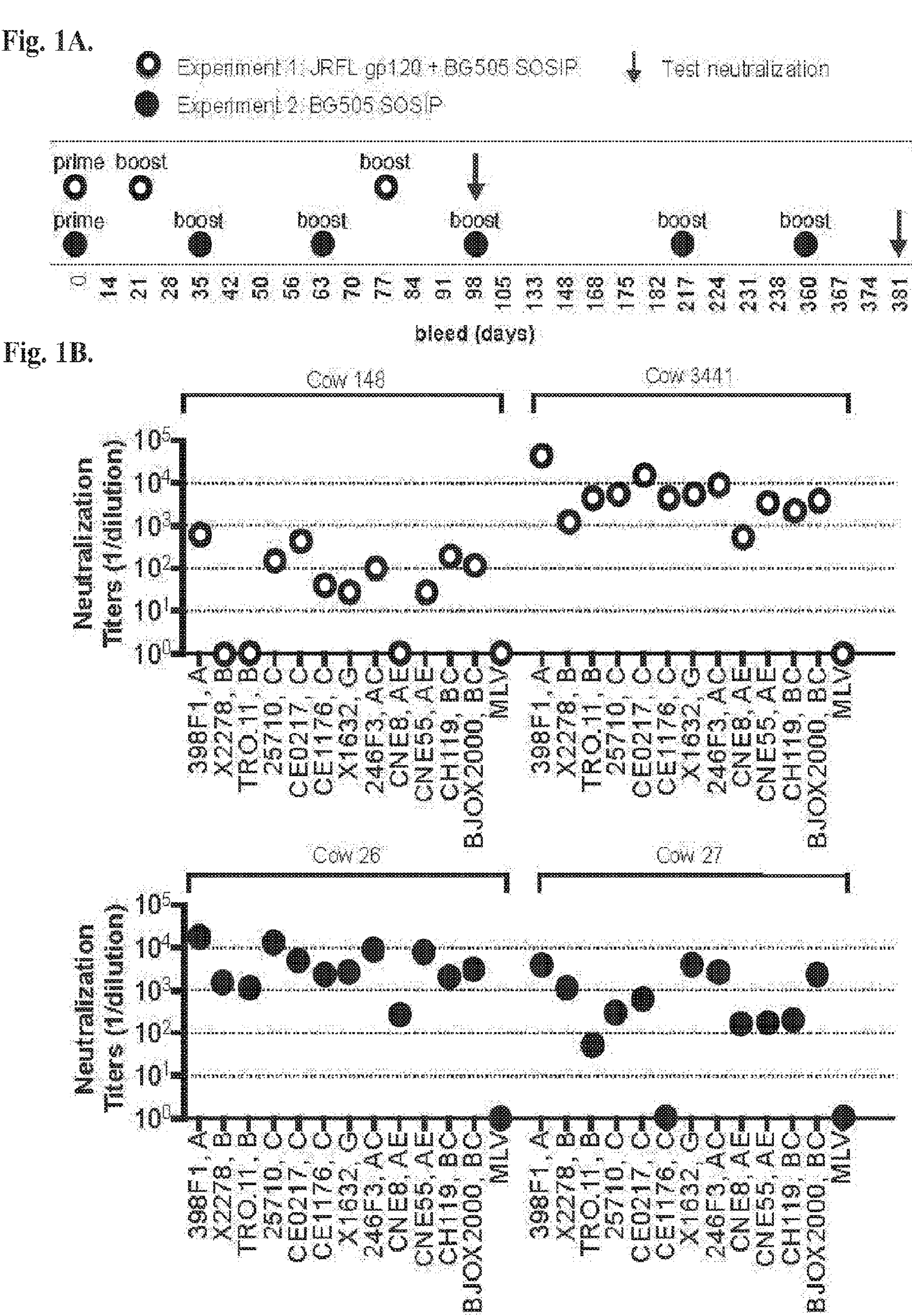
FIGS. 1A-B: Cows develop broadly neutralizing serum antibodies when immunized with the HIV envelope trimer mimic BG505 SOSIP.

Here we have shown that immunization with a well-ordered HIV Env trimer in cows rapidly and reliably elicits broad and potent neutralizing serum responses in contrast to previous experiments in other animals. The results demonstrate that broadly neutralizing antibody (bnAb) epitopes on HIV Env are only immunoquiescent in a repertoire-dependent fashion. The CD4-binding-site (CD4bs) is recessed and occluded on the native on HIV Env trimer, which greatly hinders access by human neutralizing antibodies, and thereby renders the CD4bs effectively immunoquiescent in humans. The long VH CDR3 of bovine antibodies are nonetheless able to easily access the CD4bs on the trimer, therefore rendering this region immunogenic in the context of the bovine antibody repertoire. Importantly, trimer isolates from different HIV strains were not required to elicit neutralization breadth, indicating that antigen diversity is not required provided that conserved epitopes are accessible. The speed of developing a bnAb to the CD4bs of HIV Env in cows immunized with a well-ordered Env trimer is remarkable when contrasted with the length of time required to elicit similar antibodies through natural infection of humans (>5 years), or through the immunization of non-human animals with a non-well-ordered Env trimer. The rapid elicitation of functional responses against HIV Env shows that bovine immunization can lead to the isolation of broadly neutralizing antibodies, which can be humanized, that can be used in the prevention and treatment of HIV.

One aspect of the present disclosure relates to methods of immunization for producing broadly neutralizing bovine antibodies to HIV. In another aspect, it relates to broadly neutralizing bovine anti-Env antibodies (e.g., humanized bovine anti-Env antibodies), nucleotide sequences encoding, compositions comprising, and kits comprising thereof. In another aspect, it relates to methods of treatment and prevention of HIV using the antibodies. In another aspect, it relates to methods of diagnosing and monitoring of HIV infection using the antibodies.

I. Definitions

To facilitate an understanding of the present invention, a number of terms and phrases are defined below.

The terms "human immunodeficiency virus" or "HIV," as used herein, refer generally to a retrovirus that is the causative agent for acquired immunodeficiency syndrome (AIDS), variants thereof (e.g., simian acquired immunodeficiency syndrome, SAIDS), and diseases, conditions, or opportunistic infections associated with AIDS or its variants, and includes HIV-Type 1 (HIV-1) and HIV-Type 2 (HIV-2) of any clade or strain therein, related retroviruses (e.g., simian immunodeficiency virus (SIV)), and variants thereof (e.g., engineered retroviruses, e.g., chimeric HIV viruses, e.g., simian-human immunodeficiency viruses (SHIVs)). In one embodiment, an HIV virus is an HIV-Type-1 virus. Previous names for HIV include human T-lymphotropic virus-Ill (HTLV-III), lymphadenopathy-associated virus (LAV), and AIDS-associated retrovirus (ARV).

As used herein, the term "clade" refers to related human immunodeficiency viruses (HIVs) classified according to their degree of genetic similarity. There are currently four known groups of HIV-1 isolates: M, N, O, and P. Group M (major strains) viruses are responsible for the majority of the global HIV epidemic. The other three groups, i.e., N, O and P are quite uncommon and only occur in Cameroon, Gabon and Equatorial Guinea. In one embodiment, an HIV virus is a Group M HIV virus. Within group M there are known to be at least nine genetically distinct subtypes or clades of HIV-1: subtypes or clades A, B, C, D, F, G, H, J and K. Additionally, different subtypes can combine genetic material to form a hybrid virus, known as a 'circulating recombinant form' (CRFs). Subtype B is the dominant HIV subtype in the Americas, Western Europe and Australasia. Subtype C is very common in the high AIDS prevalence countries of Southern Africa, as well as in the horn of Africa and India. Just under half of all people living with HIV have subtype C. In certain exemplary embodiments, methods described herein can be used to treat a subject (e.g., a human) infected with HIV (e.g., HIV-1) or to block or prevent HIV (e.g., HIV-1) infection in subject (e.g., a human) at risk of HIV transmission. The HIV may be of two, three, four, five, six, seven, eight, nine, ten, or more clades and/or two or more groups of HIV.

Acquired immune deficiency syndrome ("AIDS") is a disease caused by the human immunodeficiency virus, or HIV.

As used herein, the term "envelope glycoprotein" or "Env" refers to the glycoprotein that is expressed on the surface of the envelope of HIV virions and the surface of the plasma membrane of HIV infected cells. "Envelope glycoprotein" or "Env" encompass, but are not limited to, native Env, an isoform of Env, or a variant of Env (e.g., SOSIP) derived from an HIV isolate, for example, BG505. Env is the sole virally encoded gene product on the surface of the virus and, as such, is the only target of neutralizing antibodies. Env is a trimer of heterodimers composed of two non-covalently associated subunits: the receptor-binding gp120 and the fusion machinery-containing gp41. Each subunit is derived from a gp160 precursor glycoprotein following cleavage by cellular furins. HIV-1 gp120 binds the CD4 molecule on the surface of human target T cells to initiate the viral entry process, and following co-receptor engagement, fusion is mediated by gp41. gp140 env is the uncleaved ectodomain of gp160. In one embodiment, Env is a BG505 Env polypeptide. UniProtKB accession number Q2NOS5-1, Q2NOS6-1, and Q2NOS7-1 provide BG505 env gp160 polypeptide sequences. In one embodiment, BG505 Env is BG505.W6M.ENV.C2 Env comprising the amino acid sequence of SEQ ID NO: 104 (MRVMGIQRNCQHL-FRWGTMILGMIIICSAAENLWVTVYYGVPVWK-DAETTLFCASDAKAYET EKHNVWATHACVPTDPNPQEIHLENVTEEFNMW-KNNMVEQMHTDIISLWDQSLKPCVKLTPLC VTLQCTNVTN-NITDDMRGELKNCSFNMTTELRDKKQKVYS-LFYRLDVVQINENQGNRSNNSNK EYRLINCNT-SAITQACPKVSFEPIPIHYCAPAGFAILKCKDKKFN-GTGPCPSVSTVQCTHGIKPVVS TQLLLNGS-LAEEEVMIRSENITNNAKNILVQFNTPVQINC-TRPNNNTRKSIRIGPGQAFYATGDIIG DIRQAHCTV-SKATWNETLGKVVKQLRKHFGNNTIIRFANSSGG-DLEVTTHSFNCGGEFFYCNTS GLFNSTWISNTSVQG-SNSTGSNDSITLPCRIKQIINMWQRIGQAMYAPPIQG-VIRCVSNITGLILTR DGGSTN-STTETFRPGGGDMRDNWRSELYKYKVVKIEPLGVAP-TRAKRRVVGREKRAVGIGAVF LGFLGAAGSTMGAASMTLTVQARNLLS-GIVQQQSNLLRAIEAQQHLLKLTVWGIKQLQARVLA VERYLRDQQLLGIWGCSGKLICTTNVPWNSS-WSNRNLSEIWDNMTWLQWDKEISNYTQIIYGLL EESQNQQEKNEQDLLALDKWASLWNWFDIS-NWLWYIKIFIMIVGGLIGLRIVFAVLSVIHRVRQG YSPLSFQTHTPNPRGLDRPERIEEEDGEQDRGR-STRLVSGFLALAWDDLRSLCLFCYHRLRDFILI AARIVELLGHSSLKGLRLGWEGLKYLWNL-LAYWGRELKISAINLFDTIAIAVAEWTDRVIEIGQR LCRAFLHIPRRIRQGLERALL). In one embodiment, BG505 Env is a variant of BG505.W6M.ENV.C2 Env comprising the T330N substitution (SEQ ID NO: 105

```
(MRVMGIQRNCQHLFRWGTMILGMIIICSAAENLWVTVYYGVPVWKDAET
TLFCASDAKAYETEKHNVWATHACVPTDPNPQEIHLENVTEEFNMWKNNM
VEQMHTDIISLWDQSLKPCVKLTPLCVTLQCTNVTNNITDDMRGELKNCS
FNMTTELRDKKQKVYSLFYRLDVVQINENQGNRSNNSNKEYRLINCNTSA
ITQACPKVSFEPIPIHYCAPAGFAILKCKDKKFNGTGPCPSVSTVQCTHG
IKPVVSTQLLLNGSLAEEEVMIRSENITNNAKNILVQFNTPVQINCTRPN
NNTRKSIRIGPGQAFYATGDIIGDIRQAHCNVSKATWNETLGKVVKQLRK
HFGNNTIIRFANSSGGDLEVTTHSFNCGGEFFYCNTSGLFNSTWISNTSV
QGSNSTGSNDSITLPCRIKQIINMWQRIGQAMYAPPIQGVIRCVSNITGL
ILTRDGGSTNSTTETFRPGGGDMRDNWRSELYKYKVVKIEPLGVAPTRAK
RRVVGREKRAVGIGAVFLGFLGAAGSTMGAASMTLTVQARNLLSGIVQQQ
SNLLRAIEAQQHLLKLTVWGIKQLQARVLAVERYLRDQQLLGIWGCSGKL
ICTTNVPWNSSWSNRNLSEIWDNMTWLQWDKEISNYTQIIYGLLEESQNQ
QEKNEQDLLALDKWASLWNWFDISNWLWYIKIFIMIVGGLIGLRIVFAVL
SVIHRVRQGYSPLSFQTHTPNPRGLDRPERIEEEDGEQDRGRSTRLVSGF
LALAWDDLRSLCLFCYHRLRDFILIAARIVELLGHSSLKGLRLGWEGLKY
LWNLLAYWGRELKISAINLFDTIAIAVAEWTDRVIEIGQRLCRAFLHIPR
RIRQGLERALL)).
```

The term "well-ordered Env trimer" or "well-ordered trimer" as used herein refers to an envelope glycoprotein trimer comprising three cleaved gp140 polypeptides that closely mimics the quaternary structure of the Env ectodomain on the surface of the envelope of HIV or SIV virions and the surface of the plasma membrane of HIV or SIV infected cells. In one embodiment, the gp120 and gp41 ectodomain is linked by a covalent linkage, for example, a disulfide bond. In one embodiment, the gp140 polypeptide comprises one or more mutations to promote trimer formation. In one embodiment, the gp140 polypeptide comprises one or more mutations to promote disulfide formation. In one embodiment, the well-ordered trimer is an SOSIP gp140 trimer. Well-ordered SOSIP trimers have been disclosed in US Patent Appl. Pub. No. 2014/0212458, Sanders, R. W. et al., *PLOS Pathog.* 9, e1003618 (2013) and Guenaga J., et al., Immunity 46 (5): 792-803.e3 (2017), each of which is incorporated by reference herein in its entirety. In one embodiment, a well ordered trimer is formed from a clade A Env. In one embodiment, a well ordered trimer is formed from a clade B Env. In one embodiment, a well ordered trimer is formed from a clade C Env. In one embodiment, a well ordered trimer is formed from a circulating recombinant form Env. In one embodiment, a well ordered trimer is BG505 SOSIP. In one embodiment, a well ordered trimer is BGS05 SOSIP.664. In one embodiment, BG505 SOSIP.664 comprises the amino acid sequence of SEQ ID NO: 106 (AENLWVTVYYGVPVWKDAETTLFCASDAKAY-ETEKHNVWATHACVPTDPNPQEIHLENVTEE FNMW-KNNMVEQMHTDIIS-LWDQSLKPCVKLTPLCVTLQCTNVTNNITDDMR-GELKNCSFNMTT ELRDKKQKVYSLFYRLDVVQI-NENQGNRSNNSNKEYRLINCNTSAITQACPKVS-FEPIPIHYCAPA GFAILKCKDKKFNGTGPCPSVSTVQCTHGIKPV-VSTQLLLNGSLAEEEVMIRSENITNNAKNILVQ FNTPVQINCTRPNNNTRKSIRIGPGQAFYATG-DIIGDIRQAHCNVSKATWNETLGKVVKQLRKHF GNNTIIRFANSSGGDLEVTTHSFNCGGEF-FYCNTSGLFNSTWISNTSVQGSNSTGSNDSITLPCRIK QIINMWQRIGQAMYAPPIQGVIRCVSNITGLIL-TRDGGSTNSTTETFRPGGGDMRDNWRSELYKY KVVKIEPLGVAPTRCKRRVVGRRRRRRAV-GIGAVFLGFLGAAGSTMGAASMTLTVQARNLLSGI VQQQSNLLRAPEAQQHLLKLTVWGIKQLQARVLAV-ERYLRDQQLLGIWGCSGKLICCTNVPWN SSWSNRNLSEIWDNMTWLQWDKEIS-NYTQIYGLLEESQNQQEKNEQDLLALD). In one embodiment, a nascent BG505 SOSIP.664 further comprises a leader sequence, wherein the nascent BG505 SOSIP.664 comprises the amino acid sequence of SEQ ID NO: 107 (MDAMKRGLCCVLLLCGAVFVSPSOEIHARFRRAE-NLWVTVYYGVPVWKDAETTLFCASDAKA YETEKHNVWATHACVPTDPNPQEIHLENV-TEEFNMWKNNMVEQMHTDIISLWDQSLKPCVKLT PLCVTLQCTNVIN-NITDDMRGELKNCSFNMTTELRDKKQKVYS-LFYRLDVVQINENQGNRSNN SNKEYRLINCNT-SAITQACPKVSFEPIPIHYCAPAGFAILKCKDKKF-NGTGPCPSVSTVQCTHGIKP VVSTQLLLNGS-LAEEEVMIRSENITNNAKNILVQFNTPVQINC-TRPNNNTRKSIRIGPGQAFYATG DIIGDIRQAHCNV-SKATWNETLGKVVKQLRKHFGNNTIIRFANSSG-GDLEVTTHSFNCGGEFFYC NTSGLFNSTWIS-NTSVQGSNSTGSNDSITLPCRIKQI-INMWQRIGQAMYAPPIQGVIRCVSNITGLIL TRDGG-STNSTTETFRPGGGDMRDNWRSELYKYKVVKIEP-LGVAPTRCKRRVVGRRRRRRAVGI GAVELGFL-GAAGSTMGAASMTLTVQARNLLSGIVQQQSNLL-RAPEAQQHLLKLTVWGIKQLQA RVLAVERY-LRDQQLLGIWGCSGKLICCTNVPWNSSWSNRNL-SEIWDNMTWLQWDKEISNYTQII YGLLEESQNQQEKNEQDLLALD). In one embodiment, a well-ordered Env trimer is a native flexibly linked (NFL) trimer as described in Sharna, et al., Cell Reports, 11 (4): 539-50 (2015). In one embodiment, a well-ordered Env trimer is a DS-SOSIP as described in Chuang, et al., J. Virology, 91 (10). pii: e02268-16 (2017). In one embodiment, a well ordered trimer is formed from a SIV Env. In one embodiment, a well ordered trimer is an SIV Env SOSIP. In one embodiment, a well ordered trimer is formed from an Env comprising a mutation (e.g., substitution or deletion) in the CD4 binding site. In one embodiment, a well ordered trimer is formed from an Env comprising a mutation (e.g., substitution or deletion) in the CD4 binding site wherein the mutation reduces or disrupts the binding between Env and CD4. In one embodiment, a well ordered trimer is a CRF or C108 SOSIP. See, e.g., Andrabi et al, Immunity 43 (5): 959-973 (2015). In some embodiments, the gp120 and gp41 ectodomain is linked by a peptide linker, for example, a Gly-Ser linker, as described in Georgiev I S, et al., J. Virology 89 (10): 5318-5329 (2015). In some embodiments, the well-ordered Env trimer is stable.

The term "bovine" as used herein refers to biological subfamily Bovinae, which includes, but is not limited to, domestic cattle, bison, African buffalo, water buffalo, and yak. The terms "domestic cattle" and "cow" can be used interchangeably herein.

The term "antibody" means an immunoglobulin molecule (or a group of immunoglobulin molecules) that recognizes and specifically binds to a target, such as a protein, polypeptide, peptide, carbohydrate, polynucleotide, lipid, or combinations of the foregoing through at least one antigen recognition site within the variable region of the immunoglobulin molecule. As used herein, the terms "antibody" and "antibodies" are terms of art and can be used interchangeably herein and refer to a molecule with an antigen-binding site that specifically binds an antigen.

Antibodies can include, for example, monoclonal antibodies, recombinantly produced antibodies, human antibodies, humanized antibodies, resurfaced antibodies, chimeric antibodies, immunoglobulins, synthetic antibodies, tetrameric antibodies comprising two heavy chain and two light chain molecules, an antibody light chain monomer, an antibody heavy chain monomer, an antibody light chain dimer, an antibody heavy chain dimer, an antibody light chain-antibody heavy chain pair, intrabodies, heteroconjugate antibodies, single domain antibodies, monovalent antibodies, single chain antibodies or single-chain Fvs (scFv), affybodies, Fab fragments, $F(ab')_2$ fragments, disulfide-linked Fvs (sdFv), anti-idiotypic (anti-Id) antibodies (including, e.g., anti-anti-Id antibodies), bispecific antibodies, and multi-specific antibodies. In certain embodiments, antibodies described herein refer to polyclonal antibody populations. Antibodies can be of any type (e.g., IgG, IgE, IgM, IgD, IgA, or IgY), any class (e.g., $IgG_1$, $IgG_2$, $IgG_3$, $IgG_4$, $IgA_1$, or $IgA_2$), or any subclasses (isotypes) thereof (e.g. IgG1, IgG2, IgG3, IgG4, IgA1 and IgA2), of immunoglobulin molecule, based on the identity of their heavy-chain constant domains referred to as alpha, delta, epsilon, gamma, and mu, respectively. The different classes of immunoglobulins have different and well known subunit structures and three-dimensional configurations. Antibodies can be naked or conjugated or fused to other molecules such as toxins, radioisotopes, other polypeptides etc.

As used herein, the terms "antigen-binding domain," "antigen-binding region," "antigen-binding site," and similar terms refer to the portion of antibody molecules which comprises the amino acid residues that confer on the antibody molecule its specificity for the antigen (e.g., BG505 SOSIP). The antigen-binding region can be derived from any animal species, such as bovine (e.g., domestic cattle) and humans.

As used herein, the terms "variable region" or "variable domain" are used interchangeably and are common in the art. The variability in sequence is concentrated in those regions called complementarity determining regions (CDRs) while the more highly conserved regions in the variable domain are called framework regions (FR). Without wishing to be bound by any particular mechanism or theory, it is believed that the CDRs of the light and heavy chains are primarily responsible for the interaction and specificity of the antibody with antigen (e.g., BG505 SOSIP). In certain embodiments, the variable region is a bovine variable region. In certain embodiments, the variable region comprises bovine (e.g., domestic cattle) CDRs and human framework regions (FRs). In certain embodiments, the variable region comprises bovine CDRs and primate (e.g., non-human primate) framework regions (FRs).

There are at least two techniques for determining CDRs: (1) an approach based on cross-species sequence variability (i.e., Kabat et al., *Sequences of Proteins of Immunological Interest*, (5th ed., 1991, National Institutes of Health, Bethesda Md.), "Kabat"); and (2) an approach based on crystallographic studies of antigen-antibody complexes (Al-lazikani et al, *J. Molec. Biol.* 273:927-948 (1997)). In addition, combinations of these two approaches are sometimes used in the art to determine CDRs.

The Kabat numbering system is generally used when referring to a residue in the variable domain (approximately residues 1-107 of the light chain and residues 1-113 of the heavy chain) (e.g., Kabat et al., *Sequences of Immunological Interest*. (5th Ed., 1991, National Institutes of Health, Bethesda, Md.) ("Kabat").

The amino acid position numbering as in Kabat, refers to the numbering system used for heavy chain variable domains or light chain variable domains of the compilation of antibodies in Kabat et al. (*Sequences of Immunological Interest*. (5th Ed., 1991, National Institutes of Health, Bethesda, Md.), "Kabat"). Using this numbering system, the actual linear amino acid sequence can contain fewer or additional amino acids corresponding to a shortening of, or insertion into, a FR or CDR of the variable domain. For example, a heavy chain variable domain can include a single amino acid insert (residue 52a according to Kabat) after residue 52 of H2 and inserted residues (e.g. residues 82a, 82b, and 82c, etc. according to Kabat) after heavy chain FR residue 82. The Kabat numbering of residues can be determined for a given antibody by alignment at regions of homology of the sequence of the antibody with a "standard" Kabat numbered sequence. Chothia refers instead to the location of the structural loops (Chothia and Lesk, *J. Mol. Biol.* 196:901-917 (1987)). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software.

| Loop | Kabat | AbM | Chothia |
|---|---|---|---|
| L1 | L24-L34 | L24-L34 | L24-L34 |
| L2 | L50-L56 | L50-L56 | L50-L56 |
| L3 | L89-L97 | L89-L97 | L89-L97 |
| H1 | H31-H35B | H26-H35B | H26-H32 . . . 34 |
| | | (Kabat Numbering) | |
| H1 | H31-H35 | H26-H35 | H26-H32 |
| | | (Chothia Numbering) | |
| H2 | H50-H65 | H50-H58 | H52-H56 |
| H3 | H95-H102 | H95-H102 | H95-H102 |

The terms "VL" and "VL domain" are used interchangeably to refer to the light chain variable region of an antibody.

The terms "VH" and "VH domain" are used interchangeably to refer to the heavy chain variable region of an antibody.

The term "antibody fragment" refers to a portion of an intact antibody. An "antigen-binding fragment" refers to a portion of an intact antibody that binds to an antigen. An antigen-binding fragment can contain the antigenic determining variable regions of an intact antibody. Examples of antibody fragments include, but are not limited to Fab, Fab', F(ab')2, and Fv fragments, linear antibodies, and single chain antibodies.

A "monoclonal" antibody or antigen-binding fragment thereof refers to a homogeneous antibody or antigen-binding fragment population involved in the highly specific recognition and binding of a single antigenic determinant, or epitope. This is in contrast to polyclonal antibodies that typically include different antibodies directed against different antigenic determinants. The term "monoclonal" antibody or antigen-binding fragment thereof encompasses both intact and full-length monoclonal antibodies as well as antibody fragments (such as Fab, Fab', F(ab')2, Fv), single chain (scFv) mutants, fusion proteins comprising an antibody portion, and any other modified immunoglobulin molecule comprising an antigen recognition site. Furthermore, "monoclonal" antibody or antigen-binding fragment thereof refers to such antibodies and antigen-binding fragments thereof made in any number of manners including but not limited to by hybridoma, phage selection, recombinant expression, and transgenic animals.

The term "polyclonal antibody" describes a composition of different (diverse) antibody molecules which are capable of binding to or reacting with several different specific antigenic determinants on the same or on different antigens. Usually, the variability of a polyclonal antibody is located in the so-called variable regions of the polyclonal antibody, in particular in the CDR regions. In the present disclosure a mixture of two or more polyclonal antibodies (a polycomposition) is produced in one mixture from a polyclonal polycomposition cell line, which is produced from two or more parental polyclonal cell lines each expressing antibody molecules which are capable of binding to a distinct target, but it may also be a mixture of two or more polyclonal antibodies produced separately. A mixture of monoclonal antibodies providing the same antigen/epitope coverage as a polyclonal antibody described herein will be considered as an equivalent of a polyclonal antibody. When stating that a member of a polyclonal antibody binds to an antigen, it is herein meant to be binding with a binding constant below 100 nM, preferably below 10 nM, even more preferred below 1 nM.

The term "humanized" antibody or antigen-binding fragment thereof refers to forms of non-human (e.g. cow) antibodies or antigen-binding fragments that are specific immunoglobulin chains, chimeric immunoglobulins, or fragments thereof that contain minimal non-human (e.g., cow) sequences. Typically, humanized antibodies or antigen-binding fragments thereof are human immunoglobulins in which residues from the complementary determining region (CDR) are replaced by residues from the CDR of a non-human species (e.g. cow) that have the desired specificity, affinity, and capability ("CDR grafted") (Jones et al., *Nature* 321:522-525 (1986); Riechmann et al., *Nature* 332: 323-327 (1988); Verhoeyen et al., *Science* 239:1534-1536 (1988)). In some instances, the Fv framework region (FR) residues of a human immunoglobulin are replaced with the corresponding residues in an antibody or fragment from a non-human species (e.g., domestic cattle) that has the desired specificity, affinity, and capability. The humanized antibody or antigen-binding fragment thereof can be further modified by the substitution of additional residues either in the Fv framework region and/or within the replaced non-human residues to refine and optimize antibody or antigen-binding fragment thereof specificity, affinity, and/or capability. In general, the humanized antibody or antigen-binding fragment thereof will comprise substantially all of at least one, and typically two or three, variable domains containing all or substantially all of the CDR regions that correspond to the non-human immunoglobulin whereas all or substantially all of the FR regions are those of a human immunoglobulin consensus sequence. The humanized antibody or antigen-binding fragment thereof can also comprise at least a portion of an immunoglobulin constant region or domain (Fc), typically that of a human immunoglobulin. Examples of methods used to generate humanized antibodies are described in U.S. Pat. No. 5,225,539; Roguska et al., *Proc. Natl. Acad. Sci., USA,* 91 (3): 969-973 (1994), and Roguska et al., *Protein Eng.* 9 (10): 895-904 (1996). In some embodiments, a "humanized antibody" is a resurfaced antibody.

The term "chimeric" antibodies or antigen-binding fragments thereof refers to antibodies or antigen-binding fragments thereof wherein the amino acid sequence is derived from two or more species. Typically, the variable region of both light and heavy chains corresponds to the variable region of antibodies or antigen-binding fragments thereof derived from one species of mammals (e.g., domestic cattle) with the desired specificity, affinity, and capability while the constant regions are homologous to the sequences in antibodies or antigen-binding fragments thereof derived from another (usually human) to avoid eliciting an immune response in that species.

The term "epitope" or "antigenic determinant" are used interchangeably herein and refer to that portion of an antigen capable of being recognized and specifically bound by a particular antibody. When the antigen is a polypeptide, epitopes can be formed both from contiguous amino acids and noncontiguous amino acids juxtaposed by tertiary folding of a protein. Epitopes formed from contiguous amino acids are typically retained upon protein denaturing, whereas epitopes formed by tertiary folding are typically lost upon protein denaturing. An epitope typically includes at least 3, and more usually, at least 5 or 8-10 amino acids in a unique spatial conformation.

"Binding affinity" generally refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Low-affinity antibodies generally bind antigen slowly and tend to dissociate readily, whereas high-affinity antibodies generally bind antigen faster and tend to remain bound longer. A variety of methods of measuring binding affinity are known in the art, any of which can be used for purposes of the present invention. Specific illustrative embodiments are described in the following.

"Or better" when used herein to refer to binding affinity refers to a stronger binding between a molecule and its binding partner. "Or better" when used herein refers to a stronger binding, represented by a smaller numerical Kd value. For example, an antibody which has an affinity for an antigen of "0.6 nM or better", the antibody's affinity for the antigen is <0.6 nM, i.e. 0.59 nM, 0.58 nM, 0.57 nM etc. or any value less than 0.6 nM.

As used herein, the terms "immunospecifically binds," "immunospecifically recognizes," "specifically binds," and "specifically recognizes" are analogous terms in the context of antibodies and refer to molecules that bind to an antigen (e.g., epitope or immune complex) as such binding is understood by one skilled in the art. For example, a molecule that specifically binds to an antigen can bind to other peptides or polypeptides, generally with lower affinity as determined by, e.g., immunoassays, BIAcore®, KinExA 3000 instrument (Sapidyne Instruments, Boise, ID), or other assays known in the art. In a specific embodiment, molecules that immunospecifically bind to an antigen bind to the antigen with a Kd that is at least 2 logs, 2.5 logs, 3 logs, or 4 logs lower than the Kd when the molecules bind non-specifically to another antigen. In one example, the antibody may specifically bind to the BG505 SOSIP Env trimer. The antibody may bind to BG505 SOSIP trimer with a Kd at least 2 logs, 2.5 logs, 3 logs, or 4 logs lower than Kd of binding to other viral or non-viral polypeptides. An antibody or fusion polypeptide that specifically binds to Env encompass, but are not limited to, antibodies and fusion polypeptides that specifically bind to native Env, an isoform of Env, or a variant of Env (e.g., SOSIP) derived from an HIV isolate, for example, BG505. In one embodiment, the antibody or fusion polypeptide specifically binds to BG505 Env. In one embodiment, the antibody or fusion polypeptide specifically binds to BG505 SOSIP.

By "preferentially binds," it is meant that the antibody specifically binds to an epitope more readily than it would bind to a related, similar, homologous, or analogous epitope. Thus, an antibody which "preferentially binds" to a given epitope would more likely bind to that epitope than to a related epitope, even though such an antibody may cross-react with the related epitope.

An antibody is said to "competitively inhibit" binding of a reference antibody to a given epitope if it preferentially binds to that epitope or an overlapping epitope to the extent that it blocks, to some degree, binding of the reference antibody to the epitope. Competitive inhibition may be determined by any method known in the art, for example, competition ELISA assays. An antibody may be said to competitively inhibit binding of the reference antibody to a given epitope by at least 90%, at least 80%, at least 70%, at least 60%, or at least 50%.

The term "broadly neutralizing antibody" or "bnAb," as used herein, with respect to HIV (e.g., HIV-1), refers to an antibody that recognizes HIV Env of more than one isolate or strain of HIV and inhibits or prevents receptor binding of target cells as evaluated in an in vitro neutralization assay. In one embodiment, a broadly neutralizing antibody inhibits infection of a susceptible target cell by HIV. In one embodiment, a broadly neutralizing antibody specifically binds an HIV Env and inhibits infection of a susceptible target cell (e.g., TZM-bl) by an HIV pseudovirus comprising an Env polypeptide. HIV pseudovirus neutralization assays have been disclosed in the art, for example, in Walker, L. M. et al., *Nature* 477, 466-470 (2011), Li M., et al., *J. Virol.* 79:10108-10125 (2005), each of which is incorporated herein by reference in its entirety for all purposes. In one embodiment, a broadly neutralizing antibody neutralizes 2, 3, 4, 5, 6, 7, 8, 9, or more HIV strains or pseudoviruses. In one embodiment, a broadly neutralizing antibody neutralizes 2, 3, 4, 5, 6, 7, 8, 9, or more HIV strains or pseudoviruses that belong to the same or different clades.

In one embodiment, the breadth of neutralization is tested on an indicator virus panel comprising cross-clade HIV isolates. In one embodiment, the virus panel comprises 6 cross-clade isolates, for example: Clade A: 94UG103, 92RW020, Clade B: 92BR020, JR-CSF, Clade C: IAVI C22, Clade A E: 92TH021. See, Simek et al, J. Virol. 83 (14): 7337-48 (2009). In one embodiment, the virus panel comprises 12 cross-clade isolates, for example: Clade A: 398F1, Clade B: TRO.11, X2278, Clade C: 25710, Ce0217, Clade C (T/F): Ce1176_A3, Clade G: X1632_S2_B10, Clade AC: 246F3, Clade CRF01_AE: CNE8, CNE55, Clade BC: CH119, BJOX2000. In one embodiment, the virus panel comprises 117 cross-clade isolates, for example: Clade A: 94UG103, 398F1, BG505, MS208, Q23.17, Q461.e2, Q769.d22, 0330.v4.c3, 0260.v5.c36, Clade A (T/F): 191084_B7-19, Clade B: 92BR020, JR-CSF, 6535.3, QH0692.42, SC422661.8, PVO.4, TRO.11, AC10.0.29, RHPA4259.7, REJO4541.67, TRJO4551.58, WITO4160.33, CAAN5342.A2, X2278, Clade B (T/F): WEAU_d15_410_5017, 1006_11_C3_1601, 1054_07_TC4_1499, 1056_10_TA11_1826, 1012_11_TC21_3257, 6240_08_TA5_4622, 6244_13_B5_4576, 62357_14_D3_4589, SC05_8C11_2344, Clade C: IAVI C22, 25710, Du156.12, Du172.17, Du422.1, ZM197M.PB7, ZM214M.PL15, ZM233M.PB6, ZM249M.PL1, ZM53M.PB12, ZM109F.PB4, ZM135M.PL10a, CAP45, CAP210.2.00.E8, HIV-001428-2.42, HIV-16055-2.3, HIV-16845-2.22, Ce0217, Ce704809221_1B3, Clade C (T/F): Ce0393_C3, Ce1176_A3, Ce2010_F5, Ce1172_H1, Ce703010054_2A2, BF1266.431a, 246F_C1G, 249M_B10, ZM247v1 (Rev-), 7030102001E5 (Rev-), 1394C9G1 (Rev), Clade D: A07412M1.vrc12, 231965.c01, Clade G: X1193_c1, P0402_c2_11, X1254_c3, X2088_c9, P1981_C5_3, X1632_S2_B10, 3016.v5.c45, Clade AC: 3301.v1.c24, 6041.v3.c23, 6540.v4.c1, 6545.v4.c1, 246F3, Clade CRF01_AE: 92TH021, 620345.c01, C1080.c03, R2184.c04, R1166.c01, R3265.c06, C3347.c11, C4118.c09, CNE8, CNE55, CNE5, BJOX009000.02.4, Clade CRF01_AE (T/F): BJOX015000.11.5, BJOX010000.06.2, BJOX025000.01.1, BJOX028000.10.3, Clade CRF02_AG: T257-31, 928-28, 263-8, T250-4, T251-18, T278-50, 235-47, Clade BC: CNE19, CNE20, CNE21, CNE17, CNE30, CNE52, CNE53, CNE58, CH119, BJOX2000, Clade CD: 3817.v2.c59, 6480.v4.c25, 6952.v1.c20, 6811.v7.c18, 89-F1_2_25, Clade ACD: 0815.v3.c3, 3103.v3.c10. In one embodiment, a broadly neutralizing antibody is capable of neutralizing at least about 50%, 60%, 70%, 80%, 90%, 95%, or 100% of cross-clade HIV isolates in the 6-member indicator virus panel. In one embodiment, a broadly neutralizing antibody is capable of neutralizing at least about 70% of cross-clade HIV isolates in the 6-member indicator virus panel. In one embodiment, a broadly neutralizing antibody is capable of neutralizing at least about 80% of cross-clade HIV isolates in the 6-member indicator virus panel. In one embodiment, a broadly neutralizing antibody is capable of neutralizing at least about 90% of cross-clade HIV isolates in the 6-member indicator virus panel. In one embodiment, a broadly neutralizing antibody is capable of neutralizing at least about 95% of cross-clade HIV isolates in the 6-member indicator virus panel. In one embodiment, a broadly neutralizing antibody is capable of neutralizing at least about 50%, 60%, 70%, 80%, 90%, 95%, or 100% of cross-clade HIV isolates in the 12-member indicator virus panel. In one embodiment, a broadly neutralizing antibody is capable of neutralizing at least about 70% of cross-clade HIV isolates in the 12-member indicator virus panel. In one embodiment, a broadly neutralizing antibody is capable of neutralizing at least about 80% of cross-clade HIV isolates in the 12-member indicator virus panel. In one embodiment, a broadly neutralizing antibody is capable of neutralizing at least about 90% of cross-clade HIV isolates in the 12-member indicator virus panel. In one embodiment, a broadly neutralizing antibody is capable of neutralizing at least about 95% of cross-clade HIV isolates in the 12-member indicator virus panel. In one embodiment, a broadly neutralizing antibody is capable of neutralizing at least about 50%, 60%, 70%, 80%, 90%, 95%, or 100% of cross-clade HIV isolates in the 117-member indicator virus panel. In one embodiment, a broadly neutralizing antibody is capable of neutralizing at least about 60% of cross-clade HIV isolates in the 117-member indicator virus panel. In one embodiment, a broadly neutralizing antibody is capable of neutralizing at least about 70% of cross-clade HIV isolates in the 117-member indicator virus panel. In one embodiment, a broadly neutralizing antibody is capable of neutralizing at least about 80% of cross-clade HIV isolates in the 117-member indicator virus panel. In one embodiment, a broadly neutralizing antibody is capable of neutralizing at least about 90% of cross-clade HIV isolates in the 117-member indicator virus panel. In one embodiment, a broadly neutralizing antibody is capable of neutralizing at least about 95% of cross-clade HIV isolates in the 117-member indicator virus panel.

In one embodiment, the potency of neutralization by a broadly neutralizing antibody is expressed as the median $IC_{50}$ neutralization activity against a virus panel, for example the 6-virus panel, 12-virus panel, or 117-virus panel disclosed herein. In one embodiment, a broadly neutralizing antibody is capable of neutralizing at least about 50%, 60%, 70%, 80%, 90%, 95%, or 100% of cross-clade HIV isolates in the 6-member indicator virus panel with a median $IC_{50}$ equal to or less than about 0.1 microg/ml, 0.07 microg/ml, 0.06 microg/ml, 0.05 microg/ml, 0.025 microg/ml, 0.01 microg/ml or 0.005 microg/ml. In one embodiment, a broadly neutralizing antibody is capable of neutralizing at least about 90% of cross-clade HIV isolates in the 6-member indicator virus panel with a median $IC_{50}$ equal to or less than 0.05 microg/ml. In one embodiment, a broadly neutralizing antibody is capable of neutralizing at least about 50%, 60%, 70%, 80%, 90%, 95%, or 100% of cross-clade HIV isolates in the 12-member indicator virus panel with a median $IC_{50}$ equal to or less than about 0.1 microg/ml, 0.07 microg/ml, 0.06 microg/ml, 0.05 microg/ml, 0.025 microg/ml, 0.01 microg/ml or 0.005 microg/ml. In one embodiment, a broadly neutralizing antibody is capable of neutralizing at least about 90% of cross-clade HIV isolates in the 12-member indicator virus panel with a median $IC_{50}$ equal to or less than 0.05 microg/ml. In one embodiment, a broadly neutralizing antibody is capable of neutralizing at least about 50%, 60%, 70%, 80%, 90%, 95%, or 100% of cross-clade HIV isolates in the 117-member indicator virus panel with a median $IC_{50}$ equal to or less than about 0.1 microg/ml, 0.07 microg/ml, 0.06 microg/ml, 0.05 microg/ml, 0.025 microg/ml, 0.01 microg/ml or 0.005 microg/ml. In one embodiment, a broadly neutralizing antibody is capable of neutralizing at least about 60% of cross-clade HIV isolates in the 117-member indicator virus panel with a median $IC_{50}$ equal to or less than about 0.05 microg/ml. In one embodiment, a broadly neutralizing antibody is capable of neutralizing at least about 70% of cross-clade HIV isolates in the 117-member indicator virus panel with a median $IC_{50}$ equal to or less than about 0.05 microg/ml. In one embodiment, a broadly neutralizing antibody is capable of neutralizing at least about 80% of cross-clade HIV isolates in the 117-member indicator virus panel with a median $IC_{50}$ equal to or less than about 0.05 microg/ml. In one embodiment, a broadly neutralizing antibody is capable of neutralizing at least about 90% of cross-clade HIV isolates in the 117-member indicator virus panel with a median $IC_{50}$ equal to or less than about 0.05 microg/ml. In one embodiment, a broadly neutralizing antibody is capable of neutralizing at least about 95% of cross-clade HIV isolates in the 117-member indicator virus panel with a median $IC_{50}$ equal to or less than about 0.05 microg/ml.

In one embodiment, the potency of neutralization by a broadly neutralizing antibody, for example, a polyclonal serum, is expressed as the median $ID_{50}$ neutralization activity against a virus panel, for example, the 6-virus panel, 12-virus panel, or 117-virus panel. In one embodiment, a broadly neutralizing antibody is capable of neutralizing at least about 50%, 60%, 70%, 80%, 90%, 95%, or 100% of cross-clade HIV isolates in the 6-member indicator virus panel with a median $ID_{50}$ of at least about 50, 100, 500, 1000, 5000, or 10000. In one embodiment, a broadly neutralizing antibody is capable of neutralizing at least about 90% of cross-clade HIV isolates in the 6-member indicator virus panel with a median $ID_{50}$ of at least about 1000. In one embodiment, a broadly neutralizing antibody is capable of neutralizing at least about 50%, 60%, 70%, 80%, 90%, 95%, or 100% of cross-clade HIV isolates in the 12-member indicator virus panel with a median $ID_{50}$ of at least about 50, 100, 500, 1000, 5000, or 10000. In one embodiment, a broadly neutralizing antibody is capable of neutralizing at least about 90% of cross-clade HIV isolates in the 12-member indicator virus panel with a median $ID_{50}$ of at least about 1000. In one embodiment, a broadly neutralizing antibody is capable of neutralizing at least about 20%, 30%, 40%, 50%, 60%, 70%, 80%, 90%, 95%, or 100% of cross-clade HIV isolates in the 117-member indicator virus panel with a median $ID_{50}$ of at least about 50, 100, 500, 1000, 5000, or 10000. In one embodiment, a broadly neutralizing antibody is capable of neutralizing at least about 90% of cross-clade HIV isolates in the 117-member indicator virus panel with a median $ID_{50}$ of at least about 1000.

The term "$IC_{50}$" refers to the half maximal inhibitory concentration of an inhibitor, e.g., a broadly neutralizing antibody. For example, $IC_{50}$ is the concentration of an inhibitor, e.g., a broadly neutralizing antibody, where the response, e.g., infection by pseudovirus, is reduced by half.

The term "$ID_{50}$" refers to the half maximal inhibitory dilution of an inhibitor, e.g., a broadly neutralizing antibody. For example, $ID_{50}$ is the fold dilution of an inhibitor, e.g., a bovine serum comprising a broadly neutralizing antibody, where the response, e.g., infection by pseudovirus, is reduced by half.

The phrase "substantially similar," or "substantially the same", as used herein, denotes a sufficiently high degree of similarity between two numeric values (generally one associated with an antibody described herein and the other associated with a reference/comparator antibody) such that one of skill in the art would consider the difference between the two values to be of little or no biological and/or statistical significance within the context of the biological characteristic measured by said values (e.g., Kd values). The difference between said two values can be less than about 50%, less than about 40%, less than about 30%, less than about 20%, or less than about 10% as a function of the value for the reference/comparator antibody.

A polypeptide, antibody, polynucleotide, vector, cell, or composition which is "isolated" is a polypeptide, antibody, polynucleotide, vector, cell, or composition which is in a form not found in nature. Isolated polypeptides, antibodies, polynucleotides, vectors, cell or compositions include those which have been purified to a degree that they are no longer in a form in which they are found in nature. In some embodiments, an antibody, polynucleotide, vector, cell, or composition which is isolated is substantially pure.

As used herein, "substantially pure" refers to material which is at least 50% pure (i.e., free from contaminants), at least 90% pure, at least 95% pure, at least 98% pure, or at least 99% pure.

The terms "polypeptide," "peptide," and "protein" are used interchangeably herein to refer to polymers of amino acids of any length. The polymer can be linear or branched, it can comprise modified amino acids, and it can be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides described herein are based upon antibodies, in certain embodiments, the polypeptides can occur as single chains or associated chains.

The terms "identical" or percent "identity" in the context of two or more nucleic acids or polypeptides, refer to two or more sequences or subsequences that are the same or have a specified percentage of nucleotides or amino acid residues that are the same, when compared and aligned (introducing gaps, if necessary) for maximum correspondence, not considering any conservative amino acid substitutions as part of the sequence identity. The percent identity can be measured using sequence comparison software or algorithms or by visual inspection. Various algorithms and software are known in the art that can be used to obtain alignments of amino acid or nucleotide sequences. One such non-limiting example of a sequence alignment algorithm is the algorithm described in Karlin et al, *Proc. Natl. Acad. Sci.,* 87:2264-2268 (1990), as modified in Karlin et al., *Proc. Natl. Acad. Sci.,* 90:5873-5877 (1993), and incorporated into the NBLAST and XBLAST programs (Altschul et al., *Nucleic Acids Res.,* 25:3389-3402 (1991)). In certain embodiments, Gapped BLAST can be used as described in Altschul et al., *Nucleic Acids Res.* 25:3389-3402 (1997). BLAST-2, WU-BLAST-2 (Altschul et al., *Methods in Enzymology,* 266:460-480 (1996)), ALIGN, ALIGN-2 (Genentech, South San Francisco, California) or Megalign (DNASTAR) are additional publicly available software programs that can be used to align sequences. In certain embodiments, the percent identity between two nucleotide sequences is determined using the GAP program in GCG software (e.g., using a NWSgapdna.CMP matrix and a gap weight of 40, 50, 60, 70, or 90 and a length weight of 1, 2, 3, 4, 5, or 6). In certain alternative embodiments, the GAP program in the GCG software package, which incorporates the algorithm of Needleman and Wunsch (*J. Mol. Biol.* (48): 444-453 (1970)) can be used to determine the percent identity between two amino acid sequences (e.g., using either a Blossum 62 matrix or a PAM250 matrix, and a gap weight of 16, 14, 12, 10, 8, 6, or 4 and a length weight of 1, 2, 3, 4, 5). Alternatively, in certain embodiments, the percent identity between nucleotide or amino acid sequences is determined using the algorithm of Myers and Miller (*CABIOS,* 4:11-17 (1989)). For example, the percent identity can be determined using the ALIGN program (version 2.0) and using a PAM120 with residue table, a gap length penalty of 12 and a gap penalty of 4. Appropriate parameters for maximal alignment by particular alignment software can be determined by one skilled in the art. In certain embodiments, the default parameters of the alignment software are used. In certain embodiments, the percentage identity "X" of a first amino acid sequence to a second sequence amino acid is calculated as 100×(Y/Z), where Y is the number of amino acid residues scored as identical matches in the alignment of the first and second sequences (as aligned by visual inspection or a particular sequence alignment program) and Z is the total number of residues in the second sequence. If the length of a first sequence is longer than the second sequence, the percent identity of the first sequence to the second sequence will be longer than the percent identity of the second sequence to the first sequence.

As a non-limiting example, whether any particular polynucleotide has a certain percentage sequence identity (e.g., is at least 80% identical, at least 85% identical, at least 90% identical, and in some embodiments, at least 95%, 96%, 97%, 98%, or 99% identical) to a reference sequence can, in certain embodiments, be determined using the Bestfit program (Wisconsin Sequence Analysis Package, Version 8 for Unix, Genetics Computer Group, University Research Park, 575 Science Drive, Madison, WI 53711). Bestfit uses the local homology algorithm of Smith and Waterman (*Advances in Applied Mathematics* 2:482 489 (1981)) to find the best segment of homology between two sequences. When using Bestfit or any other sequence alignment program to determine whether a particular sequence is, for instance, 95% identical to a reference sequence described herein, the parameters are set such that the percentage of identity is calculated over the full length of the reference nucleotide sequence and that gaps in homology of up to 5% of the total number of nucleotides in the reference sequence are allowed.

In some embodiments, two nucleic acids or polypeptides described herein are substantially identical, meaning they have at least 70%, at least 75%, at least 80%, at least 85%, at least 90%, and in some embodiments at least 95%, 96%, 97%, 98%, 99% nucleotide or amino acid residue identity, when compared and aligned for maximum correspondence, as measured using a sequence comparison algorithm or by visual inspection. Identity can exist over a region of the sequences that is at least about 10, about 20, about 40-60 residues in length or any integral value there between, and can be over a longer region than 60-80 residues, for example, at least about 90-100 residues, and in some embodiments, the sequences are substantially identical over the full length of the sequences being compared, such as the coding region of a nucleotide sequence for example.

A "conservative amino acid substitution" is one in which one amino acid residue is replaced with another amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). For example, substitution of a phenylalanine for a tyrosine is a conservative substitution. In some embodiments, conservative substitutions in the sequences of the polypeptides and antibodies described herein do not abrogate the binding of the polypeptide or antibody containing the amino acid sequence, to the antigen(s). Methods of identifying nucleotide and amino acid conservative substitutions which do not eliminate antigen binding are well-known in the art (see, e.g., Brummell et al., *Biochem.* 32:1180-1 187 (1993); Kobayashi et al., *Protein Eng.* 12 (10): 879-884 (1999); and Burks et al., *Proc. Natl. Acad. Sci. USA* 94:412-417 (1997)).

Vectors that can be used include, but are not limited to, plasmids, bacterial vectors, and viral vectors. Viral vectors include cytomegalovirus (CMV) vectors. An advantage of these CMV vectors for use in therapeutic vaccine delivery is that they create a new CD8+ T cell epitope paradigm and induce more potent and enduring responses. It has been shown in animal models that vaccines based on these viral vectors can clear viral infections (Hansen, S. G. 2013. Science 340:1237874), and so these approaches have promise for a therapeutic vaccine, a setting in which tailored vaccines can be useful.

Other viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. Alternatively, the vaccine antigens could be delivered as DNA, RNA or protein components of a vaccine.

As used herein, the terms "treatment" or "therapy" (as well as different forms thereof, including curative or palliative) refer to treatment of an infected person. As used herein, the term "treating" includes alleviating or reducing at least one adverse or negative effect or symptom of a condition, disease or disorder. This condition, disease or disorder can be HIV infection.

Terms such as "treating" or "treatment" or "to treat" or "alleviating" or "to alleviate" refer to therapeutic measures that cure, slow down, lessen symptoms of, and/or halt progression of a diagnosed pathologic condition or disorder, such as HIV or AIDS. Thus, those in need of treatment include those already diagnosed with or suspected of having the disorder. In certain embodiments, a subject is successfully "treated" for the disorder according to the methods described herein if the patient shows one or more of the following: a reduction in the number of or complete absence of viral load; a reduction in the viral burden; inhibition of or an absence of the virus into peripheral organs; relief of one or more symptoms associated with the disorder; reduced morbidity and mortality; improvement in quality of life; increased progression-free survival (PFS), disease-free survival (DFS), or overall survival (OS), complete response (CR), partial response (PR), stable disease (SD), a decrease in progressive disease (PD), a reduced time to progression (TTP), or any combination thereof.

As used herein, the terms "prevention" or "prophylaxis" refer to preventing a subject from becoming infected with, or reducing the risk of a subject from becoming infected with, or halting transmission of, or the reducing the risk of transmission of a virus. Prophylactic or preventative measures refer to measures that prevent and/or slow the development of a targeted pathological condition or disorder. Thus, those in need of prophylactic or preventative measures include those prone to have the disorder and those in whom the disorder is to be prevented. In one embodiment, prevention encompasses passive immunization of a subject in need thereof comprising administering an effective amount of a broadly neutralizing antibody disclosed herein or a fusion polypeptide disclosed herein.

As employed above and throughout the disclosure the term "effective amount" refers to an amount effective, at dosages, and for periods of time necessary, to achieve the desired result with respect to the treatment of the relevant disorder, condition, or side effect. An "effective amount" can be determined empirically and in a routine manner, in relation to the stated purpose. It will be appreciated that the effective amount of components of the present invention will vary from patient to patient not only with the particular vaccine, component or composition selected, the route of administration, and the ability of the components to elicit a desired result in the individual, but also with factors such as the disease state or severity of the condition to be alleviated, hormone levels, age, sex, weight of the individual, the state of being of the patient, and the severity of the pathological condition being treated, concurrent medication or special diets then being followed by the particular patient, and other factors which those skilled in the art will recognize, with the appropriate dosage being at the discretion of the attending physician. Dosage regimes may be adjusted to provide the improved therapeutic response. An effective amount is also one in which any toxic or detrimental effects of the components are outweighed by the therapeutically beneficial effects.

The term "therapeutically effective amount" refers to an amount of an antibody, immunoconjugate, or other drug effective to "treat" a disease or disorder in a subject or mammal. To the extent an antibody can prevent growth and/or kill existing cells, it can be cytostatic and/or cytotoxic. A "prophylactically effective amount" refers to an amount effective, at dosages and for periods of time necessary, to achieve the desired prophylactic result. Typically but not necessarily, since a prophylactic dose is used in subjects prior to or at an earlier stage of disease, the prophylactically effective amount will be less than the therapeutically effective amount.

The terms "subject," "individual," and "patient" are used interchangeably herein, and refer to an animal, for example a human, to whom treatment, including prophylactic treatment, with the antibody or pharmaceutical composition according to the present disclosure, is provided. In one embodiment, the subject, individual, or patient has been infected with HIV. In one embodiment, the subject, individual, or patient suffers from AIDS. In one embodiment, the subject, individual, or patient has been exposed to HIV. In one embodiment, the subject, individual, or patient is at risk of being exposed to HIV.

Administration "in combination with" one or more further therapeutic agents includes simultaneous (concurrent) or consecutive administration in any order.

The terms "pharmaceutically composition," "pharmaceutical formulation," "pharmaceutically acceptable formulation," or "pharmaceutically acceptable composition" all of which are used interchangeably, refer to those compounds, materials, compositions, and/or dosage forms which are, within the scope of sound medical judgment, suitable for contact with the tissues of human beings and animals without excessive toxicity, irritation, allergic response, or other problem complications commensurate with a reasonable benefit/risk ratio. "Pharmaceutically acceptable" or "pharmaceutical formulation" refers to a preparation which is in such form as to permit the biological activity of the active ingredient to be effective, and which contains no additional components which are unacceptably toxic to a subject to which the formulation would be administered. The formulation can be sterile.

The term "antiretroviral therapy" or "ART," as used herein, refers to any of the therapies used to manage progression of a retrovirus (e.g., HIV) infection in a subject (e.g., a human), including, for example, nucleoside reverse transcriptase inhibitors (NRTIs), non-nucleoside reverse transcriptase inhibitors (NNRTIs), protease inhibitors (PIs), fusion inhibitors, entry inhibitors, maturation inhibitors, cellular inhibitors, integrase strand transfer inhibitors, and multi-class combinations. Such drugs include, but are not limited to, lamivudine and zidovudine, emtricitabine (FTC), zidovudine (ZDV), azidothymidine (AZT), lamivudine (3TC), zalcitabine, dideoxycytidine (ddC), tenofovir disoproxil fumarate (TDF), didanosine (ddl), stavudine (d4T), abacavir sulfate (ABC), etravirine, delavirdine (DLV), efavirenz (EFV), nevirapine (NVP), amprenavir (APV), tipranavir (TPV), indinavir (IDV), saquinavir, saquinavir mesylate (SQV), lopinavir (LPV), ritonavir (RTV), fosamprenavir calcium (FOS-APV), ritonavir, RTV, darunavir, atazanavir sulfate (ATV), nelfinavir mesylate (NFV), enfuvirtide, T-20, maraviroc and raltegravir. ART drugs can also include antibodies that target HIV proteins or cellular proteins associated with disease progression. Also included are immune-based therapies, such as IL-2, IL-12, and alpha-epibromide. Each of these drugs can be administered alone or in combination with any other ART drug or any HIV-specific neutralizing antibody, such as a broadly neutralizing antibody, e.g. a broadly neutralizing antibody disclosed in US Patent Appl. Pub. No. 2015/0361160, which is incorporated by reference herein in its entirety for all purposes.

The term "immunomodulator," as used herein, refers to an agent, such as an antibody or peptide, which is capable of increasing, inducing, or extending an immune response (e.g., a cell-mediated immune response and/or a humoral immune response) when administered to a subject (e.g., a human, e.g., a human infected with HIV or at risk of an HIV infection or transmission). Immunomodulators include, but are not limited to immune checkpoint inhibitors, for example, a PD-1, PD-L1, LAG-3, or TIGIT antagonist. In one embodiment, an immunomodulator used in the methods described herein comprises an anti-PD-1 antibody, anti-PD-L1 antibody, anti-LAG3 antibody, or an anti-TIGIT antibody. An immunomodulator can be administered in conjunction with (e.g., prior to, concurrently with, or subsequent to, or within the context of a treatment regimen that includes the administration of a broadly neutralizing antibody described herein.

As used in this specification and the appended claims, the singular forms "a," "an," and "the" include plural referents unless the content clearly dictates otherwise. Thus, for example, reference to "a cell" includes a combination of two or more cells, and the like.

The term "and/or" as used in a phrase such as "A and/or B" herein is intended to include both "A and B," "A or B," "A," and "B." Likewise, the term "and/or" as used in a phrase such as "A, B, and/or C" is intended to encompass each of the following embodiments: A, B, and C; A, B, or C; A or C; A or B; B or C; A and C; A and B; B and C; A (alone); B (alone); and C (alone).

The term "about" as used herein when referring to a measurable value such as an amount, a temporal duration, and the like, is meant to encompass variations of up to +20% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope described herein are approximations, the numerical values set forth in the specific examples are reported as precisely as possible. Any numerical value, however, inherently contain certain errors necessarily resulting from the standard deviation found in their respective testing measurements.

It is understood that wherever embodiments are described herein with the language "comprising," otherwise analogous embodiments described in terms of "consisting of" and/or "consisting essentially of" are also provided.

II. Methods of Producing a Broadly Neutralizing Anti-Env Antibody

In one aspect, provided herein are methods for generating a broadly neutralizing anti-Env antibody. In one embodiment, the antibody is polyclonal. In one embodiment, the antibody is monoclonal (e.g., a chimeric or humanized).

In one embodiment, a method of producing a broadly neutralizing anti-Env antibody described herein comprises immunizing a bovine by administering at least one dose of an antigenic composition comprising an HIV specific antigen to produce a broadly neutralizing anti-Env antibody. In one embodiment, the HIV specific antigen comprises a well-ordered Env trimer polypeptide. In one embodiment, the HIV specific antigen comprises a polynucleotide encoding a well-ordered Env trimer polypeptide.

In one embodiment, method of producing a broadly neutralizing anti-Env antibody, comprises immunizing a bovine by administering at least one dose of an antigenic composition comprising an HIV specific antigen to produce a broadly neutralizing anti-Env antibody, wherein the HIV specific antigen comprises a well-ordered Env trimer polypeptide or a polynucleotide encoding a well-ordered Env trimer polypeptide, and wherein the bovine produces the broadly neutralizing anti-Env antibody.

In one embodiment, the bovine is domestic cattle, bison, African buffalo, water buffalo, or yak. In one embodiment, the bovine is domestic cattle. In one embodiment, the domestic cattle is a dairy cow. In one embodiment, the cow is pregnant.

In one embodiment, the HIV specific antigen comprises a virus, pseudovirus, or virus-like particle comprising a well-ordered Env trimer polypeptide. In one embodiment, the HIV specific antigen comprises an isolated well-ordered Env trimer polypeptide. In one embodiment, the well-ordered Env trimer polypeptide comprises an SOSIP trimer. A well-ordered Env trimer polypeptide may be produced by a number of different means, for example, as described in US Patent Appl. Pub. No. 2014/0212458, Sanders, R. W. et al., *PLOS Pathog.* 9, e1003618 (2013) and Guenaga J., et al., Immunity 46 (5): 792-803.e3 (2017), each of which is incorporated by reference herein in its entirety. For example, HEK293F cells can be co-transfected with a pg140 encoding plasmid and a furin encoding plasmid. Supernatants comprising the SOSIP are purified using a lectin column. The affinity-purified SOSIP can be further purified to size homogeneity using size exclusion chromatography.

In one embodiment, a well ordered trimer is formed from a clade A Env. In one embodiment, a well ordered trimer is formed from a clade B Env. In one embodiment, a well ordered trimer is formed from a clade C Env.

In one embodiment, the SOSIP is formed from Env derived from a virus selected from the group consisting of Clade A: 94UG103, 398F1, BG505, MS208, Q23.17, Q461.e2, Q769.d22, 0330.v4.c3, 0260.v5.c36, Clade A (T/F): 191084_B7-19, Clade B: 92BR020, JR-CSF, 6535.3, QH0692.42, SC422661.8, PVO.4, TRO.11, AC10.0.29, RHPA4259.7, REJO4541.67, TRJO4551.58, WITO4160.33, CAAN5342.A2, X2278, Clade B (T/F): WEAU_d15_410_5017, 1006_11_C3_1601, 1054_07_TC4_1499, 1056_10_TA11_1826, 1012_11_TC21_3257, 6240_08_TA5_4622, 6244_13_B5_4576, 62357_14_D3_4589, SC05_8C11_2344, Clade C: IAVI C22, 25710, Du156.12, Du172.17, Du422.1, ZM197M.PB7, ZM214M.PL15, ZM233M.PB6, ZM249M.PL1, ZM53M.PB12, ZM109F.PB4, ZM135M.PL10a, CAP45, CAP210.2.00.E8, HIV-001428-2.42, HIV-16055-2.3, HIV-16845-2.22, Ce0217, Ce704809221_1B3, Clade C (T/F): Ce0393_C3, Ce1176_A3, Ce2010_F5, Ce1172_H1, Ce703010054_2A2, BF1266.431a, 246F_C1G, 249M_B10, ZM247v1 (Rev-), 7030102001E5 (Rev-), 1394C9G1 (Rev), Clade D: A07412M1.vrc12, 231965.c01, Clade G: X1193_c1, P0402_c2_11, X1254_c3, X2088_c9, P1981_C5_3, X1632_S2_B10, 3016.v5.c45, Clade AC: 3301.v1.c24, 6041.v3.c23, 6540.v4.c1, 6545.v4.c1, 246F3, Clade CRF01_AE: 92TH021, 620345.c01, C1080.c03, R2184.c04, R1166.c01, R3265.c06, C3347.c11, C4118.c09, CNE8, CNE55, CNE5, BJOX009000.02.4, Clade CRF01_AE (T/F): BJOX015000.11.5, BJOX010000.06.2, BJOX025000.01.1, BJOX028000.10.3, Clade CRF02_AG: T257-31, 928-28, 263-8, T250-4, T251-18, T278-50, 235-47, Clade BC: CNE19, CNE20, CNE21, CNE17, CNE30, CNE52, CNE53, CNE58, CH119, BJOX2000, Clade CD: 3817.v2.c59, 6480.v4.c25, 6952.v1.c20, 6811.v7.c18, 89-F1_2_25, Clade ACD: 0815.v3.c3, and 3103.v3.c10.

In one embodiment, the SOSIP is formed from Env derived from a virus selected from the group consisting of Clade A: 398F1, Clade B: TRO.11, X2278, Clade C: 25710, Ce0217, Clade C (T/F): Ce1176_A3, Clade G: X1632_S2_B10, Clade AC: 246F3, Clade CRF01_AE: CNE8, CNE55, Clade BC: CH119, and BJOX2000.

In one embodiment, the SOSIP is formed from BG505 Env.

In one embodiment, the well-ordered trimer is BG505 SOSIP. In one embodiment, the well-ordered trimer is BG505 SOSIP.664. In one embodiment, BG505 SOSIP.664 comprises the amino acid sequence of SEQ ID NO: 106.

In one embodiment, a well ordered trimer is formed from a SIV Env. In one embodiment, a well ordered trimer is an SIV Env SOSIP. In one embodiment, a well ordered trimer is formed from an Env comprising a mutation (e.g., substitution or deletion) in the CD4 binding site. In one embodiment, a well ordered trimer is formed from an Env comprising a mutation (e.g., substitution or deletion) in the CD4 binding site wherein the mutation reduces or disrupts the binding between Env and CD4. In one embodiment, a well ordered trimer is a CRF or C108 SOSIP. See, e.g., Andrabi et al, *Immunity* 43 (5): 959-973 (2015).

In one embodiment, the antigenic composition further comprises an adjuvant. The skilled person is familiar with many potentially useful adjuvants, such as Freund's complete adjuvant, alum, and squalene. See, e.g., US Patent Appl. Pub. No. 20150361160, which is incorporated by reference herein in its entirety for all purposes. Adjuvants which may be used in compositions of the invention include, but are not limited to oil emulsion compositions (oil-in-water emulsions and water-in-oil emulsions), complete Freund's adjuvant (CFA) and incomplete Freund's adjuvant (IFA). In one embodiment, the adjuvant comprises RIBI, Iscomatrix, or ENABL C1 (VaxLiant). Adjuvants suitable for use in the invention include bacterial or microbial derivatives such as derivatives of enterobacterial lipopolysaccharide (LPS), Lipid A derivatives, immunostimulatory oligonucleotides and ADP-ribosylating toxins and detoxified derivatives thereof.

Methods for immunizing a bovine, such as a cattle, to produce, for example, high titer colostrum, milk, serum, or immune tissues (e.g., PBMC), are known in in the art. Such methods are disclosed, for example, in US Patent Appl. Pub. Nos US20070053917 and US20130022619, each of which is incorporated by reference herein in its entirety for all purposes.

In one embodiment, the immunizing comprises administering a priming dose and at least one booster dose of the antigenic composition. In one embodiment, the immunizing comprises administering more than one booster doses of the antigenic composition. In one embodiment, the priming dose and at least one booster dose comprise the same antigenic composition. In one embodiment, the more than one booster doses comprise the same antigenic composition. The animal may be dosed with the immunogenic composition at intervals over a period of days, weeks or months. At the conclusion of the immunization regime, the hyperimmune material such as blood, milk or colostrum is harvested. In one embodiment, the hyperimmune material is collected less than 2 months, less than 3 months, less than 4 months, less than 5 months, less than 6 months, less than 9 months, or less than 12 months after administering the priming dose. In one embodiment, the hyperimmune material is collected between about 3 months and about 6 months after administering the priming dose. In one embodiment, the hyperimmune material is collected between about 3 months and about 9 months after administering the priming dose. In one embodiment, the hyperimmune material is collected between about 3 months and about 12 months after administering the priming dose. In one embodiment, the hyperimmune material is collected between about 6 months and about 12 months after administering the priming dose.

In one embodiment, the immunogenic composition comprises an HIV specific antigen derived from a single HIV isolate. In one embodiment, the immunogenic composition comprises an HIV specific antigen derived from more than one the HIV isolates. In one embodiment, the more than one HIV isolates belong to the same clade. In one embodiment, the more than one HIV isolates belong to different clades. For example, the more than one isolates can belong to clades A and B, clades A and C, clades B and C, or clades A, B, and C. In one embodiment, the more than one HIV isolates belong to clades A and B. In one embodiment, the more than one HIV isolates belong to clades A and C. In one embodiment, the more than one HIV isolates belong to clades C and B. In one embodiment, the more than one HIV isolates belong to clades A, B, and C. One or more of the HIV isolates can be a circulating recombinant form HIV.

In one embodiment, a method of producing a broadly neutralizing anti-Env antibody further comprises isolating from the bovine a biological sample comprising the broadly neutralizing anti-Env antibody. In one embodiment, the biological sample is milk, blood, serum, colostrum, or peripheral blood mononuclear cells (PBMC). In one embodiment, the biological sample is collected less than 2 months, less than 3 months, less than 4 months, less than 5 months, less than 6 months, less than 9 months, or less than 12 months after administering the priming dose. In one embodiment, the biological sample is collected between about 3 months and about 6 months after administering the priming dose. In one embodiment, the biological sample is collected between about 3 months and about 9 months after administering the priming dose. In one embodiment, the biological sample is collected between about 3 months and about 12 months after administering the priming dose. In one embodiment, the biological sample is collected between about 6 months and about 12 months after administering the priming dose.

The term "colostrum" as used herein includes colostral milk; processed colostral milk such as colostral milk processed to partly or completely remove one or more of fat, cellular debris, lactose and casein; and colostral milk or processed colostral milk which has been dried by for example, freeze drying, spray drying or other methods of drying known in the art. Colostral milk is generally taken from a mammal such as a cow within five days after parturition. Preferably the mammalian colostrum is bovine colostrum retained from the first 4 days post parturition, more preferably bovine colostrum retained from the first 2 days post parturition, even more preferably bovine colostrum retained from the first day post parturition, and most preferably bovine colostrum retained from the first milking post parturition.

In one embodiment, a method of producing a broadly neutralizing anti-Env antibody further comprises purifying the broadly neutralizing anti-Env antibody. In one embodiment, the antibody is a polyclonal antibody.

In one embodiment, a method of producing a broadly neutralizing anti-Env antibody further comprises isolating from the bovine a biological sample comprising the broadly neutralizing anti-Env antibody; purifying the broadly neutralizing anti-Env antibody; processing the broadly neutralizing anti-Env antibody to prepare an F(ab) or F(ab')2 fragment; and recovering the F(ab) or F(ab')2 fragment. In one embodiment, the antibody is a polyclonal antibody. In one embodiment, the antibody is a polyclonal F(ab) or F(ab')2 fragment. Methods for producing an F(ab')2 fragment and compositions thereof are known in in the art, for example, as disclosed in U.S. Pat. No. 6,709,655, which is incorporated by reference herein in its entirety for all purposes.

In one embodiment, a method of producing a broadly neutralizing anti-Env antibody further comprises isolating a peripheral blood mononuclear cell (PMBCs) from the bovine, and cloning a polynucleotide that encodes a broadly neutralizing anti-Env antibody. In one embodiment, the cloning the polynucleotide comprises performing single-cell RT-PCR amplification.

In one embodiment, a method of producing a broadly neutralizing anti-Env antibody further comprises expressing the polynucleotide that encodes the broadly neutralizing anti-Env antibody in a host cell.

In one embodiment, a method of producing a broadly neutralizing anti-Env antibody further comprises expressing the polynucleotide that encodes the broadly neutralizing anti-Env antibody in a cell-free expression system.

In one embodiment, the immunizing elicits production of polyclonal serum capable of neutralizing at least about 50%, 60%, 70%, 80%, 90%, or 100% of cross-clade HIV isolates in the 6-member indicator virus panel. In one embodiment, the immunizing elicits production of polyclonal serum capable of neutralizing at least about 90% of cross-clade HIV isolates in the 6-member indicator virus panel. In one embodiment, the immunizing elicits production of polyclonal serum capable of neutralizing at least about 50%, 60%, 70%, 80%, 90%, or 100% of cross-clade HIV isolates in the 12-member indicator virus panel. In one embodiment, the immunizing elicits production of polyclonal serum capable of neutralizing at least about 90% of cross-clade HIV isolates in the 12-member indicator virus panel. In one embodiment, the immunizing elicits production of polyclonal serum capable of neutralizing at least about 50%, 60%, 70%, 80%, 90%, or 100% of cross-clade HIV isolates in the 117-member indicator virus panel. In one embodiment, the immunizing elicits production of polyclonal serum capable of neutralizing at least about 80% of cross-clade HIV isolates in the 117-member indicator virus panel. In one embodiment, the polyclonal serum comprises an antibody capable of neutralizing the cross-clade HIV isolates with a median $IC_{50}$ equal to or less than about 0.1 microg/ml, 0.05 microg/ml, 0.025 microg/ml, 0.01 microg/ml, or 0.005 microg/ml. In one embodiment, the polyclonal serum comprises an antibody capable of neutralizing the cross-clade HIV isolates with a median $IC_{50}$ equal to or less than 0.05 microg/ml. In one embodiment, the polyclonal serum is capable of neutralizing the cross-clade HIV isolates with a median $ID_{50}$ of at least about 50, 100, 500, 1000, 5000, or 10000. In one embodiment, the polyclonal serum is capable of neutralizing the cross-clade HIV isolates with a median $ID_{50}$ of at least about 500. In one embodiment, the polyclonal serum is collected less than about 2 months, 3 months, 4 months, 5 months, 6 months, 9 months, or 12 months after administering the first dose of the antigenic composition. In one embodiment, the polyclonal serum is collected between about 3 months and about 6 months after administering the first dose of the antigenic composition. In one embodiment, the polyclonal serum is collected between about 3 months and about 9 months after administering the first dose of the antigenic composition. In one embodiment, the polyclonal serum is collected between about 3 months and about 12 months after administering the first dose of the antigenic composition. In one embodiment, the polyclonal serum is collected between about 6 months and about 12 months after administering the first dose of the antigenic composition.

In one embodiment, the immunizing elicits production of polyclonal serum capable of neutralizing at least about 10%, 15%, 20%, 25%, 30%, or 40% of cross-clade HIV isolates in the 6-member indicator virus panel with a median $ID_{50}$ of at least about 1000, wherein the serum is collected less than about 2 months, 3 months, 4 months, 5 months, or 6 months after administering the first dose of the antigenic composition.

In one embodiment, the immunizing elicits production of polyclonal serum capable of neutralizing at least about 40%, 50%, 60%, 70%, 80%, 90%, 95%, or 100% of cross-clade HIV isolates in the 6-member indicator virus panel with a median $ID_{50}$ of at least about 1000, wherein the serum is collected less than about 6 months, 9 months or 12 months after administering the first dose of the antigenic composition. In one embodiment, the immunizing elicits production of polyclonal serum capable of neutralizing at least about 90% of cross-clade HIV isolates in the 6-member indicator virus panel with a median $ID_{50}$ of at least about 500, wherein the serum is collected less than about 6 months, 9 months or 12 months after administering the first dose of the antigenic composition. In one embodiment, the serum is collected between about 3 months and about 12 months after administering the first dose of the antigenic composition.

In one embodiment, the immunizing elicits production of polyclonal serum capable of neutralizing at least about 10%, 15%, 20%, 25%, 30%, or 40% of cross-clade HIV isolates in the 12-member indicator virus panel with a median $ID_{50}$ of at least about 1000, wherein the serum is collected less than about 2 months, 3 months, 4 months, 5 months, or 6 months after administering the first dose of the antigenic composition.

In one embodiment, the immunizing elicits production of polyclonal serum capable of neutralizing at least about 40%, 50%, 60%, 70%, 80%, 90%, 95%, or 100% of cross-clade HIV isolates in the 12-member indicator virus panel with a median $ID_{50}$ of at least about 1000, wherein the serum is collected less than about 6 months, 9 months or 12 months after administering the first dose of the antigenic composition. In one embodiment, the immunizing elicits production of polyclonal serum capable of neutralizing at least about 80% of cross-clade HIV isolates in the 12-member indicator virus panel with a median $ID_{50}$ of at least about 500, wherein the serum is collected less than about 6 months, 9 months or 12 months after administering the first dose of the antigenic composition. In one embodiment, the serum is collected between about 3 months and about 12 months after administering the first dose of the antigenic composition.

In one embodiment, the immunizing elicits production of polyclonal serum capable of neutralizing at least about 10%, 15%, 20%, 25%, 30%, or 40% of cross-clade HIV isolates in the 117-member indicator virus panel with a median $ID_{50}$ of at least about 1000, wherein the serum is collected less than about 2 months, 3 months, 4 months, 5 months, or 6 months after administering the first dose of the antigenic composition.

In one embodiment, the immunizing elicits production of polyclonal serum capable of neutralizing at least about 40%, 50%, 60%, 70%, 80%, 90%, 95%, or 100% of cross-clade HIV isolates in the 117-member indicator virus panel with a median $ID_{50}$ of at least about 1000, wherein the serum is collected less than about 6 months, 9 months or 12 months after administering the first dose of the antigenic composition. In one embodiment, the immunizing elicits production of polyclonal serum capable of neutralizing at least about 80% of cross-clade HIV isolates in the 117-member indicator virus panel with a median $ID_{50}$ of at least about 500, wherein the serum is collected less than about 6 months, 9 months or 12 months after administering the first dose of the antigenic composition. In one embodiment, the serum is collected between about 3 months and about 12 months after administering the first dose of the antigenic composition.

In one embodiment, the broadly neutralizing anti-Env antibody is polyclonal. In one embodiment, the broadly neutralizing anti-Env antibody is monoclonal. In one embodiment, the broadly neutralizing anti-Env antibody is an F(ab) fragment. In one embodiment, the broadly neutralizing anti-Env antibody is an F(ab')2 fragment.

III. Broadly Neutralizing Anti-HIV Antibodies and Fusion Polypeptides

In one aspect, provided herein are broadly neutralizing anti-Env antibodies. In one embodiment, a broadly neutralizing antibody specifically binds to Env. In one embodiment, an anti-HIV antibody disclosed herein is capable of binding to Env at pH 4.5. In one embodiment, an anti-HIV antibody disclosed herein is capable of binding to Env simulated vaginal fluid at pH 4.5. In one embodiment, a broadly neutralizing antibody specifically binds to a well-ordered HIV Env trimer. In one embodiment, a broadly neutralizing antibody is an F(ab) or F(ab')2. In one embodiment, the antibody is a bovine antibody. In one embodiment, a broadly neutralizing antibody is produced by a method disclosed herein. In one embodiment, the antibody is a polyclonal antibody. In one embodiment, the antibody is a monoclonal antibody. In one embodiment, antibody is a recombinant antibody, a chimeric antibody, a humanized antibody, an antibody fragment, a bispecific antibody, or a trispecific antibody.

In one embodiment, a broadly neutralizing antibody described herein specifically binds to Env and is capable of neutralizing at least two isolates of HIV. In one embodiment, the two isolates are two cross-clade isolates. In one embodiment, the antibody is capable of neutralizing at least about 50%, 60%, 70%, 80%, 90%, or 100% of cross-clade HIV isolates in the 6-member indicator virus panel. In one embodiment, the antibody is capable of neutralizing at least about 90% of cross-clade HIV isolates in the 6-member indicator virus panel. In one embodiment, the antibody is capable of neutralizing at least about 50%, 60%, 70%, 80%, 90%, or 100% of cross-clade HIV isolates in the 12-member indicator virus panel. In one embodiment, the antibody is capable of neutralizing at least about 80% of cross-clade HIV isolates in the 12-member indicator virus panel. In one embodiment, the antibody is capable of neutralizing at least about 50%, 60%, 70%, 80%, 90%, or 100% of cross-clade HIV isolates in the 117-member indicator virus panel. In one embodiment, the antibody is capable of neutralizing at least about 80% of cross-clade HIV isolates in the 117-member indicator virus panel. In one embodiment, the antibody is capable of neutralizing the cross-clade HIV isolates with a median IC50 equal to or less than about 0.1 microg/ml, 0.05 microg/ml, 0.025 microg/ml, 0.01 microg/ml, or 0.005 microg/ml. In one embodiment, the antibody is capable of neutralizing the cross-clade HIV isolates with a median IC50 equal to or less than about 0.05 microg/ml. In one embodiment, the antibody is capable of neutralizing the cross-clade HIV isolates with a median ID50 of at least about 50, 100, 500, 1000, 5000, or 10000. In one embodiment, the antibody is capable of neutralizing the cross-clade HIV isolates with a median ID50 of at least about 500. In one embodiment, the antibody is capable of neutralizing the cross-clade HIV isolates with a median ID50 of at least about 1000. In one embodiment, a broadly neutralizing antibody is a bovine antibody. In one embodiment, the antibody is an F(ab) or F(ab')2. In one embodiment, the antibody is a polyclonal antibody. In one embodiment, the antibody is a monoclonal antibody. In one embodiment, antibody is a recombinant antibody, a chimeric antibody, a humanized antibody, an antibody fragment, a bispecific antibody, or a trispecific antibody.

In one embodiment, the bovine is domestic cattle, bison, African buffalo, water buffalo, or yak. In one embodiment, the bovine is domestic cattle.

In one embodiment, the antibody is an F(ab) fragment. In one embodiment, the antibody is an F(ab')2 fragment.

In one embodiment, the antibody is produced by a method described herein, wherein the antibody is a F(ab) or F(ab')2 fragment.

In one aspect, provided herein are broadly neutralizing monoclonal anti-Env antibodies. In one embodiment, the antibody specifically binds to Env. In one embodiment, the antibody specifically binds to a well-ordered HIV Env trimer. In one embodiment, the antibody is a humanized bovine antibody.

In one embodiment, an isolated monoclonal antibody described herein comprises a VH, a VL, or a VH and VL as shown in Tables 1 and 2.

In one embodiment, an isolated monoclonal antibody described herein comprises one, two, three, four, five or six of the VH CDR1, VH CDR2, VH CDR3, VL CDR1, VL CDR2, and VL CDR3 sequences as shown in Table 3.

In one embodiment, an isolated monoclonal antibody described herein comprises a VH CDR3 sequence as shown in Table 3.

In one embodiment, an isolated monoclonal antibody described herein comprises a VH CDR1, VH CDR2, VH CDR3, VL CDR1, VL CDR2, and VL CDR3 sequence as shown in Table 3.

Also provided herein are polypeptides that comprise an amino acid sequence having at least about 80% sequence identity, at least about 85% sequence identity, at least about 90% sequence identity, at least about 95% sequence identity, at least about 96% sequence identity, at least about 97% sequence identity, at least about 98% sequence identity, or at least about 99% sequence, or is identical to the sequences listed in Tables 1 to 3.

TABLE 1

Variable heavy chain (VH) and light chain (VL) domains.

| | VH | VL |
|---|---|---|
| NC-Cow1 | QVQLRESGPSLMKPSQTLSLTCTVSGSSLNDKSVGWVRQAPGKALQWLGSVDTSGNTDYNPGLKSRLSITKDNSKSRISLTVTGMTTEDSATYYCITAHQKTNKKECPEDYTYNPRCPQQYGWSDCDCMGDRFGGYCRQDGCSNYIHRSTYEWYVSAWGQGLLVTVSS (SEQ ID NO: 7) | SYELTQPSSVSGSLGQRVSVTCSGSSSNVGNGYVSWYQLIPGSAPRTHYGDTSRASGVPERFSGSRSGNTATLTISSLQAEDEADFFCASPDDSSSNAVFGSGTTLTVL (SEQ ID NO: 8) |
| NC-Cow2 | KVQLRESGPSLVKPSQTLSLTCMVSGSSLSDKAVGWVRQAPGKALEWLGIISAGGNRGYNSGLRSRLTISKDNSKNEVSLRVRSVTTEDSATYFCGTVHQKTQRKPICPDGYSDDSTLRYYSRCSDRDCWRCTGTTYYDTCQCGTYTWIDTHELHVDAWGQGLLVTVSS (SEQ ID NO: 17) | QAVLNQPSSVSGSLGQRVSITCSGSSSNVGNGYVSWYQLIPGSAPRTLIYGDTSRASGVPDRFSGSRSGNTATLTISSLQAEDEADYFCASAEDSSSNAVFGSGTTLTVL (SEQ ID NO: 18) |
| NC-Cow3 | QVQLRESGPSLVKPSQTLSLTCMVSGFSLNDKAVGWVRQAPGKALEWLGSIGTGGNKGYNPGLKSRLSISKDSSKNQVSLSMSSVTTEDSATYYCGTVHQRTHRKQNCPGGYSDDNALRYRSRCDDRDCWRCTGTTYYDTCQCASYFYTDTYEFYVDAWGQGLLVTVSS (SEQ ID NO: 27) | QAVLNQPSSVSGSLGQRVSITCSGSSSNVGNGYVSWYQLIPGSAPRTLIYGDTSRASGVPDRFSGSRSGNTATLTISSLQAEDEADYFCASAEDSSSNAVFGSGTTLTVL (SEQ ID NO: 28) |
| NC-Cow4 | KVQLRESGPSLVKPSQTLSLTCMVSGFSLNDEAVGWVRQAPGKALEWLGSIDAGGSTGYNPGLKSRLSISKDNSKNQVSLSVSSVTTEDSATYYCGTVHQRTQPKQTCPNGYSDDSALRYYSRCSDRDCWRCTGTTYYDTCQCSSYTYIHTYELYVDAWGQGLLVTVSS (SEQ ID NO: 37) | QAVLTQPSSVSGSLGQRVSITCSGSSSNVGNGYVSWYQLIPGSAPRTLIYGDTSRASGVPDRFSGSRSGNTATLTISSLQAEDEADYFCASPEDSSSNAVFGSGTTLTVL (SEQ ID NO: 38) |
| NC-Cow5 | QVQLQESGPSLVKPSQTLSLTCMVSGFSLNDKAVGWVRQAPGKALEWLGSIDAGGSTGYNPGLKSRLSISKDNSKNQVSLSVSSVTTEDSATYYCGTVHQRTQPKQTCPNGYSDDSALRYYSRCSDRDCWRCTGTTYYDTCQCSSYTYIHTYELYVDAWGQGLLVTVSS (SEQ ID NO: 47) | QDVLTQPSSVSGSLGQRVSITCSGSSSNVGNGYVSWYQLIPGSAPRTLIYGDTSRASGVPDRFSGSRSGNTATLTISSLQAEDEADYFCASPEDSSSNAVFGSGTTLTVL (SEQ ID NO: 48) |
| NC-Cow6 | QVQLRESGPSLVKPSQTLSLTCMVSGFSLNDKAVGWVRQAPGKALEWLGSIDAGGSTGYNPGLKSRLSISKDNSKNQVSLSVSSVTTEDSATYYCGTVHQRTQPKQTCPNGYSDDSALRYYSRCSDRDCWRCTGTTYYDTCQCSSYTYIHTYELYVDAWGQGLLVTVSS (SEQ ID NO: 57) | QAVLTQPSSVSGSLGQRVSITCSGSSSNVGNGYVSWYQLIPGSAPRTLIYGDTSRASGVPDRFSGSRSGNTATLTISSLQAEDEADYFCASPEDSSSNAVFGSGTTLTVL (SEQ ID NO: 58) |
| NC-Cow7 | KVQLRESGPSLVKPFETLSLTCTGSGFSLSDKAAGWVRQAPGKAPEWLGSIDTGGNTGYNPGLKYRLSITKDNSKSQVSLSVSSMTSEDSATYYCTTVHQKAYKKVCPDDYSSNPDCVRLYGWSHCDCMRDSFGGWCRADGCSSTVEIGPYEWYVNAWGQGLLVTVSS (SEQ ID NO: 67) | QAVLTQPSSVSGSLGQRVSITCSGSSSNVGNGYVSWYQLIPGSAPRSLIYGDTSRASGVPDRFSGSRSGNTATLTISSLQAEDEADYFCASPEDSSSNGVFGSGTTLTVL (SEQ ID NO: 68) |

TABLE 1-continued

| Variable heavy chain (VH) and light chain (VL) domains. | | |
|---|---|---|
| | VH | VL |
| NC-Cow8 | KVQLQESGPSLVKPSQTLSLTCTVS GFSLSDVAVGWVRQAPGKALEWL GTIYTSGNTNVNPGLKSRLSITKDN AKSQVSLSVTSLTTDDSATYYCTT VYQKTTKKDCPEYYTYNPDCARR YGWSDCECMADKFGGYCRHDGC ATNTVRSTYEWHLDAWGQGLLVT VSS (SEQ ID NO: 77) | QAVLTQPSSVSGSLGRRVSITCS GSSSNVGNGYVSWYQVIPGSAP RTLIYGDSNRASGVPDRFSGSRS GNTATLTISSLQAEDEADYFCGS AEDGSGSGVFGSGTTLTVL (SEQ ID NO: 78) |
| NC-Cow9 | QVQLQESGPSLVKPSQTLSLTCTVS GFSLSDVAVGWVRQAPGKALEWL GTIYTSGNTNVNPGLKSRLSITKDN AKSQVSLSVTSLTTDDSATYYCTT VYQKTTKKDCPEYYTYNPDCARR YGWSDCECMADKFGGYCRHDGC ATNTVRSTYEWHLDAWGQGLLVT VSS (SEQ ID NO: 87) | QAVLTQPSSVSGSLGRRVSITCS GSSSNVGNGYVSWYQVIPGSAP RTLIYGDSNRASGVPDRFSGSRS GNTATLTISSLQAEDEADYFCGS AEDGSGSGVFGSGTTLTVL (SEQ ID NO: 88) |
| NC-Cow10 | KVQLQESGPSLVKPSQTLSLTCTVS GFSLSDKAVGWVRQAPGKALEWL GTIDTNRNTNYHPGLKSRLSITKDN SKSRVSLSVSTMTTEDSATYYCTT VHQKTNEKDCPEYYSYNPDCPRRY GWSNCDCMADKFGGWCRHDGCS DYADMTTDEWYVDAWGQGLLVT VSS (SEQ ID NO: 97) | DVLTQPSSVSGSLGQRVSITCSG SSSNVGNGYVSWYQLISGSAPR TLIYGDTSRASGIPDRFSGSRSGN TATLTITSLQAEDEADYFCASAE DRRSNAIFGSGTTLTVL (SEQ ID NO: 98) |
| Germline | QVQLRESGPSLVKPSQTLSLTCTAS GFSLSDKAVGWVRQAPGKALEWL GGIDTGGSTGYNPGLKSRLSITKDN SKSQVSLSVSSVTTEDSATYYCTTV HQ (SEQ ID NO: 111) | QAVLTQPSSVSGSLGQRVSITCS GSSSNVGNGYVSWYQLIPGSAP RTLIYGDTSRASGVPDRFSGSRS GNTATLTISSLQAEDEADYFCAS AEDSSSNA (SEQ ID NO: 112) |
| Consensus NC-Cow1, NC-Cow7-10 | KVQLQESGPSLVKPSQTLSLTCTVS GFSLSDKAVGWVRQAPGKALEWL GTIDTSGNTNYNPGLKSRLSITKDN SKSQVSLSVTSMTTEDSATYYCTT VHQKTXKKDCPEYYTYNPDCXRR YGWSDCDCMADKFGGYCRHDGC STXTVRSTYEWYVDAWGQGLLVT VSS (SEQ ID NO: 113) | QAVLTQPSSVSGSLGQRVSITCS GSSSNVGNGYVSWYQLIPGSAP RTLIYGDTSRASGVPDRFSGSRS GNTATLTISSLQAEDEADYFCAS XEDSSSNAVFGSGTTLTVL (SEQ ID NO: 114) |
| Consensus NC-Cow2 to NC-Cow6 | QVQLRESGPSLVKPSQTLSLTCMVS GFSLNDKAVGWVRQAPGKALEWL GSIDAGGSTGYNPGLKSRLSISKDN SKNQVSLSVSSVTTEDSATYYCGT VHQRTQPKQTCPNGYSDDSALRYY SRCSDRDCWRCTGTTYYDTCQCSS YTYIHTYELYVDAWGQGLLVTVSS (SEQ ID NO: 115) | QAVLTQPSSVSGSLGQRVSITCS GSSSNVGNGYVSWYQLIPGSAP RTLIYGDTSRASGVPDRFSGSRS GNTATLTISSLQAEDEADYFCAS XEDSSSNAVFGSGTTLTVL (SEQ ID NO: 116) |

TABLE 2

| Variable heavy chain (VH) and light chain (VL) domains. | | |
|---|---|---|
| | VH | VL |
| mature NC-Cow1 HC + mature NC-Cow1 LC | QVQLRESGPSLMKPSQTLSLT CTVSGSSLNDKSVGWVRQAP GKALQWLGSVDTSGNTDYNP GLKSRLSITKDNSKSRISLTVT GMTTEDSATYYCITAHQKTNK KECPEDYTYNPRCPQQYGWS DCDCMGDRFGGYCRQDGCSN YIHRSTYEWYVSAWGQGLLV TVSS (SEQ ID NO: 7) | SYELTQPSSVSGSLGQRVSVTCS GSSSNVGNGYVSWYQLIPGSAP RTIIYGDTSRASGVPERFSGSRSG NTATLTISSLQAEDEADFFCASP DDSSSNAVFGSGTTLTVL(SEQ ID NO: 8) |
| germline NC-Cow1 HC mature NC-Cow1 LC | QVQLQESGPGLVKPSETLSLTC TVSGYSISSGYYWGWIRQPPG KGLEWIGSIYHSGSTYYNPSLK SRVTISVDTSKNQFSLKLSSVT AADTAVYYCITAHQKTNKKE | SYELTQPSSVSGSLGQRVSVTCS GSSSNVGNGYVSWYQLIPGSAP RTIIYGDTSRASGVPERFSGSRSG NTATLTISSLQAEDEADFFCASP DDSSSNAVFGSGTTLTVL (SEQ |

TABLE 2-continued

| Variable heavy chain (VH) and light chain (VL) domains. | | |
|---|---|---|
| | VH | VL |
| | CPEDYTYNPRCPQQYGWSDC DCMGDRFGGYCRQDGCSNYI HRSTYEWYVSAWGQGTLVTV SS (SEQ ID NO: 117) | ID NO: 8) |
| germline NC-Cow1 HC germline NC-Cow1 LC | QVQLQESGPGLVKPSETLSLTC TVSGYSISSGYYWGWIRQPPG KGLEWIGSIYHSGSTYYNPSLK SRVTISVDTSKNQFSLKLSSVT AADTAVYYCITAHQKTNKKE CPEDYTYNPRCPQQYGWSDC DCMGDRFGGYCRQDGCSNYI HRSTYEWYVSAWGQGTLVTV SS (SEQ ID NO: 117) | QSVLTQPPSASGTPGQRVTISCS GSSSNIGSNTVNWYQQLPGTAP KLLIYSNNQRPSGVPDRFSGSKS GTSASLAISGLQSEDEADYYCAA WDDSLNGPVVFGGGTKLTVL (SEQ ID NO: 118) |
| germline PG9 HC (NC-Cow1 VH CDR3) + mature PG9 LC | QVQLVESGGGVVQPGRSLRLS CAASGFTFSSYGMEIWVRQAP GKGLEWVAVISYDGSNKYYA DSVKGRFTISRDNSKNTLYLQ MNSLRAEDTAVYYCITAHQKT NKKECPEDYTYNPRCPQQYG WSDCDCMGDRFGGYCRQDG CSNYIHRSTYEWYVSAWGKG TTVTVSS (SEQ ID NO: 119) | QSALTQPASVSGSPGQSITISCNG TSNDVGGYESVSWYQQHPGKA PKVVIYDVSKRPSGVSNRFSGSK SGNTASLTISGLQAEDEGDYYC KSLTSTRRRVFGTGTKLTVL (SEQ ID NO: 120) |

TABLE 3

| VH and VL CDR sequences. The CDRs have been determined according to Kabat. | | | | | | |
|---|---|---|---|---|---|---|
| | VH CDR1 | VH CDR2 | VH CDR3 | VL CDR1 | VL CDR2 | VL CDR3 |
| NC-Cow1 | GSSLN DKS (SEQ ID NO: 1) | VDTSGN T (SEQ ID NO: 2) | ITAHQKTNKKE CPEDYTYNPRC PQQYGWSDCD CMGDRFGGYC RQDGCSNYIHR STYEWYVSA (SEQ ID NO: 3) | SSNVG NGY SEQ ID NO: 4) | GDT | ASPDDSSSNA V (SEQ ID NO: 6) |
| NC-Cow2 | GSSLS DKA (SEQ ID NO: 11) | ISAGGN R (SEQ ID NO: 12) | GTVHQKTQRK PICPDGYSDDS TLRYYSRCSDR DCWRCTGTTY YDTCQCGTYT WIDTHELHVD A (SEQ ID NO: 13) | SSNVG NGY (SEQ ID NO: 14) | GDT | ASAEDSSSNA V (SEQ ID NO: 16) |
| NC-Cow3 | GFSLN DKA (SEQ ID NO: 21) | IGTGGN K (SEQ ID NO: 22) | GTVHQRTHRK QNCPGGYSDD NALRYRSRCD DRDCWRCTGT TYYDTCQCAS YFYTDTYEFYV DA (SEQ ID NO: 23) | SSNVG NGY (SEQ ID NO: 24) | GDT | ASAEDSSSNA V (SEQ ID NO: 26) |
| NC-Cow4 | GFSLN DEA (SEQ ID NO: 31) | IDAGGS T (SEQ ID NO: 32) | GTVHQRTQPK QTCPNGYSDDS ALRYYSRCSDR DCWRCTGTTY YDTCQCSSYTY IHTYELYVDA (SEQ ID NO: 33) | SSNVG NGY (SEQ ID NO: 34) | GDT (SEQ | ASPEDSSSNA V (SEQ ID NO: 36) |
| NC-Cow5 | GFSLN DKA (SEQ ID NO: 41) | IDAGGS T (SEQ ID NO: 42) | GTVHQRTQPK QTCPNGYSDDS ALRYYSRCSDR DCWRCTGTTY YDTCQCSSYTY IHTYELYVDA (SEQ ID NO: 43) | SSNVG NGY (SEQ ID NO: 44) | GDT | ASPEDSSSNA V (SEQ ID NO: 46) |

TABLE 3-continued

VH and VL CDR sequences. The CDRs have been determined according to Kabat.

| | VH CDR1 | VH CDR2 | VH CDR3 | VL CDR1 | VL CDR2 | VL CDR3 |
|---|---|---|---|---|---|---|
| NC-Cow6 | GFSLNDKA (SEQ ID NO: 51) | IDAGGST (SEQ ID NO: 52) | GTVHQRTQPKQTCPNGYSDDSALRYYSRCSDRDCWRCTGTTYYDTCQCSSYTYIHTYELYVDA (SEQ ID NO: 53) | SSNVGNGY (SEQ ID NO: 54) | GDT | ASPEDSSSNAV (SEQ ID NO: 56) |
| NC-Cow7 | GFSLSDKA (SEQ ID NO: 61) | IDTGGNT (SEQ ID NO: 62) | TTVHQKAYKKVCPDDYSSNPDCVRLYGWSHCDCMRDSFGGWCRADGCSSTVEIGPYEWYVNA (SEQ ID NO: 63) | SSNVGNGY (SEQ ID NO: 64) | GDT | ASPEDSSSNGV (SEQ ID NO: 66) |
| NC-Cow8 | GFSLSDVA (SEQ ID NO: 71) | IYTSGNT (SEQ ID NO: 72) | TTVYQKTTKKDCPEYYTYNPDCARRYGWSDCECMADKFGGYCRHDGCATNTVRSTYEWHLDA (SEQ ID NO: 73) | SSNVGNGY (SEQ ID NO: 74) | GDS | GSAEDGSGSGV (SEQ ID NO: 76) |
| NC-Cow9 | GFSLSDVA (SEQ ID NO: 81) | IYTSGNT (SEQ ID NO: 82) | TTVYQKTTKKDCPEYYTYNPDCARRYGWSDCECMADKFGGYCRHDGCATNTVRSTYEWHLDA (SEQ ID NO: 83) | SSNVGNGY (SEQ ID NO: 84) | GDS | GSAEDGSGSGV (SEQ ID NO: 86) |
| NC-Cow10 | GFSLSDKA (SEQ ID NO: 91) | IDTNRNT (SEQ ID NO: 92) | TTVHQKTNEKDCPEYYSYNPDCPRRYGWSNCDCMADKFGGWCRHDGCSDYADMTTDEWYVDA (SEQ ID NO: 93) | SSNVGNGY (SEQ ID NO: 94) | GDT | ASAEDRRSNAI (SEQ ID NO: 96) |
| NC-Cow11 | | | TTVYQKTTKKDCPEYYTYNPDCARRYGWSDCDCMADKFGGSCRLDGCATNTVRSTYEWHLDA (SEQ ID NO: 227) | | | |
| NC-Cow12 | | | TTVYQKTTKKDCPEYYTYNRDCERRYGWSDCECRADNVGGHCRHEGCATNTVRSTYEWHLDA (SEQ ID NO: 228) | | | |
| NC-Cow13 | | | TTVYLKTTKQDCPEYYTYNPDCARRYGWSDCECMADKFGGYCRHDGCATNTVRSTDEWHLDA (SEQ ID NO: 229) | | | |
| NC-Cow14 | | | TTVYLKTTKQDCPEYYTYNPDCARRYGWRDCECLADKVGGYCRHVGCANNTV | | | |

TABLE 3-continued

VH and VL CDR sequences. The CDRs have been determined according to Kabat.

| | VH CDR1 | VH CDR2 | VH CDR3 | VL CDR1 | VL CDR2 | VL CDR3 |
|---|---|---|---|---|---|---|
| | | | RSTDEWHLDA (SEQ ID NO: 230) | | | |
| NC-Cow15 | | | TTVYLKTTKQDCPEYYTYNPDCARRYGWSDCECMADKVGGECRHDGCATNTVRSNDEWHLDA (SEQ ID NO: 231) | | | |
| NC-Cow16 | | | TTVYQKTTKKDCPEYYTYNPDCARRSGWSDCECMADKFGGYCRHDGCATNTVRSTYEWHLDA (SEQ ID NO: 232) | | | |
| NC-Cow17 | | | TTVYLKTTKQDCPEYYTYNPDCARRYGWSDCECMADKFGGYCRHDGCATNPVRSTDEWHLDA (SEQ ID NO: 233) | | | |
| NC-Cow18 | | | TTVYLKTTKQDCPEYYTYNPDCARRYGWSDCECMADKFGGYCRHDGCATNTVRSTDGFHLDA (SEQ ID NO: 234) | | | |
| NC-Cow19 | | | TTVYQKTTKQDCPEYYTYNPDCARRYGWSDCECMADKFGGYCRHDGCATNTVRSTYE HLDA W | | | |
| NC-Cow20 | | | TTVYLKTTKQDCPEYYTYNPDRARRSGWSDCECMADKFGGYCRHDGCATNTVRSTDEWHLDA (SEQ ID NO: 236) | | | |
| NC-Cow21 | | | TTVYQKTTKQDCPEYYTYNPDCARRYGWSDCECMADKFGGYCRHEGFATHTVRSPYEWHLHA (SEQ ID NO: 237) | | | |
| NC-Cow22 | | | TTVYQKTTKKDCPEYYTYNPDCAMRYGWSYCECMAGKFWGYWCHESCATNTVRSTYEGPRDA (SEQ ID NO: 238) | | | |

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the antibody specifically binds to BG505 Env. In one embodiment, the antibody is a humanized antibody.

In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3, 13, 23, 33, 43, 53, 63, 73, 83, 93, or 121. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 227-238. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 75%, 80%, 85%, 90%, 95%, 97%, 98%, 99% or 100% identical to SEQ ID NO: 3, 13, 23, 33, 43, 53, 63, 73, 83, 93, 121, or 227-238. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3 or SEQ ID NO: 121 (CITAHQKTNKKECPEDYTYNPRCPQQYGWSDCDCMGDRFGGYCRQDGCSNYIHRSTYEWYVS AW). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow2, NC-Cow3, NC-Cow4, NC-Cow5, NC-Cow 6, NC-Cow7, NC-Cow8, NC-Cow9, or NC-Cow10 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow7, NC-Cow8, NC-Cow9, or NC-Cow10 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein.

In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3, 13, 23, 33, 43, 53, 63, 73, 83, 93, or 121 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 227-238 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3, 13, 23, 33, 43, 53, 63, 73, 83, 93, 121, 227-238 comprising 2, 3, 4, 5, 5, 6, 7, 8, 9, 10, 11, 12, 13, 14, or 15 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the VH CDR3 of NC-Cow1 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3 or SEQ ID NO: 121 comprising 0, 1, 2, 3, 4, or 5 substitutions, insertions, or deletions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of TTVHQKTXKKDCPEYYTYNPDCXR-RYGWSDCDCMADKFGGYCRHDGC-STXTVRSTYEWYVD A (SEQ ID NO: 101). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of $X_1TX_3X_4QKX_7X_8 X_9KX_{11}CPX_{14}X_{15}YX_{17}X_{18}NPX_{21}CX_{23}X_{24}X_{25}YGW SX_{30}CX_{32}CMX_{35}DX_{37}FGGX_{41}CRX_{44} DGCX_{48}X_{49}X_{50}X_{51}X_{52}X_{53}X_{54}X_{55}X_{56}EWX_{59}X_{60}X_{61}A$ wherein $X_1$ is Tor I, $X_3$ is V or A, $X_4$ is H or Y, $X_7$ is T or A, $X_8$ is N, Y, or T, $X_9$ is Kor E, $X_{11}$ is D, E, or V, $X_{14}$ is E or D, $X_{15}$ is Y or D, $X_{17}$ is T or S, $X_{18}$ is Y or S, $X_{21}$ is D or R, $X_{23}$ is P, V, or A, $X_{24}$ is R or Q, $X_{25}$ is R, Q, or L, $X_{30}$ is D, H, or N, $X_{32}$ is D or E, $X_{35}$ is A, G, or R, $X_{37}$ is K, R, or S, $X_{41}$ is Y or W, $X_{44}$ is H, Q, or A, $X_{48}$ is S or A, $X_{49}$ is T, N, S, or D, $X_{50}$ is Y, T, or N, $X_{51}$ is V, T, I, or A, $X_{52}$ is V, H, E, or D, $X_{53}$ is R, I, or M, $X_{54}$ is S, G, or T, $X_{55}$ is T, or P, $X_{56}$ is Y, or D, $X_{59}$ is Y, or H, $X_{60}$ is V, or L, and $X_{61}$ is D, or S (SEQ ID NO: 102). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of $X_1TX_2X_3X_4KX_5X_6X_7KX_8CPX_9X_{10}YX_{11}X_{12}NX_{13}X_{14}CX_{15}X_{16}X_{17}X_{18}GWSX_{19}CX_{20}CX_{21}X_{22}X_{23}X_{24}X_{25}GGX_{26}CRX_{27}X_{28}X_{29}CX_{30}X_{31}X_{32}X_{33}X_{34}X_{35}X_{36}X_{37}X_{38}EWX_{39}X_{40}X_{41}A$ wherein $X_1$ is I or T, $X_2$ is A or V, $X_3$ is H or Y, $X_4$ is Q or L, $X_5$ is T or A, $X_6$ is N, Y, or T, $X_7$ is K or E, $X_8$ is E, V, or D, $X_9$ is E or D, $X_{10}$ is D or Y, $X_{11}$ is T or S, $X_{12}$ is Y or S, $X_{13}$ is P or R, $X_{14}$ is R or D, $X_{15}$ is P, V, E or A, $X_{16}$ is Q, M or R, $X_{17}$ is Q, L, or R, $X_{18}$ is Y or S, $X_{19}$ is D, H, Y, or N, $X_{20}$ is D or E, $X_{21}$ is M, R, or L, $X_{22}$ is G, R, or A, $X_{23}$ is D or G, $X_{24}$ is R, S, Nor K, $X_{25}$ is For V, $X_{26}$ is Y or W, $X_{27}$ is Q, A, or H, $X_{28}$ is D, E, or V, $X_{29}$ is G or S, $X_{30}$ is S or A, $X_{31}$ is N, S, T, or D, $X_{32}$ is Y, T, H or N, $X_{33}$ is I, V, T, P or A, $X_{34}$ is H, E, V, or D, $X_{35}$ is R, I, or M, $X_{36}$ is S, G, or T, $X_{37}$ is T, N or P, $X_{38}$ is Y or D, $X_{39}$ is Y, or H, $X_{40}$ is V or L, and $X_{41}$ is S, N, H or D (SEQ ID NO: 268). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of $X_1TX_2X_3X_4KX_5X_6X_7KX_8CPX_9X_{10}YX_{11}X_{12}NX_{13}X_{14}CX_{15}X_{16}X_{17}X_{18}GWSX_{19}CX_{20}CX_{21}X_{22}X_{23}X_{24}X_{25}GGX_{26}CRX_{27}X_{28}X_{29}CX_{30}X_{31}X_{32}X_{33}X_{34}X_{35}X_{36}X_{37}X_{38}EWX_{39}X_{40}X_{41}A$ wherein $X_1$ is I, A or T, $X_2$ is A or V, $X_3$ is H, A or Y, $X_4$ is Q, A or L, $X_5$ is T or A, $X_6$ is N, Y, A or T, $X_7$ is K, A or E, $X_8$ is E, V, A or D, $X_9$ is E, A or D, $X_{10}$ is D, A or Y, $X_{11}$ is T, A or S, $X_{12}$ is Y, A or S, $X_{13}$ is P, A or R, $X_{14}$ is R or D, $X_{15}$ is P, V, E or A, $X_{16}$ is Q, M, A or R, $X_{17}$ is Q, L, A or R, $X_{18}$ is Y or S, $X_{19}$ is D, H, Y, A or N, $X_{20}$ is D, A or E, $X_{21}$ is M, R, A or L, $X_{22}$ is G, R, or A, $X_{23}$ is D, A or G, $X_{24}$ is R, S, N, A or K, $X_{25}$ is For V, $X_{26}$ is Y, A or W, $X_{27}$ is Q, A, or H, $X_{28}$ is D, E, or V, $X_{29}$ is G, A or S, $X_{30}$ is S or A, $X_{31}$ is N, S, T, A or D, $X_{32}$ is Y, T, H, A or N, $X_{33}$ is I, V, T, P or A, $X_{34}$ is H, E, V, A or D, $X_{35}$ is R, I, A or M, $X_{36}$ is S, G, A or T, $X_{37}$ is T, N, A or P, $X_{38}$ is Y, A or D, $X_{39}$ is Y, A or H, $X_{40}$ is V, A or L, and $X_{41}$ is S, N, H, A or D (SEQ ID NO: 269). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of $GTVHQX_1TX_2X_3KX_4X_5CPX_6GYSDDX_7X_8LRYX_9SRCX_{10}DRDCWRCTGTTYYDTCQCX_{11}X_{12}YX_{13}X_{14}X_{15}X_{16}TX_{17}EX_{18}X_{19}VDA$ wherein $X_1$ is R or K, $X_2$ is Q or H, $X_3$ is Por R, $X_4$ is Q or P, $X_5$ is T, I or N, $X_6$ is N, D, or G, $X_7$ is S or N, $X_8$ is A or T, $X_9$ is Y or R, $X_{10}$ is S or D, Xu is S, G or A, $X_{12}$ is S or T, $X_{13}$ is Tor F, $X_{14}$ is Y or W, $X_{15}$ is I or T, $X_{16}$ is H or D, $X_{17}$ is Y or H, $X_{18}$ is L or F, and $X_{19}$ is Y or H (SEQ ID NO: 122). In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 or 253-260. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 140. In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 141. In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 142. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow 9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence with at least about 80%, 90%, 95% or 100% identity to the amino acid sequence of SEQ ID NO:133. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133 comprising 0, 1, 2, 3, 4, or 5 substitutions, deletions or insertions. In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133 comprising 0, 1, 2, 3, 4, or 5 substitutions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence with at least about 80%, 90%, 95% or 100% identity to the amino acid sequence of SEQ ID NO: 134-139 or 253-260. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 or 253-260 comprising 0, 1, 2, 3, 4, or 5 substitutions, deletions or insertions. In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 comprising 0, 1, 2, 3, 4, or 5 substitutions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises an amino acid sequence with at least about 70%, 75%, 80%, 85%, or 90% identity to the amino acid sequence of SEQ ID NO: 133-139 or 253-260. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133-139 or 253-260 comprising 5, 6, 7, 8, 9, 10, 11, 12, 13, 14, or 15 substitutions, deletions or insertions. In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133-139 comprising 5, 6, 7, 8, 9, 10, 11, 12, 13, 14, or 15 substitutions. In one embodiment, the antibody specifically binds to BG505 Env. In one embodiment, the antibody is a humanized antibody. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises a Stalk A amino acid sequence listed in Table 4, the knob comprises a knob amino acid sequence listed in Table 4, and the stalk B comprises a stalk B amino acid sequence listed in Table 4. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions. In one embodiment, the knob comprises a knob amino sequence listed in Table 4 comprising 0, 1, 2, 3, 4, 5, 6, 7, 8, 9, 10, 11, 12, 13, 14, or 15 substitutions. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions. In one embodiment, the knob comprises a knob amino sequence listed in Table 4 comprising 0, 1, 2, 3, 4, 5, 6, 7, 8, 9, 10, 11, 12, 13, 14, or 15 substitutions, deletions, or insertions. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

TABLE 4

| VH CDR3 stalk 1, knob, and stalk 2 sequences | |
|---|---|
| Stalk A sequences | |
| Stalk A1 | ITAHQKTNKKE (SEQ ID NO: 123) |
| Stalk A2 | TTVHQKAYKKV (SEQ ID NO: 124) |
| Stalk A3 | TTVYQKTTKKD (SEQ ID NO: 125) |
| Stalk A4 | TTVHQKTNEKD (SEQ ID NO: 126) |
| Stalk A5 | GTVHQKTQRKPI (SEQ ID NO: 127) |
| Stalk A6 | GTVHQRTHRKQN (SEQ ID NO: 128) |
| Stalk A7 | GTVHQRTQPKQT (SEQ ID NO: 129) |
| Stalk A8 | TTVYLKTTKQD (SEQ ID NO: 251) |
| Stalk A9 | TTVYQKTTKQD (SEQ ID NO: 252) |
| Stalk A10 | $X_1TX_2X_3X_4KX_5X_6X_7KX_8$ wherein $X_1$ is I or T, $X_2$ is A or V, $X_3$ is H or Y, $X_4$ is Q or L, $X_5$ is T or A, $X_6$ is N, Y, or T, $X_7$ is K or E, and $X_8$ is E, V, or D (SEQ ID NO: 130) |
| Stalk A11 | $X_1TX_2X_3X_4KX_5X_6X_7KX_8$ wherein $X_1$ is I, A or T, $X_2$ is A or V, $X_3$ is H, A or Y, $X_4$ is Q, A or L, $X_5$ is T or A, $X_6$ is N, Y, A or T, $X_7$ is K, A or E, and $X_8$ is E, V, A or D (SEQ ID NO: 131) |
| Stalk A12 | $GTVHQX_1TX_2X_3KX_4X_5$ wherein $X_1$ is K or R, $X_2$ is Q or H, $X_3$ is R or P, $X_4$ is P or Q, and $X_5$ is I, N, or T (SEQ ID NO: 132) |
| Knob sequences | |
| Knob 1 | CPEDYTYNPRCPQQYGWSDCDCMGDRFGGYCRQDGC (SEQ ID NO: 133) |
| Knob 2 | CPDDYSSNPDCVRLYGWSHCDCMRDSFGGWCRADGC (SEQ ID NO: 134) |
| Knob 3 | CPEYYTYNPDCARRYGWSDCECMADKFGGYCRHDGC (SEQ ID NO: 135) |
| Knob 4 | CPEYYSYNPDCPRRYGWSNCDCMADKFGGWCRHDGC (SEQ ID NO: 136) |
| Knob 5 | CPDGYSDDSTLRYYSRCSDRDCWRCTGTTYYDTCQC (SEQ ID NO: 137) |
| Knob 6 | CPGGYSDDNALRYRSRCDDRDCWRCTGTTYYDTCQC (SEQ ID NO: 138) |
| Knob 7 | CPNGYSDDSALRYYSRCSDRDCWRCTGTTYYDTCQC (SEQ ID NO: 139) |
| Knob 8 | CPEYYTYNPDCARRYGWSDCDCMADKFGGSCRLDGC (SEQ ID NO: 253) |
| Knob 9 | CPEYYTYNRDCERRYGWSDCECRADNVGGHCRHEGC (SEQ ID NO: 254) |
| Knob 10 | CPEYYTYNPDCARRYGWRDCECLADKVGGYCRHVGC (SEQ ID NO: 255) |
| Knob 11 | CPEYYTYNPDCARRYGWSDCECMADKVGGECRHDGC (SEQ ID NO: 256) |
| Knob 12 | CPEYYTYNPDCARRSGWSDCECMADKFGGYCRHDGC (SEQ ID NO: 257) |
| Knob 13 | CPEYYTYNPDRARRSGWSDCECMADKFGGYCRHDGC (SEQ ID NO: 258) |
| Knob 14 | CPEYYTYNPDCARRYGWSDCECMADKFGGYCRHEGF (SEQ ID NO: 259) |
| Knob 15 | CPEYYTYNPDCAMRYGWSYCECMAGKFWGYWCHESC (SEQ ID NO: 260) |
| Knob 16 | $CPX_1X_2YX_3X_4NX_5X_6CX_7X_8X_9X_{10}GWSX_{11}CX_{12}CX_{13}X_{14}X_{15}X_{16}X_{17}GGX_{18}CRX_{19}X_{20}X_{21}C$ wherein $X_1$ is E or D, $X_2$ is D or Y, $X_3$ is T or S, $X_4$ is Y or S, $X_5$ is P or R, $X_6$ is R or D, $X_7$ is P, V, E or A, $X_8$ is Q, M or R, $X_9$ is Q, L, or R, $X_{10}$ is Y or S, $X_{11}$ is D, H, Y, or N, $X_{12}$ is D or E, $X_{13}$ is M, R, or L, $X_{14}$ is G, R, or A, $X_{15}$ is D or G, $X_{16}$ is R, S, N or K, $X_{17}$ is F or V, $X_{18}$ is Y or W, and $X_{19}$ is Q, A, or H, $X_{20}$ is D, E, or V, $X_{21}$ is G or S (SEQ ID NO: 140) |
| Knob 17 | $CPX_1X_2YX_3X_4NX_5X_6CX_7X_8X_9X_{10}GWSX_{11}CX_{12}CX_{13}X_{14}X_{15}X_{16}X_{17}GGX_{18}CRX_{19}X_{20}X_{21}C$ wherein $X_1$ is E, A or D, $X_2$ is D, A or Y, $X_3$ is T, A or S, $X_4$ is Y, A or S, $X_5$ is P, A or R, $X_6$ is R or D, $X_7$ is P, V, E or A, $X_8$ is Q, M, a or R, $X_9$ is Q, L, A or R, $X_{10}$ is Y or S, $X_{11}$ is D, H, Y, A or N, $X_{12}$ is D, A or E, $X_{13}$ is M, R, A or L, $X_{14}$ is G, R, or A, $X_{15}$ is D, A or G, $X_{16}$ is R, S, N, A or K, $X_{17}$ is F or V, $X_{18}$ is Y, A or W, and $X_{19}$ is Q, A, or H, $X_{20}$ is D, E, or V, $X_{21}$ is G, A or S (SEQ ID NO: 141) |
| Knob 18 | $CPX_1GYSDDX_2X_3LRYX_4SRCX_5DRDCWRCTGTTYYDTCQC$ wherein $X_1$ is D, G, or N, $X_2$ is S or N, $X_3$ is T or A, $X_4$ is Y or R, and $X_5$ is S or D (SEQ ID NO: 142) |

TABLE 4-continued

| VH CDR3 stalk 1, knob, and stalk 2 sequences | |
|---|---|
| Stalk B sequences | |
| Stalk B1 | SNYIHRSTYEWYVSA (SEQ ID NO: 143) |
| Stalk B2 | SSTVEIGPYEWYVNA (SEQ ID NO: 144) |
| Stalk B3 | ATNTVRSTYEWHLDA (SEQ ID NO: 145) |
| Stalk B4 | SDYADMTTDEWYVDA (SEQ ID NO: 146) |
| Stalk B5 | GTYTWIDTHELHVDA (SEQ ID NO: 147) |
| Stalk B6 | ASYFYTDTYEFYVDA (SEQ ID NO: 148) |
| Stalk B7 | SSYTYIHTYELYVDA (SEQ ID NO: 149) |
| Stalk B8 | ATNTVRSTDEWHLDA (SEQ ID NO: 261) |
| Stalk B9 | ANNTVRSTDEWHLDA (SEQ ID NO: 262) |
| Stalk B10 | ATNTVRSNDEWHLDA (SEQ ID NO: 263) |
| Stalk B11 | ATNPVRSTDEWHLDA (SEQ ID NO: 264) |
| Stalk B12 | ATNTVRSTDGFHLDA (SEQ ID NO: 265) |
| Stalk B13 | ATHTVRSPYEWHLHA (SEQ ID NO: 266) |
| Stalk B14 | ATNTVRSTYEGPRDA (SEQ ID NO: 267) |
| Stalk B15 | $X_1X_2X_3X_4X_5X_6X_7X_8X_9EWX_{10}X_{11}X_{12}A$ wherein $X_1$ is S or A, $X_2$ is N, S, T, or D, $X_3$ is Y, T, H or N, $X_4$ is I, V, T, P or A, $X_5$ is H, E, V, or D, $X_6$ is R, I, or M, $X_7$ is S, G, or T, $X_8$ is T, N or P, $X_9$ is Y or D, $X_{10}$ is Y, or H, $X_{11}$ is V or L, and $X_{12}$ is S, N, H or D (SEQ ID NO: 150) |
| Stalk B16 | $X_1X_2X_3X_4X_5X_6X_7X_8X_9EWX_{10}X_{11}X_{12}A$ wherein $X_1$ is S or A, $X_2$ is N, S, T, A or D, $X_3$ is Y, T, H, A or N, $X_4$ is I, V, T, P or A, $X_5$ is H, E, V, A or D, $X_6$ is R, I, A or M, $X_7$ is S, G, A or T, $X_8$ is T, N, A or P, $X_9$ is Y, A or D, $X_{10}$ is Y, A or H, $X_{11}$ is V, A or L, and $X_{12}$ is S, N, H, A or D (SEQ ID NO: 151) |
| Stalk B17 | $X_1X_2YX_3X_4X_5X_6TX_7EX_8X_9X_{10}VDA$ wherein $X_1$ is G or A, $X_2$ is T or S, $X_3$ is T or F, $X_4$ is W or Y, $X_5$ is I or T, $X_6$ is D or H, $X_7$ is T, $X_8$ is H or Y, $X_9$ is L or F, and $X_{10}$ is H or Y (SEQ ID NO: 152) |

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 131; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 151. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 131; the knob comprises an amino acid sequence with at least about 80% 90%, 95%, or 100% identity to any one of SEQ ID NO:133-139 or 253-260, and the stalk B comprises an amino acid sequence of SEQ ID NO: 151. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 130; the knob comprises an amino acid sequence with at least about 80% 90%, 95%, or 100% identity to any one of SEQ ID NO: 133-139 or 253-260, and the stalk B comprises an amino acid sequence of SEQ ID NO: 150. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 131; the knob comprises an amino acid sequence of SEQ ID NO: 141, and the stalk B comprises an amino acid sequence of SEQ ID NO: 151. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 132; the knob comprises an amino acid sequence of SEQ ID NO: 142, and the stalk B comprises an amino acid sequence of SEQ ID NO: 152. In one embodiment, the antibody specifically binds to BG505 Env. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, an isolated monoclonal antibody described herein specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein the stalk A comprises an amino acid sequence of SEQ ID NO: 130-132; the knob comprises an amino acid sequence of SEQ ID NO: 140-142, and the stalk B comprises an amino acid sequence of SEQ ID NO: 150-152. In one embodiment, the antibody comprises the VH CDR1, VH CDR2, VL CDR1, VL CDR2, and VL CDR3 of an antibody disclosed herein. In one embodiment, the antibody comprises the VH CDR1, VH CDR2, VL CDR1, VL CDR2, and VL CDR3 of NC-Cow1, NC-Cow7, NC-Cow8, NC-Cow9, or NC-Cow10. In one embodiment, the antibody comprises the VH CDR1, VH CDR2, VL CDR1, VL CDR2, and VL CDR3 of NC-Cow1.

In one embodiment, the VL CDR1 comprises the VL CDR1 of NC-Cow1, NC-Cow2, NC-Cow3, NC-Cow4, NC-Cow5, NC-Cow6, NC-Cow7, NC-Cow8, NC-Cow9, or NC-Cow10; the VL CDR2 comprises the VL CDR2 of NC-Cow1, NC-Cow2, NC-Cow3, NC-Cow4, NC-Cow5, NC-Cow6, NC-Cow7, NC-Cow8, NC-Cow9, or NC-Cow10; and the VL CDR3 comprises the VL CDR3 of NC-Cow1, NC-Cow2, NC-Cow3, NC-Cow4, NC-Cow5, NC-Cow6, NC-Cow7, NC-Cow8, NC-Cow9, or NC-Cow10.

In one embodiment, the VL CDR1 comprises the VL CDR1 of NC-Cow1, NC-Cow7, NC-Cow8, NC-Cow9, or NC-Cow10; the VL CDR2 comprises the VL CDR2 of NC-Cow1, NC-Cow7, NC-Cow8, NC-Cow9, or NC-Cow10; and the VL CDR3 comprises the VL CDR3 of NC-Cow1, NC-Cow7, NC-Cow8, NC-Cow9, or NC-Cow10.

In one embodiment, the VL CDR1 comprises the amino acid sequence of SEQ ID NO: 4, 14, 24, 34, 44, 54, 64, 74, 84, or 94; the VL CDR2 comprises the amino acid sequence of GDT or GDS; and the VL CDR3 comprises the amino acid sequence of SEQ ID NO: 6, 16, 26, 36, 46, 56, 66, 76, 86, 96, or 121.

In one embodiment, the VH CDR3 is derived from a first donor antibody and the VH CDR1, VH CDR2, VL CDR1, VL CDR2, and VL CDR3 are derived from a second donor antibody. In one embodiment, the second donor antibody is an anti-Env antibody.

In one embodiment, the second donor antibody is a broadly neutralizing anti-Env antibody. In one embodiment, the second donor antibody is a human antibody. In one embodiment, the second donor antibody is PG9. In one embodiment, the second donor antibody is germline reverted variant of PG9.

In one embodiment, the second donor antibody is a broadly neutralizing anti-Env antibody. In one embodiment, the second donor antibody is a VRC01 class broadly neutralizing anti-Env antibody. In one embodiment, the second donor antibody is a CD4bs class broadly neutralizing anti-Env antibody. In one embodiment, the second donor antibody is a CD4bs epitope specific broadly neutralizing anti-Env antibody. In one embodiment, the second donor antibody is a V3 glycan epitope specific broadly neutralizing anti-Env antibody. In one embodiment, the second donor antibody is a V2-apex epitope specific broadly neutralizing anti-Env antibody.

In one embodiment, the second donor antibody is a bovine anti-Env antibody. In one embodiment, the second donor antibody is a broadly neutralizing bovine anti-Env antibody. In one embodiment, the second donor antibody is a bovine anti-Env antibody produced by a method described herein.

In one embodiment, the VL CDR1, VL CDR2, and VL CDR3 are derived from a bovine germline encoded light chain variable region (VL). In one embodiment, the bovine germline encoded VL is V30. In one embodiment, the bovine germline encoded VL comprises the amino acid sequence of (SEQ ID NO: 103)

QAVLTQPSSVSGSLGQRVSITCSGSSSNVGNGYVSWYQLIPGSAPRTLI

YGDTSRASGVPDRFSGSRSGNTATLTISSLQAEDEADYFCASAEDSSSN

AVFGSGTTLTVL.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10; the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the antibody specifically binds to BG505 Env. In one embodiment, the antibody is a humanized antibody.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10; the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and the VH CDR3 comprises the VH CDR3 of NC-Cow11, NC-Cow12, NC-Cow13, NC-Cow14, NC-Cow15, NC-Cow16, NC-Cow17, NC-Cow18, NC-Cow19, NC-Cow20, NC-Cow21 or NC-Cow22. In one embodiment, the antibody specifically binds to BG505 Env. In one embodiment, the antibody is a humanized antibody.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the VH CDR1 of NC-Cow1, NC-Cow7, NC-Cow8, NC-Cow9, or NC-Cow10; the VH CDR2 comprises the VH CDR2 of NC-Cow1, NC-Cow7, NC-Cow8, NC-Cow9, or NC-Cow10; and the VH CDR3 comprises the VH CDR3 of NC-Cow1, NC-Cow7, NC-Cow8, NC-Cow9, or NC-Cow10. In one embodiment, the antibody specifically binds to BG505 Env. In one embodiment, the antibody is a humanized antibody.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the amino acid sequence of SEQ ID NO: 1, 11, 21, 31, 41, 51, 61, 71, 81, or 91; the VH CDR2 comprises the amino acid sequence of SEQ ID NO: 2, 12, 22, 32, 42, 52, 62, 72, 82, or 92; and the VH CDR3 comprises the amino acid sequence of SEQ ID NO: 3, 13, 23, 33, 43, 53, 63, 73, 83, 93, or 121. In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the amino acid sequence of SEQ ID NO: 1, 11, 21, 31, 41, 51, 61, 71, 81, or 91; the VH CDR2 comprises the amino acid sequence of SEQ ID NO: 2, 12, 22, 32, 42, 52, 62, 72, 82, or 92; and the VH CDR3 comprises the amino acid sequence of SEQ ID NO: 227-238. In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1 comprises the amino acid sequence of SEQ ID NO: 1, 11, 21, 31, 41, 51, 61, 71, 81, or 91; the VH CDR2 comprises the amino acid sequence of SEQ ID NO: 2, 12, 22, 32, 42, 52, 62, 72, 82, or 92; and the VH CDR3 comprises the amino acid sequence of SEQ ID NO: 101, 102, 122, 133-142, 268, or 269. In one embodiment, the antibody specifically binds to BG505 Env. In one embodiment, the antibody is a humanized antibody.

In one embodiment, the VL CDR1 comprises the VL CDR1 of NC-Cow1, NC-Cow2, NC-Cow3, NC-Cow4, NC-Cow5, NC-Cow6, NC-Cow7, NC-Cow8, NC-Cow9, or NC-Cow10; the VL CDR2 comprises the VL CDR2 of NC-Cow1, NC-Cow2, NC-Cow3, NC-Cow4, NC-Cow5, NC-Cow6, NC-Cow7, NC-Cow8, NC-Cow9, or NC-Cow10; and the VL CDR3 comprises the VL CDR3 of NC-Cow1, NC-Cow2, NC-Cow3, NC-Cow4, NC-Cow5, NC-Cow6, NC-Cow7, NC-Cow8, NC-Cow9, or NC-Cow10.

In one embodiment, the VL CDR1 comprises the VL CDR1 of NC-Cow1, NC-Cow7, NC-Cow8, NC-Cow9, or NC-Cow10; the VL CDR2 comprises the VL CDR2 of NC-Cow1, NC-Cow7, NC-Cow8, NC-Cow9, or NC-Cow10; and the VL CDR3 comprises the VL CDR3 of NC-Cow1, NC-Cow7, NC-Cow8, NC-Cow9, or NC-Cow10.

In one embodiment, the VL CDR1 comprises the amino acid sequence of SEQ ID NO: 4, 14, 24, 34, 44, 54, 64, 74, 84, or 94; the VL CDR2 comprises the amino acid sequence of GDT or GDS; and the VL CDR3 comprises the amino acid sequence of SEQ ID NO: 6, 16, 26, 36, 46, 56, 66, 76, 86, or 96.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR1, VH CDR2, VH CDR3, VL CDR1, VL CDR2, and VL CDR3, respectively. In one embodiment, the antibody specifically binds to BG505 Env. In one embodiment, the antibody is a humanized antibody.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow7, NC-Cow8, NC-Cow9, or NC-Cow10 VH CDR1, VH CDR2, VH CDR3, VL CDR1, VL CDR2, and VL CDR3, respectively. In one embodiment, the antibody specifically binds to BG505 Env. In one embodiment, the antibody is a humanized antibody.

In one embodiment, an isolated monoclonal antibody described herein specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of SEQ ID NO: 1-4, GDT and SEQ ID NO: 6, respectively; SEQ ID NO: 11-14, GDT and SEQ ID NO: 16, respectively; SEQ ID NO: 21-24, GDT and SEQ ID NO: 26, respectively; SEQ ID NO: 31-34, GDT and SEQ ID NO: 36, respectively; SEQ ID NO: 41-44, GDT and SEQ ID NO: 46, respectively; SEQ ID NO: 51-54, GDT and SEQ ID NO: 56, respectively; SEQ ID NO: 61-64, GDT and SEQ ID NO: 66, respectively; SEQ ID NO: 71-74, GDS and SEQ ID NO: 76, respectively; SEQ ID NO: 81-84. GDS and SEQ ID NO: 86, respectively; or SEQ ID NO: 91-94, GDT and SEQ ID NO: 96, respectively. In one embodiment, the antibody specifically binds to BG505 Env. In one embodiment, the antibody is a humanized antibody.

In one embodiment, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the antibody specifically binds to BG505 Env. In one embodiment, the antibody is a humanized antibody.

In one embodiment, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow7, NC-Cow8, NC-Cow9, or NC-Cow10. In one embodiment, the antibody specifically binds to BG505 Env. In one embodiment, the antibody is a humanized antibody.

In one embodiment, an isolated monoclonal antibody described herein specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 7, 17, 27, 37, 47, 57, 67, 77, 87, 97, 113, 115, 117, or 119. In one embodiment, the antibody specifically binds to BG505 Env. In one embodiment, the antibody is a humanized antibody.

In one embodiment, the VL comprises an amino acid sequence that is at least about 90%, 95%, 97%, 98%, 99% or 100% identical to the VL of NC-Cow1, NC-Cow2, NC-Cow3, NC-Cow4, NC-Cow5, NC-Cow6, NC-Cow7, NC-Cow8, NC-Cow9, or NC-Cow10.

In one embodiment, the VL comprises an amino acid sequence that is at least about 90%, 95%, 97%, 98%, 99% or 100% identical to the VL of NC-Cow1, NC-Cow7, NC-Cow8, NC-Cow9, or NC-Cow10.

In one embodiment, the VL comprises an amino acid sequence that is at least about 90%, 95%, 97%, 98%, 99% or 100% identical to SEQ ID NO: 8, 18, 28, 38, 48, 58, 68, 87, 88, 98, 114, 116, 118, or 120.

In one embodiment, the VL comprises a bovine germline encoded light chain variable region (VL). In one embodiment, the bovine germline encoded VL is V30. In one embodiment, the bovine germline encoded VL comprises the amino acid sequence of SEQ ID NO: 103.

In one embodiment, the VL comprises the NC-Cow1 VL. In one embodiment, the VL comprises the amino acid sequence of SEQ ID NO: 8.

In one embodiment, an isolated monoclonal antibody described herein specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow2, NC-Cow3, NC-Cow4, NC-Cow5, NC-Cow6, NC-Cow7, NC-Cow8, NC-Cow9, or NC-Cow10 VH and VL, respectively. In one embodiment, the antibody specifically binds to BG505 Env. In one embodiment, the antibody is a humanized antibody.

In one embodiment, an isolated monoclonal antibody described herein specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow7, NC-Cow8, NC-Cow9, or NC-Cow10 VH and VL, respectively. In one embodiment, the antibody specifically binds to BG505 Env. In one embodiment, the antibody is a humanized antibody.

In one embodiment, an isolated monoclonal antibody described herein specifically binds to Env and comprises a heavy chain variable region (VH) and light chain variable region (VL), wherein the VH and VL comprise an amino acid sequence that is at least about 90%, 95%, 97%, 98%, 99% or 100% identical to SEQ ID NO: 7 and 8, respectively; SEQ ID NO: 17 and 18, respectively; SEQ ID NO: 27 and 28, respectively; SEQ ID NO: 37 and 38, respectively; SEQ ID NO: 47 and 48, respectively; SEQ ID NO: 57 and 58, respectively; SEQ ID NO: 67 and 68, respectively; SEQ ID NO: 77 and 78, respectively; SEQ ID NO: 87 and 88, respectively; SEQ ID NO: 97 and 98, respectively; SEQ ID NO: 113 and 114, respectively; SEQ ID NO: 115 and 116, respectively; SEQ ID NO: 117 and 8, respectively; SEQ ID NO: 117 and 118, respectively; or SEQ ID NO: 119 and 120, respectively. In one embodiment, the antibody specifically binds to BG505 Env. In one embodiment, the antibody is a humanized antibody.

In one embodiment, the antibody is not NC-Cow1, NC-Cow2, NC-Cow3, NC-Cow4, NC-Cow5, NC-Cow6, NC-Cow7, NC-Cow8, NC-Cow9, or NC-Cow10.

In one embodiment, an isolated monoclonal antibody described herein further comprises heavy and/or light chain constant regions.

In one embodiment, an isolated monoclonal antibody described herein further comprises human heavy and/or light chain constant regions.

In one embodiment, the heavy chain constant region is selected from the group consisting of human immunoglobulins IgG1, IgG2, IgG3, IgG4, IgA1, and IgA2.

In one embodiment, the heavy chain constant region comprises a native amino acid sequence.

In one embodiment, the heavy chain constant region comprises a variant amino acid sequence.

In one embodiment, the antibody is a recombinant antibody, a chimeric antibody, a humanized antibody, an antibody fragment, a bispecific antibody, or a trispecific antibody.

In one embodiment, the antibody fragment comprises a single-chain Fv (scFv), F(ab) fragment, F(ab')2 fragment, or an isolated VH domain.

In one embodiment, the antibody is capable of neutralizing at least two cross-clade isolates of HIV.

In one embodiment, the antibody is capable of neutralizing at least about 50%, 60%, 70%, 80%, 90%, or 100% of cross-clade HIV isolates in the 6-member indicator virus panel. In one embodiment, the antibody is capable of neutralizing at least about 50%, 60%, 70%, 80%, 90%, or 100% of cross-clade HIV isolates in the 12-member indicator virus panel. In one embodiment, the antibody is capable of neutralizing at least about 50%, 60%, 70%, 80%, 90%, or 100% of cross-clade HIV isolates in the 117-member indicator virus panel. In one embodiment, the antibody is capable of neutralizing the cross-clade HIV isolates with a median IC50 equal to or less than about 0.1 microg/ml, 0.05 microg/ml, 0.025 microg/ml, 0.01 microg/ml, or 0.005 microg/ml. In one embodiment, the antibody is capable of neutralizing the cross-clade HIV isolates with a median ID50 of at least about 50, 100, 500, 1000, 5000, or 10000.

In one aspect, provided herein are broadly neutralizing fusion polypeptides comprising a fragment (VH CDR3) of a broadly neutralizing antibody described herein. In one embodiment, a broadly neutralizing fusion polypeptide specifically binds to Env. In one embodiment, a broadly neutralizing fusion polypeptide specifically binds to a well-ordered HIV Env trimer.

In one embodiment, a fusion polypeptide described herein specifically binds to Env and comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10. In one embodiment, the fusion polypeptide specifically binds to BG505 Env. In one embodiment, the fusion polypeptide comprises an Fc domain.

In one embodiment, a fusion polypeptide described herein specifically binds to Env and comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10. In one embodiment, the fusion polypeptide specifically binds to BG505 Env. In one embodiment, the fusion polypeptide comprises an Fc domain.

In one embodiment, a fusion polypeptide described herein specifically binds to Env and comprises an amino acid sequence that is at least about 90%, 95%, 97%, 98%, 99% or 100% identical to SEQ ID NO: 3, 13, 23, 33, 43, 53, 63, 73, 83, 93, or 121. In one embodiment, the fusion polypeptide specifically binds to BG505 Env. In one embodiment, the fusion polypeptide comprises an Fc domain.

In one embodiment, a fusion polypeptide described herein specifically binds to Env and comprises an amino acid sequence that is at least about 90%, 95%, 97%, 98%, 99% or 100% identical to the VH CDR3 of NC-Cow1. In one embodiment, the fusion polypeptide specifically binds to BG505 Env. In one embodiment, the fusion polypeptide comprises an Fc domain.

In one embodiment, a fusion polypeptide described herein specifically binds to Env and comprises an amino acid sequence that is at least about 90%, 95%, 97%, 98%, 99% or 100% identical to SEQ ID NO: 3 or SEQ ID NO: 121. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR3 comprising 0, 1, 2, 3, 4, or 5 substitutions, insertions, or deletions. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of the NC-Cow1, NC-Cow7, NC-Cow8, NC-Cow9, or NC-Cow10 VH CDR3 comprising 0, 1, 2, 3, 4, or 5 substitutions, insertions, or deletions. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of SEQ ID NO: 3, 13, 23, 33, 43, 53, 63, 73, 83, 93, or 121 comprising 0, 1, 2, 3, 4, or 5 substitutions, insertions, or deletions. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of the NC-Cow1 VH CDR3 comprising 0, 1, 2, 3, 4, or 5 substitutions, insertions, or deletions. In one embodiment, the fusion polypeptide specifically binds to BG505 Env.

In one embodiment, a fusion polypeptide described herein specifically binds to Env and comprises the amino acid sequence of SEQ ID NO: 3 or SEQ ID NO: 121 comprising 0, 1, 2, 3, 4, or 5 substitutions, insertions, or deletions. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of the NC-Cow1 VH CDR3. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of SEQ ID NO: 3 or SEQ ID NO: 121. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of TTVHQKTXKKDCPEYYTYNPDCXRRYGWSDCDCMADKFGGYCRHDGCSTXTVRSTYEWYVD A (SEQ ID NO: 101). In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of $X_1TX_3X_4QKX_7X_8X_9KX_{11}CPX_{14}X_{15}YX_{17}X_{18}NPX_{21}CX_{23}X_{24}X_{25}YGWSX_{30}CX_{32}CMX_{35}DX_{37}FGGX_{41}CRX_{44}DGCX_{48}X_{49}X_{50}X_{51}X_{52}X_{53}X_{54}X_{55}X_{56}EWX_{59}X_{60}X_{61}A$ wherein $X_1$ is Tor I, $X_3$ is V or A, $X_4$ is H or Y, $X_7$ is T or A, $X_8$ is N, Y, or T, $X_9$ is K or E, $X_{11}$ is D, E, or V, $X_{14}$ is E or D, $X_{15}$ is Y or D, $X_{17}$ is T or S, $X_{18}$ is Y or S, $X_{21}$ is D or R, $X_{23}$ is P, V, or A, $X_{24}$ is R or Q, $X_{25}$ is R, Q, or L, $X_{30}$ is D, H, or N, $X_{32}$ is D or E, $X_{35}$ is A, G, or R, $X_{37}$ is K, R, or S, $X_{41}$ is Y or W, $X_{44}$ is H, Q, or A, $X_{48}$ is S or A, $X_{49}$ is T, N, S, or D, $X_{50}$ is Y, T, or N, $X_{51}$ is V, T, I, or A, $X_{52}$ is V, H, E, or D, $X_{53}$ is R, I, or M, $X_{54}$ is S, G, or T, $X_{55}$ is T, or P, $X_{56}$ is Y, or D, $X_{59}$ is Y, or H, $X_{60}$ is V, or L, and $X_{61}$ is D, or S (SEQ ID NO: 102). In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of SEQ ID NO: 268. In one embodiment, a fusion polypeptide described herein specifically binds to Env and comprises the amino acid sequence of SEQ ID NO: 269. In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of GTVHQ$X_1$T$X_2$$X_3$K$X_4$$X_5$CP$X_6$GYSDD$X_7$$X_8$LRY$X_9$SRC$X_{10}$DRDCWRCTGTTYYDTCQC$X_{11}$$X_{12}$Y$X_{13}$$X_{14}$$X_{15}$$X_{16}$T$X_{17}$E$X_{18}$$X_{19}$VDA wherein $X_1$ is R or K, $X_2$ is Q or H, $X_3$ is Por R, $X_4$ is Q or P, $X_5$ is T, I or N, $X_6$ is N, D, or G, $X_7$ is S or N, $X_8$ is A or T, $X_9$ is Y or R, $X_{10}$ is S or D, $X_{11}$ is S, G or A, $X_{12}$ is S or T, $X_{13}$ is Tor F, $X_{14}$ is Y or W, $X_{15}$ is I or T, $X_{16}$ is H or D, $X_{17}$ is Y or H, $X_{18}$ is L or F, and $X_{19}$ is Y or H (SEQ ID NO: 122). In one embodiment, the fusion polypeptide specifically binds to BG505 Env. In one embodiment, the fusion polypeptide comprises an Fc domain.

In one embodiment, a fusion polypeptide described herein specifically binds to Env and comprises the amino acid sequence of SEQ ID NO: 133-139 or 253-260. In one embodiment, a fusion polypeptide described herein specifically binds to Env and comprises the amino acid sequence of SEQ ID NO: 140. In one embodiment, a fusion polypeptide described herein specifically binds to Env and comprises the amino acid sequence of SEQ ID NO: 141. In one embodiment, a fusion polypeptide described herein specifically binds to Env and comprises the amino acid sequence of SEQ ID NO: 142. In one embodiment, the fusion polypeptide specifically binds to BG505 Env. In one embodiment, the fusion polypeptide comprises an Fc domain.

In one embodiment, a fusion polypeptide described herein specifically binds to Env and comprises an amino acid sequence with at least about 80%, 90%, 95% or 100% identity to the amino acid sequence of SEQ ID NO: 133. In one embodiment, a fusion polypeptide described herein specifically binds to Env and comprises the amino acid sequence of SEQ ID NO: 133 comprising 0, 1, 2, 3, 4, or 5 substitutions, deletions or insertions. In one embodiment, a fusion polypeptide described herein specifically binds to Env and comprises the amino acid sequence of SEQ ID NO: 133 comprising 0, 1, 2, 3, 4, or 5 substitutions. In one embodiment, a fusion polypeptide described herein specifically binds to Env and comprises an amino acid sequence with at least about 80%, 90%, 95% or 100% identity to the amino acid sequence of SEQ ID NO: 134-139 or 253-260. In one embodiment, a fusion polypeptide described herein specifically binds to Env and comprises the amino acid sequence of SEQ ID NO: 134-139 or 253-260 comprising 0, 1, 2, 3, 4, or 5 substitutions, deletions or insertions. In one embodiment, a fusion polypeptide described herein specifically binds to Env and comprises the amino acid sequence of SEQ ID NO: 134-139 or 253-260 comprising 0, 1, 2, 3, 4, or 5 substitutions. In one embodiment, the fusion polypeptide specifically binds to BG505 Env. In one embodiment, the fusion polypeptide comprises an Fc domain.

In one embodiment, a fusion polypeptide described herein specifically binds to Env and comprises a domain having the structure, from N to C terminus, of stalk A-knob-stalk B, wherein the stalk A comprises a Stalk A amino acid sequence of SEQ ID NO: 123-132, 251, or 252 or a variant thereof, the knob comprises a knob amino acid sequence of SEQ ID NO: 133-142 or 253-260 or a variant thereof, and the stalk B comprises a stalk B amino acid sequence of SEQ ID NO: 143-152 or 261-267 or a variant thereof. In one embodiment, the stalk A comprises a Stalk A amino acid sequence of SEQ ID NO: 123-132, 251 or 252, the knob comprises a knob amino acid sequence of SEQ ID NO: 133-142 or 253-260, and the stalk B comprises a stalk B amino acid sequence of SEQ ID NO: 143-152 or 261-267. In one embodiment, the fusion polypeptide comprises an Fc domain.

In one embodiment, a fusion polypeptide described herein specifically binds to Env and comprises a domain having the structure, from N to C terminus, of stalk A-knob-stalk B, wherein the stalk A comprises a Stalk A amino acid sequence of SEQ ID NO: 123-129, 251, or 252 or a variant thereof, the knob comprises a knob amino acid sequence of SEQ ID NO: 133-139 or 253-260 or a variant thereof, and the stalk B comprises a stalk B amino acid sequence of SEQ ID NO: 143-149 or 261-267 or a variant thereof. In one embodiment, the stalk A comprises a Stalk A amino acid sequence of SEQ ID NO: 123-129, 251 or 252, the knob comprises a knob amino acid sequence of SEQ ID NO: 133-139 or 253-260, and the stalk B comprises a stalk B amino acid sequence of SEQ ID NO: 143-149 or 261-267. In one embodiment, the fusion polypeptide comprises an Fc domain.

In one embodiment, the stalk A comprises a Stalk A amino acid sequence listed in Table 4, the knob comprises a knob amino acid sequence listed in Table 4, and the stalk B comprises a stalk B amino acid sequence listed in Table 4. In one embodiment, the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4. In one embodiment, the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4. In one embodiment, the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions. In one embodiment, the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions. In one embodiment, the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions. In one embodiment, the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions.

In one embodiment, the stalk A comprises an amino acid sequence of SEQ ID NO: 131; the knob comprises a knob amino sequence of SEQ ID NO:133-139 comprising 0, 1, 2, 3, 4, or 5 substitutions, insertions, or deletions, and the stalk B comprises an amino acid sequence of SEQ ID NO: 151. In one embodiment, the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150. In one embodiment, the stalk A comprises an amino acid sequence of SEQ ID NO: 131; the knob comprises an amino acid sequence with at least about 80% 90%, 95%, or 100% identity to any one of SEQ ID NO:133-139 or 253-260, and the stalk B comprises an amino acid sequence of SEQ ID NO: 151.

In one embodiment, the stalk A comprises an amino acid sequence of SEQ ID NO: 130; the knob comprises an amino acid sequence with at least about 80% 90%, 95%, or 100% identity to any one of SEQ ID NO:133-139 or 253-260, and the stalk B comprises an amino acid sequence of SEQ ID NO: 150. In one embodiment, the stalk A comprises an amino acid sequence of SEQ ID NO: 131; the knob comprises an amino acid sequence of SEQ ID NO: 141, and the stalk B comprises an amino acid sequence of SEQ ID NO: 151. In one embodiment, the stalk A comprises an amino acid sequence of SEQ ID NO: 132; the knob comprises an amino acid sequence of SEQ ID NO: 142, and the stalk B comprises an amino acid sequence of SEQ ID NO: 152. In one embodiment, the stalk A comprises an amino acid sequence of SEQ ID NO: 130-132; the knob comprises an amino acid sequence of SEQ ID NO: 140-142, and the stalk B comprises an amino acid sequence of SEQ ID NO: 150-152. In one embodiment, the fusion polypeptide specifically binds to BG505 Env.

In one embodiment, the fusion polypeptide comprises a non-immunoglobulin polypeptide or a fragment thereof. In certain embodiments, the non-immunoglobulin polypeptide comprises a protein scaffold of a type selected from the group consisting of protein A, protein G, a lipocalin, a fibronectin domain, an ankyrin consensus repeat domain, and thioredoxin. In one embodiment, the non-immunoglobulin polypeptide comprises human serum albumin, ferritin, or a fragment thereof.

In one embodiment, the fusion polypeptide comprises an Fc domain.

In one embodiment, the Fc domain is a human IgG1, IgG2, IgG3, IgG4, IgA1, or IgA2 Fc domain.

In one embodiment, the fusion polypeptide is capable of neutralizing at least two cross-clade isolates of HIV. In one embodiment, the fusion polypeptide is capable of neutralizing at least about 50%, 60%, 70%, 80%, 90%, or 100% of cross-clade HIV isolates in the 6-member indicator virus panel. In one embodiment, the fusion polypeptide is capable of neutralizing at least about 90% of cross-clade HIV isolates in the 6-member indicator virus panel. In one embodiment, the fusion polypeptide is capable of neutralizing at least two cross-clade isolates of HIV. In one embodiment, the fusion polypeptide is capable of neutralizing at least about 50%, 60%, 70%, 80%, 90%, or 100% of cross-clade HIV isolates in the 12-member indicator virus panel. In one embodiment, the fusion polypeptide is capable of neutralizing at least about 90% of cross-clade HIV isolates in the 12-member indicator virus panel. In one embodiment, the fusion polypeptide is capable of neutralizing at least about 50%, 60%, 70%, 80%, 90%, or 100% of cross-clade HIV isolates in the 117-member indicator virus panel. In one embodiment, the fusion polypeptide is capable of neutralizing at least about 80% of cross-clade HIV isolates in the 117-member indicator virus panel. In one embodiment, the fusion polypeptide is capable of neutralizing the cross-clade HIV isolates with a median IC50 equal to or less than about 0.1 microg/ml, 0.05 microg/ml, 0.025 microg/ml, 0.01 microg/ml, or 0.005 microg/ml. In one embodiment, the fusion polypeptide is capable of neutralizing the cross-clade HIV isolates with a median IC50 equal to or less than about 0.05 microg/ml. In one embodiment, the fusion polypeptide is capable of neutralizing the cross-clade HIV isolates with a median ID50 of at least about 50, 100, 500, 1000, 5000, or 10000. In one embodiment, the fusion polypeptide is capable of neutralizing the cross-clade HIV isolates with a median ID50 of at least about 1000. In one embodiment, the fusion polypeptide is capable of neutralizing the cross-clade HIV isolates with a median ID50 of at least about 500.

In another aspect, provided herein are antibodies that bind the same or an overlapping epitope of Env (e.g., an epitope of BG505 Env) as an antibody described herein (e.g., NC-Cow1). In certain embodiments, the epitope of an antibody can be determined by, e.g., NMR spectroscopy, X-ray diffraction crystallography studies, ELISA assays, hydrogen/deuterium exchange coupled with mass spectrometry (e.g., liquid chromatography electrospray mass spectrometry), array-based oligo-peptide scanning assays, and/or mutagenesis mapping (e.g., site-directed mutagenesis mapping). For X-ray crystallography, crystallization may be accomplished using any of the known methods in the art (e.g., Giegé R et al., (1994) Acta Crystallogr D Biol Crystallogr 50 (Pt 4): 339-350; McPherson A (1990) Eur J Biochem 189:1-23; Chayen NE (1997) Structure 5:1269-1274; McPherson A (1976) J Biol Chem 251:6300-6303). Antibody: antigen crystals may be studied using well known X-ray diffraction techniques and may be refined using computer software such as X-PLOR (Yale University, 1992, distributed by Molecular Simulations, Inc.; see, e.g., Meth Enzymol (1985) volumes 114 & 115, eds Wyckoff H W et al.; U.S. Patent Application No. 2004/0014194), and BUSTER (Bricogne G (1993) Acta Crystallogr D Biol Crystallogr 49 (Pt 1): 37-60; Bricogne G (1997) Meth Enzymol 276A: 361-423, ed Carter CW; Roversi P et al., (2000) Acta Crystallogr D Biol Crystallogr 56 (Pt 10): 1316-1323). Mutagenesis mapping studies may be accomplished using any method known to one of skill in the art. See, e.g., Champe M et al., (1995) supra and Cunningham BC & Wells JA (1989) supra for a description of mutagenesis techniques, including alanine scanning mutagenesis techniques. In a specific embodiment, the epitope of an antibody is determined using alanine scanning mutagenesis studies. Usually, binding to the antigen is reduced or disrupted when a residue within the epitope is substituted to alanine. In one embodiment, the Kd of binding to the antigen is increased by about 5-fold, 10-fold, 20-fold, 10-fold or more when a residue within the epitope is substituted for alanine. In one embodiment, binding affinity is determined by ELISA. In addition, antibodies that recognize and bind to the same or overlapping epitopes of Env (e.g., an epitope of BG505 Env) can be identified using routine techniques such as an immunoassay, for example, by showing the ability of one antibody to block the binding of another antibody to a target antigen, i.e., a competitive binding assay.

In specific aspects, provided herein is an antibody, which immunospecifically binds to the same epitope as that of NC-Cow1, NC-Cow2, NC-Cow3, NC-Cow4, NC-Cow5, NC-Cow6, NC-Cow7, NC-Cow8, NC-Cow9, or NC-Cow10 for specific binding to Env (e.g., an epitope of BG505 Env). Assays known to one of skill in the art or described herein (e.g., X-ray crystallography, hydrogen/deuterium exchange coupled with mass spectrometry (e.g., liquid chromatography electrospray mass spectrometry), alanine scanning, ELISA assays, etc.) can be used to determine if two antibodies bind to the same epitope.

In a specific embodiment, an antibody described herein immunospecifically binds to the same epitope as that bound by Nc-Cow1 or an epitope that overlaps the epitope.

In another specific embodiment, an antibody described herein, immunospecifically binds to the same epitope as that of an antibody comprising a heavy chain variable region (VH) and light chain variable region (VL), wherein the VH and VL comprise the amino acid sequence of SEQ ID NO: 7 and 8, SEQ ID NO: 17 and 18, SEQ ID NO: 27 and 28, SEQ ID NO: 37 and 38, SEQ ID NO: 47 and 48, SEQ ID NO: 57 and 58, SEQ ID NO: 67 and 68, SEQ ID NO: 77 and 78, SEQ ID NO: 87 and 88, or SEQ ID NO: 97 and 98, respectively. In one embodiment, an antibody described herein, immunospecifically binds to the same epitope as that of an antibody comprising a heavy chain variable region (VH) and light chain variable region (VL), wherein the VH and VL comprise the amino acid sequence of SEQ ID NO: 7 and 8, respectively.

In a specific aspect, the binding between an antibody described herein and a variant BG505 Env is substantially weakened relative to the binding between the antibody and BG505 Env, wherein the variant BG505 Env comprises the amino 1 sequence of SEQ ID NO: 108 (MRVMGIQRNCQHLFRWGTMILGMIIICSAAE-NLWVTVYYGVPVWKDAETTLFCASDAKAYET EKHNVWATHACVPTDPNPQEIHLENVTEEFNMW-KNNMVEQMHTDIISLWDQSLKPCVKLTPLC VTLQCTNVTN-NITDDMRGELKNCSFNMTTELRDKKQKVYS-LFYRLDVVQINENQGNRSNNSNK EYRLINCNT-SAITQACPKVSFEPIPIHYCAPAGFAILKCKDKKF-NGTGPCPSVSTVQCTHGIKPVVS TQLLLNGS-LAEEEVMIRSENITNNAKNILVQFNTPVQINC-TRPNNNTRKSIRIGPGQAFYATGDIIG DIRQAHCNV-SKATWNETLGKVVKQLRKHFGNNTIIRFANSSGG-DLEVTTHSFNCGGEFFYCNTS GLFNSTWISNTSVQG-SNSTGSNDSITLPCRIKQIINMWQRIGQAMYAPPIQG-VIRCVSNITGLILTR DGGSTN-STTETFRPGGGDMRDNWRSELYKYKVVKIEPLGVAP-TRAKRRVVGREKRAVGIGAVF LGFLGAAGSTMGAASMTLTVQARNLLS-GIVQQQSNLLRAIEAQQHLLKLTVWGIKQLQARVLA VERYLRDQQLLGIWGCSGKLICTTNVPWNSS-WSNRNLSEIWDNMTWLQWDKEISNYTQIIYGLL EESQNQQEKNEQDLLALDKWASLWNWFDIS-NWLWYIKIFIMIVGGLIGLRIVFAVLSVIHRVRQG YSPLSFQTHTPNPRGLDRPERIEEEDGEQDRGR-STRLVSGFLALAWDDLRSLCLFCYHRLRDFILI AARIVELLGHSSLKGLRLGWEGLKYLWNL-LAYWGRELKISAINLFDTIAIA VAEWTDR VIEIGQR LCRAFLHIPRRIRQGLERALL) except for an amino acid mutation (e.g., substitution) selected from the group consisting of: K282A, G367A, G472A, and a combination thereof. The position of the K282A, G367A, and G472A substitutions within SEQ ID NO: 108 are defined in reference to the HXB2 reference Env sequence of SEQ ID NO: 110 (MRVKEKYQHLWRW-GWRWGTMLLGMLMICSATEKLWVTVYYGVPVWKE-ATTTLFCASDAK AYDTE-VHNVWATHACVPTDPNPQEVVLVNVTENFNMW-KNDMVEQMHEDIISLWDQSLKPCV KLTPLCVSLKCTDLKNDTNTNSSSGRMIME-KGEIKNCSFNISTSIRGKVQKEYAFFYKLDIIPIDND TTSYKLTSCNTSVITQACPKVSFEPIPIHYCA-PAGFAILKCNNKTFNGTGPCTNVSTVQCTHGIRPV VSTQLLLNGSLAEEEVVIRSVNFTDNAKTIIVQLNTS-VEINCTRPNNNTRKRIRIQRGPGRAFVTIG KIGNMRQAHCNISRAKWNNTLKQIASKL-REQFGNNKTIIFKQSSGGDPEIVTHSFNCGGEFFYCNS TQLFNSTWFNSTWSTEGSNNTEGSDTITLPCRIKQI-INMWQKVGKAMYAPPISGQIRCSSNITGLL LTRDGG-NSNNESEIFRPGGGDMRDNWRSELYKYKVVKIE-PLGVAPTKAKRRVVQREKRAVGIG ALFLGFLGAAGSTMGAASMTLTVQARQLLS-GIVQQQNNLLRAIEAQQHLLQLTVWGIKQLQARI LAVERYLKDQQLLGIWGCSGKLICTTAVPWNAS-WSNKSLEQIWNHTTWMEWDREINNYTSLIH SLIEESQNQQEKNEQELLELDK-WASLWNWFNITNWLWYIKLFIMIVGGLVGL-RIVFAVLSIVNRV RQGYSPLSFQTHLPTPRGPDRP-EGIEEEGGERDRDRSIRLVNGSLALIWDDLRSLC-LFSYHRLRDL LLIVTRIVELL-GRRGWEALKYWWNLLQYWSQELKNSAVSLLNA-TAIAVAEGTDRVIEVVQGAC RAIRHIPRRIRQGLER-ILL). In particular, residues 282, 367, and 472 of SEQ ID NO: 108 are the residues corresponding to residues 282, 367, and 472, respectively, of the HXB2 reference Env sequence of SEQ ID NO: 110. In some embodiments, the variant BG505 Env comprises the sequence of SEQ ID NO: 108 except for any one mutation selected from the group consisting of: K282A, G367A, and G472A. In some embodiments, the variant BG505 Env comprises the sequence of SEQ ID NO: 106 except for any two mutations selected from the group consisting of: K282A, G367A, and G472A. In some embodiments, the variant BG505 Env comprises the sequence of SEQ ID NO: 106 except for the amino acid mutations K282A, G367A, and G472A. In one embodiment, the binding between an antibody described herein and a variant BG505 Env is not substantially weakened relative to the binding between the antibody and BG505 Env, wherein the variant BG505 Env comprises the amino acid sequence of SEQ ID NO: 108 except for the N279A substitution. In one embodiment, binding affinity is determined by ELISA. In one embodiment, the antibody is a chimeric, human or humanized antibody.

In a specific aspect, the binding between an antibody described herein and a variant JR-CSF Env is substantially weakened relative to the binding between the antibody and JR-CSF Env, wherein the variant JR-CSF Env comprises the amino acid sequence of SEQ ID NO: 109 (MRVKEKYQHLWRWGWRWGTMLLGMLMICS-ATEKLWVTVYYGVPVWKETTTTLFCASDAK AYDTEVHNVWATHACVPTDPNPQEVVLENVT-EDFNMWKNNMVEQMQEDVINLWDQSLKPCV KLTPLCVTLNCKDVNATNTTSSSEGMMER-GEIKNCSFNITKSIRDKVQKEYALFYKLDVVPIDNK NNTKYRLISCNTSVITQACPKVSFEPIPIHYCA-PAGFAILKCNNKTFNGKGQCKNVSTVQCTHGIR PVVSTQLLLNGSLAEEKVVIRSDNFTDNAKTIIVQL-NESVKINCTRPSNNTRKSIHIGPGRAFYTTG EIIGDIRQAHCNISRAQWNNTLKQIVEKLREQFNNK-TIVFTHSSGGDPEIVMHSFNCGGEFFYCNS TQLFNSTWNDTEKSSGTEGNDTIILPCRIKQI-INMWQEVGKAMYAPPIKGQIRCSSNITGLLLTRD GGKNESEIEIFRPGGGDMRDNWRSELYKYKVVKIE-PLGVAPTKAKRRVVQREKRAVGIGALFLG FLGAAGSTMGAASMTLTVQARQLLSGIVQQQNNLL-RAIEAQQHMLQLTVWGIKQLQARVLAVE RYLKDQQLMGIWGCSGKLICTTAVPWN-TSWSNKSLDSIWNNMTWMEWEKEIENYTNTIYTLIE ESQIQQEKNEQELLELDK-WASLWNWFDITKWLWYIKIFIMIVGGLIGLRIVESVL-SIVNRVRQGYS PLSFQTLLPATRGPDRPEGIEEEGG-ERDRDRSGQLVNGFLALIWVDLRSLFLFSYHRL-RDLLLTVT RIVELLGRRG-WEILKYWWNLLQYWSQELKNSAVSLLNATAIAVAE-GTDRIIEVVQRVYRAILHIP TRIRQGLERALL) except for an amino acid mutation (e.g., substitution) selected from the group consisting of: N262A, D368A, E370A, V371A, G472A, G473A, and a combination thereof. The position of the N262A, D368A, E370A, V371A, G472A, and G473A substitutions within SEQ ID NO: 109 are defined in reference to the HXB2 reference Env sequence of SEQ ID NO: 110. In particular, residues 262, 368, 370, 371, 472, and 473 of SEQ ID NO: 109 are the residues corresponding to residues 262, 368, 370, 371, 472, and 473, respectively, of the HXB2 reference Env sequence of SEQ ID NO: 110. In some embodiments, the variant JR-CSF Env comprises the sequence of SEQ ID NO: 109 except for any one mutation selected from the group consisting of: N262A, D368A, E370A, V371A, G472A, and G473A. In some embodiments, the variant JR-CSF Env comprises the sequence of SEQ ID NO: 109 except for any two, three, four, or five mutations selected from the group consisting of: N262A, D368A, E370A, V371A, G472A, and G473A. In some embodiments, the variant JR-CSF Env comprises the sequence of SEQ ID NO: 109 except for the amino acid mutations N262A, D368A, E370A, V371A, G472A, and G473A. In one embodiment, the binding between an antibody described herein and a variant JR-CSF Env is not substantially weakened relative to the binding between the antibody and JR-CSF Env, wherein the variant JR-CSF Env comprises the amino acid sequence of SEQ ID NO: 109 except for the N279A substitution. In one embodiment, binding affinity is determined by ELISA. In one embodiment, the antibody is a chimeric, human or humanized antibody.

In a specific aspect, an antibody described herein specifically binds to an epitope of a Env (e.g., BG505 Env) sequence comprising, consisting essentially of, or consisting of a residue of SEQ ID NO: 108 selected from the group consisting of: 282, 367, 472, and a combination thereof. Residues 282, 367, and 472 of SEQ ID NO: 108 are the residues corresponding to residues 282, 367, and 472, respectively, of the HXB2 reference Env sequence of SEQ ID NO: 110. In some embodiments, the epitope comprises, consists essentially of, or consists of any one residue selected from the group consisting of: 282, 367, and 472 of SEQ ID NO: 108. In some embodiments, the epitope comprises, consists essentially of, or consists of any two residues selected from the group consisting of: 282, 367, and 472 of SEQ ID NO: 108. In some embodiments, the epitope comprises, consists essentially of, or consists of residues 282, 367, and 472 of SEQ ID NO: 108. In one embodiment, the epitope does not comprise residue 279 of SEQ ID NO: 108. In one embodiment, the antibody is a chimeric, human or humanized antibody.

In a specific aspect, an antibody described herein specifically binds to an epitope of a Env (e.g., JR-CSF Env) sequence comprising, consisting essentially of, or consisting of a residue of SEQ ID NO: 109 selected from the group consisting of: 262, 368, 370, 371, 472, 473, and a combination thereof. Residues 262, 368, 370, 371, 472, and 473 of SEQ ID NO: 109 are the residues corresponding to residues 262, 368, 370, 371, 472, and 473, respectively, of the HXB2 reference Env sequence of SEQ ID NO: 110. In some embodiments, the epitope comprises, consists essentially of, or consists of any one residue selected from the group consisting of: 262, 368, 370, 371, 472, and 473 of SEQ ID NO: 109. In some embodiments, the epitope comprises, consists essentially of, or consists of any two, three, four, or five residues selected from the group consisting of: 262, 368, 370, 371, 472, and 473 of SEQ ID NO: 109. In some embodiments, the epitope comprises, consists essentially of, or consists of residues 262, 368, 370, 371, 472, and 473 of SEQ ID NO: 109. In one embodiment, the epitope does not comprise residue 279 of SEQ ID NO: 109. In one embodiment, the antibody is a chimeric, human or humanized antibody.

In a specific aspect, an antibody described herein specifically binds to at least one residue of SEQ ID NO: 108 selected from the group consisting of: 282, 367, 472, and a combination thereof. Residues 282, 367, and 472 of SEQ ID NO: 108 are the residues corresponding to residues 282, 367, and 472, respectively, of the HXB2 reference Env sequence of SEQ ID NO: 110. In some embodiments, an antibody described herein specifically binds to any one residue, or any two residues, selected from the group consisting of: 282, 367, and 472 of SEQ ID NO: 105. In some embodiments, an antibody described herein specifically binds to any two, three, four, five, six, or seven residues selected from the group consisting of: 282, 367, and 472 of SEQ ID NO: 105. In some embodiments, an antibody described herein specifically binds to residues 282, 367, and 472 of SEQ ID NO: 108. In one embodiment, the epitope does not comprise residue 279 of SEQ ID NO: 105. In one embodiment, the antibody is a chimeric, human or humanized antibody.

In a specific aspect, an antibody described herein specifically binds to at least one residue of SEQ ID NO: 109 selected from the group consisting of: 262, 368, 370, 371, 472, 473, and a combination thereof. Residues 262, 368, 370, 371, 472, and 473 of SEQ ID NO: 109 are the residues corresponding to residues 262, 368, 370, 371, 472, and 473, respectively, of the HXB2 reference Env sequence of SEQ ID NO: 110. In some embodiments, an antibody described herein specifically binds to any one residue, or any two, three, four, or five residues, selected from the group consisting of: 262, 368, 370, 371, 472, and 473 of SEQ ID NO: 109. In some embodiments, an antibody described herein specifically binds to any two, three, four, or five residues selected from the group consisting of: 262, 368, 370, 371, 472, and 473 of SEQ ID NO: 108. In some embodiments, an antibody described herein specifically binds to residues 262, 368, 370, 371, 472, and 473 of SEQ ID NO: 109. In one embodiment, the epitope does not comprise residue 279 of SEQ ID NO: 109. In one embodiment, the antibody is a chimeric, human or humanized antibody.

In a specific aspect, an antibody described herein exhibits, as compared to binding to a BG505 Env sequence of SEQ ID NO: 108, reduced or absent binding to a protein identical to SEQ ID NO: 108 except for the presence of an amino acid mutation (e.g., substitution) selected from the group consisting of:

K282A, G367A, G472A, and a combination thereof. The position of the K282A, G367A, and G472A substitutions within SEQ ID NO: 108 are defined in reference to the HXB2 reference Env sequence of SEQ ID NO: 110. In some embodiments, the protein is identical to SEQ ID NO: 108 except for the presence of an amino acid mutation comprising any one mutation, or any two mutations selected from the group consisting of: K282A, G367A, and G472A. In some embodiments, the protein is identical to SEQ ID NO: 108 except for the presence of an amino acid mutation comprising any two mutations selected from the group consisting of: K282A, G367A, and G472A. In some embodiments, the protein is identical to SEQ ID NO: 108 except for the presence of an amino acid substitution comprising the mutations K282A, G367A, and G472A. In one embodiment, the antibody described herein does not exhibit, as compared to binding to a BG505 Env sequence of SEQ ID NO: 108, reduced or absent binding to a protein identical to SEQ ID NO: 108 except for the presence of the amino acid mutation N279A. In one embodiment, the antibody is a chimeric, human or humanized antibody.

In a specific aspect, an antibody described herein exhibits, as compared to binding to a JR-CSF Env sequence of SEQ ID NO: 109, reduced or absent binding to a protein identical to SEQ ID NO: 109 except for the presence of an amino acid mutation (e.g., substitution) selected from the group consisting of: N262A, D368A, E370A, V371A, G472A, G473A, and a combination thereof. The position of the N262A, D368A, E370A, V371A, G472A, and G473A substitutions within SEQ ID NO: 109 are defined in reference to the HXB2 reference Env sequence of SEQ ID NO: 110. In some embodiments, the protein is identical to SEQ ID NO: 109 except for the presence of an amino acid mutation comprising any one mutation, or any two, three, four, or five mutations, selected from the group consisting of: N262A, D368A, E370A, V371A, G472A, and G473A. In some embodiments, the protein is identical to SEQ ID NO: 109 except for the presence of an amino acid mutation comprising any two, three, four, or five mutations selected from the group consisting of: N262A, D368A, E370A, V371A, G472A, and G473A. In some embodiments, the protein is identical to SEQ ID NO: 109 except for the presence of an amino acid substitution comprising the mutations N262A, D368A, E370A, V371A, G472A, and G473A. In one embodiment, the antibody described herein does not exhibit, as compared to binding to a JR-CSF Env sequence of SEQ ID NO: 109, reduced or absent binding to a protein identical to SEQ ID NO: 109 except for the presence of the amino acid mutation N279A. In one embodiment, the antibody is a chimeric, human or humanized antibody.

In another aspect, provided herein are antibodies that compete (e.g., in a dose dependent manner) for binding to Env (e.g., an epitope of BG505 Env) with an antibody described herein (e.g., NC-Cow1), as determined using assays known to one of skill in the art or described herein (e.g., ELISA competitive assays or surface plasmon resonance). In another aspect, provided herein are antibodies that competitively inhibit (e.g., in a dose dependent manner) an antibody described herein (e.g., NC-Cow1) from binding to Env (e.g., an epitope of BG505 Env), as determined using assays known to one of skill in the art or described herein (e.g., ELISA competitive assays, or suspension array or surface plasmon resonance assay).

In certain embodiments, the epitope of an antibody described herein is used as an immunogen to produce antibodies.

The affinity or avidity of an antibody or fusion polypeptide for an antigen can be determined experimentally using any suitable method well known in the art, e.g., flow cytometry, enzyme-linked immunoabsorbent assay (ELISA), or radioimmunoassay (RIA), or kinetics (e.g., BIACORE™ analysis). Direct binding assays as well as competitive binding assay formats can be readily employed. (See, for example, Berzofsky, et al., "Antibody-Antigen Interactions," In Fundamental Immunology, Paul, W. E., Ed., Raven Press: New York, N.Y. (1984); Kuby, Janis Immunology, W. H. Freeman and Company: New York, N.Y. (1992); and methods described herein. The measured affinity of a particular antibody-antigen interaction can vary if measured under different conditions (e.g., salt concentration, pH, temperature). Thus, measurements of affinity and other antigen-binding parameters (e.g., KD or Kd, Kon, Koff) are made with standardized solutions of antibody and antigen, and a standardized buffer, as known in the art and such as the buffer described herein.

In some embodiments, the broadly neutralizing anti-Env antibody described herein is a monoclonal antibody. Monoclonal antibodies can be prepared using hybridoma methods, such as those described by Kohler and Milstein (1975) Nature 256:495. Using the hybridoma method, a bovine host (e.g., cow) is immunized to elicit the production by lymphocytes of antibodies that will specifically bind to an immunizing antigen. Lymphocytes can also be immunized in vitro. Following immunization, the lymphocytes are isolated and fused with a suitable myeloma cell line using, for example, polyethylene glycol, to form hybridoma cells that can then be selected away from unfused lymphocytes and myeloma cells. Hybridomas that produce monoclonal antibodies directed specifically against a chosen antigen as determined by immunoprecipitation, immunoblotting, or by an in vitro binding assay (e.g., radioimmunoassay (RIA); enzyme-linked immunosorbent assay (ELISA)) can then be propagated either in vitro culture using standard methods (Goding, Monoclonal Antibodies: Principles and Practice, Academic Press, 1986) or in vivo as ascites tumors in an animal. The monoclonal antibodies can then be purified from the culture medium or ascites fluid using any method known in the art.

Alternatively monoclonal antibodies can also be made using recombinant DNA methods as described in U.S. Pat. No. 4,816,567. The polynucleotides encoding a monoclonal antibody are isolated from mature B-cells or hybridoma cells, such as by RT-PCR using oligonucleotide primers that specifically amplify the genes encoding the heavy and light chains of the antibody, and their sequence is determined using conventional procedures. The isolated polynucleotides encoding the heavy and light chains are then cloned into suitable expression vectors, which when transfected into host cells such as *E. coli* cells, simian COS cells, Chinese hamster ovary (CHO) cells, or myeloma cells that do not otherwise produce immunoglobulin protein, monoclonal antibodies are generated by the host cells. Also, recombinant monoclonal antibodies or fragments thereof of the desired species can be isolated from phage display libraries expressing CDRs of the desired species as described (McCafferty et al., 1990, Nature, 348:552-554; Clackson et al., 1991, Nature, 352:624-628; and Marks et al., 1991, J. Mol. Biol., 222:581-597).

The polynucleotide(s) encoding a monoclonal antibody can further be modified in a number of different manners using recombinant DNA technology to generate alternative antibodies. In some embodiments, the constant domains of the light and heavy chains of, for example, a mouse monoclonal antibody can be substituted 1) for those regions of, for example, a human antibody to generate a chimeric antibody or 2) for a non-immunoglobulin polypeptide to generate a fusion antibody. In some embodiments, the constant regions are truncated or removed to generate the desired antibody fragment of a monoclonal antibody. Site-directed or high-density mutagenesis of the variable region can be used to optimize specificity, affinity, etc. of a monoclonal antibody.

Methods for engineering, humanizing or resurfacing non-human or human antibodies can also be used and are well known in the art. A humanized, resurfaced or similarly engineered antibody can have one or more amino acid residues from a source that is non-human, e.g., but not limited to, mouse, rat, rabbit, non-human primate or other mammal. These non-human amino acid residues are replaced by residues that are often referred to as "import" residues, which are typically taken from an "import" variable, constant or other domain of a known human sequence.

Such imported sequences can be used to reduce immunogenicity or reduce, enhance or modify binding, affinity, on-rate, off-rate, avidity, specificity, half-life, or any other suitable characteristic, as known in the art. In general, the CDR residues are directly and most substantially involved in influencing antibody binding. Accordingly, part or all of the non-human or human CDR sequences are maintained while the non-human sequences of the variable and constant regions can be replaced with human or other amino acids.

Antibodies can also optionally be humanized, resurfaced, engineered or human antibodies engineered with retention of high affinity for the antigen and other favorable biological properties. To achieve this goal, humanized (or human) or engineered antibodies and resurfaced antibodies can be optionally prepared by a process of analysis of the parental sequences and various conceptual humanized and engineered products using three-dimensional models of the parental, engineered, and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, framework (FR) residues can be selected and combined from the consensus and import sequences so that the desired antibody characteristic, such as increased affinity for the target antigen(s), is achieved.

Humanization, resurfacing or engineering of antibodies described herein can be performed using any known method, such as but not limited to those described in, Winter (Jones et al., Nature 321:522 (1986); Riechmann et al., Nature 332:323 (1988); Verhoeyen et al., Science 239:1534 (1988)), Sims et al., J. Immunol. 151:2296 (1993); Chothia and Lesk, J. Mol. Biol. 196:901 (1987), Carter et al., Proc. Natl. Acad. Sci. U.S.A. 89:4285 (1992); Presta et al., J. Immunol. 151:2623 (1993), U.S. Pat. Nos. 5,639,641, 5,723,323; 5,976,862; 5,824,514; 5,817,483; 5,814,476; 5,763,192; 5,723,323; 5,766,886; 5,714,352; 6,204,023; 6,180,370; 5,693,762; 5,530,101; 5,585,089; 5,225,539; 4,816,567; PCT/: US98/16280; US96/18978; US91/09630; US91/05939; US94/01234; GB89/01334; GB91/01134; GB92/01755; WO90/14443; WO90/14424; WO90/14430; EP 229246; 7,557,189; 7,538,195; and 7,342,110, each of which is entirely incorporated herein by reference, including the references cited therein.

In certain alternative embodiments, the antibody is a human antibody. Human antibodies can be directly prepared using various techniques known in the art. Immortalized human B lymphocytes immunized in vitro or isolated from an immunized individual (e.g., a cow) that produce an antibody directed against a target antigen can be generated (See, e.g., Cole et al., Monoclonal Antibodies and Cancer Therapy, Alan R. Liss, p. 77 (1985); Boemer et al., 1991, J. Immunol., 147 (1): 86-95; and U.S. Pat. No. 5,750,373). Also, the human antibody can be selected from a phage library, where that phage library expresses human antibodies, as described, for example, in Vaughan et al., 1996, Nat. Biotech., 14:309-314, Sheets et al., 1998, Proc. Nat'l. Acad. Sci., 95:6157-6162, Hoogenboom and Winter, 1991, J. Mol. Biol., 227:381, and Marks et al., 1991, J. Mol. Biol., 222:581). Techniques for the generation and use of antibody phage libraries are also described in U.S. Pat. Nos. 5,969,108, 6,172,197, 5,885,793, 6,521,404; 6,544,731; 6,555,313; 6,582,915; 6,593,081; 6,300,064; 6,653,068; 6,706,484; and 7,264,963; and Rothe et al., 2007, *J. Mol. Bio*., doi: 10.1016/j.jmb.2007.12.018 (each of which is incorporated by reference in its entirety). Affinity maturation strategies and chain shuffling strategies (Marks et al., 1992, Bio/Technology 10:779-783, incorporated by reference in its entirety) are known in the art and can be employed to generate high affinity human antibodies.

In certain embodiments an antibody fragment is provided. Various techniques are known for the production of antibody fragments. Traditionally, these fragments are derived via proteolytic digestion of intact antibodies (for example Morimoto et al., 1993, Journal of Biochemical and Biophysical Methods 24:107-117; Brennan et al., 1985, *Science*, 229:81). In certain embodiments, antibody fragments are produced recombinantly. Fab, Fv, and scFv antibody fragments can all be expressed in and secreted from *E. coli* or other host cells, thus allowing the production of large amounts of these fragments. Such antibody fragments can also be isolated from antibody phage libraries. The antibody fragment can also be linear antibodies as described in U.S. Pat. No. 5,641,870, for example, and can be monospecific or bispecific. Other techniques for the production of antibody fragments will be apparent to the skilled practitioner.

In certain embodiments, the variable domains in both the heavy and light chains are altered by at least partial replacement of one or more CDRs and, if necessary, by partial framework region replacement and sequence changing. Although the CDRs can be derived from an antibody of the same class or even subclass as the antibody from which the framework regions are derived, it is envisaged that the CDRs will be derived from an antibody of different class and in certain embodiments from an antibody from a different species. It may not be necessary to replace all of the CDRs with the complete CDRs from the donor variable region to transfer the antigen-binding capacity of one variable domain to another. Rather, it may only be necessary to transfer those residues that are necessary to maintain the activity of the antigen-binding site. Given the explanations set forth in U.S. Pat. Nos. 5,585,089, 5,693,761 and 5,693,762, it will be well within the competence of those skilled in the art, either by carrying out routine experimentation or by trial and error testing to obtain a functional antibody with reduced immunogenicity.

Alterations to the variable region notwithstanding, those skilled in the art will appreciate that the modified antibodies described herein will comprise antibodies (e.g., full-length antibodies or immunoreactive fragments thereof) in which at least a fraction of one or more of the constant region domains has been deleted or otherwise altered so as to provide desired biochemical characteristics such as increased serum half-life when compared with an antibody of approximately the same immunogenicity comprising a native or unaltered constant region. In some embodiments, the constant region of the modified antibodies will comprise a human constant region. Modifications to the constant region compatible with this invention comprise additions, deletions or substitutions of one or more amino acids in one or more domains. That is, the modified antibodies described herein can comprise alterations or modifications to one or more of the three heavy chain constant domains (CH1, CH2 or CH3) and/or to the light chain constant domain (CL). In some embodiments, modified constant regions wherein one or more domains are partially or entirely deleted are contemplated. In some embodiments, the modified antibodies will comprise domain deleted constructs or variants wherein the entire CH2 domain has been removed (ΔCH2 constructs). In some embodiments, the omitted constant region domain will be replaced by a short amino acid spacer (e.g., 10 residues) that provides some of the molecular flexibility typically imparted by the absent constant region.

It will be noted that in certain embodiments, the modified antibodies can be engineered to fuse the CH3 domain directly to the hinge region of the respective modified antibodies. In other constructs it may be desirable to provide a peptide spacer between the hinge region and the modified CH2 and/or CH3 domains. For example, compatible constructs could be expressed wherein the CH2 domain has been deleted and the remaining CH3 domain (modified or unmodified) is joined to the hinge region with a 5-20 amino acid spacer. Such a spacer can be added, for instance, to ensure that the regulatory elements of the constant domain remain free and accessible or that the hinge region remains flexible. However, it should be noted that amino acid spacers can, in some cases, prove to be immunogenic and elicit an unwanted immune response against the construct. Accordingly, in certain embodiments, any spacer added to the construct will be relatively non-immunogenic, or even omitted altogether, so as to maintain the desired biochemical qualities of the modified antibodies.

Besides the deletion of whole constant region domains, it will be appreciated that the antibodies described herein can be provided by the partial deletion or substitution of a few or even a single amino acid. For example, it may be desirable to simply delete that part of one or more constant region domains that control the effector function (e.g., complement C1Q binding) to be modulated. Such partial deletions of the constant regions can improve selected characteristics of the antibody (serum half-life) while leaving other desirable functions associated with the subject constant region domain intact. Moreover, as alluded to above, the constant regions of the disclosed antibodies can be modified through the mutation or substitution of one or more amino acids that enhances the profile of the resulting construct. In this respect it may be possible to disrupt the activity provided by a conserved binding site (e.g., Fc binding) while substantially maintaining the configuration and immunogenic profile of the modified antibody. Certain embodiments can comprise the addition of one or more amino acids to the constant region to enhance desirable characteristics such as decreasing or increasing effector function or provide for more cytotoxin or carbohydrate attachment. In such embodiments it can be desirable to insert or replicate specific sequences derived from selected constant region domains.

The present invention further embraces variants and equivalents which are substantially homologous to the chimeric, humanized and human antibodies, or antibody fragments thereof, set forth herein. These can contain, for example, conservative substitution mutations, i.e., the substitution of one or more amino acids by similar amino acids. For example, conservative substitution refers to the substitution of an amino acid with another within the same general class such as, for example, one acidic amino acid with another acidic amino acid, one basic amino acid with another basic amino acid or one neutral amino acid by another neutral amino acid. What is intended by a conservative amino acid substitution is well known in the art.

The polypeptides provided herein can be recombinant polypeptides, natural polypeptides, or synthetic polypeptides comprising an antibody, or fragment thereof. It will be recognized in the art that some amino acid sequences described herein can be varied without significant effect of the structure or function of the protein. Thus, the invention further includes variations of the polypeptides which show substantial activity or which include regions of an antibody, or fragment thereof, against a human folate receptor protein. Such mutants include deletions, insertions, inversions, repeats, and type substitutions.

The polypeptides and analogs can be further modified to contain additional chemical moieties not normally part of the protein. Those derivatized moieties can improve the solubility, the biological half-life or absorption of the protein. The moieties can also reduce or eliminate any desirable side effects of the proteins and the like. An overview for those moieties can be found in REMINGTON'S PHARMACEUTICAL SCIENCES, 21th ed., Mack Publishing Co., Easton, PA (2005).

IV. Polynucleotides

In certain aspects, provided herein are polynucleotides comprising a nucleotide sequence or nucleotide sequences encoding a broadly neutralizing anti-Env antibody described herein or a fragment thereof (e.g., a humanized variable light chain and/or variable heavy chain region) and vectors, e.g., vectors comprising such polynucleotides. In one embodiment, the vectors can be used for recombinant expression of an antibody described herein in host cells (e.g., *E. coli* and mammalian cells). In one embodiment, the vectors can be used for administration of an antibody described herein to a patient in need thereof.

In one aspect, provided herein are isolated polynucleotides encoding the heavy chain variable region or heavy chain of a broadly neutralizing antibody described herein.

In one aspect, provided herein are isolated polynucleotides encoding the light chain variable region or light chain of a broadly neutralizing antibody described herein.

In one aspect, provided herein are isolated polynucleotides encoding the heavy chain variable region or heavy chain of a broadly neutralizing antibody described herein and the light chain variable region or light chain of a broadly neutralizing antibody described herein.

In one embodiment, the polynucleotide encodes a heavy chain variable region comprising the amino acid sequence of SEQ ID NO: 7, 17, 27, 37, 47, 57, 67, 77, 87, or 97.

In one embodiment, the polynucleotide encodes a light chain variable region comprising the amino acid sequence of SEQ ID NO: 8, 18, 28, 38, 48, 58, 68, 87, 88, or 98.

In one embodiment, an isolated polynucleotide described herein encodes a broadly neutralizing antibody described herein and comprises an mRNA. In one embodiment, the mRNA comprises at least one modified nucleotide. In one embodiment, a modified mRNA encoding an antibody disclosed herein is for administering to a subject to treat or prevent HIV infection.

In one aspect, provided herein are isolated polynucleotides encoding a fusion polypeptide described herein.

As used herein, an "isolated" polynucleotide or nucleic acid molecule is one which is separated from other nucleic acid molecules which are present in the natural source (e.g., in a mouse or a human) of the nucleic acid molecule. Moreover, an "isolated" nucleic acid molecule, such as a cDNA molecule, can be substantially free of other cellular material, or culture medium when produced by recombinant techniques, or substantially free of chemical precursors or other chemicals when chemically synthesized. For example, the language "substantially free" includes preparations of polynucleotide or nucleic acid molecule having less than about 15%, 10%, 5%, 2%, 1%, 0.5%, or 0.1% (in particular less than about 10%) of other material, e.g., cellular material, culture medium, other nucleic acid molecules, chemical precursors and/or other chemicals. In a specific embodiment, a nucleic acid molecule(s) encoding an antibody or fusion polypeptide described herein is isolated or purified.

In particular aspects, provided herein are polynucleotides comprising nucleotide sequences encoding broadly neutralizing bovine anti-Env antibodies described herein, as well as antibodies that compete with such antibodies for binding to HIV, or which binds to the same epitope as that of such antibodies.

In certain aspects, provided herein are polynucleotides comprising a nucleotide sequence encoding the light chain or heavy chain of a broadly neutralizing anti-Env antibody described herein. The polynucleotides can comprise nucleotide sequences encoding a light chain comprising the VL of antibodies described herein (see, e.g., Table 1 and 2). The polynucleotides can comprise nucleotide sequences encoding a heavy chain comprising the VH of antibodies described herein (see, e.g., Table 1 and 2). In specific embodiments, a polynucleotide described herein encodes a VL domain comprising the amino acid sequence set forth in SEQ ID NO: 8, 18, 28, 38, 48, 58, 68, 87, 88, and 98. In specific embodiments, a polynucleotide described herein encodes a VH domain comprising the amino acid sequence set forth in SEQ ID NO: 7, 17, 27, 37, 47, 57, 67, 77, 87, and 97. In one embodiment, the antibody is a chimeric antibody.

In particular embodiments, provided herein are polynucleotides comprising a nucleotide sequence encoding a broadly neutralizing anti-Env antibody comprising three VL chain CDRs, e.g., containing VL CDR1, VL CDR2, and VL CDR3 of any one of antibodies described herein (e.g., see Table 3). In specific embodiments, provided herein are polynucleotides comprising three VH chain CDRs, e.g., containing VH CDR1, VH CDR2, and VH CDR3 of any one of antibodies described herein (e.g., see Table 3). In specific embodiments, provided herein are polynucleotides comprising a nucleotide sequence encoding an anti-Env antibody comprising three VL CDRs, e.g., containing VL CDR1, VL CDR2, and VL CDR3 of any one of antibodies described herein (e.g., see Table 3) and three VH chain CDRs, e.g., containing VH CDR1, VH CDR2, and VH CDR3 of any one of antibodies described herein (e.g., see Table 3). In one embodiment, the antibody is a humanized antibody.

In some embodiments, provided herein are polynucleotides comprising a nucleotide sequence encoding a broadly neutralizing anti-Env antibody comprising the VH CDR3 of an antibody described herein (e.g., see Table 3). In one embodiment, the VH CDR3 comprises the amino acid sequence of SEQ ID NO: 3, 13, 23, 33, 43, 53, 63, 73, 83, or 93. In one embodiment, the VH CDR3 comprises the amino acid sequence of SEQ ID NO: 227-238. In one embodiment, the VH CDR3 comprises the amino acid sequence of SEQ ID NO: 3 or SEQ ID NO: 121. In one embodiment, the VH CDR3 comprises the amino acid sequence of SEQ ID NO: 101. In one embodiment, the VH CDR3 comprises the amino acid sequence of SEQ ID NO: 102. In one embodiment, the VH CDR3 comprises the amino acid sequence of SEQ ID NO: 268. In one embodiment, the VH CDR3 comprises the amino acid sequence of SEQ ID NO: 269. In one embodiment, the VH CDR3 comprises the amino acid sequence of SEQ ID NO: 122. In one embodiment, the antibody is a humanized antibody.

In some embodiments, provided herein are polynucleotides comprising a nucleotide sequence encoding fusion polypeptide, which is capable of binding and broadly neutralizing HIV, wherein the fusion polypeptide comprises the VH CDR3 of an antibody described herein (e.g., see Table 3). In one embodiment, the VH CDR3 comprises the amino acid sequence of SEQ ID NO: 3, 13, 23, 33, 43, 53, 63, 73, 83, or 93. In one embodiment, the VH CDR3 comprises the amino acid sequence of SEQ ID NO: 227-238. In one embodiment, the VH CDR3 comprises the amino acid sequence of SEQ ID NO: 3 or SEQ ID NO: 121. In one embodiment, the VH CDR3 comprises the amino acid sequence of SEQ ID NO: 101. In one embodiment, the VH CDR3 comprises the amino acid sequence of SEQ ID NO: 102. In one embodiment, the VH CDR3 comprises the amino acid sequence of SEQ ID NO: 122. In one embodiment, the VH CDR3 comprises the amino acid sequence of SEQ ID NO: 268. In one embodiment, the VH CDR3 comprises the amino acid sequence of SEQ ID NO: 269.

In specific embodiments, a polynucleotide provided herein comprises a nucleotide sequence encoding an antibody or fragment thereof described herein comprising: framework regions (e.g., framework regions of the VL domain and VH domain) that are human framework regions, wherein the antibody immunospecifically binds Env. In certain embodiments, a polynucleotide provided herein comprises a nucleotide sequence encoding an antibody or fragment thereof (e.g., CDRs or variable domain) described herein.

In specific aspects, provided herein is a polynucleotide comprising a nucleotide sequence encoding an antibody comprising a light chain and a heavy chain, e.g., a separate light chain and heavy chain. With respect to the light chain, in a specific embodiment, a polynucleotide provided herein comprises a nucleotide sequence encoding a kappa light chain. In another specific embodiment, a polynucleotide provided herein comprises a nucleotide sequence encoding a lambda light chain. In yet another specific embodiment, a polynucleotide provided herein comprises a nucleotide sequence encoding an antibody described herein comprising a human kappa light chain or a human lambda light chain. In a particular embodiment, a polynucleotide provided herein comprises a nucleotide sequence encoding an antibody, which immunospecifically binds to Env, wherein the antibody comprises a light chain, and wherein the amino acid sequence of the VL domain can comprise the amino acid sequence set forth in Tables 1 and 2, and wherein the constant region of the light chain comprises the amino acid sequence of a human kappa light chain constant region. In another particular embodiment, a polynucleotide provided herein comprises a nucleotide sequence encoding an antibody, which immunospecifically binds to Env, and comprises a light chain, wherein the amino acid sequence of the VL domain can comprise the amino acid sequence set forth in Tables 1 and 2, and wherein the constant region of the light chain comprises the amino acid sequence of a human lambda light chain constant region. For example, human constant region sequences can be those described in U.S. Pat. No. 5,693,780.

In a particular embodiment, a polynucleotide provided herein comprises a nucleotide sequence encoding an antibody described herein, which immunospecifically binds to Env, wherein the antibody comprises a heavy chain, wherein the amino acid sequence of the VH domain can comprise the amino acid sequence set forth in Table 1 and 2, and wherein the constant region of the heavy chain comprises the amino acid sequence of a human alpha or gamma heavy chain constant region.

In yet another specific embodiment, a polynucleotide provided herein comprises a nucleotide sequence encoding an antibody described herein, which immunospecifically binds Env, wherein the antibody comprises a VL domain and a VH domain comprising any amino acid sequences described herein, and wherein the constant regions comprise the amino acid sequences of the constant regions of a human $IgA_1$, human $IgA_2$' human $IgG_1$ (e.g., allotype 1, 17, or 3), human $IgG_2$, or human $IgG_4$.

In a specific embodiment, provided herein are polynucleotides comprising a nucleotide sequence encoding an anti-Env antibody or domain thereof, designated herein NC-Cow1, NC-Cow2, NC-Cow3, NC-Cow4, NC-Cow5, NC-Cow6, NC-Cow7, NC-Cow8, NC-Cow9, and NC-Cow10.

In one embodiment, a polynucleotide provided herein comprises the nucleotide sequence of SEQ ID NO: 9, 19, 29, 39, 49, 59, 69, 79, 89, or 99.

In one embodiment, a polynucleotide provided herein comprises the nucleotide sequence of SEQ ID NO: 10, 20, 30, 40, 50, 60, 70, 80, 90, or 100.

Also provided herein are polynucleotides encoding an anti-Env antibody or a fragment thereof that are optimized, e.g., by codon/RNA optimization, replacement with heterologous signal sequences, and elimination of mRNA instability elements. Methods to generate optimized nucleic acids encoding an anti-Env antibody or a fragment thereof (e.g., light chain, heavy chain, VH domain, or VL domain) for recombinant expression by introducing codon changes and/or eliminating inhibitory regions in the mRNA can be carried out by adapting the optimization methods described in, e.g., U.S. Pat. Nos. 5,965,726; 6,174,666; 6,291,664; 6,414,132; and 6,794,498, accordingly. For example, potential splice sites and instability elements (e.g., A/T or A/U rich elements) within the RNA can be mutated without altering the amino acids encoded by the nucleic acid sequences to increase stability of the RNA for recombinant expression. The alterations utilize the degeneracy of the genetic code, e.g., using an alternative codon for an identical amino acid. In some embodiments, it can be desirable to alter one or more codons to encode a conservative mutation, e.g., a similar amino acid with similar chemical structure and properties and/or function as the original amino acid.

In certain embodiments, an optimized polynucleotide sequence encoding an anti-Env antibody described herein or a fragment thereof (e.g., VL domain or VH domain) can hybridize to an antisense (e.g., complementary) polynucleotide of an unoptimized polynucleotide sequence encoding an anti-Env antibody described herein or a fragment thereof (e.g., VL domain or VH domain). In specific embodiments, an optimized nucleotide sequence encoding an anti-Env antibody described herein or a fragment hybridizes under high stringency conditions to antisense polynucleotide of an unoptimized polynucleotide sequence encoding an anti-Env antibody described herein or a fragment thereof. In a specific embodiment, an optimized nucleotide sequence encoding an anti-Env antibody described herein or a fragment thereof hybridizes under high stringency, intermediate or lower stringency hybridization conditions to an antisense polynucleotide of an unoptimized nucleotide sequence encoding an anti-Env antibody described herein or a fragment thereof.

Information regarding hybridization conditions has been described, see, e.g., U.S. Patent Application Publication No. US 2005/0048549 (e.g., paragraphs 72-73), which is incorporated herein by reference.

The polynucleotides can be obtained, and the nucleotide sequence of the polynucleotides determined, by any method known in the art. Nucleotide sequences encoding antibodies described herein, and modified versions of these antibodies can be determined using methods well known in the art, i.e., nucleotide codons known to encode particular amino acids are assembled in such a way to generate a nucleic acid that encodes the antibody. Such a polynucleotide encoding the antibody can be assembled from chemically synthesized oligonucleotides (e.g., as described in Kutmeier G et al., (1994), *BioTechniques* 17:242-246), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody or fragment thereof described herein can be generated from nucleic acid from a suitable source (e.g., PBMCs) using methods well known in the art (e.g., PCR and other molecular cloning methods). For example, PCR amplification using synthetic primers hybridizable to the 3' and 5' ends of a known sequence can be performed using genomic DNA obtained from hybridoma cells producing the antibody of interest. Such PCR amplification methods can be used to obtain nucleic acids comprising the sequence encoding the light chain and/or heavy chain of an antibody. Such PCR amplification methods can be used to obtain nucleic acids comprising the sequence encoding the variable light chain region and/or the variable heavy chain region of an antibody. The amplified nucleic acids can be cloned into vectors for expression in host cells and for further cloning, for example, to generate chimeric and humanized antibodies.

If a clone containing a nucleic acid encoding a particular antibody or fragment thereof is not available, but the sequence of the antibody molecule or fragment thereof is known, a nucleic acid encoding the immunoglobulin or fragment can be chemically synthesized or obtained from a suitable source (e.g., an antibody cDNA library or a cDNA library generated from, or nucleic acid, preferably poly A+RNA, isolated from, any tissue or cells expressing the antibody, such as hybridoma cells selected to express an antibody described herein) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR can then be cloned into replicable cloning vectors using any method well known in the art.

DNA encoding anti-Env antibodies described herein can be readily isolated and sequenced using conventional procedures (e.g., by using oligonucleotide probes that are capable of binding specifically to genes encoding the heavy and light chains of the anti-Env antibodies). PBMCs can serve as a source of such DNA. Once isolated, the DNA can be placed into expression vectors, which are then transfected into host cells such as *E. coli* cells, simian COS cells, Chinese hamster ovary (CHO) cells (e.g., CHO cells from the CHO GS System™ (Lonza)), or myeloma cells that do not otherwise produce immunoglobulin protein, to obtain the synthesis of anti-Env antibodies in the recombinant host cells.

The DNA also can be modified, for example, by substituting the coding sequence for human heavy and light chain constant domains in place of the bovine sequences, or by covalently joining to the immunoglobulin coding sequence all or part of the coding sequence for a non-immunoglobulin polypeptide.

Also provided are polynucleotides that hybridize under high stringency, intermediate or lower stringency hybridization conditions to polynucleotides that encode an antibody described herein. In specific embodiments, polynucleotides described herein hybridize under high stringency, intermediate or lower stringency hybridization conditions to polynucleotides encoding a VH domain and/or VL domain provided herein.

Hybridization conditions have been described in the art and are known to one of skill in the art. For example, hybridization under stringent conditions can involve hybridization to filter-bound DNA in 6× sodium chloride/sodium citrate (SSC) at about 45° C. followed by one or more washes in 0.2×SSC/0.1% SDS at about 50-65° C.; hybridization under highly stringent conditions can involve hybridization to filter-bound nucleic acid in 6×SSC at about 45° C. followed by one or more washes in 0.1×SSC/0.2% SDS at about 68° C. Hybridization under other stringent hybridization conditions are known to those of skill in the art and have been described, see, for example, Ausubel F M et al., eds., (1989) *Current Protocols in Molecular Biology*, Vol. I, Green Publishing Associates, Inc. and John Wiley & Sons, Inc., New York at pages 6.3.1-6.3.6 and 2.10.3.

V. Vectors, Cells, and Methods of Producing a Broadly Neutralizing Agent

In certain aspects, provided herein are cells (e.g., host cells) expressing (e.g., recombinantly) antibodies or fusion polypeptides (e.g., fusion polypeptide comprising a VH CDR3 of NC-Cow1) described herein which specifically bind to Env and related polynucleotides and expression vectors. Provided herein are vectors (e.g., expression vectors) comprising polynucleotides comprising nucleotide sequences encoding anti-Env antibodies or a fragment thereof described herein or a fusion polypeptide described herein. In one embodiment, the vectors can be used for recombinant expression of an antibody or fusion polypeptide described herein in host cells (e.g., mammalian cells). In one embodiment, the vectors can be used for administration of an antibody or fusion polypeptide described herein to a patient in need thereof. Also provided herein are host cells comprising such vectors for recombinantly expressing anti-Env antibodies described herein (e.g., humanized antibody) or fusion polypeptides described herein. In a particular aspect, provided herein are methods for producing an antibody or fusion polypeptide described herein, comprising expressing such antibody in a host cell.

In certain aspects, provided herein is an isolated vector comprising a polynucleotide described herein. In one embodiment, the vector is a viral vector.

In certain aspects, provided herein is a recombinant virus comprising a polynucleotide described herein. In one embodiment, the recombinant virus encodes an antibody (e.g., a humanized broadly neutralizing antibody) or a fusion polypeptide described herein. In one embodiment, the recombinant virus is an adeno-associated virus (AAV). In one embodiment, the recombinant virus is for administration to a subject to prevent or treat HIV infection.

In certain aspects, provided herein is a host cell comprising a polynucleotide described herein, or a vector described herein. In one embodiment, the vector encodes an antibody described herein. In one embodiment, a vector comprises a first vector encoding an VH described herein and a second vector encoding a VL described herein. In one embodiment, the vector encodes a chimeric or humanized broadly neutralizing antibody described herein. In one embodiment, the vector encodes a fusion polypeptide described herein.

In one embodiment, the host cell is selected from the group consisting of *E. coli, Pseudomonas, Bacillus, Streptomyces*, yeast, CHO, YB/20, NS0, PER-C6, HEK-293T, NIH-3T3, Helga, BHK, Hep G2, SP2/0, R1.1, B-W, L-M, COS 1, COS 7, BSC1, BSC40, BMT10 cell, plant cell, insect cell, and human cell in tissue culture. In one embodiment, the host cell is CHO.

In certain aspects, provided herein is a method of producing an antibody or fusion polypeptide that binds to HIV comprising culturing a host cell described herein so that the polynucleotide is expressed and the antibody or fusion polypeptide is produced. In one embodiment, the method further comprises recovering the antibody or fusion polypeptide.

The isolated polypeptides (e.g., broadly neutralizing bovine anti-Env antibody or fusion polypeptide) described herein can be produced by any suitable method known in the art. Such methods range from direct protein synthetic methods to constructing a DNA sequence encoding isolated polypeptide sequences and expressing those sequences in a suitable transformed host. In some embodiments, a DNA sequence is constructed using recombinant technology by isolating or synthesizing a DNA sequence encoding a wild-type protein of interest. Optionally, the sequence can be mutagenized by site-specific mutagenesis to provide functional analogs thereof. See, e.g., Zoeller et al., Proc. Nat'l. Acad. Sci. USA 81:5662-5066 (1984) and U.S. Pat. No. 4,588,585.

In some embodiments a DNA sequence encoding a polypeptide of interest would be constructed by chemical synthesis using an oligonucleotide synthesizer. Such oligonucleotides can be designed based on the amino acid sequence of the desired polypeptide and selecting those codons that are favored in the host cell in which the recombinant polypeptide of interest will be produced. Standard methods can be applied to synthesize an isolated polynucleotide sequence encoding an isolated polypeptide of interest. For example, a complete amino acid sequence can be used to construct a back-translated gene. Further, a DNA oligomer containing a nucleotide sequence coding for the particular isolated polypeptide can be synthesized. For example, several small oligonucleotides coding for portions of the desired polypeptide can be synthesized and then ligated. The individual oligonucleotides typically contain 5' or 3' overhangs for complementary assembly.

Once assembled (by synthesis, site-directed mutagenesis or another method), the polynucleotide sequences encoding a particular isolated polypeptide of interest will be inserted into an expression vector and operatively linked to an expression control sequence appropriate for expression of the protein in a desired host. Proper assembly can be confirmed by nucleotide sequencing, restriction mapping, and expression of a biologically active polypeptide in a suitable host. As is well known in the art, in order to obtain high expression levels of a transfected gene in a host, the gene must be operatively linked to transcriptional and translational expression control sequences that are functional in the chosen expression host.

In certain embodiments, recombinant expression vectors are used to amplify and express DNA encoding antibodies, fragments thereof, or fusion polypeptides. Recombinant expression vectors are replicable DNA constructs which have synthetic or cDNA-derived DNA fragments encoding a polypeptide chain of an antibody, or fragment thereof, or a fusion polypeptide operatively linked to suitable transcriptional or translational regulatory elements derived from mammalian, microbial, viral or insect genes. A transcriptional unit generally comprises an assembly of (1) a genetic element or elements having a regulatory role in gene expression, for example, transcriptional promoters or enhancers, (2) a structural or coding sequence which is transcribed into mRNA and translated into protein, and (3) appropriate transcription and translation initiation and termination sequences. Such regulatory elements can include an operator sequence to control transcription. The ability to replicate in a host, usually conferred by an origin of replication, and a selection gene to facilitate recognition of transformants can additionally be incorporated. DNA regions are operatively linked when they are functionally related to each other. For example, DNA for a signal peptide (secretory leader) is operatively linked to DNA for a polypeptide if it is expressed as a precursor which participates in the secretion of the polypeptide; a promoter is operatively linked to a coding sequence if it controls the transcription of the sequence; or a ribosome binding site is operatively linked to a coding sequence if it is positioned so as to permit translation. Structural elements intended for use in yeast expression systems include a leader sequence enabling extracellular secretion of translated protein by a host cell. Alternatively, where recombinant protein is expressed without a leader or transport sequence, it can include an N-terminal methionine residue. This residue can optionally be subsequently cleaved from the expressed recombinant protein to provide a final product.

The choice of expression control sequence and expression vector will depend upon the choice of host. A variety of host-expression vector systems can be utilized to express antibody molecules described herein (e.g., a broadly neutralizing humanized or chimeric bovine antibody) (see, e.g., U.S. Pat. No. 5,807,715) or fusion polypeptides described herein. Such host-expression systems represent vehicles by which the coding sequences of interest can be produced and subsequently purified, but also represent cells which can, when transformed or transfected with the appropriate nucleotide coding sequences, express an antibody molecule or fusion polypeptide described herein in situ. These include but are not limited to microorganisms such as bacteria (e.g., *E. coli* and *B. subtilis*) transformed with recombinant bacteriophage DNA, plasmid DNA or cosmid DNA expression vectors containing antibody or fusion polypeptide coding sequences; yeast (e.g., *Saccharomyces Pichia*) transformed with recombinant yeast expression vectors containing antibody or fusion polypeptide coding sequences; insect cell systems infected with recombinant virus expression vectors (e.g., baculovirus) containing antibody or fusion polypeptide coding sequences; plant cell systems (e.g., green algae such as *Chlamydomonas reinhardtii*) infected with recombinant virus expression vectors (e.g., cauliflower mosaic virus, CaMV; tobacco mosaic virus, TMV) or transformed with recombinant plasmid expression vectors (e.g., Ti plasmid) containing antibody or fusion polypeptide coding sequences; or mammalian cell systems (e.g., COS (e.g., COS1 or COS), CHO, BHK, MDCK, HEK 293, NS0, PER.C6, VERO, CRL7030, HsS78Bst, Helga, and NIH 3T3, HEK-293T, HepG2, SP210, R1.1, B-W, L-M, BSC1, BSC40, YB/20 and BMT10 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). In a specific embodiment, cells for expressing antibodies or fusion polypeptides described herein are CHO cells, for example CHO cells from the CHO GS System™ (Lonza). In a particular embodiment, cells for expressing antibodies or fusion polypeptides described herein are human cells, e.g., human cell lines. In a specific embodiment, a mammalian expression vector is pOptiVEC™ or pcDNA3.3. In a particular embodiment, bacterial cells such as *Escherichia coli*, or eukaryotic cells (e.g., mammalian cells), especially for the expression of whole recombinant antibody molecule, are used for the expression of a recombinant antibody molecule. For example, mammalian cells such as Chinese hamster ovary (CHO) cells in conjunction with a vector such as the major intermediate early gene promoter element from human cytomegalovirus is an effective expression system for antibodies (Foecking MK & Hofstetter H (1986) Gene 45:101-105; and Cockett M I et al., (1990) Biotechnology 8:662-667). In certain embodiments, antibodies or fusion polypeptides described herein are produced by CHO cells or NS0 cells. In a specific embodiment, the expression of nucleotide sequences encoding antibodies described herein which immunospecifically bind Env (e.g., a broadly neutralizing humanized or chimeric bovine antibody) is regulated by a constitutive promoter, inducible promoter or tissue specific promoter.

For applications where it is desired that the antibodies or fusion polypeptides described herein be expressed in vivo, for example in a subject in need of treatment with an antibody or fusion polypeptide described herein, any vector that allows for the expression of the antibodies or fusion polypeptides and is safe for use in vivo may be used. In one embodiment, the vector is a viral vector. Viral vectors can include poxvirus (vaccinia), including vaccinia Ankara and canarypox; adenoviruses, including adenovirus type 5 (Ad5); rubella; sendai virus; rhabdovirus; alphaviruses; and adeno-associated viruses. In one embodiment, the viral vector is an adeno-associated virus. Alternatively, a polynucleotide encoding the antibody or fusion polypeptide could be delivered as DNA or RNA to the subject for in vivo expression of the antibody or fusion polypeptide.

Suitable host cells for expression of a polypeptide of interest (e.g., antibody of fusion polypeptide described herein) include prokaryotes, yeast, insect or higher eukaryotic cells under the control of appropriate promoters. Prokaryotes include gram negative or gram positive organisms, for example *E. coli* or bacilli. Higher eukaryotic cells include established cell lines of mammalian origin. Cell-free translation systems could also be employed. Appropriate cloning and expression vectors for use with bacterial, fungal, yeast, and mammalian cellular hosts are described by Pouwels et al. (Cloning Vectors: A Laboratory Manual, Elsevier, N.Y., 1985), the relevant disclosure of which is hereby incorporated by reference. Additional information regarding methods of protein production, including antibody production, can be found, e.g., in U.S. Patent Publication No. 2008/0187954, U.S. Pat. Nos. 6,413,746 and 6,660,501, and International Patent Publication No. WO 04009823, each of which is hereby incorporated by reference herein in its entirety.

Various mammalian or insect cell culture systems are also advantageously employed to express recombinant protein. Expression of recombinant proteins in mammalian cells can be performed because such proteins are generally correctly folded, appropriately modified and completely functional.

Examples of suitable mammalian host cell lines include but are not limited to CHO, VERO, BHK, Hela, MDCK, HEK 293, NIH 3T3, W138, BT483, Hs578T, HTB2, BT20 and T47D, NS0 (a murine myeloma cell line that does not endogenously produce any immunoglobulin chains), CRL7030, COS (e.g., COS1 or COS), PER.C6, VERO, HsS78Bst, HEK-293T, HepG2, SP210, R1.1, B-W, L-M, BSC1, BSC40, YB/20, BMT10 and HsS78Bst cells. Mammalian expression vectors can comprise nontranscribed elements such as an origin of replication, a suitable promoter and enhancer linked to the gene to be expressed, and other 5' or 3' flanking nontranscribed sequences, and 5' or 3' nontranslated sequences, such as necessary ribosome binding sites, a polyadenylation site, splice donor and acceptor sites, and transcriptional termination sequences. Baculovirus systems for production of heterologous proteins in insect cells are reviewed by Luckow and Summers, Bio/Technology 6:47 (1988).

The proteins produced by a transformed host can be purified according to any suitable method. Such standard methods include chromatography (e.g., ion exchange, affinity and sizing column chromatography), centrifugation, differential solubility, or by any other standard technique for protein purification. Affinity tags such as hexahistidine, maltose binding domain, influenza coat sequence and glutathione-S-transferase can be attached to the protein to allow easy purification by passage over an appropriate affinity column. Isolated proteins can also be physically characterized using such techniques as proteolysis, nuclear magnetic resonance and x-ray crystallography.

For example, supernatants from systems which secrete recombinant protein into culture media can be first concentrated using a commercially available protein concentration filter, for example, an Amicon or Millipore Pellicon ultrafiltration unit. Following the concentration step, the concentrate can be applied to a suitable purification matrix. Alternatively, an anion exchange resin can be employed, for example, a matrix or substrate having pendant diethylaminoethyl (DEAE) groups. The matrices can be acrylamide, agarose, dextran, cellulose or other types commonly employed in protein purification. Alternatively, a cation exchange step can be employed. Suitable cation exchangers include various insoluble matrices comprising sulfopropyl or carboxymethyl groups. Finally, one or more reversed-phase high performance liquid chromatography (RP-HPLC) steps employing hydrophobic RP-HPLC media, e.g., silica gel having pendant methyl or other aliphatic groups, can be employed to further an agent. Some or all of the foregoing purification steps, in various combinations, can also be employed to provide a homogeneous recombinant protein.

Recombinant protein produced in bacterial culture can be isolated, for example, by initial extraction from cell pellets, followed by one or more concentration, salting-out, aqueous ion exchange or size exclusion chromatography steps. High performance liquid chromatography (HPLC) can be employed for final purification steps. Microbial cells employed in expression of a recombinant protein can be disrupted by any convenient method, including freeze-thaw cycling, sonication, mechanical disruption, or use of cell lysing agents.

Methods known in the art for purifying antibodies and other proteins also include, for example, those described in U.S. Patent Publication Nos. 2008/0312425, 2008/0177048, and 2009/0187005, each of which is hereby incorporated by reference herein in its entirety.

In specific embodiments, an antibody or fusion polypeptide described herein is isolated or purified. Generally, an isolated antibody or fusion polypeptide is one that is substantially free of other antibodies with different antigenic specificities than the isolated antibody. For example, in a particular embodiment, a preparation of an antibody or fusion polypeptide described herein is substantially free of cellular material and/or chemical precursors. The language "substantially free of cellular material" includes preparations of an antibody or fusion polypeptide in which the antibody or fusion polypeptide is separated from cellular components of the cells from which it is isolated or recombinantly produced. Thus, an antibody or fusion polypeptide that is substantially free of cellular material includes preparations of antibody or fusion polypeptide having less than about 30%, 20%, 10%, 5%, 2%, 1%, 0.5%, or 0.1% (by dry weight) of heterologous protein (also referred to herein as a "contaminating protein") and/or variants of an antibody or fusion polypeptide, for example, different post-translational modified forms of an antibody or fusion polypeptide. When the polypeptide (e.g., antibody of fusion polypeptide described herein) is recombinantly produced, it is also generally substantially free of culture medium, i.e., culture medium represents less than about 20%, 10%, 2%, 1%, 0.5%, or 0.1% of the volume of the protein preparation. When the polypeptide (e.g., antibody of fusion polypeptide described herein) is produced by chemical synthesis, it is generally substantially free of chemical precursors or other chemicals, i.e., it is separated from chemical precursors or other chemicals which are involved in the synthesis of the protein. Accordingly, such preparations of the polypeptide (e.g., antibody of fusion polypeptide described herein) have less than about 30%, 20%, 10%, or 5% (by dry weight) of chemical precursors or compounds other than the polypeptidelypetide of interest. In one embodiment, antibodies described herein are isolated or purified. In one embodiment, fusion polypeptides described herein are isolated or purified.

VI. Pharmaceutical Compositions

Compositions comprising the antibodies or antigen-binding fragments described herein or fusion polypeptides (e.g., fusion polypeptide comprising a VH CDR3 of NC-Cow1) are also provided. In one embodiment, a composition comprises a broadly neutralizing anti-Env antibody (e.g., bovine antibody or humanized bovine antibody) or antigen-binding fragment described herein. In one embodiment, a composition comprises a fusion polypeptide comprising a VH CDR3 of NC-Cow1.

Further provided herein are compositions comprising a polynucleotide or polynucleotides encoding the antibodies or antigen-binding fragments described herein or fusion polypeptides described herein. In one embodiment, the polynucleotide comprises mRNA.

In one embodiment, a composition described herein comprises bovine serum, colostrum, or milk, wherein the serum, colostrum, or milk is produced according to a method described herein. In one embodiment, the composition is a lyophilized composition. In one embodiment, the composition is formulated for topical administration, and in certain embodiments the composition is formulated for vaginal or rectal administration.

In one embodiment, a composition described herein comprises a broadly neutralizing bovine polyclonal anti-Env antibody. In one embodiment, the antibody comprises an F(ab) or F(ab')2 fragment. In one embodiment, the composition is a lyophilized composition. In one embodiment, the formulation is a pharmaceutical composition. In one embodiment, the composition is formulated for topical administration, and in certain embodiments the composition is formulated for vaginal or rectal administration.

In certain aspects, provided herein is a pharmaceutical composition comprising an antibody or a fusion polypeptide described herein and a pharmaceutically acceptable excipient. In one embodiment, the antibody is monoclonal. In one embodiment, the antibody is polyclonal. In one embodiment, the fusion polypeptide comprises a VH CDR3 of NC-Cow1. In one embodiment, the composition is formulated for topical administration, and in certain embodiments the composition is formulated for vaginal or rectal administration.

In another embodiment, the disclosure provides a pharmaceutical composition comprising an antibody described herein (e.g., broadly neutralizing bovine antibody or humanized bovine antibody) or a fusion polypeptide described herein. Such compositions are intended for prevention and treatment of HIV infection.

In further embodiments of the present disclosure, a composition comprising the antibody described herein or the fusion polypeptide described herein can additionally be combined with other compositions for the treatment of HIV infection or the prevention of HIV transmission.

In some embodiments, an antibody or fusion polypeptide described herein may be administered within a pharmaceutically-acceptable diluent, carrier, or excipient, in unit dose form. Conventional pharmaceutical practice may be employed to provide suitable formulations or compositions to administer to individuals being treated for HIV infection. In one embodiment, the administration is prophylactic. Any appropriate route of administration may be employed, for example, administration may be parenteral, intravenous, intra-arterial, subcutaneous, intramuscular, intraperitoneal, intranasal, aerosol, suppository, oral administration, vaginally, or anally.

The pharmaceutical compositions described herein are prepared in a manner known per se, for example, by means of conventional dissolving, lyophilizing, mixing, granulating or confectioning processes. The pharmaceutical compositions may be formulated according to conventional pharmaceutical practice (see for example, in Remington: The Science and Practice of Pharmacy (21st ed.), ed. A. R. Gennaro, 2005, Lippincott Williams & Wilkins, Philadelphia, PA, and Encyclopedia of Pharmaceutical Technology, eds. J. Swarbrick and J. C. Boylan, 2013, Marcel Dekker, New York, NY).

The injection compositions are prepared in customary manner under sterile conditions; the same applies also to introducing the compositions into ampoules or vials and sealing the containers.

Pharmaceutical compositions according to the invention may be, for example, in unit dose form, such as in the form of ampoules, vials, suppositories, tablets, pills, or capsules. The formulations can be administered to human individuals in therapeutically or prophylactic effective amounts (e.g., amounts which prevent, eliminate, or reduce a pathological condition) to provide therapy for a disease or condition. The preferred dosage of therapeutic agent to be administered is likely to depend on such variables as the type and extent of the disorder, the overall health status of the particular patient, the formulation of the compound excipients, and its route of administration.

In certain embodiments, the compositions described herein can be formulated for topical administration, and in certain embodiments the composition is formulated for vaginal or rectal administration. The composition may be formulated as a gel, or formulated as a topical cream, ointment, lotion or foam formulation. Useful formulations are known in the art, for example, as disclosed in U.S. Patent Appl. Pub. No. 20130022619, which is incorporated by reference herein in its entirety for all purposes.

In certain embodiments, the composition may further comprise a pharmaceutically acceptable excipient, a lubricant, or an antiviral agent.

The topical formulations of the present invention can be used to prevent HIV infection in a human, or to inhibit transmission of the HIV virus from an infected human to another human. The topical formulations of the present invention can inhibit the growth or replication of HIV. The topical formulations are useful in the prophylactic treatment of humans who are at risk for HIV infection. The topical formulations also can be used to treat objects or materials, such as contraceptive devices (for example condoms or intrauterine devices), medical equipment, supplies, or fluids, including biological fluids, such as blood, blood products, and tissues, to prevent or inhibit viral infection of a human. Such topical formulations also are useful to prevent transmission, such as sexual transmission of viral infections, e.g., HIV, which is the primary way in which HIV is transmitted globally. The methods of prevention or inhibition or retardation of transmission of viral infection, e.g., HIV infection, in accordance with the present invention, comprise vaginal, rectal, penile or other topical treatment with an antiviral effective amount of a topical preparation of the present invention, alone or in combination with another antiviral compound as described herein.

In one embodiment the composition is in the form of a cream, lotion, gel, or foam that is applied to the affected skin or epithelial cavity, and preferably spread over the entire skin or epithelial surface which is at risk of contact with bodily fluids. Such formulations, which are suitable for vaginal or rectal administration, may be present as aqueous or oily suspensions, solutions or emulsions (liquid formulations) containing in addition to the active ingredient, such carriers as are known in the art to be appropriate. These formulations are useful to protect not only against sexual transmission of HIV, but also to prevent infection of a baby during passage through the birth canal. Thus the vaginal administration can take place prior to sexual intercourse, during sexual intercourse, and immediately prior to childbirth.

As a vaginal formulation, the active ingredient may be used in conjunction with a spermicide and may be employed with a condom, diaphragm, sponge or other contraceptive device. Examples of suitable spermicides include nonylphenoxypolyoxyethylene glycol (nonoxynol 9), benzethonium chloride, and chlorindanol. Suitably, the pH of the composition is 4.5 to 8.5. Vaginal compositions preferably have a pH of 4.5 to 6, most preferably about 5.

Vaginal formulations include suppositories (for example, gel-covered creams), tablets and films. The suppositories can be administered by insertion with an applicator using methods well known in the art.

Buccal formulations include creams, ointments, gels, tablets or films that comprise ingredients that are safe when administered via the mouth cavity. Buccal formulations can also comprise a taste-masking or flavoring agent.

The present compositions may be associated with a contraceptive device or article, such as a vaginal ring device, an intrauterine device (IUD), vaginal diaphragm, vaginal sponge, pessary, condom, etc.

In one embodiment the compositions described herein are used in conjunction with condoms, to enhance the risk-reducing effectiveness of condoms and provide maximum protection for users. The composition can either be coated onto condoms during manufacture, and enclosed within conventional watertight plastic or foil packages that contain one condom per package, or it can be manually applied by a user to either the inside or the outside of a condom, immediately before use. As used herein, “condom” refers to a barrier device which is used to provide a watertight physical barrier between male and female genitalia during sexual intercourse, and which is removed after intercourse. This term includes conventional condoms that cover the penis; it also includes so-called “female condoms” which are inserted into the vaginal cavity prior to intercourse.

In another embodiment a composition described herein is in the form of an intra-vaginal pill, an intra-rectal pill, or a suppository. The suppository or pill should be inserted into the vaginal or rectal cavity in a manner that permits the suppository or pill, as it dissolves or erodes, to coat the vaginal or rectal walls with a prophylactic layer of the anti-Env agent (e.g., a broadly neutralizing antibody or fusion polypeptide described herein).

In certain embodiments, the composition may further comprise a pharmaceutically acceptable excipient, a lubricant, or an antiviral agent.

Compositions used in the methods of this invention may also comprise other active agents, such as another agent to prevent HIV infection, and agents that protect individuals from conception and other sexually transmitted diseases. Thus, in another embodiment the compositions used in this invention further comprise a second anti-Env agent, a virucide effective against viral infections other than HIV, and/or a spermicide.

The compositions used in this invention may also contain a lubricant that facilitates application of the composition to the desired areas of skin and epithelial tissue, and reduces friction during sexual intercourse. In the case of a pill or suppository, the lubricant can be applied to the exterior of the dosage form to facilitate insertion.

In the cream or ointment embodiments of the present invention, the topical formulation comprises one or more lubricants. The gels and foams of the present invention optionally can include one or more lubricants.

Non-limiting examples of useful lubricants include cetyl esters wax, hydrogenated vegetable oil, magnesium stearate, methyl stearate, mineral oil, polyoxyethylene-polyoxypropylene copolymer, polyethylene glycol, polyvinyl alcohol, sodium lauryl sulfate, white wax, or mixtures of two or more of the above.

The gel formulations of the present invention comprise one or more gelling agents. Non-limiting examples of useful gelling agents include carboxylic acid polymers including acrylic acid polymers crosslinked with cross links such as allyl ethers of sucrose (e.g. carbomer brand thickeners), cetostearyl alcohol, hydroxymethyl cellulose, polyoxyethylene-polyoxypropylene copolymer, sodium carboxymethylcellulose, polyvinyl pyrrolidone, or mixtures of two or more thereof.

VII. Uses and Methods

Therapeutic Uses and Methods

In one aspect, provided herein is a method of treating HIV or inhibiting transmission of HIV. In one embodiment, the method of inhibiting transmission of HIV comprises generating a broadly neutralizing anti-HIV antibody by immunizing a bovine with an antigenic composition comprising a well-ordered Env trimer polypeptide to produce a broadly neutralizing anti-HIV antibody; and administering the broadly neutralizing anti-HIV antibody to a subject.

In one embodiment, the method of inhibiting transmission of HIV comprises administering an effective amount of a broadly neutralizing anti-HIV antibody disclosed herein to a subject in need thereof. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject at risk of being exposed to HIV is a newborn.

In one aspect, provided herein is a method of treating HIV or inhibiting transmission of HIV, which comprises forming a bovine colostrum, serum, or milk comprising a broadly neutralizing anti-HIV antibody by immunizing a bovine with an antigenic composition comprising a well-ordered Env trimer polypeptide to produce a broadly neutralizing anti-HIV antibody; and administering the colostrum, serum, or milk to a subject.

In one embodiment, a method of inhibiting transmission of HIV described herein comprises administering to a subject in need thereof an effective amount of a bovine colostrum, serum, or milk disclosed herein comprising a broadly neutralizing anti-HIV antibody. In one embodiment, a method of treating HIV described herein comprises administering to a subject in need thereof a therapeutically effective amount of a bovine colostrum, serum, or milk disclosed herein comprising a broadly neutralizing anti-HIV antibody. In one embodiment, the subject is at risk of being exposed to HIV. In one embodiment, the subject at risk of being exposed to HIV is a health care worker, a sexual partner of an HIV infected individual, or a sex worker. In one embodiment, the subject at risk of being exposed to HIV is a newborn. In one aspect, provided herein is bovine colostrum, serum, or milk for inhibiting transmission of HIV. In one aspect, provided herein is bovine colostrum, serum, or milk for treating HIV.

In one aspect, provided herein is a method of treating HIV or inhibiting transmission of HIV comprising administering to a subject in need thereof a therapeutically sufficient amount of a fusion polypeptide (e.g., fusion polypeptide comprising a VH CDR3 of NC-Cow1) described herein. In one aspect, provided herein is a fusion polypeptide (e.g., fusion polypeptide comprising a VH CDR3 of NC-Cow1) for treating HIV.

In one aspect, provided herein is a method of reducing the risk of a subject becoming infected with HIV comprising administering to the subject in need thereof an effective amount of a broadly neutralizing anti-HIV antibody disclosed herein, a composition disclosed herein, or a fusion polypeptide disclosed herein. In one embodiment, the subject is administered a broadly neutralizing antibody disclosed herein. In one embodiment, the subject is administered a composition comprising a bovine colostrum, serum, or milk disclosed herein comprising a broadly neutralizing antibody. In one embodiment, the subject is administered a fusion polypeptide disclosed herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject at risk of being exposed to HIV is a newborn. In one aspect, provided herein is a composition comprising a bovine colostrum, serum, or milk comprising a broadly neutralizing antibody for reducing the risk of a subject becoming infected with HIV.

In one aspect, provided herein is a method for passively immunizing a subject comprising administering to the subject in need thereof an effective amount of a broadly neutralizing anti-HIV antibody disclosed herein, a composition disclosed herein, or a fusion polypeptide disclosed herein. In one embodiment, the subject is administered a broadly neutralizing antibody disclosed herein. In one embodiment, the subject is administered a composition comprising a bovine colostrum, serum, or milk disclosed herein comprising a broadly neutralizing antibody. In one embodiment, the subject is administered a fusion polypeptide disclosed herein. In one embodiment, the subject has been exposed to HIV. In one embodiment, the subject is at risk of being exposed to HIV. In one embodiment, the subject at risk of being exposed to HIV is a health care worker, a sexual partner of an HIV infected individual, or a sex worker. In one embodiment, the subject at risk of being exposed to HIV is a newborn. In one aspect, provided herein is a broadly neutralizing anti-HIV antibody, a composition, or a fusion polypeptide for passively immunizing a subject.

Further provided herein is a method of neutralizing an HIV virus comprising contacting the virus with an effective amount of an antibody or fusion polypeptide described herein. In one embodiment, the virus is comprised by a composition, for example, a fluid, including a biological fluid, such as blood or blood product. In certain embodiments, the method comprises adding an antibody or fusion polypeptide described herein to a composition comprising HIV at a sufficient amount tor concentration to neutralize the HIV.

In one embodiment of a method described herein, the antibody can be a polyclonal antibody, chimeric antibody, humanized antibody, or a monoclonal antibody described herein. In one embodiment, the antibody is a full antibody, an F(ab) fragment, or an F(ab)2 fragment described herein. In a specific embodiment, the antibody is a chimeric monoclonal antibody described herein. In a specific embodiment, the antibody is a monoclonal humanized antibody described herein. In a specific embodiment, the antibody is a polyclonal F(ab) described herein. In a specific embodiment, the antibody is a polyclonal F(ab')2 fragment described herein.

In one embodiment, a method of preventing HIV infection provided herein comprises administering to a subject in need thereof a therapeutically sufficient amount of an antibody described herein, a composition described herein, a pharmaceutical composition described herein, an isolated polynucleotide described herein, a fusion polypeptide described herein, or a recombinant virus described herein.

In one embodiment, a method of treating HIV/AIDS provided herein comprises administering to a subject in need thereof a therapeutically sufficient amount of an antibody described herein, a composition described herein, a pharmaceutical composition described herein, an isolated polynucleotide described herein, a fusion polypeptide described herein, or a recombinant virus described herein. In one embodiment, a method of treating HIV/AIDS comprises administering an antibody described herein. In one embodiment, a method of treating HIV/AIDS comprises administering a composition comprising a bovine colostrum, serum, or milk disclosed herein comprising a broadly neutralizing antibody. In one embodiment, a method of treating HIV/AIDS comprises administering a composition described herein. In one embodiment, a method of treating HIV/AIDS comprises administering a pharmaceutical composition described herein. In one embodiment, a method of treating HIV/AIDS comprises administering an isolated polynucleotide described herein. In one embodiment, a method of treating HIV/AIDS comprises administering a fusion polypeptide described herein. In one embodiment, a method of treating HIV/AIDS comprises administering a recombinant virus described herein. In one aspect, provided herein is an antibody, a composition, a pharmaceutical composition, an isolated polynucleotide, a fusion polypeptide, or a recombinant virus for treating HIV/AIDS.

In one embodiment, the administering to the subject is by at least one mode selected from oral, parenteral, subcutaneous, intramuscular, intravenous, vaginal, rectal, buccal, sublingual, and transdermal In one embodiment, a method of treatment described herein further comprises administering at least one additional therapeutic agent. In one embodiment, the additional therapeutic agent is an antiretroviral therapy (ART) agent, immunomodulator, or a second antibody. In one embodiment, the additional therapeutic agent is a second broadly neutralizing antibody. In one embodiment, the additional therapeutic agent is a second and third broadly neutralizing antibody. In one embodiment, the second (and optionally third) broadly neutralizing antibody binds to a different epitope class than the antibody disclosed herein. In one embodiment, the second (and optionally third) broadly neutralizing antibody is a VRC01 class broadly neutralizing anti-Env antibody. In one embodiment, the second (and optionally third) broadly neutralizing antibody is a CD4bs class broadly neutralizing anti-Env antibody. In one embodiment, the second (and optionally third) broadly neutralizing antibody is a CD4bs epitope specific broadly neutralizing anti-Env antibody. In one embodiment, the second (and optionally third) broadly neutralizing antibody is a V3 glycan epitope specific broadly neutralizing anti-Env antibody. In one embodiment, the second (and optionally third) broadly neutralizing antibody is a V2-apex epitope specific broadly neutralizing anti-Env antibody.

In certain embodiments, the subject is at risk for exposure to HIV. In some embodiments, the subject is infected with HIV. In some embodiments, the subject is diagnosed with AIDS. In certain embodiments, the subject at risk for exposure to HIV is a health care worker. In certain embodiments, the subject at risk for exposure to HIV is a sex worker. In certain embodiments, the subject at risk for exposure to HIV is a sexual partner of an HIV infected individual. In certain embodiments, the subject at risk for exposure to HIV is a newborn.

In certain embodiments, the subject is treated with a composition comprising a broadly neutralizing antibody described herein, wherein the composition comprises a milk, colostrum, and/or serum described herein.

The invention also features methods of blocking HIV infection in a subject (e.g., a human) at risk of HIV transmission. For example, in one aspect, the subject may be a fetus of an HIV-infected pregnant female and the method includes administering to the HIV-infected pregnant female a broadly neutralizing antibody or fusion polypeptide described herein, thereby blocking the HIV infection in the fetus. In other instances, the subject is a newborn having an HIV-infected mother, a subject at risk of HIV transmission following a needle stick injury, or a subject at risk of HIV transmission following a sexual exposure to an HIV-infected individual.

In instances when the subject is a newborn having an HIV-infected mother, the newborn can be administered a broadly neutralizing antibody or fusion polypeptide described herein peripartum and/or postpartum, for example, prior to, during, and/or following breastfeeding from the HIV-infected mother, in order to block an HIV infection in the newborn.

In instances when the subject is at risk of HIV transmission following a sexual exposure to an HIV-infected individual, the subject can be administered a broadly neutralizing antibody or fusion polypeptide described herein following the sexual exposure in order to block an HIV infection in the subject.

In some embodiments, a broadly neutralizing antibody or fusion polypeptide described herein can be used as a microbicides to prevent mucosal HIV acquisition. In some embodiments, a broadly neutralizing antibody or fusion polypeptide described herein is used to prevent vaginal or rectal acquisition of HIV. In some embodiments, a broadly neutralizing antibody or fusion polypeptide described herein can be used as a microbicides to reduce the likelihood of mucosal HIV acquisition. In some embodiments, a broadly neutralizing antibody or fusion polypeptide described herein is used to reduce the likelihood of vaginal or rectal acquisition of HIV.

In any of the methods described above, further administration of ART and/or an immunomodulator is contemplated. For example, the ART and/or immunomodulator can be administered in conjunction with, prior to, concurrently with, subsequent to, or within the context of a treatment regimen that includes administration of a broadly neutralizing antibody or fusion polypeptide described herein.

A broadly neutralizing antibody or fusion polypeptide described herein, or a composition described herein can be delivered to a subject by a variety of routes, such as oral, parenteral, subcutaneous, intravenous, intradermal, transdermal, intranasal, vaginally, or anally. In one embodiment, the antibody or composition is administered by an intravenous, vaginally, or anally.

The amount of a broadly neutralizing antibody or fusion polypeptide described herein, or a composition described herein which will be effective in the treatment and/or prevention of a condition will depend on the nature of the disease, and can be determined by standard clinical techniques.

The precise dose to be employed in a composition will also depend on the route of administration, and the seriousness of the disease, and should be decided according to the judgment of the practitioner and each subject's circumstances. For example, effective doses may also vary depending upon means of administration, target site, physiological state of the patient (including age, body weight and health), whether the patient is human or an animal, other medications administered, or whether treatment is prophylactic or therapeutic. Usually, the patient is a human but non-human mammals including transgenic mammals can also be treated. Treatment dosages are optimally titrated to optimize safety and efficacy.

In certain embodiments, an in vitro assay is employed to help identify optimal dosage ranges. Effective doses may be extrapolated from dose response curves derived from in vitro or animal model test systems.

Detection & Diagnostic Uses

An anti-Env antibody or fusion polypeptide (e.g., fusion polypeptide comprising a VH CDR3 of NC-Cow1) described herein can be used to detect HIV and/or assay HIV levels in a biological sample using classical immunohistological methods known to those of skill in the art, including immunoassays, such as the enzyme linked immunosorbent assay (ELISA), immunoprecipitation, or Western blotting. An anti-Env antibody or fusion polypeptide (e.g., fusion polypeptide comprising a VH CDR3 of NC-Cow1) described herein can also be used as an imaging agent, for example, a tissue-penetrating imaging agent. In one embodiment, an anti-Env antibody or fusion polypeptide described herein is conjugated with a detectable label. Suitable assay labels are known in the art and include enzyme labels, such as, glucose oxidase; radioisotopes, such as iodine ($^{125}I$, $^{121}I$), carbon ($^{14}C$), sulfur ($^{35}S$), tritium ($^{3}H$), indium ($^{121}In$), and technetium ($^{99}Tc$); luminescent labels, such as luminol; and fluorescent labels, such as fluorescein and rhodamine, and biotin. Such labels can be used to label an antibody or fusion polypeptide described herein. Alternatively, a second antibody that recognizes an anti-Env antibody or fusion polypeptide described herein can be labeled and used in combination with an anti-HIV antibody or fusion polypeptide to detect HIV levels.

As used herein, the term "biological sample" refers to any biological sample obtained from a subject, cell line, tissue, or other source potentially comprising HIV. Methods for obtaining tissue biopsies and body fluids from animals (e.g., humans) are well known in the art.

In another embodiment, an anti-Env antibody or fusion polypeptide (e.g., fusion polypeptide comprising a VH CDR3 of NC-Cow1) can be used to detect levels of HIV, which levels can then be linked to certain disease symptoms. Anti-Env antibodies or fusion polypeptides described herein may carry a detectable or functional label. Anti-Env antibodies described herein can carry a fluorescence label. Exemplary fluorescence labels include, for example, reactive and conjugated probes, e.g., Aminocoumarin, Fluorescein and Texas red, Alexa Fluor dyes, Cy dyes and DyLight dyes. An anti-Env antibody can carry a radioactive label, such as the isotopes $^{3}H$, $^{14}C$, $^{32}P$, $^{35}S$, $^{36}Cl$, $^{51}Cr$, $^{57}Co$, $^{58}Co$, $^{59}Fe$, $^{67}Cu$, $^{90}Y$, $^{99}Tc$, $^{111}In$, $^{117}Lu$, $^{121}I$, $^{124}I$, $^{125}I$, $^{131}I$, $^{198}Au$, $^{211}At$, $^{213}Bi$, $^{225}Ac$ and $^{186}Re$. When radioactive labels are used, currently available counting procedures known in the art may be utilized to identify and quantitate the specific binding of anti-Env antibody or fusion polypeptide to HIV. In the instance where the label is an enzyme, detection may be accomplished by any of the presently utilized colorimetric, spectrophotometric, fluorospectrophotometric, amperometric or gasometric techniques as known in the art. This can be achieved by contacting a sample or a control sample with an anti-Env antibody or fusion polypeptide under conditions that allow for the formation of a complex between the antibody or fusion polypeptide and HIV. Any complexes formed between the antibody or fusion polypeptide and HIV are detected and compared in the sample and the control. The antibodies or fusion polypeptides described herein can also be used to purify HIV via immunoaffinity purification.

In some aspects, provided herein are methods for in vitro detecting HIV in a sample, comprising contacting said sample with an antibody described herein. In some aspects, provided herein is the use of an antibody described herein, for in vitro detecting HIV in a sample. In one aspect, provided herein is an antibody or pharmaceutical composition described herein for use in the detection of HIV in a subject. In one aspect, provided herein is an antibody or pharmaceutical composition described herein for use as a diagnostic. In one preferred embodiment, the antibody comprises a detectable label. In one embodiment, the subject is a human. In one embodiment, the method of detecting HIV in a sample comprises contacting the sample with an antibody described herein.

In some embodiments, the present disclosure provides methods of purifying HIV from a sample. In some embodiments, the method of purifying HIV from a sample comprises contacting the sample with an antibody described herein under conditions that allow the antibody to bind to HIV. In some embodiments, the antibody comprises a tag, for example, hexa-histidine tag or FLAG-tag to facilitate the purification of HIV.

In some aspects, provided herein are methods for in vitro detecting HIV in a sample, comprising contacting said sample with a fusion polypeptide described herein. In some aspects, provided herein is the use of a fusion polypeptide described herein for in vitro detecting HIV in a sample. In one aspect, provided herein is a fusion polypeptide or pharmaceutical composition described herein for use in the detection of HIV in a subject. In one aspect, provided herein is a fusion polypeptide or pharmaceutical composition described herein for use as a diagnostic. In one preferred embodiment, the fusion polypeptide comprises a detectable label. In one embodiment, the subject is a human. In one embodiment, the method of detecting HIV in a sample comprises contacting the sample with a fusion polypeptide described herein.

In some embodiments, the present disclosure provides methods of purifying HIV from a sample. In some embodiments, the method of purifying HIV from a sample comprises contacting the sample with a fusion polypeptide described herein under conditions that allow the antibody to bind to HIV. In some embodiments, the fusion polypeptide comprises a tag, for example, hexa-histidine tag or FLAG-tag to facilitate the purification of HIV.

VIII. Kits

Provided herein are kits comprising one or more antibodies described herein or one or more fusion polypeptides (e.g., fusion polypeptides comprising H CDR3 of NC-Cow1) described herein. In some embodiments, a pharmaceutical pack or kit described herein comprises one or more containers filled with one or more of the ingredients of the pharmaceutical compositions described herein, such as one or more antibodies or fusion polypeptides described herein. In some embodiments, a kit contains an antibody or fusion polypeptide described herein or a pharmaceutical composition described herein, and a second prophylactic or therapeutic agent used in the treatment or prevention of HIV. In one embodiment, the second agent is an antiretroviral agent. In one embodiment, the second agent is an immunomodulator. In some embodiments, a kit contains an antibody or fusion polypeptide described herein or a pharmaceutical composition described herein, and a reagent used in the detection of HIV. In one embodiment, the detection reagent comprises DNA primers for the detection of HIV. Optionally associated with such container(s) can be a notice in the form prescribed by a governmental agency regulating the manufacture, use or sale of pharmaceuticals or biological products, which notice reflects approval by the agency of manufacture, use or sale for human administration.

In one embodiment, a kit described herein comprises an antibody described herein or a pharmaceutical composition described herein and a) a detection reagent, b) an HIV antigen, c) a notice that reflects approval for use or sale for human administration, or d) any combination thereof.

In one embodiment, a kit described herein comprises a fusion polypeptide described herein or a pharmaceutical composition described herein and a) a detection reagent, b) an HIV antigen, c) a notice that reflects approval for use or sale for human administration, or d) any combination thereof.

IX. Further Embodiments

In some embodiments, the disclosure provides:

[1.] a method of producing a broadly neutralizing anti-Env antibody, comprising immunizing a bovine by administering at least one dose of an antigenic composition comprising an HIV specific antigen to produce a broadly neutralizing anti-Env antibody, wherein the HIV specific antigen comprises a well-ordered Env trimer polypeptide or a polynucleotide encoding a well-ordered Env trimer polypeptide;

[2.] the method of [1], wherein a virus, pseudovirus, or virus-like particle comprises the well-ordered Env trimer polypeptide;

[3.] the method of [1], wherein the well-ordered Env trimer polypeptide is an isolated polypeptide;

[4.] the method of [1] or [3], wherein the well-ordered Env trimer polypeptide comprises a SOSIP trimer;

[5.] the method of [4], wherein the SOSIP trimer comprises BG505 SOSIP;

[6.] the method of any one of [1] to [5], wherein the antigenic composition further comprises an adjuvant;

[7.] the method of any one of [1] to [6], wherein the immunizing comprises administering a priming dose and at least one booster dose of the antigenic composition;

[8.] the method of [7], comprising administering more than one booster dose of the antigenic composition;

[9.] the method of [7], wherein the priming dose and at least one booster dose comprise the same antigenic composition;

[10.] the method of [8], wherein the more than one booster doses comprise the same antigenic composition;

[11.] the method of any one of [1] to [10], wherein the HIV specific antigen is derived from a single HIV isolate;

[12.] the method of any one of [1] to [11], wherein the HIV specific antigen is derived from a BG505 HIV isolate;

[13.] the method of any one of [1] to [12], further comprising isolating from the bovine a biological sample comprising the broadly neutralizing anti-Env antibody;

[14.] the method of any one of [1] to [12], further comprising isolating from the bovine a biological sample comprising the broadly neutralizing anti-Env antibody; purifying the broadly neutralizing anti-Env antibody; processing the broadly neutralizing anti-Env antibody to prepare an F(ab) or F(ab')2 fragment; and recovering the F(ab) or F(ab')2 fragment;

[15.] the method of [13] or [14], wherein the biological sample is milk, blood, serum, colostrum, or peripheral blood mononuclear cells;

[16.] the method of [13] or [14], wherein the biological sample is milk;

[17.] the method of [13] or [14], wherein the biological sample is serum;

[18.] the method of [13] or [14], wherein the biological sample is colostrum;

[19.] the method of [13] or [14], wherein the biological sample is peripheral blood mononuclear cells;

[20.] the method of any one of [13] to [19], further comprising purifying the broadly neutralizing anti-Env antibody;

[21.] the method of any one of [1] to [12], further comprising isolating a peripheral blood mononuclear cell (PMBC) from the bovine, and cloning a polynucleotide from the PBMC that encodes a broadly neutralizing anti-Env antibody;

[22.] the method of [21], wherein the cloning the polynucleotide comprises performing single-cell RT-PCR amplification;

[23.] the method of [13] or [22], further comprising expressing the polynucleotide that encodes the broadly neutralizing anti-Env antibody in a host cell;

[24.] the method of [13] or [22], further comprising expressing the polynucleotide that encodes the broadly neutralizing anti-Env antibody in a cell-free expression system;

[25.] the method of any one of [1] to [24], wherein the bovine is a domestic cattle, bison, African buffalo, water buffalo, or yak;

[26.] the method of [25], wherein the bovine is a domestic cattle;

[27.] the method of any one of [1] to [26], wherein the bovine is pregnant;

[28.] the method of any one of [1] to [27], wherein the immunizing elicits production of polyclonal serum capable of neutralizing at least about 50%, 60%, 70%, 80%, 90%, or 100% of cross-clade HIV isolates in the 6-member indicator virus panel;

[29.] the method of any one of [1] to [27], wherein the immunizing elicits production of polyclonal serum capable of neutralizing 100% of cross-clade HIV isolates in the 6-member indicator virus panel;

[30.] the method of any one of [1] to [27], wherein the immunizing elicits production of polyclonal serum capable of neutralizing at least about 90% of cross-clade HIV isolates in the 6-member indicator virus panel;

[31.] the method of any one of [1] to [27], wherein the immunizing elicits production of polyclonal serum capable of neutralizing at least about 50%, 60%, 70%, 80%, 90%, or 100% of cross-clade HIV isolates in the 12-member indicator virus panel;

[32.] the method of any one of [1] to [27], wherein the immunizing elicits production of polyclonal serum capable of neutralizing
  a) at least about 80% of cross-clade HIV isolates in the 12-member indicator virus panel; or
  b) at least about 90% of cross-clade HIV isolates in the 12-member indicator virus panel;

[33.] the method of any one of [1] to [27], wherein the immunizing elicits production of polyclonal serum capable of neutralizing 100% of cross-clade HIV isolates in the 12-member indicator virus panel;

[34.] the method of any one of [1] to [27], wherein the immunizing elicits production of polyclonal serum capable of neutralizing at least about 50%, 60%, 70%, 80%, 90%, or 100% of cross-clade HIV isolates in the 117-member indicator virus panel;

[35.] the method of any one of [1] to [27], wherein the immunizing elicits production of polyclonal serum capable of neutralizing at least about 80% of cross-clade HIV isolates in the 117-member indicator virus panel;

[36.] the method of any one of [1] to [27], wherein the immunizing elicits production of polyclonal serum capable of neutralizing at least about 90% of cross-clade HIV isolates in the 117-member indicator virus panel;

[37.] the method of any one of [1] to [27], wherein the immunizing elicits production of polyclonal serum capable of neutralizing 100% of cross-clade HIV isolates in the 117-member indicator virus panel;

[38.] the method of any one of [28] to [37], wherein the polyclonal serum comprises an antibody capable of neutralizing the cross-clade HIV isolates with a median IC50 equal to or less than about 0.1 microg/ml, 0.05 microg/ml, 0.025 microg/ml, 0.01 microg/ml, or 0.005 microg/ml;

[39.] the method of any one of [28] to [37], wherein the polyclonal serum comprises an antibody capable of neutralizing the cross-clade HIV isolates with a median IC50 equal to or less than about 0.05 microg/ml;

[40.] the method of any one of [28] to [39], wherein the polyclonal serum is capable of neutralizing the cross-clade HIV isolates with a median ID50 of at least about 50, 100, 500, 1000, 5000, or 10000;

[41.] the method of any one of [28] to [39], wherein the polyclonal serum is capable of neutralizing the cross-clade HIV isolates with a median ID50 of at least about 500;

[42.] the method of any one of [28] to [39], wherein the polyclonal serum is capable of neutralizing the cross-clade HIV isolates with a median ID50 of at least about 1000;

[43.] the method of any one of [1] to [27], wherein the immunizing elicits production of polyclonal serum capable of neutralizing at least about 10%, 15%, 20%, 25% or 30% of cross-clade HIV isolates in the 117-member indicator virus panel with a median ID50 of at least about 1000 within less than about 3 month after administering the first dose of the antigenic composition;

[44.] the method of any one of [1] to [27], wherein the immunizing elicits production of polyclonal serum capable of neutralizing at least about 30% of cross-clade HIV isolates in the 117-member indicator virus panel with a median ID50 of at least about 1000 within less than about 3 month after administering the first dose of the antigenic composition;

[45.] the method of any one of [1] to [27], wherein the immunizing elicits production of polyclonal serum capable of neutralizing at least about 50%, 60%, 70%, 80%, or 90% of cross-clade HIV isolates in the 117-member indicator virus panel with a median ID50 of at least about 1000 within less than about 6 months, 9 months, or 12 months after administering the first dose of the antigenic composition;

[46.] the method of any one of [1] to [27], wherein the immunizing elicits production of polyclonal serum capable of neutralizing at least about 80% of cross-clade HIV isolates in the 117-member indicator virus panel with a median ID50 of at least about 500 within less than about 9 months after administering the first dose of the antigenic composition;

[47.] the method of any one of [1] to [27], wherein the immunizing elicits production of polyclonal serum capable of neutralizing at least about 70%, 80%, 90%, 95%, 97%, 98%, 99% or 100% of cross-clade HIV isolates in the 12-member indicator virus panel with a median ID50 of at least about 1000 less within than about 3 months, 6 months, 9 months, or 12 months after administering the first dose of the antigenic composition;

[48.] the method of any one of [1] to [27], wherein the immunizing elicits production of polyclonal serum capable of neutralizing at least about 90% of cross-clade HIV isolates in the 12-member indicator virus panel with a median ID50 of at least about 500 less within than about 9 months after administering the first dose of the antigenic composition;

[49.] the method of any one of [1] to [20] and [25] to [48], wherein the broadly neutralizing anti-Env antibody is polyclonal;

[50.] the method of any one of [21] to [48], wherein the broadly neutralizing anti-Env antibody is monoclonal;

[51.] the method of any one of [1] to [50], wherein the broadly neutralizing anti-Env antibody is an F(ab) fragment;

[52.] the method of any one of [1] to [50], wherein the broadly neutralizing anti-Env antibody is an F(ab')2 fragment;

[53.] a broadly neutralizing antibody that specifically binds to Env, wherein the broadly neutralizing antibody is produced by the method of any one of [1] to [52];

[54.] the antibody of [53], wherein the antibody is polyclonal;

[55.] the antibody of [53], wherein the antibody is monoclonal;

[56.] the antibody of [54] or [55], wherein the antibody is an F(ab) fragment;

[57.] the antibody of [54] or [55], wherein the antibody is an F(ab')2 fragment;

[58.] a composition comprising bovine serum, colostrum, or milk, wherein the serum, colostrum, or milk is produced according to the method of any one of [1] to [14] and [25] to [52];

[59.] a composition comprising bovine serum produced according to the method of any one of [1] to [14] and [25] to [52];

[60.] a composition comprising bovine colostrum produced according to the method of any one of [1] to [14] and [25] to [52];

[61.] a composition comprising bovine milk produced according to the method of any one of [1] to [14] and [25] to [52];

[62.] the composition of any one of [58] to [61], which is a lyophilized composition;

[63.] a bovine antibody that specifically binds to Env and is capable of neutralizing at least two cross-clade isolates of HIV;

[64.] a bovine antibody that specifically binds to Env and is capable of neutralizing at least two cross-clade isolates of HIV from clades A and B;

[65.] a bovine antibody that specifically binds to Env and is capable of neutralizing at least two cross-clade isolates of HIV from clades A and C;

[66.] a bovine antibody that specifically binds to Env and is capable of neutralizing at least two cross-clade isolates of HIV from clades B and C;

[67.] the bovine antibody of any one of [63] to [66], wherein the antibody is capable of neutralizing at least about 50%, 60%, 70%, 80%, 90%, or 100% of cross-clade HIV isolates in the 6-member indicator virus panel;

[68.] the bovine antibody of any one of [63] to [66], wherein the antibody is capable of neutralizing at least about 90% of cross-clade HIV isolates in the 6-member indicator virus panel;

[69.] the bovine antibody of any one of [63] to [66], wherein the antibody is capable of neutralizing at least about 50%, 60%, 70%, 80%, 90%, or 100% of cross-clade HIV isolates in the 12-member indicator virus panel;

[70.] the bovine antibody of any one of [63] to [66], wherein the antibody is capable of neutralizing at least about 90% of cross-clade HIV isolates in the 12-member indicator virus panel;

[71.] the bovine antibody of any one of [63] to [66], wherein the antibody is capable of neutralizing at least about 50%, 60%, 70%, 80%, 90%, or 100% of cross-clade HIV isolates in the 117-member indicator virus panel;

[72.] the bovine antibody of any one of [63] to [66], wherein the antibody is capable of neutralizing at least about 80% of cross-clade HIV isolates in the 117-member indicator virus panel;

[73.] the bovine antibody of any one of [63] to [66], wherein the antibody is capable of neutralizing at least about 90% of cross-clade HIV isolates in the 117-member indicator virus panel;

[74.] the bovine antibody of any one of [63] to [73], wherein the antibody is capable of neutralizing the cross-clade HIV isolates with a median IC50 equal to or less than about 0.1 microg/ml, 0.05 microg/ml, 0.025 microg/ml, 0.01 microg/ml, or 0.005 microg/ml;

[75.] the bovine antibody of any one of [63] to [73], wherein the antibody is capable of neutralizing the cross-clade HIV isolates with a median IC50 equal to or less than about 0.05 microg/ml;

[76.] the bovine antibody of any one of [63] to [75], wherein the antibody is capable of neutralizing the cross-clade HIV isolates with a median ID50 of at least about 50, 100, 500, 1000, 5000, or 10000;

[77.] the bovine antibody of any one of [63] to [75], wherein the antibody is capable of neutralizing the cross-clade HIV isolates with a median ID50 of at least about 500;

[78.] the bovine antibody of any one of [63] to [75], wherein the antibody is capable of neutralizing the cross-clade HIV isolates with a median ID50 of at least about 1000;

[79.] the antibody of any one of [63] to [78], wherein the bovine is a domestic cattle, bison, African buffalo, water buffalo, or yak;

[80.] the antibody of [79], wherein the bovine is a domestic cattle;

[81.] the antibody of any one of [63] to [80], wherein the antibody is an F(ab) fragment;

[82.] the antibody of any one of [63] to [80], wherein the antibody is an F(ab')2 fragment;

[83.] the antibody of any one of [63] to [82], wherein the antibody is produced by a method according to any one of [1] to [35];

[84.] the antibody of any one of [63] to [83], wherein the antibody is a polyclonal antibody;

[85.] the antibody of any one of [63] to [83], wherein the antibody is a monoclonal antibody;

[86.] the antibody of [85], wherein the antibody is a recombinant antibody, a chimeric antibody, a humanized antibody, an antibody fragment, a bispecific antibody, or a trispecific antibody;

[87.] the antibody of [85], wherein the antibody is a chimeric antibody;

[88.] the antibody of [85], wherein the antibody is a humanized antibody;

[89.] the antibody of [85], wherein the antibody is an antibody fragment;

[90.] the antibody of [85], wherein the antibody is a bispecific antibody;

[91.] the antibody of [85], wherein the antibody is a trispecific antibody;

[92.] a composition comprising the bovine antibody of any one of [63] to [91];

[93.] the composition of [92], which is a lyophilized composition;

[94.] the composition of [92] or [93], which is a pharmaceutical composition further comprising a pharmaceutical excipient;

[95.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[96.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[97.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[98.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10;

[99.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to the VH CDR3 of NC-Cow1, NC-Cow7, NC-Cow8, NC-Cow9, or NC-Cow10;

[100.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to the VH CDR3 of NC-Cow1, NC-Cow7, NC-Cow8, NC-Cow9, or NC-Cow10;

[101.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3, 13, 23, 33, 43, 53, 63, 73, 83, or 93;

[102.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to SEQ ID NO: 3, 13, 23, 33, 43, 53, 63, 73, 83, or 93;

[103.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to SEQ ID NO: 3, 13, 23, 33, 43, 53, 63, 73, 83, or 93;

[104.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 227-238;

[105.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to SEQ ID NO: 227-238;

[106.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to SEQ ID NO: 227-238;

[107.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to the VH CDR3 of NC-Cow1;

[108.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to the VH CDR3 of NC-Cow1;

[109.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to the VH CDR3 of NC-Cow1;

[110.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90%, 95%, 97%, 98%, 99% or 100% identical to SEQ ID NO: 3 or SEQ ID NO: 121;

[111.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to SEQ ID NO: 3;

[112.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is at least about 90% identical to SEQ ID NO: 121;

[113.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to SEQ ID NO: 3;

[114.] an isolated monoclonal antibody that specifically binds to Env and comprises a VH CDR1, VH CDR2, VH CDR3, VL CDR1, VL CDR2, and VL CDR3, wherein the VH CDR3 comprises an amino acid sequence that is identical to SEQ ID NO: 121;

[115.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10 comprising 0, 1, 2, 3, 4, or 5 substitutions, insertions, or deletions;

[116.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10 comprising 0, 1, 2, 3, 4, or 5 substitutions;

[117.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow7, NC-Cow8, NC-Cow9, or NC-Cow10 comprising 0, 1, 2, 3, 4, or 5 substitutions, insertions, or deletions;

[118.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1, NC-Cow7, NC-Cow8, NC-Cow9, or NC-Cow10 comprising 0, 1, 2, 3, 4, or 5 substitutions; [119.] an isolated monoclonal antibody that specifically binds to Env and comprises a VH CDR1, VH amino acid sequence of SEQ ID NO: 3, 13, 23, 33, 43, 53, 63, 73, 83, or 93 comprising 0, 1, 2, 3, 4, or 5 substitutions, insertions, or deletions;

[120.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3, 13, 23, 33, 43, 53, 63, 73, 83, or 93 comprising 0, 1, 2, 3, 4, or 5 substitutions;

[121.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 227-238 comprising 0, 1, 2, 3, 4, or 5 substitutions, insertions, or deletions;

[122.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 227-238 comprising 0, 1, 2, 3, 4, or 5 substitutions;

[123.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1 comprising 0, 1, 2, 3, 4, or 5 substitutions, insertions, or deletions;

[124.] an isolated monoclonal antibody that specifically binds to Env and comprises a VH CDR1, VH CDR2, VH CDR3, VL CDR1, VL CDR2, and VL CDR3, wherein the VH CDR3 comprises the VH CDR3 of NC-Cow1 comprising 0, 1, 2, 3, 4, or 5 substitutions;

[125.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3 or SEQ ID NO: 121 comprising 0, 1, 2, 3, 4, or 5 substitutions, insertions, or deletions;

[126.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 3 comprising 0, 1, 2, 3, 4, or 5 substitutions, insertions, or deletions;

[127.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 121 comprising 0, 1, 2, 3, 4, or 5 substitutions, insertions, or deletions;

[128.] an isolated monoclonal antibody that specifically binds to Env and comprises a VH CDR1, VH amino acid sequence of SEQ ID NO: 101;

[129.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 102;

[130.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 122;

[131.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 268;

[132.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 269;

[133.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133;

[134.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 134-139 or 253-260;

[135.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 140;

[136.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 141;

[137.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 142;

[138.] an isolated monoclonal antibody that specifically binds to Env and comprises a VH CDR1, VH CDR2, VH CDR3, VL CDR1, VL CDR2, and VL CDR3, wherein the VH CDR3 comprises the amino acid sequence of SEQ ID NO: 133 comprising 0, 1, 2, 3, 4, or 5 substitutions, insertions, or deletions;

[139.] an isolated monoclonal antibody that specifically binds to Env and comprises a VH CDR1, VH amino acid sequence of SEQ ID NO: 134-139 or 253-260 comprising 0, 1, 2, 3, 4, or 5 substitutions, insertions, or deletions;

[140.] an isolated monoclonal antibody that specifically binds to Env and comprises a VH CDR1, VH CDR2, VH CDR3, VL CDR1, VL CDR2, and VL CDR3, wherein the VH CDR3 comprises the structure of stalk A-knob-stalk B from N to C terminus, wherein a) the stalk A comprises a Stalk A amino acid sequence listed in Table 4, the knob comprises a knob amino acid sequence listed in Table 4, and the stalk B comprises a stalk B amino acid sequence listed in Table 4;

b) the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4;

c) the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4;

d) the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions;

e) the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions;

f) the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions;

g) the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions;

h) the stalk A comprises an amino acid sequence of SEQ ID NO: 131; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 151;

i) the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150;

j) the stalk A comprises an amino acid sequence of SEQ ID NO: 131; the knob comprises an amino acid sequence with at least about 80% 90%, 95%, or 100% identity to any one of SEQ ID NO: 133-139 or 253-260, and the stalk B comprises an amino acid sequence of SEQ ID NO: 151;

k) the stalk A comprises an amino acid sequence of SEQ ID NO: 130; the knob comprises an amino acid sequence with at least about 80% 90%, 95%, or 100% identity to any one of SEQ ID NO: 133-139 or 253-260, and the stalk B comprises an amino acid sequence of SEQ ID NO: 150;

l) the stalk A comprises an amino acid sequence of SEQ ID NO: 131; the knob comprises an amino acid sequence of SEQ ID NO: 141, and the stalk B comprises an amino acid sequence of SEQ ID NO: 151;

m) the stalk A comprises an amino acid sequence of SEQ ID NO: 132; the knob comprises an amino acid sequence of SEQ ID NO: 142, and the stalk B comprises an amino acid sequence of SEQ ID NO: 152; or n) the stalk A comprises an amino acid sequence of SEQ ID NO: 130-132; the knob comprises an amino acid sequence of SEQ ID NO: 140-142, and the stalk B comprises an amino acid sequence of SEQ ID NO: 150-152;

[141.] the isolated monoclonal antibody of any one of [95] to [140], wherein the VH CDR3 is derived from a first donor antibody and the VH CDR1, VH CDR2, VL CDR1, VL CDR2, and VL CDR3 are derived from a second donor antibody;

[142.] the isolated monoclonal antibody of [141], wherein the second donor antibody is an anti-Env antibody;

[143.] the isolated monoclonal antibody of [143], wherein the second donor antibody is a broadly neutralizing anti-Env antibody;

[144.] the isolated monoclonal antibody of any one of [141] to [143], wherein the second donor antibody is a human antibody;

[145.] the isolated monoclonal antibody of [141], wherein the second donor antibody is PG9;

[146.] the isolated monoclonal antibody of [141], wherein the second donor antibody is a germline reverted variant of PG9;

[147.] the isolated monoclonal antibody of [141], wherein the second donor antibody is a bovine anti-Env antibody;

[148.] the isolated monoclonal antibody of [141], wherein the second donor antibody is NC-Cow1, NC-Cow2, NC-Cow3, NC-Cow4, NC-Cow5, NC-Cow6, NC-Cow7, NC-Cow8, NC-Cow9, or NC-Cow10;

[149.] the isolated monoclonal antibody of [141], wherein the second donor antibody is NC-Cow1, NC-Cow7, NC-Cow8, NC-Cow9, or NC-Cow10;

[150.] the isolated monoclonal antibody of [141], wherein the second donor antibody is NC-Cow2, NC-Cow3, NC-Cow4, NC-Cow5, or NC-Cow6;

[151.] the isolated monoclonal antibody of [141], wherein the second donor antibody is NC-Cow1;

[152.] the isolated monoclonal antibody of any one of [147] to [151], wherein the second donor antibody is a broadly neutralizing bovine anti-Env antibody;

[153.] the isolated monoclonal antibody of [141], wherein the second donor antibody is a bovine anti-Env antibody produced by a method according to any one of [1] to [52];

[154.] the isolated monoclonal antibody of any one of [95] to [141], wherein the VL CDR1, VL CDR2, and VL CDR3 are derived from a bovine germline encoded light chain variable region (VL);

[155.] the isolated monoclonal antibody of [154] wherein the bovine germline encoded VL is V30;

[156.] the isolated monoclonal antibody of [155] wherein the bovine germline encoded VL comprises the amino acid sequence of SEQ ID NO: 103;

[157.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein
- (a) the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10;
- (b) the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and
- (c) the VH CDR3 comprises the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[158.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein
- (a) the VH CDR1 comprises the VH CDR1 of NC-Cow1, NC-Cow2, NC-Cow3, NC-Cow4, NC-Cow5, NC-Cow6, NC-Cow7, NC-Cow8, NC-Cow9, or NC-Cow10;
- (b) the VH CDR2 comprises the VH CDR2 of NC-Cow1, NC-Cow2, NC-Cow3, NC-Cow4, NC-Cow5, NC-Cow6, NC-Cow7, NC-Cow8, NC-Cow9, or NC-Cow10; and
- (c) the VH CDR3 comprises the VH CDR3 of NC-Cow11, NC-Cow12, NC-Cow13, NC-Cow14, NC-Cow15, NC-Cow16, NC-Cow17, NC-Cow18, NC-Cow19, NC-Cow20, NC-Cow21 or NC-Cow22;

[159.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein
- (a) the VH CDR1 comprises the VH CDR1 of NC-Cow1, NC-Cow7, NC-Cow8, NC-Cow9, or NC-Cow10;
- (b) the VH CDR2 comprises the VH CDR2 of NC-Cow1, NC-Cow7, NC-Cow8, NC-Cow9, or NC-Cow10; and
- (c) the VH CDR3 comprises the VH CDR3 of NC-Cow1, NC-Cow7, NC-Cow8, NC-Cow9, or NC-Cow10;

[160.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein
- (a) the VH CDR1 comprises the amino acid sequence of SEQ ID NO: 1, 11, 21, 31, 41, 51, 61, 71, 81, or 91;
- (b) the VH CDR2 comprises the amino acid sequence of SEQ ID NO: 2, 12, 22, 32, 42, 52, 62, 72, 82, or 92; and
- (c) the VH CDR3 comprises the amino acid sequence of SEQ ID NO: 3, 13, 23, 33, 43, 53, 63, 73, 83, 93, or 121;

[161.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein
- (a) the VH CDR1 comprises the amino acid sequence of SEQ ID NO: 1, 11, 21, 31, 41, 51, 61, 71, 81, or 91;
- (b) the VH CDR2 comprises the amino acid sequence of SEQ ID NO: 2, 12, 22, 32, 42, 52, 62, 72, 82, or 92; and
- (c) the VH CDR3 comprises the amino acid sequence of SEQ ID NO: 227-238;

[162.] the isolated monoclonal antibody of any one of [157] to [161], wherein
- (a) the VL CDR1 comprises the VL CDR1 of NC-Cow1, NC-Cow2, NC-Cow3, NC-Cow4, NC-Cow5, NC-Cow6, NC-Cow7, NC-Cow8, NC-Cow9, or NC-Cow10;
- (b) the VL CDR2 comprises the VL CDR2 of NC-Cow1, NC-Cow2, NC-Cow3, NC-Cow4, NC-Cow5, NC-Cow6, NC-Cow7, NC-Cow8, NC-Cow9, or NC-Cow10; and
- (c) the VL CDR3 comprises the VL CDR3 of NC-Cow1, NC-Cow2, NC-Cow3, NC-Cow4, NC-Cow5, NC-Cow6, NC-Cow7, NC-Cow8, NC-Cow9, or NC-Cow10;

[163.] the isolated monoclonal antibody of any one of [157] to [161], wherein
- (a) the VL CDR1 comprises the VL CDR1 of NC-Cow1, NC-Cow7, NC-Cow8, NC-Cow9, or NC-Cow10;
- (b) the VL CDR2 comprises the VL CDR2 of NC-Cow1, NC-Cow7, NC-Cow8, NC-Cow9, or NC-Cow10; and
- (c) the VL CDR3 comprises the VL CDR3 of NC-Cow1, NC-Cow7, NC-Cow8, NC-Cow9, or NC-Cow10;

[164.] the isolated monoclonal antibody of any one of [157] to [161], wherein (a) the VL CDR1 comprises the amino acid sequence of SEQ ID NO: 4, 14, 24, 34, 44, 54, 64, 74, 84, or 94;

(b) the VL CDR2 comprises the amino acid sequence of GDT or GDS; and (c) the VL CDR3 comprises the amino acid sequence of SEQ ID NO: 6, 16, 26, 36, 46, 56, 66, 76, 86, or 96;

[165.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR1, VH CDR2, VH CDR3, VL CDR1, VL CDR2, and VL CDR3, respectively;

[166.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of the NC-Cow1, NC-Cow7, NC-Cow8, NC-Cow9, or NC-Cow10 VH CDR1, VH CDR2, VH CDR3, VL CDR1, VL CDR2, and VL CDR3, respectively;

[167.] an isolated monoclonal antibody that specifically binds to Env and comprises a heavy chain variable region comprising a VH CDR1, VH CDR2, and VH CDR3 and a light chain variable region comprising a VL CDR1, VL CDR2, and VL CDR3, wherein the VH CDR1, VH CDR2, VH CDR3, VL CDR1, VL CDR2, and VL CDR3 comprise the amino acid sequence of (a) SEQ ID NO: 1-4, GDT and SEQ ID NO: 6, respectively;

(b) SEQ ID NO: 11-14, GDT and SEQ ID NO: 16, respectively;

(c) SEQ ID NO: 21-24, GDT and SEQ ID NO: 26, respectively;

(d) SEQ ID NO: 31-34, GDT and SEQ ID NO: 36, respectively;

(e) SEQ ID NO: 41-44, GDT and SEQ ID NO: 46, respectively;

(f) SEQ ID NO: 51-54, GDT and SEQ ID NO: 56, respectively;

(g) SEQ ID NO: 61-64. GDT and SEQ ID NO: 66, respectively;

(h) SEQ ID NO: 71-74, GDS and SEQ ID NO: 76, respectively;

(i) SEQ ID NO: 81-84, GDS and SEQ ID NO: 86, respectively; or (j) SEQ ID NO: 91-94. GDT and SEQ ID NO: 96, respectively;

[168.] an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow2, NC-Cow3, NC-Cow4, NC-Cow5, NC-Cow6, NC-Cow7, NC-Cow8, NC-Cow9, or NC-Cow10;

[169.] an isolated monoclonal antibody that specifically binds to Env and comprises a heavy chain variable region (VH) and a light chain variable region (VL), wherein the VH comprises an amino acid sequence that is at least about 90% identical to the VH of NC-Cow1, NC-Cow2, NC-Cow3, NC-Cow4, NC-Cow5, NC-Cow6, NC-Cow7, NC-Cow8, NC-Cow9, or NC-Cow10;

[170.] an isolated monoclonal antibody that specifically binds to Env and comprises a heavy chain variable region (VH) and a light chain variable region (VL), wherein the VH comprises an amino acid sequence that is identical to the VH of NC-Cow1, NC-Cow2, NC-Cow3, NC-Cow4, NC-Cow5, NC-Cow6, NC-Cow7, NC-Cow8, NC-Cow9, or NC-Cow10;

[171.] an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to the VH of NC-Cow1, NC-Cow7, NC-Cow8, NC-Cow9, or NC-Cow10;

[172.] an isolated monoclonal antibody that specifically binds to Env and comprises a heavy chain variable region (VH) and a light chain variable region (VL), wherein the VH comprises an amino acid sequence that is at least about 90% identical to the VH of NC-Cow1, NC-Cow7, NC-Cow8, NC-Cow9, or NC-Cow10;

[173.] an isolated monoclonal antibody that specifically binds to Env and comprises a heavy chain variable region (VH) and a light chain variable region (VL), wherein the VH comprises an amino acid sequence that is identical to the VH of NC-Cow1, NC-Cow7, NC-Cow8, NC-Cow9, or NC-Cow10;

[174.] an isolated monoclonal antibody that specifically binds to Env and comprises a heavy chain variable region (VH) and a light chain variable region (VL), wherein the VH comprises an amino acid sequence that is at least about 90%, 95%, 97%, 98%, 99% or 100% identical to SEQ ID NO: 7, 17, 27, 37, 47, 57, 67, 77, 87, 97, 113, 115, 117, or 119;

[175.] an isolated monoclonal antibody that specifically binds to Env and comprises a heavy chain variable region (VH) and a light chain variable region (VL), wherein the VH comprises an amino acid sequence that is at least about 90% identical to SEQ ID NO: 7, 17, 27, 37, 47, 57, 67, 77, 87, 97, 113, 115, 117, or 119;

[176.] an isolated monoclonal antibody that specifically binds to Env and comprises a heavy chain variable region (VH) and a light chain variable region (VL), wherein the VH comprises an amino acid sequence that is identical to SEQ ID NO: 7, 17, 27, 37, 47, 57, 67, 77, 87, 97, 113, 115, 117, or 119;

[177.] the isolated monoclonal antibody of any one of [168] to [176], wherein the VL comprises an amino acid sequence that is at least about 90%, 95%, 97%, 98%, 99% or 100% identical to the VL of NC-Cow1, NC-Cow2, NC-Cow3, NC-Cow4, NC-Cow5, NC-Cow6, NC-Cow7, NC-Cow8, NC-Cow9, or NC-Cow10;

[178.] the isolated monoclonal antibody of any one of [168] to [176], wherein the VL comprises an amino acid sequence that is at least about 90% identical to the VL of NC-Cow1, NC-Cow2, NC-Cow3, NC-Cow4, NC-Cow5, NC-Cow6, NC-Cow7, NC-Cow8, NC-Cow9, or NC-Cow10;

[179.] the isolated monoclonal antibody of any one of [168] to [176], wherein the VL comprises an amino acid sequence that is identical to the VL of NC-Cow1, NC-Cow2, NC-Cow3, NC-Cow4, NC-Cow5, NC-Cow6, NC-Cow7, NC-Cow8, NC-Cow9, or NC-Cow10;

[180.] the isolated monoclonal antibody of any one of [168] to [176], wherein the VL comprises an amino acid sequence that is at least about 90%, 95%, 97%, 98%, 99% or 100% identical to the VL of NC-Cow1, NC-Cow7, NC-Cow8, NC-Cow9, or NC-Cow10;

[181.] the isolated monoclonal antibody of any one of [168] to [176], wherein the VL comprises an amino acid sequence that is at least about 90% identical to the VL of NC-Cow1, NC-Cow7, NC-Cow8, NC-Cow9, or NC-Cow10;

[182.] the isolated monoclonal antibody of any one of [168] to [176], wherein the VL comprises an amino acid sequence that is identical to the VL of NC-Cow1, NC-Cow7, NC-Cow8, NC-Cow9, or NC-Cow10;

[183.] the isolated monoclonal antibody of any one of [168] to [176], wherein the VL comprises an amino acid sequence that is at least about 90%, 95%, 97%, 98%, 99% or 100% identical to SEQ ID NO: 8, 18, 28, 38, 48, 58, 68, 87, 88, 98, 114, 116, 118, or 120;

[184.] the isolated monoclonal antibody of any one of [168] to [176], wherein the VL comprises an amino acid sequence that is at least about 90% identical to SEQ ID NO: 8, 18, 28, 38, 48, 58, 68, 87, 88, 98, 114, 116, 118, or 120;

[185.] the isolated monoclonal antibody of any one of [168] to [176], wherein the VL comprises an amino acid sequence that is identical to SEQ ID NO: 8, 18, 28, 38, 48, 58, 68, 87, 88, 98, 114, 116, 118, or 120;

[186.] the isolated monoclonal antibody of any one of [168] to [176], wherein the VL comprises a bovine germline encoded light chain variable region (VL);

[187.] the isolated monoclonal antibody of any one of [177] to [179 wherein the bovine germline encoded VL is V30;

[188.] the isolated monoclonal antibody of any one of [180] to [182 wherein the bovine germline encoded VL comprises the amino acid sequence of SEQ ID NO: 103;

[189.] the isolated monoclonal antibody of any one of [168] to [176], wherein the VL comprises the NC-Cow1 VL;

[190.] the isolated monoclonal antibody of any one of [168] to [176], wherein the VL comprises the amino acid sequence of SEQ ID NO: 8;

[191.] an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow2, NC-Cow3, NC-Cow4, NC-Cow5, NC-Cow6, NC-Cow7, NC-Cow8, NC-Cow9, or NC-Cow10 VH and VL, respectively;

[192.] an isolated monoclonal antibody that specifically binds to Env and comprises a heavy chain variable region (VH) and light chain variable region (VL), wherein the VH and VL comprise an amino acid sequence that is at least about 90% identical to the NC-Cow1, NC-Cow2, NC-Cow3, NC-Cow4, NC-Cow5, NC-Cow6, NC-Cow7, NC-Cow8, NC-Cow9, or NC-Cow10 VH and VL, respectively;

[193.] an isolated monoclonal antibody that specifically binds to Env and comprises a heavy chain variable region (VH) and light chain variable region (VL), wherein the VH and VL comprise an amino acid sequence that is identical to the NC-Cow1, NC-Cow2, NC-Cow3, NC-Cow4, NC-Cow5, NC-Cow6, NC-Cow7, NC-Cow8, NC-Cow9, or NC-Cow10 VH and VL, respectively;

[194.] an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to the NC-Cow1, NC-Cow7, NC-Cow8, NC-Cow9, or NC-Cow10 VH and VL, respectively;

[195.] an isolated monoclonal antibody that specifically binds to Env and comprises a heavy chain variable region (VH) and light chain variable region (VL), wherein the VH and VL comprise an amino acid sequence that is at least about 90% identical to the NC-Cow1, NC-Cow7, NC-Cow8, NC-Cow9, or NC-Cow10 VH and VL, respectively;

[196.] an isolated monoclonal antibody that specifically binds to Env and comprises a heavy chain variable region (VH) and light chain variable region (VL), wherein the VH and VL comprise an amino acid sequence that is identical to the NC-Cow1, NC-Cow7, NC-Cow8, NC-Cow9, or NC-Cow10 VH and VL, respectively;

[197.] an isolated monoclonal antibody that specifically binds to Env and comprises a heavy chain variable region (VH) and light chain variable region (VL), wherein the VH and VL comprise an amino acid sequence that is at least about 90%, 95%, 97%, 98%, 99% or 100% identical to (a) SEQ ID NO: 7 and 8, respectively;
(b) SEQ ID NO: 17 and 18, respectively;
(c) SEQ ID NO: 27 and 28, respectively;
(d) SEQ ID NO: 37 and 38, respectively;
(e) SEQ ID NO: 47 and 48, respectively;
(f) SEQ ID NO: 57 and 58, respectively;
(g) SEQ ID NO: 67 and 68, respectively;
(h) SEQ ID NO: 77 and 78, respectively;
(i) SEQ ID NO: 87 and 88, respectively;
(j) SEQ ID NO: 97 and 98, respectively;
(k) SEQ ID NO: 113 and 114, respectively;
(l) SEQ ID NO: 115 and 116, respectively;
(m) SEQ ID NO: 117 and 8, respectively;
(n) SEQ ID NO: 117 and 118, respectively; or
(o) SEQ ID NO: 119 and 120, respectively;

[198.] an isolated monoclonal antibody that specifically binds to Env and comprises a heavy chain variable region (VH) and light chain variable region (VL), wherein the VH and VL comprise an amino acid sequence that is at least about 90% identical to (a) SEQ ID NO: 7 and 8, respectively;
(b) SEQ ID NO: 17 and 18, respectively;
(c) SEQ ID NO: 27 and 28, respectively;
(d) SEQ ID NO: 37 and 38, respectively;
(e) SEQ ID NO: 47 and 48, respectively;
(f) SEQ ID NO: 57 and 58, respectively;
(g) SEQ ID NO: 67 and 68, respectively;
(h) SEQ ID NO: 77 and 78, respectively;
(i) SEQ ID NO: 87 and 88, respectively;
(j) SEQ ID NO: 97 and 98, respectively;
(k) SEQ ID NO: 113 and 114, respectively;
(l) SEQ ID NO: 115 and 116, respectively;
(m) SEQ ID NO: 117 and 8, respectively;
(n) SEQ ID NO: 117 and 118, respectively; or (o) SEQ ID NO: 119 and 120, respectively;

[199.] an isolated monoclonal antibody that specifically binds to Env and comprises a heavy chain variable region (VH) and light chain variable region (VL), wherein the VH and VL comprise an amino acid sequence that is identical to (a) SEQ ID NO: 7 and 8, respectively;
(b) SEQ ID NO: 17 and 18, respectively;
(c) SEQ ID NO: 27 and 28, respectively;
(d) SEQ ID NO: 37 and 38, respectively;
(e) SEQ ID NO: 47 and 48, respectively;
(f) SEQ ID NO: 57 and 58, respectively;
(g) SEQ ID NO: 67 and 68, respectively;
(h) SEQ ID NO: 77 and 78, respectively;
(i) SEQ ID NO: 87 and 88, respectively;
(j) SEQ ID NO: 97 and 98, respectively;
(k) SEQ ID NO: 113 and 114, respectively;
(l) SEQ ID NO: 115 and 116, respectively;
(m) SEQ ID NO: 117 and 8, respectively;
(n) SEQ ID NO: 117 and 118, respectively; or
(o) SEQ ID NO: 119 and 120, respectively;

[200.] the isolated antibody of any one of [95] to [199], wherein the antibody is not NC-Cow1, NC-Cow2, NC-Cow3, NC-Cow4, NC-Cow5, NC-Cow6, NC-Cow7, NC-Cow8, NC-Cow9, or NC-Cow10;

[201.] the isolated antibody of any one of [95] to [199], wherein the antibody is not NC-Cow11, NC-Cow12, NC-Cow13, NC-Cow14, NC-Cow15, NC-Cow16, NC-Cow17, NC-Cow18, NC-Cow19, NC-Cow20, NC-Cow21 or NC-Cow22;

[202.] the isolated antibody of any one of [95] to [199], wherein the antibody is not NC-Cow1, NC-Cow7, NC-Cow8, NC-Cow9, or NC-Cow10;

[203.] the monoclonal antibody of any one of [95] to [202], further comprising a heavy and/or light chain constant region;

[204.] the monoclonal antibody of any one of [95] to [203], further comprising a human heavy and/or light chain constant region;

[205.] the antibody of [203 or [204], wherein the heavy chain constant region is selected from the group consisting of a human immunoglobulin IgG1, IgG2, IgG3, IgG4, IgA1, and IgA2 constant region;

[206.] the antibody of any one of [203] to [205], wherein the heavy chain constant region comprises a native amino acid sequence;

[207.] the antibody of any one of [203] to [205], wherein the heavy chain constant region comprises a variant amino acid sequence;

[208.] the isolated monoclonal antibody of any one of [95] to [207], wherein the antibody is a recombinant antibody, a chimeric antibody, a humanized antibody, an antibody fragment, a bispecific antibody, or a trispecific antibody;

[209.] the antibody of [208], wherein the antibody is a chimeric antibody;

[210.] the antibody of [208], wherein the antibody is a humanized antibody;

[211.] the antibody of [208], wherein the antibody is an antibody fragment;

[212.] the antibody of [208], wherein the antibody is a bispecific antibody;

[213.] the antibody of [208], wherein the antibody is a trispecific antibody;

[214.] the isolated monoclonal antibody of [208] or [208], wherein the antibody fragment comprises a single-chain Fv (scFv), F(ab) fragment, F(ab')2 fragment, or an isolated VH domain;

[215.] a fusion polypeptide that specifically binds to Env and comprises an amino acid sequence that is at least about 90%, 95%, 97%, 98%, 99% or 100% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[216.] a fusion polypeptide that specifically binds to Env and comprises an amino acid sequence that is at least about 90% identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[217.] a fusion polypeptide that specifically binds to Env and comprises an amino acid sequence that is identical to the VH CDR3 of NC-Cow1, NC-Cow2, NC-Cow3, NC-Cow4, NC-Cow5, NC-Cow6, NC-Cow7, NC-Cow8, NC-Cow9, or NC-Cow10;

[218.] a fusion polypeptide that specifically binds to Env and comprises an amino acid sequence that is at least about 90%, 95%, 97%, 98%, 99% or 100% identical to the VH CDR3 of NC-Cow1, NC-Cow7, NC-Cow8, NC-Cow9, or NC-Cow10;

[219.] a fusion polypeptide that specifically binds to Env and comprises an amino acid sequence that is at least about 90% identical to the VH CDR3 of NC-Cow1, NC-Cow7, NC-Cow8, NC-Cow9, or NC-Cow10;

[220.] a fusion polypeptide that specifically binds to Env and comprises an amino acid sequence that is identical to the VH CDR3 of NC-Cow1, NC-Cow7, NC-Cow8, NC-Cow9, or NC-Cow10;

[221.] a fusion polypeptide that specifically binds to Env and comprises an amino acid sequence that is at least about 90%, 95%, 97%, 98%, 99% or 100% identical to SEQ ID NO: 3, 13, 23, 33, 43, 53, 63, 73, 83, or 93;

[222.] a fusion polypeptide that specifically binds to Env and comprises an amino acid sequence that is at least about 90% identical to SEQ ID NO: 3, 13, 23, 33, 43, 53, 63, 73, 83, or 93;

[223.] a fusion polypeptide that specifically binds to Env and comprises an amino acid sequence that is identical to SEQ ID NO: 3, 13, 23, 33, 43, 53, 63, 73, 83, or 93;

[224.] a fusion polypeptide that specifically binds to Env and comprises an amino acid sequence that is at least about 90%, 95%, 97%, 98%, 99% or 100% identical to SEQ ID NO: 227-238;

[225.] a fusion polypeptide that specifically binds to Env and comprises an amino acid sequence that is at least about 90% identical to SEQ ID NO: 227-238;

[226.] a fusion polypeptide that specifically binds to Env and comprises an amino acid sequence that is identical to SEQ ID NO: 227-238;

[227.] a fusion polypeptide that specifically binds to Env and comprises an amino acid sequence that is at least about 90%, 95%, 97%, 98%, 99% or 100% identical to the VH CDR3 of NC-Cow1;

[228.] a fusion polypeptide that specifically binds to Env and comprises an amino acid sequence that is at least about 90% identical to the VH CDR3 of NC-Cow1;

[229.] a fusion polypeptide that specifically binds to Env and comprises an amino acid sequence that is identical to the VH CDR3 of NC-Cow1;

[230.] a fusion polypeptide that specifically binds to Env and comprises an amino acid sequence that is at least about 90%, 95%, 97%, 98%, 99% or 100% identical to SEQ ID NO: 3 or SEQ ID NO: 121;

[231.] a fusion polypeptide that specifically binds to Env and comprises an amino acid sequence that is at least about 90% identical to SEQ ID NO: 3;

[232.] a fusion polypeptide that specifically binds to Env and comprises an amino acid sequence that is at least about 90% identical to SEQ ID NO: 121;

[233.] a fusion polypeptide that specifically binds to Env and comprises an amino acid sequence that is identical to SEQ ID NO: 3;

[234.] a fusion polypeptide that specifically binds to Env and comprises the amino acid sequence that is identical to SEQ ID NO: 121;

[235.] a fusion polypeptide that specifically binds to Env and comprises the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR3 comprising 0, 1, 2, 3, 4, or 5 substitutions, insertions, or deletions;

[236.] a fusion polypeptide that specifically binds to Env and comprises the amino acid sequence of the NC-Cow1, NC-Cow2, NC-Cow3, NC-Cow4, NC-Cow5, NC-Cow6, NC-Cow7, NC-Cow8, NC-Cow9, or NC-Cow10 VH CDR3 comprising 0, 1, 2, 3, 4, or 5 substitutions;

[237.] a fusion polypeptide that specifically binds to Env and comprises the amino acid sequence of the NC-Cow1, NC-Cow7, NC-Cow8, NC-Cow9, or NC-Cow10 VH CDR3 comprising 0, 1, 2, 3, 4, or 5 substitutions, insertions, or deletions;

[238.] a fusion polypeptide that specifically binds to Env and comprises the amino acid sequence of the NC-Cow1, NC-Cow7, NC-Cow8, NC-Cow9, or NC-Cow10 VH CDR3 comprising 0, 1, 2, 3, 4, or 5 substitutions;

[239.] a fusion polypeptide that specifically binds to Env and comprises the amino acid sequence of SEQ ID NO: 3, 13, 23, 33, 43, 53, 63, 73, 83, or 93 comprising 0, 1, 2, 3, 4, or 5 substitutions, insertions, or deletions;

[240.] a fusion polypeptide that specifically binds to Env and comprises the amino acid sequence of SEQ ID NO: 3, 13, 23, 33, 43, 53, 63, 73, 83, or 93 comprising 0, 1, 2, 3, 4, or 5 substitutions;

[241.] a fusion polypeptide that specifically binds to Env and comprises the amino acid sequence of SEQ ID NO: 227-238 comprising 0, 1, 2, 3, 4, or 5 substitutions, insertions, or deletions;

[242.] a fusion polypeptide that specifically binds to Env and comprises the amino acid sequence of SEQ ID NO: 227-238 comprising 0, 1, 2, 3, 4, or 5 substitutions;

[243.] a fusion polypeptide that specifically binds to Env and comprises the amino acid sequence of the NC-Cow1 VH CDR3 comprising 0, 1, 2, 3, 4, or 5 substitutions, insertions, or deletions;

[244.] a fusion polypeptide that specifically binds to Env and comprises the amino acid sequence of the NC-Cow1 VH CDR3 comprising 0, 1, 2, 3, 4, or 5 substitutions;

[245.] a fusion polypeptide that specifically binds to Env and comprises the amino acid sequence of SEQ ID NO: 3 or SEQ ID NO: 121 comprising 0, 1, 2, 3, 4, or 5 substitutions, insertions, or deletions;

[246.] a fusion polypeptide that specifically binds to Env and comprises the amino acid sequence of SEQ ID NO: 3 comprising 0, 1, 2, 3, 4, or 5 substitutions, insertions, or deletions;

[247.] a fusion polypeptide that specifically binds to Env and comprises the amino acid sequence of SEQ ID NO: 121 comprising 0, 1, 2, 3, 4, or 5 substitutions, insertions, or deletions;

[248.] a fusion polypeptide that specifically binds to Env and comprises the amino acid sequence of SEQ ID NO: 3 comprising 0, 1, 2, 3, 4, or 5 substitutions;

[249.] a fusion polypeptide that specifically binds to Env and comprises the amino acid sequence of SEQ ID NO: 121 comprising 0, 1, 2, 3, 4, or 5 substitutions;

[250.] a fusion polypeptide that specifically binds to Env and comprises the amino acid sequence of the NC-Cow1 VH CDR3;

[251.] a fusion polypeptide that specifically binds to Env and comprises the amino acid sequence of SEQ ID NO: 3 or SEQ ID NO: 121;

[252.] a fusion polypeptide that specifically binds to Env and comprises the amino acid sequence of SEQ ID NO: 3;

[253.] a fusion polypeptide that specifically binds to Env and comprises the amino acid sequence of SEQ ID NO: 121;

[254.] a fusion polypeptide that specifically binds to Env and comprises the amino acid sequence of SEQ ID NO:101;

[255.] a fusion polypeptide that specifically binds to Env and comprises the amino acid sequence of SEQ ID NO:102;

[256.] a fusion polypeptide that specifically binds to Env and comprises the amino acid sequence of SEQ ID NO:268;

[257.] a fusion polypeptide that specifically binds to Env and comprises the amino acid sequence of SEQ ID NO:269;

[258.] a fusion polypeptide that specifically binds to Env and comprises the amino acid sequence of SEQ ID NO:122;

[259.] a fusion polypeptide that specifically binds to Env and comprises the amino acid sequence of SEQ ID NO:133;

[260.] a fusion polypeptide that specifically binds to Env and comprises the amino acid sequence of SEQ ID NO:134-139 or 253-260;

[261.] a fusion polypeptide that specifically binds to Env and comprises the amino acid sequence of SEQ ID NO:140;

[262.] a fusion polypeptide that specifically binds to Env and comprises the amino acid sequence of SEQ ID NO:141;

[263.] a fusion polypeptide that specifically binds to Env and comprises the amino acid sequence of SEQ ID NO:142;

[264.] a fusion polypeptide that specifically binds to Env and comprises the amino acid sequence of SEQ ID NO: 133 comprising 0, 1, 2, 3, 4, or 5 substitutions, insertions, or deletions;

[265.] a fusion polypeptide that specifically binds to Env and comprises the amino acid sequence of SEQ ID NO: 134-139 or 253-260 comprising 0, 1, 2, 3, 4, or 5 substitutions, insertions, or deletions;

[266.] a fusion polypeptide that specifically binds to Env and comprises a domain having the structure, from N to C terminus, of stalk A-knob-stalk B, wherein a) the stalk A comprises a Stalk A amino acid sequence listed in Table 4, the knob comprises a knob amino acid sequence listed in Table 4, and the stalk B comprises a stalk B amino acid sequence listed in Table 4;

b) the stalk A comprises an amino acid sequence with at least about 80%, 90%, 95% or 100% identity of a stalk A amino acid sequence listed in Table 4, the knob comprises a knob amino acid sequence listed in Table 4, and the stalk B comprises an amino acid sequence with at least about 80%, 90%, 95% or 100% identity of a stalk B amino acid sequence listed in Table 4;

c) the stalk A comprises an amino acid sequence with at least about 80%, 90%, 95% or 100% identity of a stalk A amino acid sequence listed in Table 4, the knob comprises an amino acid sequence with at least about 80% 90%, 95%, or 100% identity of a knob amino acid sequence listed in Table 4, and the stalk B comprises an amino acid sequence with at least about 80%, 90%, 95% or 100% identity of a stalk B amino acid sequence listed in Table 4;

d) the stalk A comprises a stalk A amino acid sequence listed in Table 4 comprising 0, 1, 2, 3, 4, or 5 substitutions, the knob comprises a knob amino sequence listed in Table 4, and the stalk B comprises a stalk B amino acid sequence listed in Table 4 comprising 0, 1, 2, 3, 4, or 5 substitutions;

e) the stalk A comprises a stalk A amino acid sequence listed in Table 4 comprising 0, 1, 2, 3, 4, or 5 substitutions, the knob comprises a knob amino sequence listed in Table 4 comprising 0, 1, 2, 3, 4, or 5 substitutions, and the stalk B comprises a stalk B amino acid sequence listed in Table 4 comprising 0, 1, 2, 3, 4, or 5 substitutions;

f) the stalk A comprises a stalk A amino acid sequence listed in Table 4 comprising 0, 1, 2, 3, 4, or 5 substitutions, insertions, or deletions, the knob comprises a knob amino sequence listed in Table 4, and the stalk B comprises a stalk B amino acid sequence listed in Table 4 comprising 0, 1, 2, 3, 4, or 5 substitutions, insertions, or deletions;

g) the stalk A comprises a stalk A amino acid sequence listed in Table 4 comprising 0, 1, 2, 3, 4, or 5 substitutions, insertions, or deletions, the knob comprises a knob amino sequence listed in Table 4 comprising 0, 1, 2, 3, 4, or 5 substitutions, insertions, or deletions, and the stalk B comprises a stalk B amino acid sequence listed in Table 4 comprising 0, 1, 2, 3, 4, or 5 substitutions, insertions, or deletions;

h) the stalk A comprises an amino acid sequence of SEQ ID NO: 131; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 151;

i) the stalk A comprises an amino acid sequence of SEQ ID NO: 130; the knob comprises a knob amino sequence of SEQ ID NO:133-139 or 253-260 comprising 0, 1, 2, 3, 4, or 5 substitutions, insertions, or deletions, and the stalk B comprises an amino acid sequence of SEQ ID NO: 150;

j) the stalk A comprises an amino acid sequence of SEQ ID NO: 131; the knob comprises an amino acid sequence with at least about 80% 90%, 95%, or 100% identity to any one of SEQ ID NO: 133-139 or 253-260, and the stalk B comprises an amino acid sequence of SEQ ID NO: 151;

k) the stalk A comprises an amino acid sequence of SEQ ID NO: 130; the knob comprises an amino acid sequence with at least about 80% 90%, 95%, or 100% identity to any one of SEQ ID NO: 133-139 or 253-260, and the stalk B comprises an amino acid sequence of SEQ ID NO: 150;

l) the stalk A comprises an amino acid sequence of SEQ ID NO: 131; the knob comprises an amino acid sequence of SEQ ID NO: 141, and the stalk B comprises an amino acid sequence of SEQ ID NO: 151;

m) the stalk A comprises an amino acid sequence of SEQ ID NO: 132; the knob comprises an amino acid sequence of SEQ ID NO: 142, and the stalk B comprises an amino acid sequence of SEQ ID NO: 152; or n) the stalk A comprises an amino acid sequence of SEQ ID NO: 130-132; the knob comprises comprises an amino acid sequence of SEQ ID NO: 140-142, and the stalk B comprises an amino acid sequence of SEQ ID NO: 150-152;

[267.] the fusion polypeptide of any one of [215] to [266], wherein the polypeptide comprises a non-immunoglobulin polypeptide or a fragment thereof;

[268.] the fusion polypeptide of [267], wherein the non-immunoglobulin polypeptide or a fragment thereof comprises human serum albumin, ferritin, or a fragment thereof;

[269.] the fusion polypeptide of any one of [215] to [268], wherein the polypeptide comprises an Fc domain;

[270.] the fusion polypeptide of [269], wherein the Fc domain is a human IgG1, IgG2, IgG3, IgG4, IgA1, or IgA2 Fc domain;

[271.] the monoclonal antibody of any one of [95] to [214], or the fusion polypeptide of any one of [215] to [270], wherein the antibody or fusion polypeptide is capable of neutralizing at least two cross-clade isolates of HIV;

[272.] the antibody or fusion polypeptide of [271], wherein the antibody or fusion polypeptide is capable of neutralizing at least about 50%, 60%, 70%, 80%, 90%, or 100% of cross-clade HIV isolates in the 6-member indicator virus panel;

[273.] the antibody or fusion polypeptide of [271], wherein the antibody or fusion polypeptide is capable of neutralizing at least about 90% of cross-clade HIV isolates in the 6-member indicator virus panel;

[274.] the antibody or fusion polypeptide of [271], wherein the antibody or fusion polypeptide is capable of neutralizing at least about 50%, 60%, 70%, 80%, 90%, or 100% of cross-clade HIV isolates in the 12-member indicator virus panel;

[275.] the antibody or fusion polypeptide of [271], wherein the antibody or fusion polypeptide is capable of neutralizing at least about 90% of cross-clade HIV isolates in the 12-member indicator virus panel;

[276.] the antibody or fusion polypeptide of [271], wherein the antibody or fusion polypeptide is capable of neutralizing at least about 50%, 60%, 70%, 80%, 90%, or 100% of cross-clade HIV isolates in the 117-member indicator virus panel;

[277.] the antibody or fusion polypeptide of [271], wherein the antibody or fusion polypeptide is capable of neutralizing at least about 80% of cross-clade HIV isolates in the 117-member indicator virus panel;

[278.] the antibody or fusion polypeptide of any one of [271] to [277], wherein the antibody or fusion polypeptide is capable of neutralizing the cross-clade HIV isolates with a median IC50 equal to or less than about 0.1 microg/ml, 0.05 microg/ml, 0.025 microg/ml, 0.01 microg/ml, or 0.005 microg/ml;

[279.] the antibody or fusion polypeptide of any one of [271] to [277], wherein the antibody or fusion polypeptide is capable of neutralizing the cross-clade HIV isolates with a median IC50 equal to or less than about 0.05 microg/ml;

[280.] the antibody or fusion polypeptide of any one of [271] to [279], wherein the antibody or fusion polypeptide is capable of neutralizing the cross-clade HIV isolates with a median ID50 of at least about 50, 100, 500, 1000, 5000, or 10000;

[281.] the antibody or fusion polypeptide of any one of [271] to [279], wherein the antibody or fusion polypeptide is capable of neutralizing the cross-clade HIV isolates with a median ID50 of at least about 500;

[282.] the antibody or fusion polypeptide of any one of [271] to [279], wherein the antibody or fusion polypeptide is capable of neutralizing the cross-clade HIV isolates with a median ID50 of at least about 1000;

[283.] a pharmaceutical composition comprising the broadly neutralizing antibody of any one of [51] to [61] and [63] to [91] or the monoclonal antibody of any one of [95] to [214] and a pharmaceutically acceptable excipient;

[284.] the pharmaceutical composition of [283], which is lyophilized;

[285.] an isolated polynucleotide encoding the heavy chain variable region or heavy chain of the antibody of any one of [63] to [91] and [95] to [214];

[286.] an isolated polynucleotide encoding the light chain variable region or light chain of the antibody of any one of [63] to [91] and [95] to [214].

[287.] an isolated polynucleotide or polynucleotides encoding the heavy chain variable region or heavy chain of the antibody of any one of [63] to [91] and [95] to [214] and the light chain variable region or light chain of the antibody of any one [63] to [91] and [95] to [214];

[288.] the isolated polynucleotide of [285] or [287], wherein the polynucleotide encodes a heavy chain variable region comprising the amino acid sequence of SEQ ID NO: 7, 17, 27, 37, 47, 57, 67, 77, 87, or 97;

[289.] the isolated polynucleotide of [286] or [287], wherein the polynucleotide encodes a light chain variable region comprising the amino acid sequence of SEQ ID NO: 8, 18, 28, 38, 48, 58, 68, 87, 88, or 98;

[290.] the isolated polynucleotide of any one of [285] to [287], which is an mRNA;

[291.] the isolated polynucleotide of [290], wherein the mRNA comprises a modified nucleotide;

[292.] an isolated polynucleotide encoding the fusion polypeptide of any one of [215] to [270];

[293.] an isolated vector or vectors comprising the polynucleotide of any one of [285] to [289] and [292];

[294.] the isolated vector of [293], wherein the vector is a viral vector;

[295.] a recombinant virus comprising the polynucleotide of any one of [285] to [289] and [292]; [296.] the recombinant virus of [295], which is a recombinant adeno-associated virus (AAV);

[297.] a host cell comprising the polynucleotide of any one of [285] to [289] and [292], the vector of [293] or [294], or a first vector comprising the nucleic acid of [285] and a second vector comprising the nucleic acid of [286];

[298.] the host cell of [297], which is selected from the group consisting of *E. coli, Pseudomonas, Bacillus, Streptomyces*, yeast, CHO, YB/20, NS0, PER-C6, HEK-293T, NIH-3T3, HeLa, BHK, Hep G2, SP2/0, R1.1, B-W, L-M, COS 1, COS 7, BSC1, BSC40, BMT10 cell, plant cell, insect cell, and human cell in tissue culture;

[299.] a method of producing an antibody or fusion polypeptide that binds to HIV comprising culturing the host cell of [298] so that the polynucleotide is expressed and the antibody or fusion polypeptide is produced;

[300.] an isolated antibody that specifically binds to Env and is encoded by the isolated polynucleotide of any one of [285] to [292];

[301.] a method of neutralizing an HIV virus comprising contacting the virus with a sufficient amount of the antibody of any one of [63] to [91] and [95] to [214], the composition of any one of [58]-[62], [92], and [93], the fusion polypeptide of any one of [215] to [270], or the pharmaceutical composition of any one of [94], [283], and [284];

[302.] a method of preventing HIV infection comprising administering to a subject in need thereof a therapeutically sufficient amount of the antibody of any one of [63] to [91] and [95] to [214], the composition of any one of [58]-[62], [92], and [93], the pharmaceutical composition of any one of [94], [283], and [284], the isolated nucleotide of any one of [285] to [292], the fusion polypeptide of any one of [215] to [270], or the recombinant virus of any [295] or [296];

[303.] a method of reducing the risk of a subject becoming infected with HIV comprising administering to the subject in need thereof an effective amount of the antibody of any one of [63] to [91] and to [214], the composition of any one of [58]-[62], [92], and [93], the pharmaceutical composition of any one of [94], [283], and [284], the isolated nucleotide of any one of [285] to [292], the fusion polypeptide of any one of [215] to [270], or the recombinant virus of any [295] or [296];

[304.] a method for passively immunizing a subject comprising administering to the subject in need thereof an effective amount of the antibody of any one of [63] to [91] and [95] to [214], the composition of any one of [58]-[62], [92], and [93], the pharmaceutical composition of any one of [94], [283], and [284], the isolated nucleotide of any one of [285] to [292], the fusion polypeptide of any one of [215] to [270], or the recombinant virus of any [295] or [296];

[305.] a method of treating HIV/AIDS comprising administering to a subject in need thereof a therapeutically sufficient amount of the antibody of any one of [63] to [91] and [95] to [214], the composition of any one of [58]-[62], [92], and [93], the pharmaceutical composition of any one of [94], [283], and [284], the isolated nucleotide of any one of [285] to [292], the fusion polypeptide of any one of [215] to [270], or the recombinant virus of any [295] or [296];

[306.] the method of any one of [301] to [305], wherein the administering to the subject is by at least one mode selected from oral, parenteral, subcutaneous, intramuscular, intravenous, vaginal, rectal, buccal, sublingual, and transdermal.

[307.] the method of any one of [301] to [306], further comprising administering at least one additional therapeutic agent.

[308.] the method of [307], wherein the additional therapeutic agent is an antiretroviral agent or a second antibody;

[309.] the method of [307], wherein the additional therapeutic agent is a second broadly neutralizing antibody;

[310.] the method of [307], wherein the additional therapeutic agent is a second and third broadly neutralizing antibody;

[311.] a method for detecting HIV in a sample comprising contacting the sample with the antibody of any one of [63] to [91] and [95] to [214] or the fusion polypeptide of any one of [215] to [270];

[312.] a method of purifying HIV from a sample comprising contacting the sample with the antibody of any one of [63] to [91] and [95] to [214] or the fusion polypeptide of any one of [215] to [270];

[313.] a kit comprising the antibody of any one of [63] to [91] and [95] to [214] or the fusion polypeptide of any one of [215] to [270], or the pharmaceutical composition of any one of [94], [283], and [284] and a) a detection reagent, b) an HIV antigen, c) a notice that reflects approval for use or sale for human administration, or d) any combination thereof;

[314] an antibody according to any one of [63] to [91] and [95] to [214], a composition according to any one of [58]-[62], [92], and [93], a pharmaceutical composition according to any one of [94], [283], and [284], an isolated polynucleotide according to any one of [285] to [292], a fusion polypeptide according to any one of [215] to [270], or a recombinant virus according to [295] or [296] for treating HIV/AIDS;

[315] a antibody according to any one of [63] to [91] and [95] to [214], a composition according to any one of [58]-[62], [92], and [93], a pharmaceutical composition according to any one of [94], [283], and [284], an isolated nucleotide according to any one of [285] to [292], a fusion polypeptide according to any one of [215] to [270], or a recombinant virus of [295] or [296] for preventing HIV infection;

[316.] an antibody according to any one of [63] to [91] and [95] to [214], a composition according to any one of [58]-[62], [92], and [93], a pharmaceutical composition according to any one of [94], [283], and [284], an isolated nucleotide according to any one of [285] to [292], a fusion polypeptide according to any one of [215] to [270], or a recombinant virus of [295] or [296] for reducing the risk of a subject becoming infected with HIV;

[317.] an antibody according to any one of [63] to [91] and [95] to [214], a composition according to any one of [58]-[62], [92], and [93], a pharmaceutical composition according to any one of [94], [283], and [284], an isolated nucleotide according to any one of [285] to [292], a fusion polypeptide according to any one of [215] to [270], or a recombinant virus of [295] or [296] a method for passively immunizing a subject;

[318.] the antibody of any one of [63] to [91] and [95] to [214] and [314]-[317] or the fusion polypeptide of any one of [215] to [270] and [314]-[317], wherein the antibody or fusion polypeptide specifically binds to BG505 Env; and

[319.] the antibody of any one of [63] to [91] and [95] to [214] and [314]-[317] or the fusion polypeptide of any one of [215] to [270] and [314]-[317], wherein the antibody or fusion polypeptide specifically binds to BG505 SOSIP.

Embodiments of the present disclosure can be further defined by reference to the following non-limiting examples, which describe in detail preparation of certain antibodies of the present disclosure and methods for using antibodies of the present disclosure. It will be apparent to those skilled in the art that many modifications, both to materials and methods, can be practiced without departing from the scope of the present disclosure.

All documents, patent, and patent applications cited herein are hereby incorporated by reference, and may be employed in the practice described herein.

EXAMPLES

It is understood that the following examples are provided to describe the embodiments described herein with greater detail. They are intended to illustrate, not to limit, the embodiments. Various modifications or changes in light thereof will be suggested to persons skilled in the art and are to be included within the spirit and purview of this application

Example 1

No immunogen to date has reliably elicited broadly neutralizing antibodies (bnAbs) to HIV in humans or animal models. Advances in the design of immunogens (BG505 SOSIP) that antigenically mimic the HIV envelope glycoprotein (Env) have improved the elicitation of potent isolate-specific Ab responses in rabbits and macaques, but so far failed to induce bnAbs. Sanders, R. W. et al., *PLoS Pathog.* 9, e1003618 (2013); McCoy, L. E. et al., *Cell Rep* 16, 2327-2338 (2016); Sanders, R. W. et al., *Science* 349, aac4223-aac4223 (2015). The difficulty in eliciting bnAbs has been attributed to the enormous antigenic diversity of the envelope glycoprotein and to the dense N-linked glycan coat that covers Env (the 'glycan shield'). One possible contributor to this failure is that the relevant antibody repertoires are poorly suited to target somewhat occluded conserved epitope regions on Env relative to exposed variable epitopes. BnAbs isolated from chronic infection have a number of unusual features that have been selected to cope with the glycan shield including much longer than average VH CDR3 loops. Walker, L. M. et al., *Nature* 477, 466-470 (2011); Doria-Rose, N. A. et al., *Nature* 509, 55-62 (2014); Bonsignori, M. et al., *J. Virol.* 85, 9998-10009 (2011). VH CDR3s in most vertebrates have restricted lengths that predominantly encode loops of 12-16 amino acids upon VDJ recombination. Shi, B. et al., *Theor Biol Med Model* 11, 30 (2014); Lee, E.-C. et al., *Nat. Biotechnol.* 32, 356-363 (2014); Kodangattil, S. et al., *MAbs* 6, 628-636 (2014). Therefore, in many species, relatively few antibody precursors can be affinity-matured to HIV bnAbs. Cows, however, produce antibodies with VH CDR3s that average ~26 amino acids in length with an ultralong subset (10-15% of the repertoire) that can be over 70 amino acids in length. Berens, S. J., Wylie, D. E. & Lopez, O. J., *Int. Immunol.* 9, 189-199 (1997); Lopez, O., Perez, C. & Wylie, D., *Immunol. Rev.* 162, 55-66 (1998); Saini, S. S. et al., *Eur. J. Immunol.* 29, 2420-2426 (1999); Saini, S. S. & Kaushik, A., *Scand. J. Immunol.* 55, 140-148 (2002); de los Rios, M. et al., *Curr. Opin. Struct. Biol.* 33, 27-41 (2015); Wang, F. et al., et al., *Cell* 153, 1379-1393 (2013); Saini, S. S., et al. *Int. Immunol.* 15, 845-853 (2003). Previous work has shown that repeated immunization over multiple years with a non-well-ordered Env trimer in cows can lead to some neutralization breadth in the immunoglobulin-rich colostrum, although with relatively low potency. Heydarchi, B. et al., *MAbs* 9, 0-00 (2016); Heydarchi, B. et al., *PLOS ONE* 11, e0157353 (2016); Kramski, M. et al., *Antimicrob. Agents Chemother.* 56, 4310-4319 (2012).

Four cows have been immunized with BG505 SOSIP. Remarkably, BG505 SOSIP immunization resulted in rapid elicitation of broad and potent serum antibody responses in all four animals. Longitudinal serum analysis for one cow showed the development of neutralization breadth (20%, n=117 cross-clade isolates) in 42 days and 96% breadth (n=117) at 381 days. A monoclonal antibody (mAb) isolated from this cow harbored an ultralong VH CDR3 of 60 amino acids and neutralized 72% of cross-clade isolates (n=117) with a potent median $IC_{50}$ of 0.028 μg/ml. The breadth was elicited with a single trimer immunogen and did not require additional envelope diversity.

Experimental Methods

Pseudovirus Neutralization Assays: Plasmids encoding HIV Env were co-transfected into HEK 293T cells (ATCC) with pSG3ΔEnv, an Env-deficient genomic backbone plasmid, in a 1:2 ratio using X-tremeGENE HP (Roche) as transfection reagent. Cell culture supernatants were harvested 3 days post transfection and sterile filtered through a 0.22 μm filter. Neutralizing activity was measured by incubating monoclonal antibodies or sera with replication incompetent pseudovirus for 1 h at 37C before transferring onto TZM-bl target cells (aidsreagent.org) as described previously. Walker, L. M. et al., *Nature* 477, 466-470 (2011).

BG505 SOSIP trimer expression and purification: BG505 SOSIP.664 gp140, BG505 SOSIP.664-His gp140, and BG505 SOSIP.664-avi gp140 were expressed in HEK293F (Invitrogen) as described previously. Sok, D. et al., *Proc. Natl. Acad. Sci. U.S.A.* 111, 17624-17629 (2014). Briefly, HEK293F cells were maintained in FreeStyle medium (Invitrogen). For gp140 trimer production, HEK293F cells were seeded at a density of $0.5\times10^6$/mL. After 24 h, cells were transfected with 1 mg of 293Fectin (Invitrogen) with 300 μg of Env plasmid and 75 μg of furin plasmid in OPTI-MEM according to the manufacturer's protocol. Supernatants were purified using a *Galanthus nivalis* lectin (Vector Labs) column and protein was eluted with 1M methyl-α-D-mannopyranoside (MMP, Sigma). Following buffer exchange into PBS, only trimers with AviTags were in vitro biotinylated using the BirA enzyme according to the manufacturer protocol (Avidity). The affinity-purified Env proteins were further purified to size homogeneity using size exclusion chromatography (SEC) on a Superose 6 10/300 GL column (GE Healthcare) in PBS. The trimer fractions were collected and pooled and protein concentrations were determined using either a bicinchonic acid-based assay (Thermo Scientific) or UV280 absorbance using theoretical extinction coefficients.

Cow immunization: *Bos taurus* calves six months of age were used to analyze the bovine immune response against HIV antigens. Animals were primed and boosted by intradermal inoculation. Two animals were selected for two different immunization experiments as a pilot study, yielding a sample size of four animals total. All four animals were bled from the jugular vein as often as once a week for serum and for the isolation of mononuclear cells from peripheral blood. Animals and subsequent analyses were not randomized or blinded. Heifers #148 and #3441 were Angus cross breeds immunized with 200 μg BG505 SOSIP trimer (200 μL antigen/800 μL adjuvant inoculations were divided into five 200 μl injections with Iscomatrix adjuvant for #148 and RIBI for #3441) on one side and 200 μg JRFL gp120 on the other (200 μL antigen/800 μL adjuvant inoculations were split into five 200 μl injections with RIBI adjuvant). Both heifers #148 and #3441 were boosted at Day 21 with 200 μg of the same antigen on the same side of the neck as previously received, and once more on Day 78 with the same delivery of immunogen as the first boost. All boosts of these two heifers employed RIBI as adjuvant. Holstein steers #26 and #27 received immunizations of 200 μg BG505 SOSIP trimer (total spread over five sites on each side of neck) emulsified in equal volume of ENABL C1 (VaxLiant) adjuvant. Boosts of equal amounts of antigen were administered on Days 36, 64, and 99, 148, 211, and 360. Exceptions were that on Day 99 the boost was administered with RIBI adjuvant instead of ENABL C1. Cows #26 and #27 were euthanized for tissue harvest into RNAlater for RNA and cDNA preparation of immune tissues. These protocols were approved by the Texas A&M Institutional Animal Care and Use Committee for MFC as AUP 2015-078.

Single Particle Negative Stain Electron Microscopy: BG505 SOSIP.664+NC-Cow1 complexes were placed on glow-discharged carbon coated copper mesh grids and stained with 2% uranyl formate. Grids were screened for appropriate stain thickness and particle distribution using an FEI Morgagni (80 keV) electron microscope. The final data set was collected on an FEI Tecnai Spirit T12 (120 keV) electron microscope with a Tietz TVIPS CMOS (4K by 4K) camera controlled with Leginon automated imaging software. Images were collected at 52,000× magnification with a −1.3 μm defocus for a final magnified pixel size of 2.05 Å/pix. Both Automated particle picking performed with DoG-Picker and reference-free 2-D classification with iterative MRA-MSA were executed through the Appion database[30]. For 3D analysis, micrographs were first CTF estimated with GCTF then particles were extracted, phase-flipped, and subjected to reference-based 3D classification and refinement in Relion version 2.0. The final 3D reconstruction contained ~3.5k particles out of the initial ~13.5k that went into 3D classification. UCSF Chimera was used to generate figures.

Single-Cell Sorting of Cow PBMCs using Flow Cytometry: Sorting of cow PBMCs was performed as described previously with some modifications. Sok, D. et al., *Proc. Natl. Acad. Sci. U.S.A.* 111, 17624-17629 (2014) Cow PBMCs were stained with primary fluorophore-conjugated antibodies binding cow IgG (AbCam) and 50 nM of biotinylated BG505 SOSIP.664-avi gp140 coupled to streptavidin-APC and PE (Life Technologies) in equimolar ratios. Cells were stained for 1 hr at 4° C. in PBS containing 1 mM EDTA and 1% FBS. Cells were sorted for $IgG^+$/BG505 SOSIP.664-avi-$PE^+$/BG505 SOSIP.664-avi-$APC^+$ events. Target cells were single-cell sorted into 96-well plates containing lysis buffer on a BD Fusion sorter and were immediately frozen on dry ice.

Single Cell PCR Amplification and Cloning of Antibody Variable Genes: cDNA synthesis from mRNA and subsequent rounds of PCR amplification of antibody variable genes were performed as previously described, but using primers for cow immunoglobulin (Table 5). PCR reactions were set up in 25 μL volume with 2.5 μL cDNA or PCR1 product using HotStarTaq Master Mix (Qiagen). Heavy and light chain paired retrieved form single sorted cells were cloned into human antibody expression vectors as described previously. Tiller, T. et al., *J Immunol Methods* 329, 112-124 (2008).

TABLE 5

Primer sequences used to amplify and clone antibody variable genes. Indicated restriction sites are underlined.

| Primer Name | Chain Amplified | Primer Direction | Primer Sequence |
|---|---|---|---|
| L leader 2 F | Light chain | Forward | CACCATGGCCTGGTCCCCTCTG (SEQ ID NO: 199) |
| L leader 35 F | Light chain | Forward | GACCCCAGACTCACCATCTC (SEQ ID NO: 200) |
| L leader 45 F | Light chain | Forward | AGGGCTGCGGGCTCAGAAGGCAGC (SEQ ID NO: 201) |
| L leader 55 F | Light chain | Forward | CTGCCCCTCCTCACTCTCTGC (SEQ ID NO: 202) |
| L leader 15 F | Light chain | Forward | GGAACCTTTCCTGCAGCTC (SEQ ID NO: 203) |
| L leader 16 F | Light chain | Forward | GCTTGCTTATGGCTCAGGTC (SEQ ID NO: 204) |
| Cow LC rev1 | Light chain | Reverse | AAGTCGCTGATGAGACACACC (SEQ ID NO: 205) |
| Cow VH fwd1 | Heavy chain | Forward | CCCTCCTCTTTGTGCTSTCAGCCC (SEQ ID NO: 206) |
| Cow IgG rev1 | Heavy chain | Reverse | GTCACCATGCTGCTGAGAGA (SEQ ID NO: 207) |
| Cow IgG rev2 | Heavy chain | Reverse | CTTTCGGGGCTGTGGTGGAGGC (SEQ ID NO: 208) |
| LV2 F | Light chain | Forward AgeI | CATCCTTTTTCTAGTAGCAACTGCAACCGGTTGA GGATGAGGCGGATTATT (SEQ ID NO: 209) |
| LV6 F | Light chain | Forward AgeI | CATCCTTTTTCTAGTAGCAACTGCAACCGGTGGG TCAGAAGGTCTCCATC (SEQ ID NO: 210) |
| LF8 F | Light chain | Forward AgeI | CATCCTTTTTCTAGTAGCAACTGCAACCGGTGAT TTTGGGTGTGAGCTGGT (SEQ ID NO: 211) |
| LV23 F | Light chain | Forward AgeI | CATCCTTTTTCTAGTAGCAACTGCAACCGGTCCC CCAAAACCCTCATCTAT (SEQ ID NO: 212) |
| LV30 F | Light chain | Forward AgeI | CATCCTTTTTCTAGTAGCAACTGCAACCGGTCAG CAGCAATGTTGGAAATG (SEQ ID NO: 213) |
| LV33 F | Light chain | Forward AgeI | CATCCTTTTTCTAGTAGCAACTGCAACCGGTCCC CCAAAACCCTGATCTAT (SEQ ID NO: 214) |
| LV35 F | Light chain | Forward AgeI | CATCCTTTTTCTAGTAGCAACTGCAACCGGTGGC GGATTATTTCTGTGCAT (SEQ ID NO: 215) |
| LV45 F | Light chain | Forward AgeI | CATCCTTTTTCTAGTAGCAACTGCAACCGGTTCT GGGAATCTGGGACAGAC (SEQ ID NO: 216) |
| LV55 F | Light chain | Forward AgeI | CATCCTTTTTCTAGTAGCAACTGCAACCGGTCTG CCAGGGAGACGACTTAG (SEQ ID NO: 217) |
| LV10 F | Light chain | Forward AgeI | CATCCTTTTTCTAGTAGCAACTGCAACCGGTCTT CAGTGTCAGTGGCCTTG (SEQ ID NO: 218) |
| LV15 F | Light chain | Forward AgeI | CATCCTTTTTCTAGTAGCAACTGCAACCGGTGCT CCAGACCAGTGAGGAAG (SEQ ID NO: 219) |
| LV16 F | Light chain | Forward AgeI | CATCCTTTTTCTAGTAGCAACTGCAACCGGTGTC ACCCTCACCTGTGGACT (SEQ ID NO: 220) |
| LV21 F | Light chain | Forward AgeI | CATCCTTTTTCTAGTAGCAACTGCAACCGGTAGC ATCAGCCAGACTCACCT (SEQ ID NO: 221) |
| LV40 F | Light chain | Forward AgeI | CATCCTTTTTCTAGTAGCAACTGCAACCGGTGTC ACCCTCACCTGTGGACT (SEQ ID NO: 222) |
| Cow LC rev | Light chain | Reverse XhoI | GTTGGCTTGAAGCTCCTCACTCGAGGGYGGGAA CAGAGTG (SEQ ID NO: 223) |
| Cow VH fwd | Heavy chain | Forward AgeI | CATCCTTTTTCTAGTAGCAACTGCAACCGGTGTA CATTCCMAGGTGCAGCTGCRGGAGTC (SEQ ID NO: 224) |
| Cow IgG rev | Heavy chain | Reverse SalI | GGAAGACCGATGGGCCCTTGGTCGACGCTGAGG AGACGGTGACCAGGAGTCCTTGGCC (SEQ ID NO: 225) |

Antibody production and purification: Antibody plasmids containing heavy chain and light chain genes were co-transfected (1:1 ratio) in either HEK 293T or 293F cells using X-tremeGENE (Roche) or 293fectin (Invitrogen) as transfection reagents, respectively. Antibody containing supernatants were harvested 4 days after transfection and 0.22 μm sterile filtered. Antibodies produced in 293T cells were quantified by anti-Fc ELISA and used directly in neutralization assays for screening purposes. Antibody supernatants produced in 293F cells were purified over Protein A Sepharose 4 Fast Flow (GE healthcare) columns as described previously. Sok, D. et al., *Proc. Natl. Acad. Sci. U.S.A.* 111, 17624-17629 (2014).

ELISA assays: ELISA plates were first coated with an anti-C5 gp120 antibody at 4° C. in 1×PBS overnight. Plates were then washed 5× with PBS+0.05% tween and blocked with 3% BSA in 1× PBS at room temperature for 1 hr. Mutant pseudovirus supernatants were lysed with 1% NP40 and then captured on ELISA plates at 37° C. for 2 hr. Plates were washed 5× with PBS+0.05% tween and then serial dilutions of mAb were added to the wells and plates were incubated at room temperature for 1 hour. Plates were washed 5× with PBS+0.05% tween and then goat anti-human IgG F(ab')2 conjugated to alkaline phosphatase (Pierce) was diluted 1:1000 in PBS containing 1% BSA and 0.05% tween and added to the wells. The plate was incubated at room temperature for 1 h and washed 5× with PBS+0.05% tween. Plates were then developed by adding 50 μL of alkaline phosphatase substrate (Sigma) dissolved in alkaline phosphatase staining buffer (pH 9.8), according to the manufacturer's instructions. The optical density at 405 nm was read on a microplate reader (Molecular Devices). For experiments involving antibody binding to antigen at different pH, serial dilutions of mAbs were incubated in PBS at different pHs or simulated vaginal fluid (SVF) for 1 hr at RT and then washed 5× with PBS+0.05% tween before addition of goat anti-human IgG F(ab')2 conjugated to alkaline phosphatase secondary. Sok, D. et al., *Proc. Natl. Acad. Sci. U.S.A.* 111, 17624-17629 (2014). SVF was made with citric acid instead of lactic acid to improve buffering at higher pH levels.

Competition ELISA: For competition ELISA experiments, competing antibodies were biotinylated using an antibody biotinylation kit (Thermo Scientific). Plates were coated with an anti-His antibody (Roche) at 5 μg/mL overnight. Following washing, plates were blocked with 3% BSA for 1 hr at RT. The stabilized BG505 SOSIP construct MD39 was then captured at 2.5 μg/mL in PBS (50 μl/well) for 2 h at 37° C. Steichen, J. M. et al., *Immunity* 45, 483-496 (2016). Following washing, serially diluted antibodies in PBS/1% BSA were added for 30 min. To this was added biotinylated antibody at a constant $EC_{70}$ concentration for 1 h. Plates were washed and detection was measured using alkaline phosphatase-conjugated streptavidin (Pierce) at 1:1000 for 1 hr at RT. Absorption was measured at 405 nm.

Polyreactivity assay: HEp-2 cell staining assay: The HEp-2 cell-staining assay was performed using kits purchased from Aesku Diagnostics (Oakland, CA) according to manufacturer's instructions. These Aesku slides use optimally fixed human epithelial (HEp-2) cells (ATCC) as substrate and affinity purified, FITC-conjugated goat anti-human IgG for the detection. Briefly, 2.5 μg or 25 μl of 100 μg/ml mAb and controls were added to wells and incubated on HEp-2 slides in a moist chamber at room temperature for 30 min. Slides were then rinsed and submerged in PBS and 25 μl of FITC-conjugated goat anti-human IgG was immediately applied to each well. Slides were allowed to incubate at room temperature in a moist chamber for another 30 min. Slides were then washed in the same manner as above and then mounted on coverslips using the provided mounting medium. Slides were viewed at 20× magnification and photographed on an EVOS f1 fluorescence microscope at a 250 ms exposure with 100% intensity. Positive and negative control sera were provided by the vendor. Samples showing fluorescence greater than the negative control were considered positive for HEp-2 staining.

Polyreactivity assay: Polyspecificity reagent (PSR) binding assay: Monoclonal antibodies were screened for reactivity with preparations of solubilized membrane proteins (SMP) and cytosolic proteins (SCP) as described 1 previously with a small modification. Jardine et al., https://doi.org/10.1371/journal.ppat.1005815. Briefly, SMP and SCP were extracted from CHO cells (ATCC). The protein concentration was determined using the Dc-protein assay kit (BioRad). SMP and SCP were then immobilized on ELISA plates for mAb screening. The results were established by reading the absorbance at 450 nm of the examined samples.

Polyreactivity assay: Single autoantigen reactivity: Single antigen ELISA assays for SSA/Ro, SS-B/La, Sm, ribonucleoprotein (RNP), Jo-1, double-stranded DNA, centromere B, and histones were purchased from Aesku Diagnostics (Oakland, CA). The 96 wells were separately coated with these eight cellular and nuclear antigens for the qualitative detection of mAbs reactivity. A cut-off calibrator was provided by the manufacturer. The negative control was diluted human serum.

Results

Production of Broadly Neutralizing Polyclonal Bovine Serum

To investigate immunization with a well-ordered Env trimer in cows, two experiments were performed (FIG. 1A). A first pilot experiment involved immunization with JR-FL gp120 and BG505 SOSIP on each flank of two cows. Evaluation of sera on an indicator virus panel showed that both cows developed neutralization breadth and potency, with one cow (#3441) developing exceptionally potent responses (FIG. 1B). Based on these initial results, two additional cows were immunized with BG505 SOSIP alone (FIG. 1A). The terminal bleeds (day 381) for these two cows were also tested on the indicator virus panel and similar cross-clade neutralizing serum responses were observed (FIG. 1B).

Figure 2A:
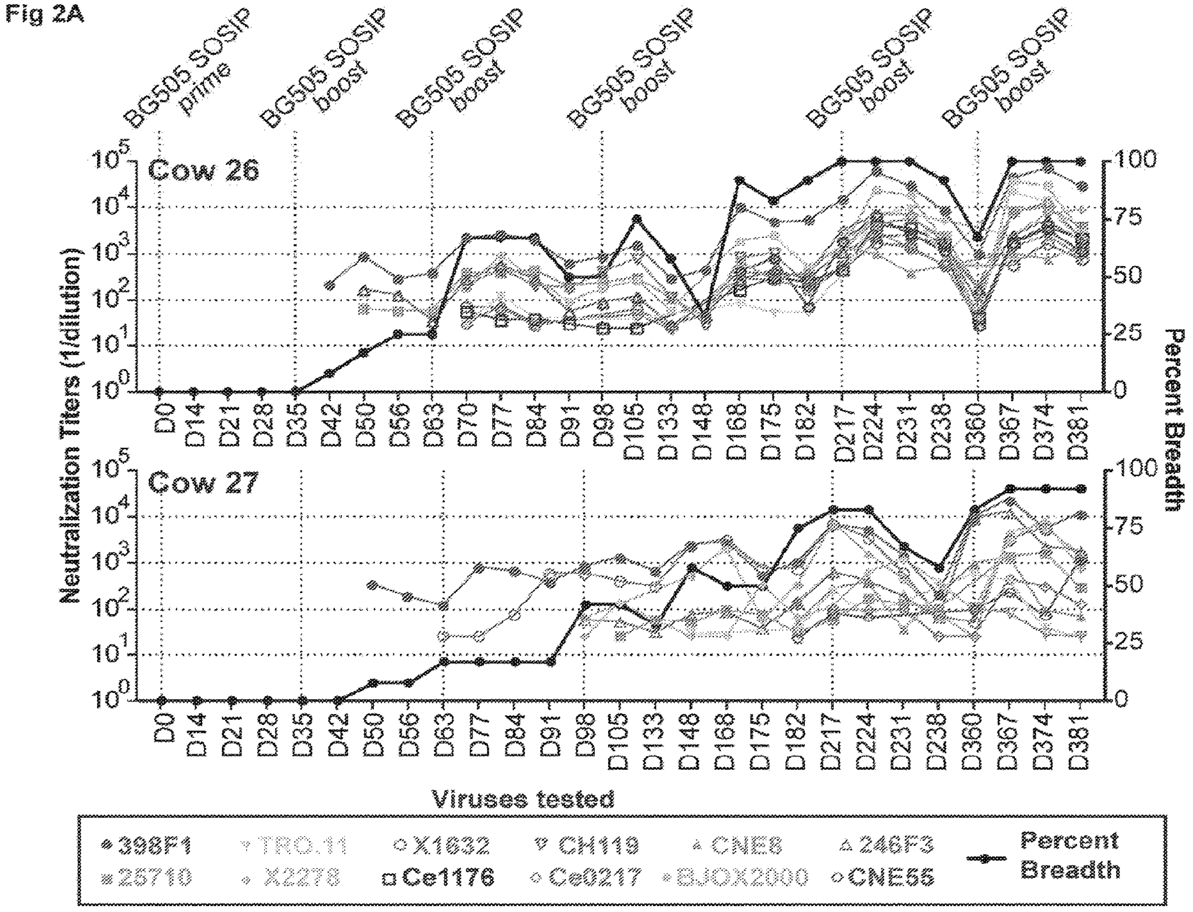
Figure 4:
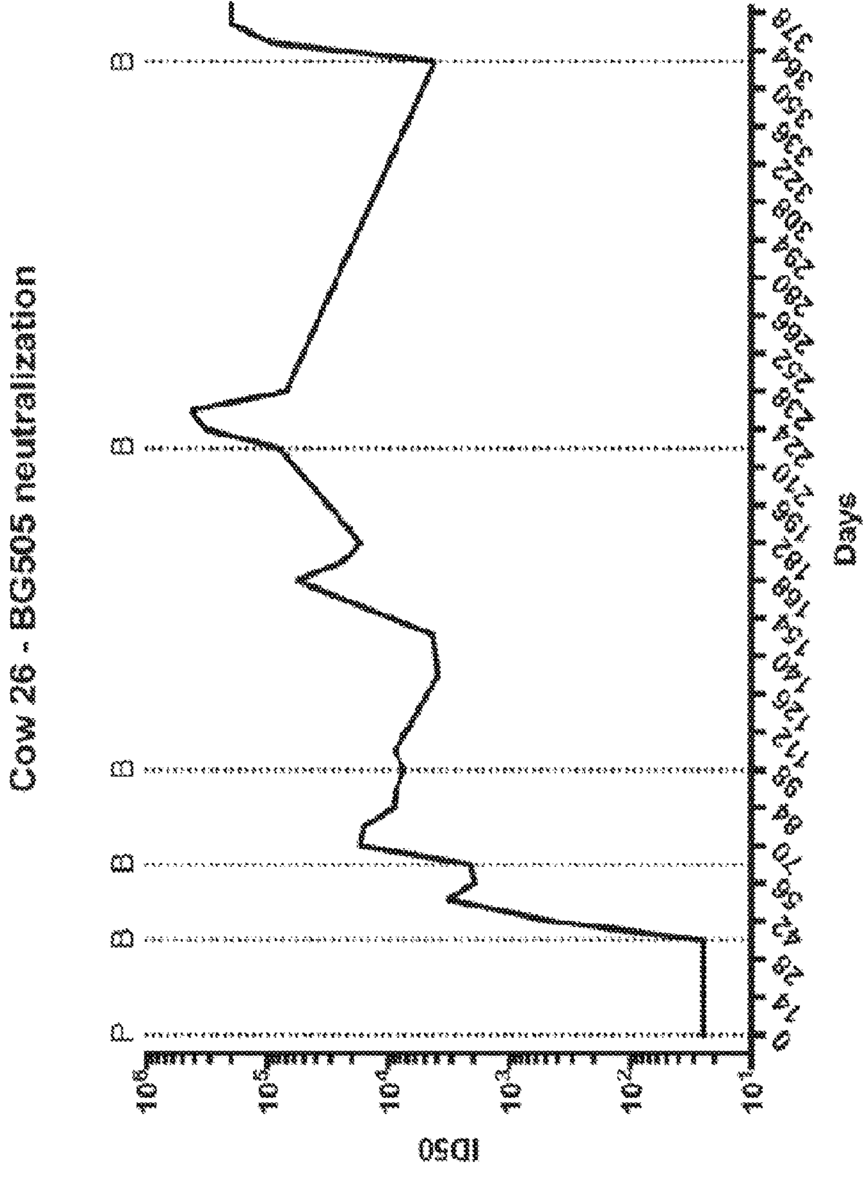
FIG. 4. Autologous serum time points tested for neutralization on BG505 pseudovirus. Neutralization against autologous virus emerged at the same time as breadth (d42) and increased in potency over time. Values represent serum $ID_{50}$.
Figures 6, 7A, 7B:
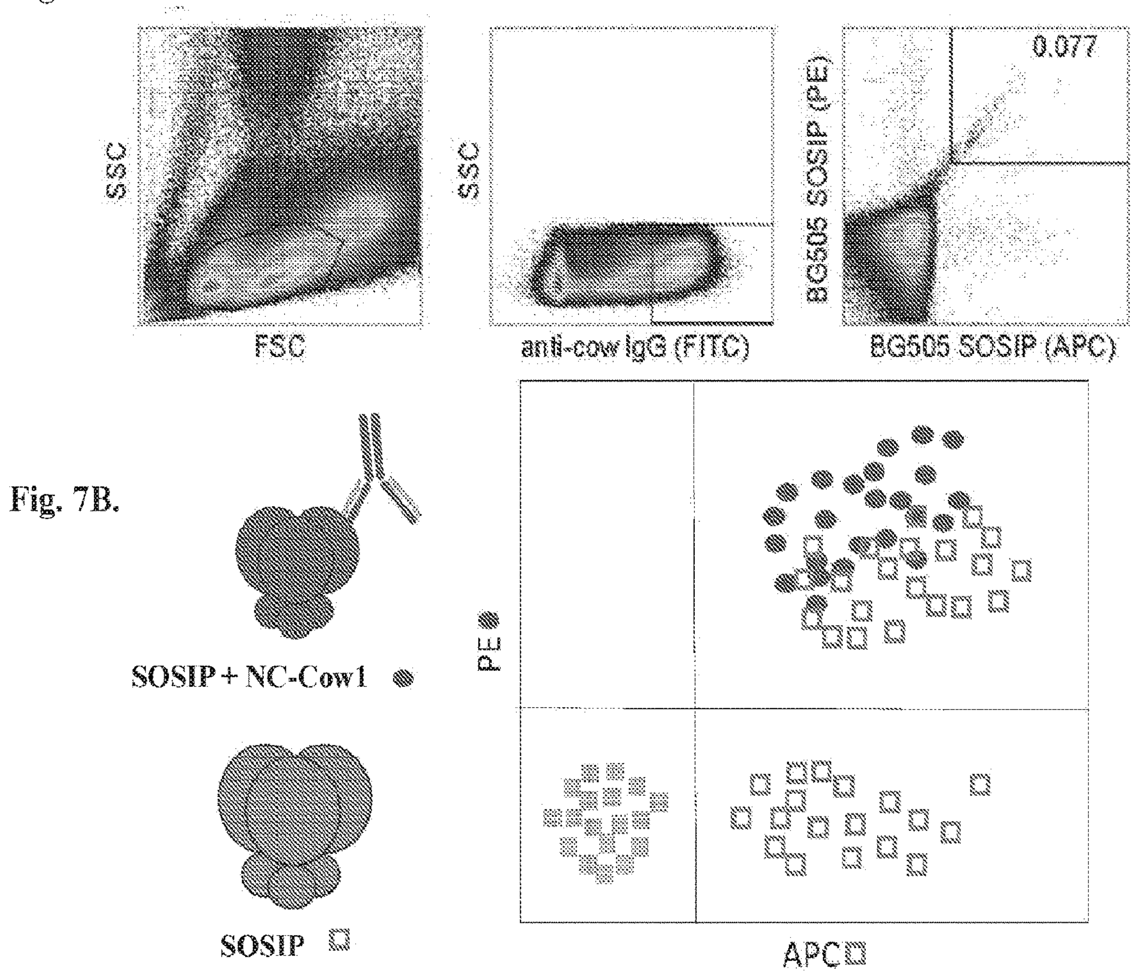
FIG. 6. Development of neutralization breadth at 35 days post immunization from cows in experiment 1. Serum collected at day 35 from experiment 1 was tested for neutralization breadth and potency on the 12-virus global indicator panel. Values represent serum $ID_{50}$.
FIGS. 7A-7B. Sorting strategy for isolating antigen-specific IgG+ B cells.

Next determined was how quickly these responses developed. Sera from cow 26 and cow 27 were sampled approximately every 7 days and tested on the same virus indicator panel (FIG. 2A and FIG. 3). Remarkably, the results show the development of cross-neutralizing activity (8% breadth, n=12) only 42 days following a prime and single homologous boost with BG505 SOSIP for cow #26. Autologous neutralization emerged at the same time as broad responses and potency increased over time (FIG. 4). Cow #27 also developed broad responses, although more delayed than for cow #26 (FIG. 2A). Evaluation of the day 35 time point (14 days after first boost) for cows #148 and #344 (FIG. 2A) from experiment 1 similarly showed rapid emergence of breadth albeit with lower potency (FIG. 6).

To fully evaluate the extent of neutralization breadth, sera from cow #26 was tested on a 117 cross-clade virus panel (FIG. 2B and FIG. 5A-C) using the following time points: d42, d77, d238, and d381. The results showed higher neutralization breadth at the earliest time point (day 42, 20% breadth) than observed for the indicator panel (8%). Following a second boost (d77), this breadth expanded to 79% of isolates. At day 238 and day 381, breadth continued to rise to 92% and 96% of isolates, respectively. Potency, determined by median $ID_{50}$ titers, also increased with consecutive boosts.

Monoclonal bnAbs were isolated from cow #26. Peripheral blood mononuclear cells (PBMCs) from time points d70 and d238 were sorted with fluorophores conjugated to anti-cow IgG, and biotinylated BG505 SOSIP was used as antigen bait as described previously (FIG. 7A-B). Sok, D. et al., *Proc. Natl. Acad. Sci. U.S.A.* 111, 17624-17629 (2014).

Generation of Neutralizing Bovine Monoclonal Antibodies

Figure 8A:
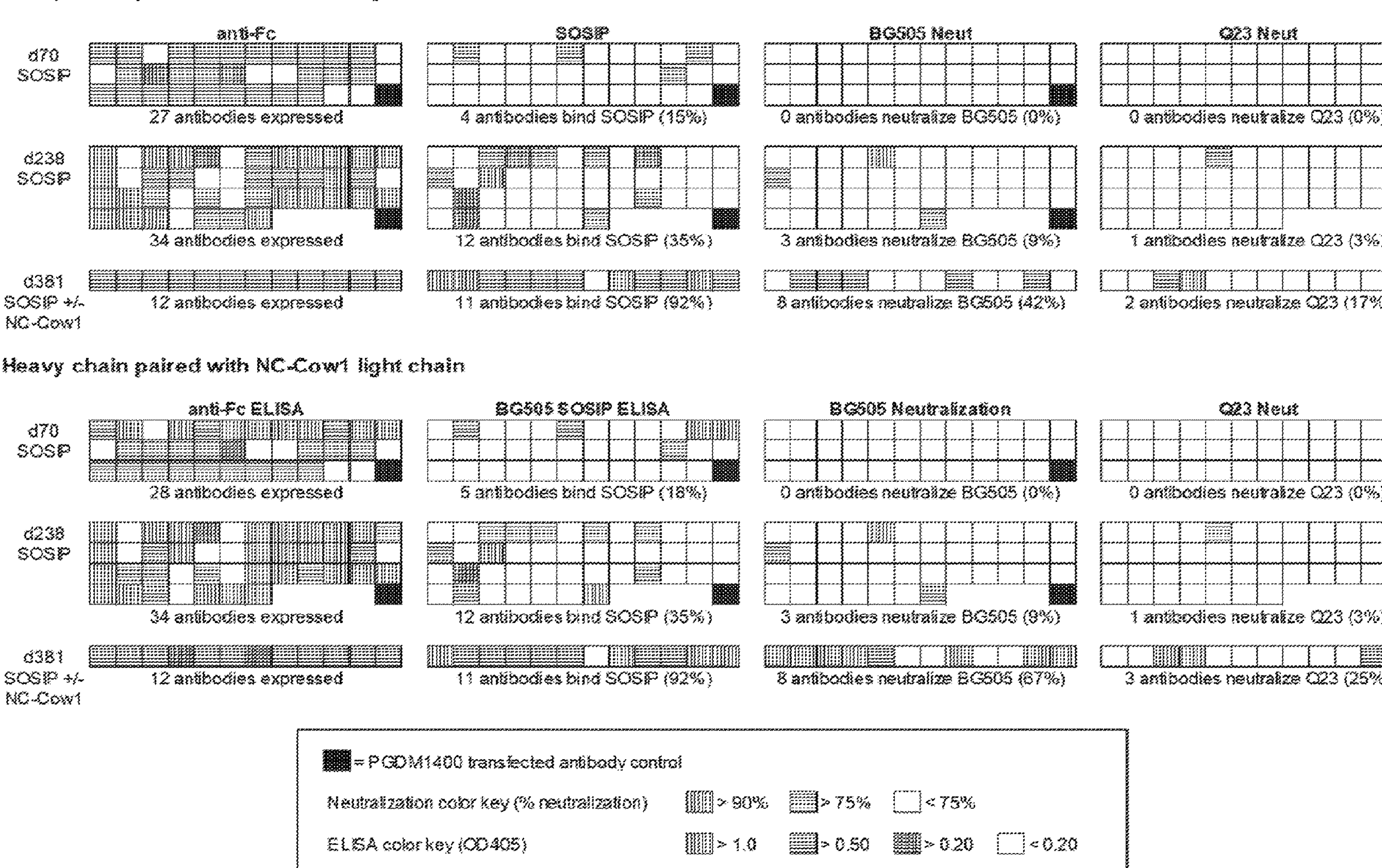
FIGS. 8A-B. Functional screening and sequencing information for isolated antibodies.
Figure 8B:
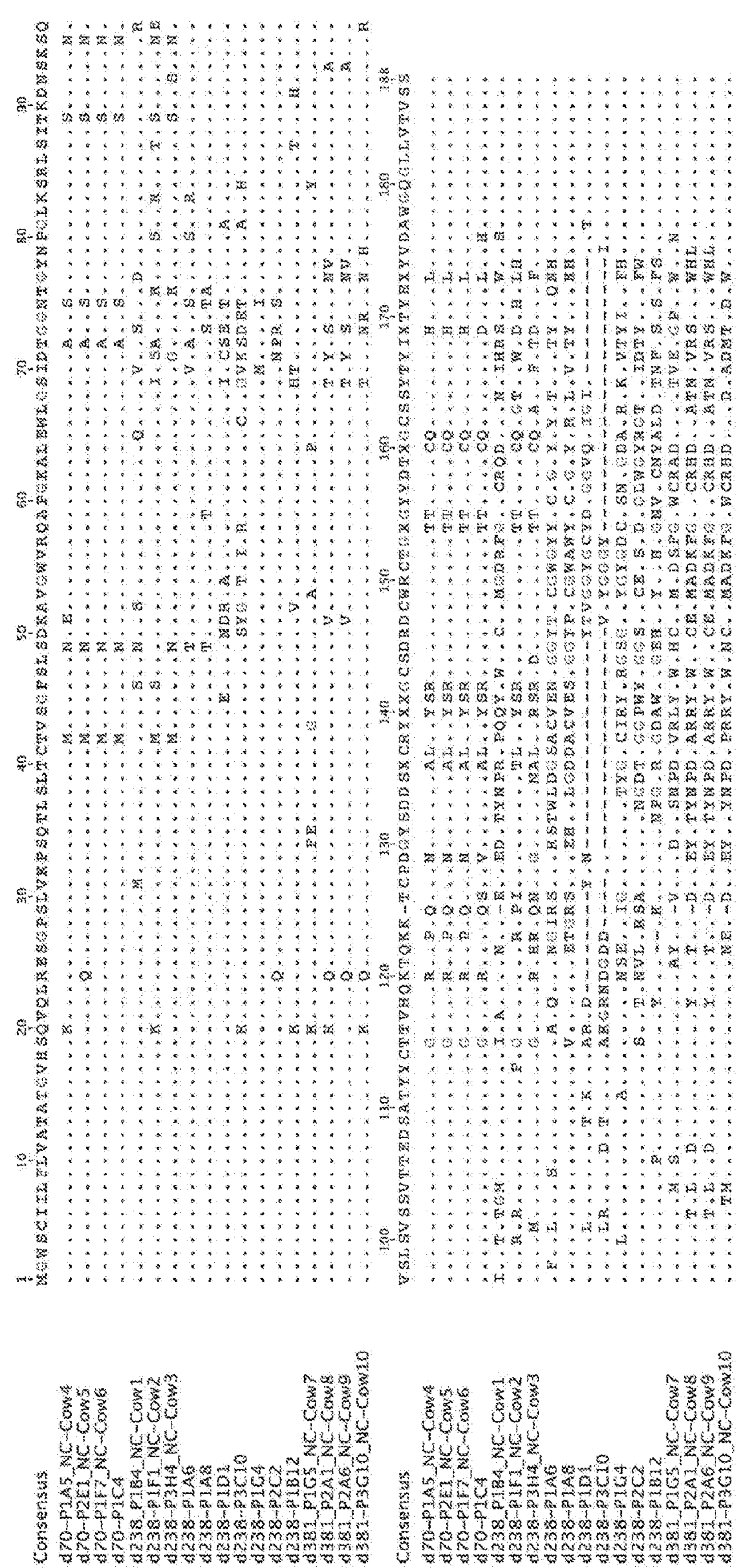
Figure 9D:
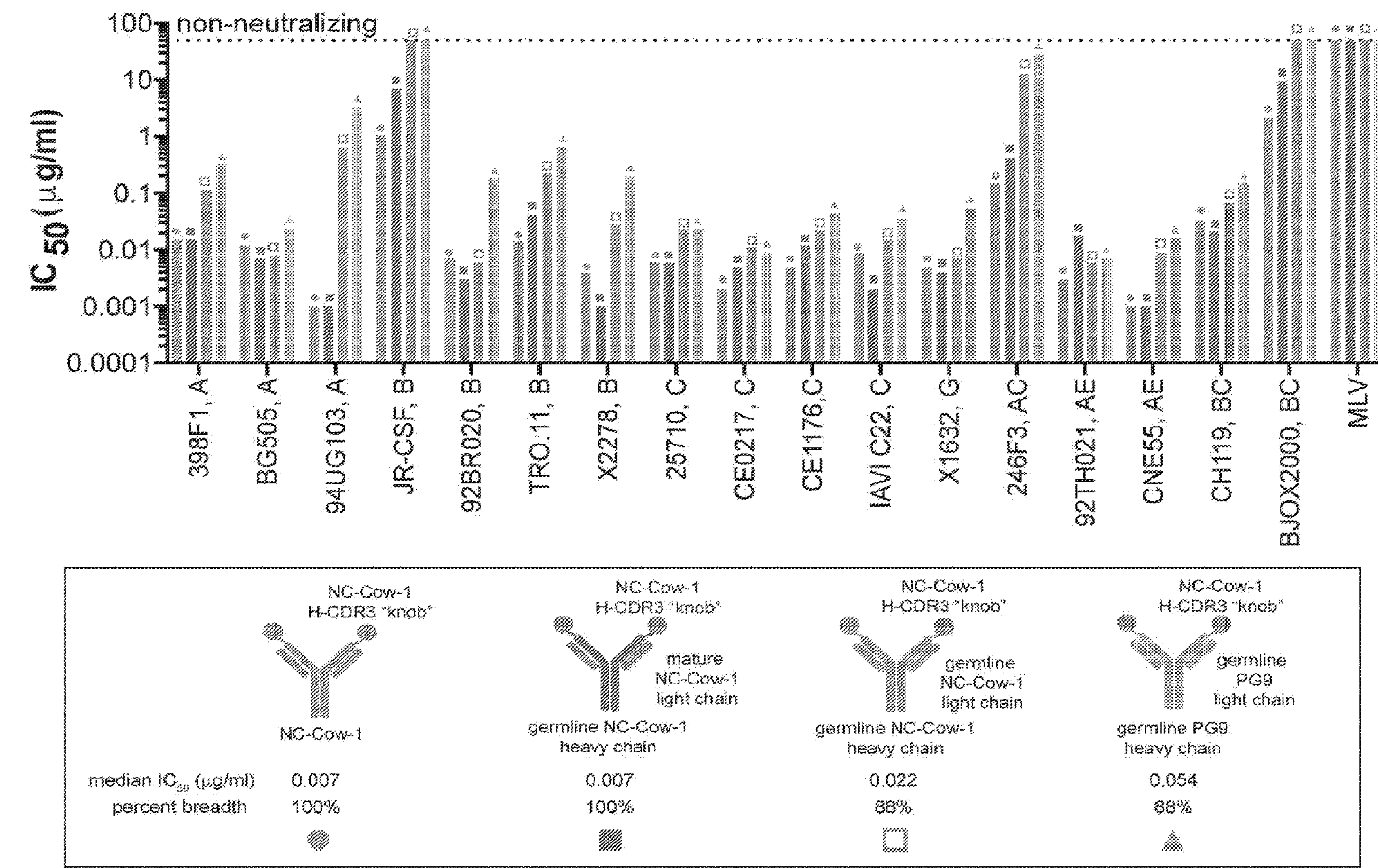
Figure 10C:
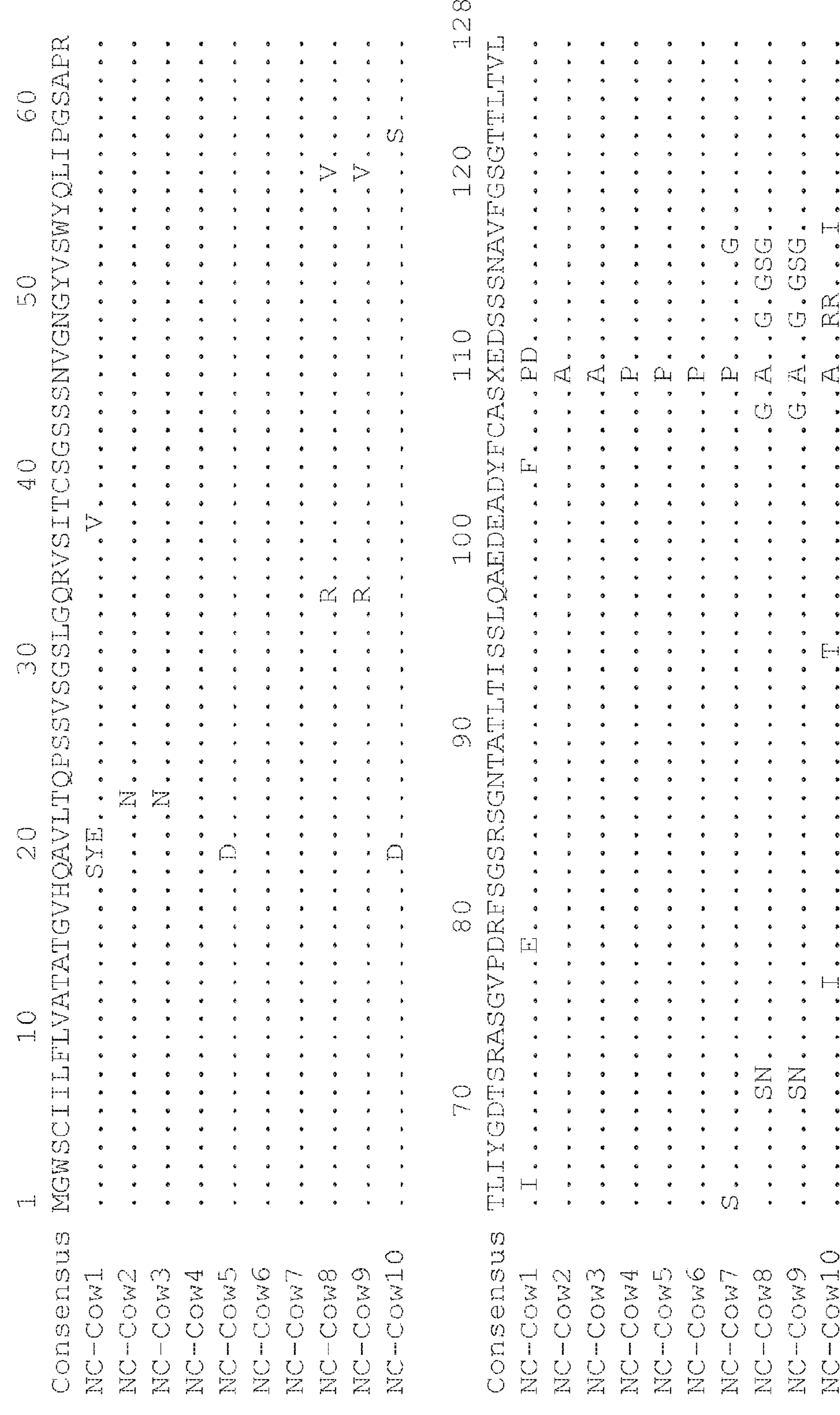

Sorting and screening of PBMCs at different time points (FIG. 8A-B) using different sort strategies (FIG. 7A-B) resulted in the isolation of 10 mAbs named NC-Cow1 to NC-Cow10. In one sorting strategy, cow PBMCs were sorted for IgG+ cells that bound to biotinylated BG505 SOSIP-AviTag conjugated on PE and APC fluorophores. This sort strategy resulted in the generation of the broadly neutralizing antibody NC-Cow1. In a second strategy, to isolate epitope-specific antibodies, unliganded BG505 SOSIP (blue) and BG505 SOSIP liganded with NC-Cow1 was used to antigen-sort memory B cells. Epitope-specific B cells were defined as binding unliganded SOSIP and not binding to liganded SOSIP. This sort strategy resulted in the generation of broadly neutralizing antibodies NC-Cow7 to NC-Cow10. Sequences and alignments of the heavy and light chain sequences for NC-Cow1 to NC-Cow10 are listed in Table 6 and FIGS. 10A-C. Interestingly, all 10 antibodies have ultralong VH CDR3s (FIG. 9A)

Following sorting PMBCs, single cell RT PCR was done to amplify and clone the heavy chain variable region coding sequences. Amplified heavy chains were paired with universal cow light chain or with NC-Cow1 light chain and tested for expression (anti-Fc ELISA), Ag binding (BG505 SOSIP), autologous neutralization (BG505 pseudovirus), and heterologous neutralization (Q23 pseudovirus). (FIG. 8A). Sequence alignment of recovered heavy chains are listed. As ultralong VH CDR3 antibodies have been reported with (V30, to pair a single germline light chain MGWSCIILFLVATATGVHQAVLNQPSSVSGSLGQRVSITCSGSSSNVGNGYVSWYQLIPGSAPRT LIYGDTSRASGVPDRFSGSRSGNTATLTISSLQAEDEADYFCASAEDSSSNAVFGSGTTLTV SEQ ID NO: 226), amplified heavy chain genes were first paired with the universal cow light chain and screened for expression, binding to BG505 SOSIP, neutralization of BG505 virus, and neutralization of a clade A heterologous virus, Q23. From this dataset, 3 antibodies (named NC-Cow1, NC-Cow2, and NC-Cow3) were selected that showed autologous neutralization (all from d238) and corresponding native light chains were amplified, with success for only NC-Cow1. These three antibodies were expressed and purified at larger scale for additional characterization by maintaining native pairing for NC-Cow1 and pairing with germline V30 for NC-Cow2 and NC-Cow3. For the d70 time point, three heavy chains were selected that showed binding to BG505 SOSIP, but no neutralization, and these antibodies were produced with their native light chain pairs (NC-Cow4 to NC-Cow6). Finally, as NC-Cow1 could neutralize isolate Q23 in the neutralization screen, an additional sort with PBMCs from d381 was performed, but used BG505 SOSIP liganded with and without NC-Cow1 to enrich for epitope-specific antibodies. The enrichment yielded an additional 5 hits by neutralization screen, and 4 out of these 5 antibodies were produced at larger scale with their native light chain pairs (NC-Cow7 to NC-Cow10). Small-scale screening was also performed with all heavy chains paired with NC-Cow1 light chain and no significant increase in neutralization breadth was observed, although there were slight improvements in BG505 SOSIP affinity or autologous potency.

TABLE 6

DNA sequences of isolated monoclonal antibodies.

| Clone | nucleotide sequence encoding leader sequence and VH | nucleotide sequence encoding leader sequence and VL |
| --- | --- | --- |
| NC-Cow1 | ATGGGATGGTCATGTATCATCCTTTT<br>TCTAGTAGCAACTGCAACCGGTGTA<br>CATTCCCAGGTGCAGCTGCGGGAGT<br>CGGGCCCCAGCCTGATGAAGCCGTC<br>ACAGACCCTCTCCCTCACCTGCACG<br>GTCTCTGGATCTTCATTGAACGACA<br>AGTCTGTAGGCTGGGTCCGCCAGGC<br>TCCAGGGAAGGCGCTGCAGTGGCTC<br>GGTAGTGTGGACACTAGTGGAAACA<br>CAGACTATAACCCAGGCCTGAAATC<br>CCGGCTCAGCATCACCAAGGACAAC<br>TCCAAGAGCCGAATCTCTCTTACAG<br>TGACTGGCATGACAACTGAAGACTC<br>GGCCACATACTACTGCATTACTGCTC<br>ACCAAAAAACAAACAAAAAAGAGT<br>GTCCGGAGGATTATACTTATAATCC<br>ACGTTGCCCTCAGCAGTATGGTTGG<br>AGTGACTGTGATTGTATGGGCGATA<br>GGTTTGGGGGTTACTGTCGACAGGA<br>TGGTTGTA<br>GTAATTATATACATCGTAGTACTTAC<br>GAATGGTACGTCAGCGCCTGGGGCC<br>AAGGACTCCTGGTCACCGTCTCCTC<br>A (SEQ ID NO: 9) | ATGGGATGGTCATGTATCATCCTTT<br>TTCTAGTAGCAACTGCAACCGGTG<br>TACATTCCTATGAGCTGACTCAGCC<br>ATCATCCGTGTCCGGGTCCCTGGGC<br>CAGAGGGTCTCCGTCACCTGCTCTG<br>GAAGCAGCAGCAATGTTGGAAATG<br>GATATGTGAGTTGGTACCAACTGA<br>TCCCAGGATCGGCCCCCAGAACGA<br>TCATCTATGGTGACACCAGTCGAG<br>CCTCGGGGGTCCCCGAGCGATTCT<br>CCGGCTCCAGGTCTGGGAACACAG<br>CCACCCTGACCATCAGCTCGCTCCA<br>GGCTGAGGACGAGGCGGATTTCTT<br>CTGTGCATCTCCTGACGATAGTAGC<br>AGTAATGCTGTTTTCGGCAGCGGG<br>ACCACACTGACCGTCCTG (SEQ ID<br>NO: 10) |
| NC-Cow2 | ATGGGATGGTCATGTATCATCCTTTT<br>TCTAGTAGCAACTGCAACCGGTGTA<br>CATTCCAAGGTGCAGCTGCGGGAGT<br>CGGGCCCCAGCCTGGTGAAGCCGTC<br>ACAGACCCTCTCTCTCACCTGCATGG | ATGGGATGGTCATGTATCATCCTTT<br>TTCTAGTAGCAACTGCAACCGGTG<br>TACATCAGGCCGTCCTGAACCAGC<br>CAAGCAGCGTCTCCGGGTCTCTGG<br>GGCAGCGGGTCTCAATCACCTGTA |

TABLE 6-continued

| DNA sequences of isolated monoclonal antibodies. | | |
|---|---|---|
| Clone | nucleotide sequence encoding leader sequence and VH | nucleotide sequence encoding leader sequence and VL |
| | TCTCTGGATCTTCATTGAGCGACAA<br>GGCTGTAGGCTGGGTCCGCCAGGCT<br>CCGGGGAAGGCGCTGGAGTGGCTCG<br>GTATTATCAGCGCTGGTGGAAACAG<br>GGGCTATAATTCGGGCCTGAGGTCC<br>CGACTCACTATCTCCAAGGACAACT<br>CCAAGAACGAGGTCTCTCTGAGAGT<br>GAGGAGCGTGACAACTGAGGACTCG<br>GCCACATACTTCTGTGGTACTGTGCA<br>CCAGAAGACACAGCGGAAACCAATT<br>TGTCCTGATGGCTATAGTGATGATA<br>GTACTCTTCGTTACTACAGTAGATGT<br>TCTGATCGTGATTGTTGGCGTTGTAC<br>CGGGACTACGTATTATGATACTTGTC<br>AATGCGGTACTTATACTTGGATTGAT<br>ACTCACGAATTACACGTCGATGCCT<br>GGGGCCAAGGACTCCTGGTCACCGT<br>CTCCTCA (SEQ ID NO: 19) | GCGGGTCTTCCTCCAATGTCGGCA<br>ACGGCTACGTGTCTTGGTATCAGCT<br>GATCCCTGGCAGTGCCCCACGAAC<br>CCTGATCTACGGCGACACATCCAG<br>AGCTTCTGGGGTCCCCGATCGGTTC<br>TCAGGGAGCAGATCCGGAAACACA<br>GCTACTCTGACCATCAGCTCCCTGC<br>AGGCTGAGGACGAAGCAGATTATT<br>TCTGCGCATCTGCCGAGGACTCTA<br>GTTCAAATGCCGTGTTTGGAAGCG<br>GCACCACACTGACAGTCCTG (SEQ<br>ID NO: 20) |
| NC-Cow3 | ATGGGATGGTCATGTATCATCCTTTT<br>TCTAGTAGCAACTGCAACCGGTGTA<br>CATTCCCAGGTGCAGCTGCGGGAGT<br>CGGGCCCCAGCCTGGTGAAGCCGTC<br>ACAGACCCTCTCCCTCACCTGCATG<br>GTCTCTGGATTCTCATTGAACGACA<br>AGGCTGTAGGCTGGGTCCGCCAGGC<br>TCCAGGGAAGGCGTTGGAGTGGCTC<br>GGTAGTATAGGCACTGGTGGAAACA<br>AAGGCTATAACCCAGGCCTGAAATC<br>CCGGCTCAGCATCTCCAAGGACAGC<br>TCCAAGAACCAAGTCTCTCTGTCAA<br>TGAGCAGCGTGACAACTGAGGACTC<br>GGCCACATACTACTGTGGTACTGTG<br>CACCAGAGGACACACCGAAAACAA<br>AATTGTCCTGGAGGGTATAGTGATG<br>ATAATGCTCTTCGTTATCGCAGTAGA<br>TGTGATGATCGTGATTGTTGGCGTTG<br>TACTGGGACTACGTATTATGATACTT<br>GTCAATGTGCCAGTTATTTTTATACT<br>GATACTTACGAATTCTACGTCGATG<br>CCTGGGGCCAAGGACTCCTGGTCAC<br>CGTCTCCTCA (SEQ ID NO: 29) | ATGGGATGGTCATGTATCATCCTTT<br>TTCTAGTAGCAACTGCAACCGGTG<br>TACATCAGGCCGTCCTGAACCAGC<br>CAAGCAGCGTCTCCGGGTCTCTGG<br>GGCAGCGGGTCTCAATCACCTGTA<br>GCGGGTCTTCCTCCAATGTCGGCA<br>ACGGCTACGTGTCTTGGTATCAGCT<br>GATCCCTGGCAGTGCCCCACGAAC<br>CCTGATCTACGGCGACACATCCAG<br>AGCTTCTGGGGTCCCCGATCGGTTC<br>TCAGGGAGCAGATCCGGAAACACA<br>GCTACTCTGACCATCAGCTCCCTGC<br>AGGCTGAGGACGAAGCAGATTATT<br>TCTGCGCATCTGCCGAGGACTCTA<br>GTTCAAATGCCGTGTTTGGAAGCG<br>GCACCACACTGACAGTCCTG (SEQ<br>ID NO: 30) |
| NC-Cow4 | ATGGGATGGTCATGTATCATCCTTTT<br>TCTAGTAGCAACTGCAACCGGTGTA<br>CATTCCAAGGTGCAGCTGCGGGAGT<br>CGGGCCCCAGCCTGGTGAAGCCGTC<br>ACAGACCCTCTCCCTCACCTGCATG<br>GTCTCTGGATTCTCATTGAACGACG<br>AGGCTGTAGGCTGGGTCCGCCAGGC<br>TCCAGGGAAGGCGCTGGAGTGGCTC<br>GGTAGTATAGACGCTGGTGGAAGCA<br>CAGGCTATAACCCAGGCCTGAAATC<br>CCGACTCAGCATCTCCAAGGACAAC<br>TCCAAGAACCAAGTTTCTCTGTCAGT<br>GAGCAGCGTGACAACTGAGGACTCG<br>GCCACATACTACTGTGGTACTGTGC<br>ACCAGAGGACACAGCCAAAACAAA<br>CTTGTCCTAATGGCTATAGTGATGAT<br>AGTGCTCTTCGTTATTACAGTAGATG<br>TTCTGATCGTGATTGTTGGCGTTGTA<br>CTGGGACTACGTATTATGATACTTGT<br>CAATGTAGTAGTTATACTTATATTCA<br>TACTTACGAATTATACGTCGATGCCT<br>GGGGCCAAGGACTCCTGGTCACCGT<br>CTCCTCA (SEQ ID NO: 39) | ATGGGATGGTCATGTATCATCCTTT<br>TTCTAGTAGCAACTGCAACCGGTG<br>TACATCAGGCTGTGCTGACTCAGC<br>CATCATCCGTGTCCGGGTCCCTGGG<br>CCAGAGGGTCTCCATCACCTGCTCT<br>GGAAGCAGCAGCAATGTTGGAAAT<br>GGATATGTGAGCTGGTACCAACTG<br>ATCCCAGGATCGGCCCCCAGAACC<br>CTCATCTATGGTGACACCAGTCGA<br>GCCTCGGGGGTCCCCGACCGATTC<br>TCCGGCTCCAGGTCTGGGAACACA<br>GCCACCCTGACCATCAGCTCGCTCC<br>AGGCTGAAGACGAGGCAGATTATT<br>TCTGTGCATCTCCTGAGGATAGTAG<br>CAAGTAAATGCTGTTTTCGGCAGCGG<br>GCCCACTGACCGTCCTG (SEQ ID<br>NO: 40) |
| NC-Cow5 | ATGGGATGGTCATGTATCATCCTTTT<br>TCTAGTAGCAACTGCAACCGGTGTA<br>CATTCCCAGGTGCAGCTGCAGGAGT<br>CGGGCCCCAGCCTGGTGAAGCCGTC<br>ACAGACCCTCTCCCTCACCTGCATG<br>GTCTCTGGATTCTCATTGAACGACA<br>AGGCTGTAGGCTGGGTCCGCCAGGC<br>TCCAGGGAAGGCGCTGGAGTGGCTC | ATGGGATGGTCATGTATCATCCTTT<br>TTCTAGTAGCAACTGCAACCGGTG<br>TACATCAGGATGTGCTGACTCAGC<br>CATCATCCGTGTCCGGGTCCCTGGG<br>CCAGAGGGTCTCCATCACCTGCTCT<br>GGAAGCAGCAGCAATGTTGGAAAT<br>GGATATGTGAGCTGGTACCAACTG<br>ATCCCAGGATCGGCCCCCAGAACC |

TABLE 6-continued

DNA sequences of isolated monoclonal antibodies.

| Clone | nucleotide sequence encoding leader sequence and VH | nucleotide sequence encoding leader sequence and VL |
|---|---|---|
| | GGTAGTATAGACGCTGGTGGAAGCA CAGGCTATAACCCAGGCCTGAAATC CCGACTCAGCATCTCCAAGGACAAC TCCAAGAACCAAGTCTCTCTGTCAG TGAGCAGCGTGACAACTGAGGACTC GGCCACATACTACTGTGGTACTGTG CACCAGAGGACACAGCCAAAACAA ACTTGTCCTAATGGCTATAGTGATG ATAGTGCTCTTCGTTATTACAGTAGA TGTTCTGATCGTGATTGTTGGCGTTG TACTGGGACTACGTATTATGATACTT GTCAATGTAGTAGTTATACTTATATT CATACTTACGAATTATACGTCGATG CCTGGGGCCAAGGACTCCTGGTCAC CGTCTCCTCA (SEQ ID NO: 49) | CTCATCTATGGTGACACCAGTCGA GCCTCGGGGGTCCCCGACCGATTC TCCGGCTCCAGGTCTGGGAACACA GCCACCCTGACCATCAGCTCGCTCC AGGCTGAAGACGAGGCAGATTATT TCTGTGCATCTCCTGAGGATAGTAG CAGTAATGCTGTTTTCGGCAGCGG GACCACACTGACCGTCCTG (SEQ ID NO: 50) |
| NC-Cow6 | ATGGGATGGTCATGTATCATCCTTTT TCTAGTAGCAACTGCAACCGGTGTA CATTCCCAGGTGCAGCTGCGGGAGT CGGGCCCCAGCCTGGTGAAGCCGTC ACAGACCCTCTCCCTCACCTGCATG GTCTCTGGATTCTCATTGAACGACA AGGCTGTAGGCTGGGTCCGCCAGGC TCCAGGGAAGGCGCTGGAGTGGCTC GGTAGTATAGACGCTGGTGGAAGCA CAGGCTATAACCCAGGCCTGAAATC CCGACTCAGCATCTCCAAGGACAAC TCCAAGAACCAAGTCTCTCTGTCAG TGAGCAGCGTGACAACTGAGGACTC GGCCACATACTACTGTGGTACTGTG CACCAGAGGACACAGCCAAAACAA ACTTGTCCTAATGGCTATAGTGATG ATAGTGCTCTTCGTTATTACAGTAGA TGTTCTGATCGTGATTGCTGGCGTTG TACTGGGACTACGTATTATGATACTT GTCAATGTAGTAGTTATACTTATATT CATACTTACGAATTATACGTCGATG CCTGGGGCCAAGGACTCCTGGTCAC CGTCTCCTCA (SEQ ID NO: 59) | ATGGGATGGTCATGTATCATCCTTT TTCTAGTAGCAACTGCAACCGGTG TACATCAGGCTGTGCTGACTCAGC CATCATCCGTGTCCGGGTCCCTGGG CCAGAGGGTCTCCATCACCTGCTCT GGAAGCAGCAGCAATGTTGGAAAT GGATATGTGAGCTGGTACCAACTG ATCCCAGGATCGGCCCCCAGAACC CTCATCTATGGTGACACCAGTCGA GCCTCGGGGGTCCCCGACCGATTC TCCGGCTCCAGGTCTGGGAACACA GCCACCCTGACCATCAGCTCGCTCC AGGCTGAAGACGAGGCAGATTATT TCTGTGCATCTCCTGAGGATAGTAG CAGTAATGCTGTTTTCGGCAGCGG GACCACACTGACCGTCCTG (SEQ ID NO: 60) |
| NC-Cow7 | ATGGGATGGTCATGTATCATCCTTTT TCTAGTAGCAACTGCAACCGGTGTA CATTCCAAGGTGCAGCTGCGGGAGT CGGGCCCCAGCCTGGTGAAGCCGTT TGAGACCCTCTCCCTCACCTGCACG GGTTCTGGATTCTCATTGAGCGACA AGGCTGCAGGCTGGGTCCGCCAGGC TCCAGGGAAGGCGCCGGAGTGGCTT GGCAGTATAGACACTGGTGGAAACA CAGGCTATAACCCAGGCCTGAAATA CCGGCTGAGTATCACCAAGGACAAC TCCAAGAGCCAAGTCTCTCTGTCAG TGAGCAGTATGACAAGTGAGGACTC GGCCACATACTACTGTACTACTGTA CACCAGAAAGCCTACAAAAAAGTTT GTCCGGATGATTATAGTAGTAATCC CGATTGCGTTCGGTTGTATGGCTGG AGTCACTGTGACTGTATGAGAGACA GTTTTGGGGGTTGGTGTCGTGCTGAT GGTTGTAGTAGTACTGTAGAGATTG GGCCTTACGAATGGTACGTCAATGC CTGGGGCCAAGGACTCCTGGTCACC GTCTCCTCA (SEQ ID NO: 69) | ATGGGATGGTCATGTATCATCCTTT TTCTAGTAGCAACTGCAACCGGTG TACATCAGGCTGTGCTGACTCAGC CATCATCCGTGTCCGGGTCCCTGGG CCAGAGGGTCTCCATCACCTGCTCT GGAAGCAGCAGCAATGTTGGAAAT GGATATGTGAGTTGGTACCAACTG ATCCCAGGATCGGCCCCCAGAAGC CTCATCTATGGTGACACTAGTCGA GCCTCGGGGGTCCCCGACCGATTC TCCGGCTCCAGGTCTGGGAACACA GCCACCCTGACCATCAGCTCGCTCC AGGCTGAGGACGAGGCAGATTATT TCTGTGCATCTCCTGAGGATAGTAG TAGTAATGGTGTTTTCGGCAGCGG GACCACACTGACCGTCCTG (SEQ ID NO: 70) |
| NC-Cow8 | ATGGGATGGTCATGTATCATCCTTTT TCTAGTAGCAACTGCAACCGGTGTA CATTCCAAGGTGCAGCTGCAGGAGT CGGGCCCCAGCCTGGTGAAGCCGTC ACAGACCCTCTCCCTCACCTGCACG GTCTCTGGATTCTCATTGAGCGACGT GGCTGTAGGCTGGGTCCGCCAGGCT CCAGGGAAGGCGCTGGAGTGGCTCG GTACGATATACACTAGTGGAAACAC AAACGTTAACCCAGGCCTGAAATCC CGGCTCAGCATCACTAAGGACAACG | ATGGGATGGTCATGTATCATCCTTT TTCTAGTAGCAACTGCAACCGGTG TACATCAGGCTGTGCTGACTCAAC CATCATCCGTGTCCGGGTCCCTGGG CCGGAGGGTCTCCATCACCTGCTCT GGAAGCAGCAGCAATGTTGGAAAT GGATATGTGAGTTGGTACCAAGTG ATCCCAGGATCGGCCCCCAGAACC CTCATCTATGGTGACAGCAATCGA GCCTCGGGGGTCCCCGACCGATTC TCCGGGTCCAGGTCTGGGAACACA |

TABLE 6-continued

| DNA sequences of isolated monoclonal antibodies. | | |
|---|---|---|
| Clone | nucleotide sequence encoding leader sequence and VH | nucleotide sequence encoding leader sequence and VL |
| | CCAAGAGCCAAGTCTCTCTATCAGT GACCAGCTTGACAACTGACGACTCG GCCACATACTACTGTACTACTGTATA CCAGAAAACAACGAAAAAAGATTGT CCGGAGTATTATACTTATAATCCCG ATTGCGCGAGGCGCTATGGTTGGAG TGACTGTGAATGTATGGCAGATAAA TTTGGGGGTTATTGTCGTCATGATGG TTGTGCTACTAATACAGTCCGTAGTA CTTACGAATGGCACCTCGATGCCTG GGGCCAAGGACTCCTGGTCACCGTC TCCTCA (SEQ ID NO: 79) | GCCACCCTGACCATCAGCTCGCTCC AGGCTGAGGACGAGGCAGATTATT TCTGTGGCTCTGCTGAGGATGGTA GCGGTAGTGGCGTTTTCGGCAGCG GGACCACACTGACCGTCCTG (SEQ ID NO: 80) |
| NC-Cow9 | ATGGGATGGTCATGTATCATCCTTTT TCTAGTAGCAACTGCAACCGGTGTA CATTCCCAGGTGCAGCTGCAGGAGT CGGGCCCCAGCCTGGTGAAGCCGTC ACAGACCCTCTCCCTCACCTGCACG GTCTCTGGATTCTCATTGAGCGACGT GGCTGTAGGCTGGGTCCGCCAGGCT CCAGGGAAGGCGCTGGAGTGGCTCG GTACGATATACACTAGTGGAAACAC AAACGTTAACCCAGGCCTGAAATCC CGGCTCAGCATCACTAAGGACAACG CCAAGAGCCAAGTCTCTCTATCAGT GACCAGCTTGACAACTGACGACTCG GCCACATACTACTGTACTACTGTATA CCAGAAAACAACGAAAAAAGATTGT CCGGAGTATTATACTTATAATCCCG ATTGCGCGAGGCGCTATGGTTGGAG TGACTGTGAATGTATGGCAGATAAA TTTGGGGGTTATTGTCGTCATGATGG TTGTGCTACTAATACAGTCCGTAGTA CTTACGAATGGCACCTCGATGCCTG GGGCCAAGGACTCCTGGTCACCGTC TCCTCA (SEQ ID NO: 89) | ATGGGATGGTCATGTATCATCCTTT TTCTAGTAGCAACTGCAACCGGTG TACATCAGGCTGTGCTGACTCAAC CATCATCCGTGTCCGGGTCCCTGGG CCGGAGGGTCTCCATCACCTGCTCT GGAAGCAGCAGCAATGTTGGAAAT GGATATGTGAGTTGGTACCAAGTG ATCCCAGGATCGGCCCCCAGAACC CTCATCTATGGTGACAGCAATCGA GCCTCGGGGGTCCCCGACCGATTC TCCGGGTCCAGGTCTGGGAACACA GCCACCCTGACCATCAGCTCGCTCC AGGCTGAGGACGAGGCAGATTATT TCTGTGGCTCTGCTGAGGATGGTA GCGGTAGTGGCGTTTTCGGCAGCG GGACCACACTGACCGTCCTG (SEQ ID NO: 90) |
| NC-Cow10 | ATGGGATGGTCATGTATCATCCTTTT TCTAGTAGCAACTGCAACCGGTGTA CATTCCAAGGTGCAGCTGCAGGAGT CGGGCCCCAGCCTGGTGAAGCCGTC ACAGACCCTCTCCCTCACCTGCACG GTCTCTGGATTCTCATTGAGCGACA AGGCTGTAGGCTGGGTCCGCCAGGC TCCAGGGAAGGCGCTGGAGTGGCTC GGTACGATAGACACTAATCGAAACA CAAACTATCACCCAGGCCTAAAATC CCGGCTCAGCATCACCAAGGACAAC TCCAAGAGTCGAGTCTCTCTGTCCGT GAGCACCATGACAACTGAGGACTCG GCCACATACTACTGTACTACTGTAC ACCAGAAAACAAACGAAAAAGATT GTCCGGAGTATTATAGTTATAACCC CGATTGCCCTAGGCGGTATGGTTGG AGTAACTGTGATTGTATGGCAGATA AATTTGGGGGTTGGTGTCGTCATGA TGGTTGTAGTGATTATGCAGATATG ACTACTGACGAATGGTACGTCGATG CCTGGGGCCAAGGACTCCTGGTCAC CGTCTCCTCA (SEQ ID NO: 99) | ATGGGATGGTCATGTATCATCCTTT TTCTAGTAGCAACTGCAACCGGTG TACATCAGGATGTGCTGACTCAGC CATCATCCGTGTCCGGGTCCCTGGG CCAGAGGGTCTCCATCACCTGCTCT GGAAGCAGCAGCAATGTTGGAAAT GGATATGTGAGTTGGTACCAATTG ATCTCAGGATCGGCCCCCAGAACC CTCATCTATGGTGACACCAGTCGA GCCTCGGGAATCCCCGACCGATTC TCCGGCTCCAGGTCTGGGAACACA GCCACCCTGACCATCACCTCGCTCC AGGCTGAGGACGAGGCAGATTATT TCTGTGCATCTGCTGAAGATAGGC GCAGTAATGCTATTTTCGGCAGCG GGACCACACTGACCGTCCTG (SEQ ID NO: 100) |

To understand the neutralization properties of these 10 antibodies, we evaluated them on the 12-virus indicator panel as well as several clade A viruses and found that NC-Cow2 to NC-Cow6 had narrow breadth, while NC-Cow1 and NC-Cow7 to NC-Cow10 have broadly neutralizing activity (FIG. 10D). NC-Cow1 demonstrated the greatest breadth, so this bnAb was evaluated on a larger 117-virus panel and was found to have 72% neutralization breadth with a potent median $IC_{50}$ of 0.028 μg/ml (FIG. 9B and FIG. 5). All 10 mAbs competed with VRC01-class antibodies on a stabilized BG505 SOSIP trimer termed MD39 (FIG. 9B). Steichen, J. M. et al., *Immunity* 45, 483-496 (2016). With the epitope specificity of NC-Cow 1 identified, serum competition experiments were performed with NC-Cow1. The results demonstrated that the main serum specificity was to the CD4bs (FIG. 14). Relatively low serum reactivity to the BG505 V3 loop was found (FIG. 14).

Figure 11A:
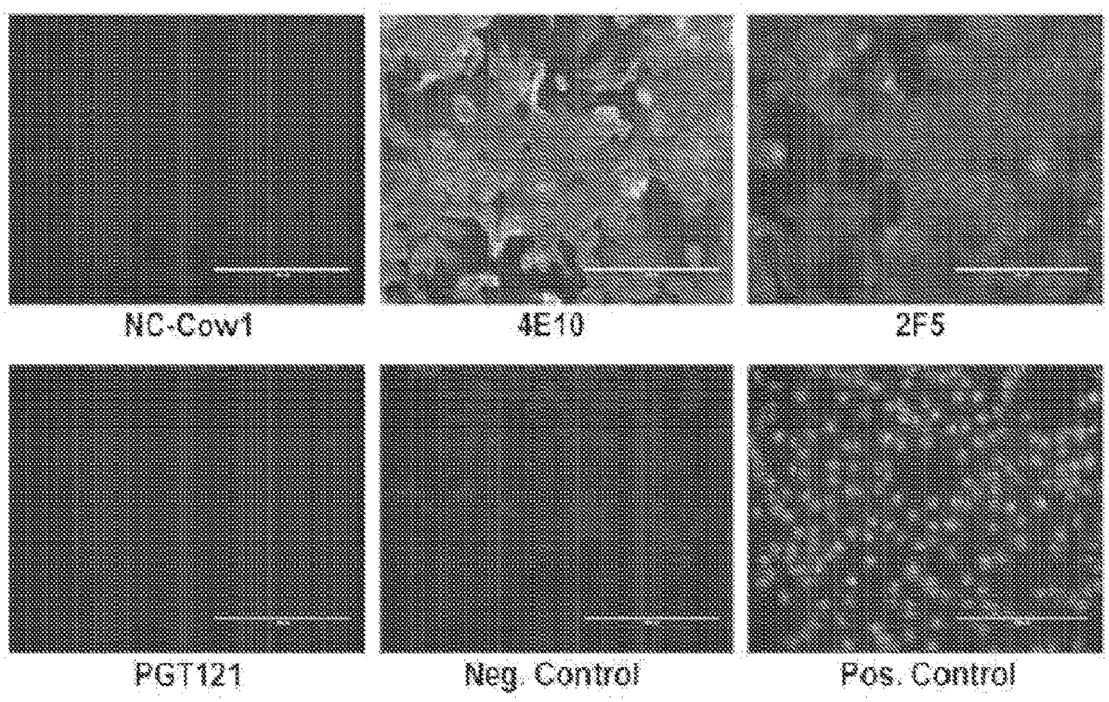
FIGS. 11A-B. NC-Cow1 is not polyreactive to human antigens.
Figure 11B:
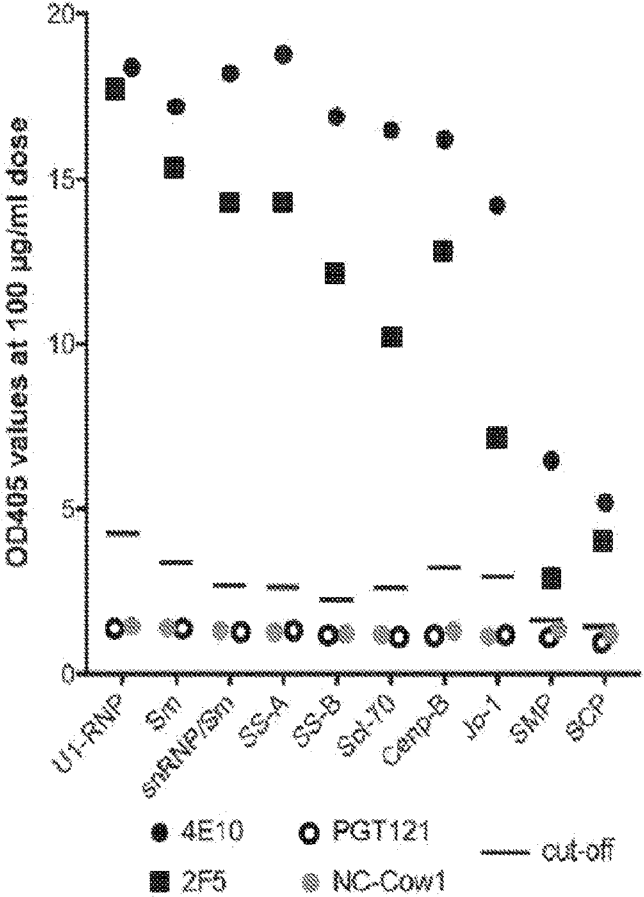

Additional tests showed that NC-Cow1 was not polyreactive to human antigens in a HEp-2 assay and in an ELISA binding assay (FIG. 11). NC-Cow1 was tested for antigen reactivity in a HEp2 assay compared to the known polyreactive antibody 4E10, and negative and positive control sera supplied by the manufacturer. (FIG. 11A). NC-Cow1 was also tested for reactivity with a range of typical human autoantigens by ELISA as well as for binding to solubilized membrane (SMP) and cytosolic preparations (SCP) from CHO cells. (FIG. 11B). Values are optical density values (OD405) at a 100 μg/ml dose. Black line indicates cut-off values as indicated by the manufacturer.

Epitope Mapping

Figures 12A, 12B, 12C:
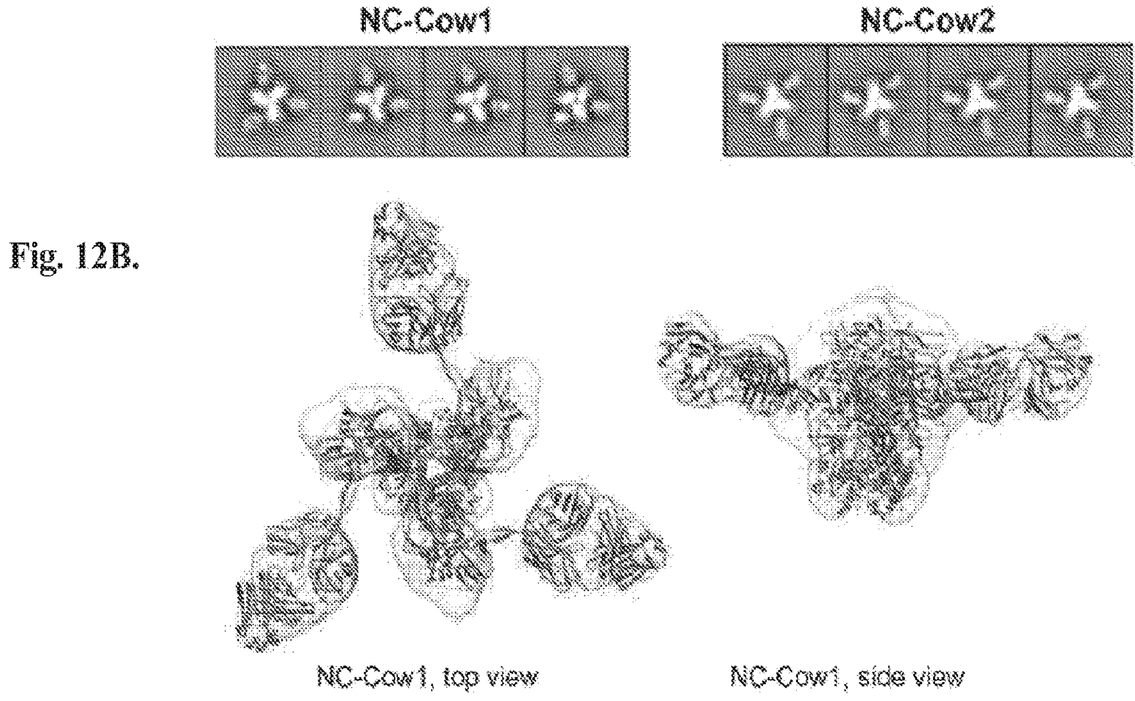
FIGS. 12A-E. Epitope mapping of NC-Cow1.
Figures 12D, 12E:
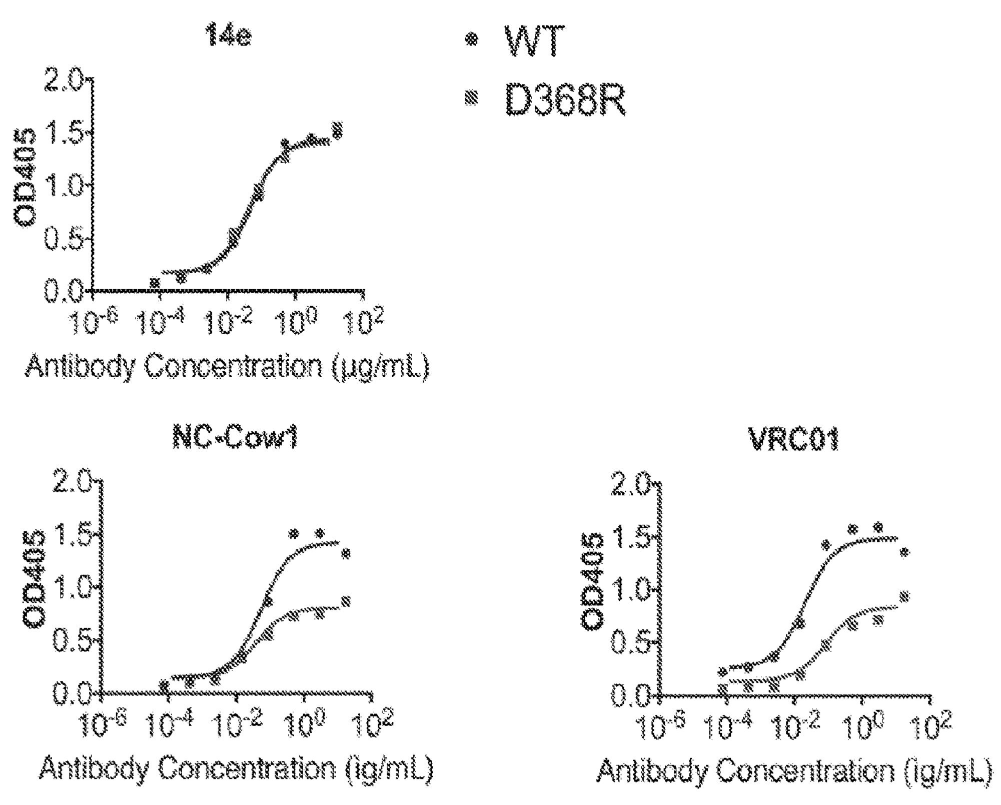

To further understand the binding mechanisms of these antibodies, single particle negative stain electron microscopy was used to visually characterize the NC-Cow1 and NC-Cow2 epitopes. In each dataset, the Fab was clearly visible adjacent to the CD4bs in 2-dimensional class averages (FIG. 12A). Representative 2D class averages of cow Fabs NC-Cow1 and NC-Cow2 bound to BG505 SOSIP trimers to demonstrate CD4bs site specificity are shown in (FIG. 12A). The Fabs appear at slightly different angles relative to the trimer, perhaps due to some flexibility between the Fab and VH CDR3. In the 2D class averages for NC-Cow1, the VH CDR3 appears as a faint density bridging between the Fab and CD4bs. Top and side views of 3D reconstruction of NC-Cow1 bound to BG505 SOSIP trimer with previously published Env trimer structure (green, PDB 5CEZ) and cow Fab (orange, PDB 5IJV) docked in are shown in (FIG. 12B). The body of NC-Cow1 Fab is approximately 20 Å away from the CD4 binding site, which is the estimated length of the ultralong VH CDR3. NC-Cow 1 was tested for binding by ELISA to BG505 or JRCSF gp120 captured from lysed virions with an anti-gp120 antibody called D3724 (C5 epitope). (FIG. 12C-D); VRC01 (CD4bs epitope) and PGT121 (V3 glycan epitope) were included for comparison. NC-Cow1 was also tested for neutralization on BG505 (SEQ ID NO: 108) or JR-CSF (SEQ ID NO: 109) and JR-CSF pseudoviruses and corresponding alanine mutants; PGT121 (V3-glycan epitope) and 12A12 (CD4bs epitope) were included for comparison. The position of the alanine substitutions within the BG505 (SEQ ID NO: 108) and JR-CSF (SEQ ID NO: 109) Env polypeptide are defined in reference to the HXB2 reference Env sequence of SEQ ID NO: 110. NC-Cow1 was also tested for binding to BG505 WT and D368R recombinant gp120 protein. (FIG. 12E). Antibodies VRC01 (CD4bs) and 14e (V3) were included for comparison.

From the above results, a 3-dimensional reconstruction of NC-Cow1 was calculated, which confirmed the CD4bs epitope specificity (FIG. 12). In the comparison of VRC01 and NC-Cow1 binding to a panel of gp120 CD4 binding site alanine mutants for isolates BG505 and JR-CSF (FIG. 12), NC-Cow 1 showed sensitivity to several known CD4bs Ab residues including D368R for binding to BG505 gp120 (FIG. 12). For both isolates, VRC01 was shown to be highly dependent on N279, as described previously. Zhou, T. et al., *Science* 329, 811-817 (2010). In contrast, NC-Cow1 was not dependent on N279, but was instead dependent on residues in the C2 and C5 regions of gp120.

NC-Cow1 VH CDR3 characterization

Experiments were done to determine if the VH CDR3 is functional on its own and/or if the antibody retains function when reverted to its inferred germline. NC-Cow1 was evaluated for neutralization on the 12-virus indicator panel, which demonstrated 100% breadth at a potent median $IC_{50}$ of 0.007 μg/ml (FIG. 9C). Compared to this affinity-matured antibody, partial or fully reverted antibody variants showed no or little decrease in neutralization breadth and potency (FIG. 9C). Next, the 60-amino acid VH CDR3 of NC-Cow1 was transplanted to a germline reverted variant of HIV bnAb PG9 and tested for neutralization on the 12-virus indicator panel. A moderate drop to 88% neutralization breadth with a reduction in potency to a median $IC_{50}$ of 0.054 μg/ml was observed. Although somewhat less active than the original antibody, the neutralization breadth and potency of a 60-amino acid VH CDR3 transplanted onto a germline antibody was remarkable, and has implications for therapeutic designs.

A number of HIV bnAbs have been or are being tested as potential microbicides to prevent mucosal HIV acquisition. Veselinovic, M., et al. *Virology* 432, 505-510 (2012). Of note, VRC01-class antibodies rely on a critical salt bridge interaction with an aspartic acid residue at position 368 of gp1202 that is disrupted at low pH (FIG. 13A), which is characteristic of conditions found in the vagina. NC-Cow1, however, retained affinity for gp120 in simulated vaginal fluid (SVF), pH 4.5, suggesting that the antibody can be useful as a potential microbicide (FIG. 13B).

These experiments demonstrated that immunization with a well-ordered Env trimer in cows reliably and rapidly elicits broad and potent neutralizing serum responses in contrast to previous experiments in other animals.

Importantly, different trimer isolates were not required to elicit breadth, indicating that diversity might not be required provided that conserved epitopes are accessible. The speed of developing a bnAb to the CD4bs of HIV Env in cows was remarkable when contrasted with the length of time required to elicit similar antibodies in humans through natural infection (>5 years).

Example 2: Characterization of NC-Cow1 VH CDR3

Figure 15A:
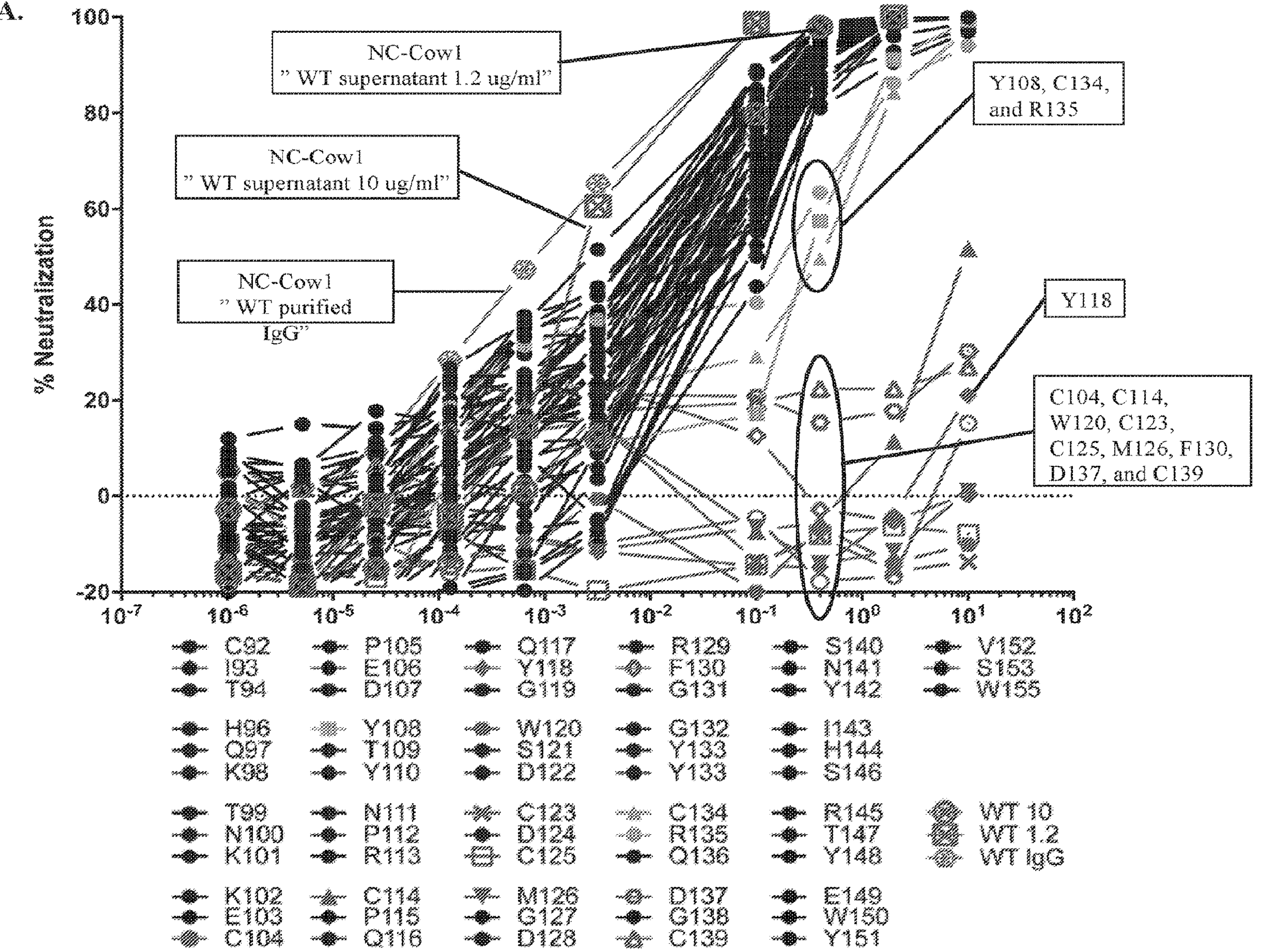

To identify amino acid residues in the VH CDR3 of NC-Cow1 that mediates virus neutralization, each residue of the VH CDR3 domain and the flanking C and W residues (CITAHQKTNKKECPEDYTYNPRCPQQYGWSDCDCMGDRFGGYCRQDGCSNYIHRSTYEWYVS AW (SEQ ID NO: 121)) was individually mutated into alanine in the context of the NC-Cow1 antibody. The heavy chain variants comprising a single alanine substitution were paired with the NC-Cow1 light chain, and NC-Cow1 antibody variants comprising a single alanine substitution in the VH CDR3 were evaluated for neutralization against BG505 pseudovirus. Results are shown in FIG. 15A. For comparision to an unmodified antibody, a purified IgG control of NC-Cow1 (WT IgG) and unpurified transfected supernatents of NC-Cow1 at two concentrations (1.2 μg/ml and 10 μg/ml) were included. NC-Cow1 variants comprising an alanine substitution at a VH CDR3 residue necessary for virus neutralization have reduced or no virus neutralizing activity. An alignment of the NC-Cow1 VH CDR3 domain scanned and the corresponding VH CDR3 sequences of NC-Cow7-10 are shown in FIG. 15B. Residues whose replacement with alanine results in loss or reduction of neutralization are bolded and underlined. Residues whose replacement with alanine resulted in loss of neutralization are C104, C114, W120, C123, C125, M126, F130, D137, and C139. Residues whose replacement with alanine resulted in reduced neutralization are Y108, Y118, C134, and R135. Residues whose replacement with alanine did not result in loss or reduction of neutralization are C92, 193, T94, H96, Q97, K98, T99, N100, K101, K102, E103, P105, E106, D107, T109, Y110, N111, P112, R113, P115, Q116, Q117, G119, S121, D122, D124, G127, D128, R129, G131, G132, Y133, Q136, G138, S140, N141, Y142, 1143, H144, R145, S146, T147, Y148, E149, W150, Y151, V152, S153, and W155.

The results demonstrate that HIV binding and neutralization is mediated by the 36 residue knob of the VH CDR3 (CPEDYTYNPRCPQQYGWSDCDCMGDRFG-GYCRQDGC (SEQ ID NO: 133)), whereas the amino acid residues within the flanking stalk regions (Stalk A and Stalk B in Table 4) do not contribute to the antibody paratope, but might offer instead secondary contributions such as VH CDR3 stabilization. The results further demonstrate that all residues in the stalk regions and 23 out of the 36 residues in the knob region could be substituted with alanine without loss of neutralization activity. Thus, in one embodiment, an antibody or fusion polypeptide that specifically binds to Env provided herein comprises a knob sequence listed in Table 4 comprising 0, 1, 2, 3, 4, 5, 6, 7, 8, 9, 10, 11, 12, 13, 14, or 15 substitutions. In one embodiment, an antibody or fusion polypeptide that specifically binds to Env provided herein comprises the NC-Cow1 knob sequence (SEQ ID NO: 133) comprising 0, 1, 2, 3, 4, 5, 6, 7, 8, 9, 10, 11, 12, 13, 14, or 15 substitutions. In one embodiment, an antibody or fusion polypeptide that specifically binds to Env provided herein comprises a VH CDR3 sequence listed in Table 3 comprising 0, 1, 2, 3, 4, 5, 6, 7, 8, 9, 10, 11, 12, 13, 14, or 15 substitutions. In one embodiment, an antibody or fusion polypeptide that specifically binds to Env provided herein comprises the NC-Cow1 VH CDR3 sequence (SEQ ID NO: 3) comprising 0, 1, 2, 3, 4, 5, 6, 7, 8, 9, 10, 11, 12, 13, 14, or 15 substitutions.

To confirm that the VH CDR3 domain of NC-Cow1 alone is capable of mediating virus neutralizing activity, the N and C termini of the VH CDR3 loop are transplanted onto albumin and/or ferritin, and the resulting chimeric fusion polypeptide is evaluated for neutralization breadth and potency on the 12-virus indicator panel. The protein is expressed and purified as a single construct. Virus neutralization by the chimeric fusion polypeptide indicates that the NC-Cow1 VH CDR3 loop maintains functional activity when transplanted into a non-immunoglobulin polypeptide.

Example 3. Treatment of HIV

Broadly neutralizing cow anti-Env antibodies described herein (e.g., polyclonal, humanized or chimeric antibodies) are used to treat patients infected with HIV. It is contemplated that the patient is diagnosed to have HIV/AIDS. The patient is administered a therapeutically effective amount of at least one broadly neutralizing cow antibody (e.g., a polyclonal, humanized or chimeric antibody) described herein or a pharmaceutical composition comprising the antibody described herein.

Administration of the antibody or pharmaceutical composition is done by one mode selected from oral, parenteral, subcutaneous, intramuscular, intravenous, vaginal, rectal, buccal, and transdermal.

In one embodiment, the patient is treated via administration of a composition comprising a broadly neutralizing cow anti-Env antibody or colostrum comprising a broadly neutralizing cow anti-Env antibody.

In one embodiment, a broadly neutralizing cow anti-Env antibody described herein is co-administered with at least one additional therapeutic agent, for example, an antiretroviral agent or a second antibody. In one embodiment, a broadly neutralizing cow anti-Env antibody described herein is co-administered with a second broadly neutralizing anti-HIV antibody. In one embodiment, a broadly neutralizing cow anti-Env antibody described herein is co-administered with a second and third broadly neutralizing anti-HIV antibody.

Example 4. Prevention of HIV

Broadly neutralizing cow anti-Env antibodies (e.g., polyclonal, humanized or chimeric antibodies) as described herein are used to prevent HIV infections in a subject. The subject is administered a therapeutically effective amount of a broadly neutralizing cow anti-Env antibody described herein or a pharmaceutical composition comprising a broadly neutralizing cow anti-Env antibody described herein.

Administration of the antibody or pharmaceutical composition is done by one mode selected from oral, parenteral, subcutaneous, intramuscular, intravenous, vaginal, rectal, buccal, and transdermal.

In one embodiment, the subject is provided administration of a composition colostrum comprising a broadly neutralizing cow anti-Env antibody described herein. In one embodiment, the subject is administered a composition comprising a broadly neutralizing cow anti-Env antibody (e.g., a polyclonal, humanized or chimeric antibody) described herein. In one embodiment, a broadly neutralizing antibody described herein is co-administered with at least one additional therapeutic agent, which is an antiretroviral agent or a second antibody. In one embodiment, a broadly neutralizing cow anti-Env antibody described herein is co-administered with a second broadly neutralizing anti-HIV antibody. In one embodiment, a broadly neutralizing cow anti-Env antibody described herein is co-administered with a second and third broadly neutralizing anti-HIV antibody.

The invention is not to be limited in scope by the specific embodiments described herein. Indeed, various modifications of the invention in addition to those described will become apparent to those skilled in the art from the foregoing description and accompanying figures. Such modifications are intended to fall within the scope of the appended claims.

All references (e.g., publications or patents or patent applications) cited herein are incorporated herein by reference in their entirety and for all purposes to the same extent as if each individual reference (e.g., publication or patent or patent application) was specifically and individually indicated to be incorporated by reference in its entirety for all purposes.

Other embodiments are within the following claims.

SEQUENCE LISTING

```
Sequence total quantity: 269
SEQ ID NO: 1            moltype = AA  length = 8
FEATURE                 Location/Qualifiers
source                  1..8
                        mol_type = protein
                        organism = Bos taurus
SEQUENCE: 1
```

```
GSSLNDKS                                                                   8

SEQ ID NO: 2            moltype = AA  length = 7
FEATURE                 Location/Qualifiers
source                  1..7
                        mol_type = protein
                        organism = Bos taurus
SEQUENCE: 2
VDTSGNT                                                                    7

SEQ ID NO: 3            moltype = AA  length = 62
FEATURE                 Location/Qualifiers
source                  1..62
                        mol_type = protein
                        organism = Bos taurus
SEQUENCE: 3
ITAHQKTNKK ECPEDYTYNP RCPQQYGWSD CDCMGDRFGG YCRQDGCSNY IHRSTYEWYV  60
SA                                                                 62

SEQ ID NO: 4            moltype = AA  length = 8
FEATURE                 Location/Qualifiers
source                  1..8
                        mol_type = protein
                        organism = Bos taurus
SEQUENCE: 4
SSNVGNGY                                                           8

SEQ ID NO: 5            moltype =   length =
SEQUENCE: 5
000

SEQ ID NO: 6            moltype = AA  length = 11
FEATURE                 Location/Qualifiers
source                  1..11
                        mol_type = protein
                        organism = Bos taurus
SEQUENCE: 6
ASPDDSSSNA V                                                       11

SEQ ID NO: 7            moltype = AA  length = 168
FEATURE                 Location/Qualifiers
source                  1..168
                        mol_type = protein
                        organism = Bos taurus
SEQUENCE: 7
QVQLRESGPS LMKPSQTLSL TCTVSGSSLN DKSVGWVRQA PGKALQWLGS VDTSGNTDYN  60
PGLKSRLSIT KDNSKSRISL TVTGMTTEDS ATYYCITAHQ KTNKKECPED YTYNPRCPQQ  120
YGWSDCDCMG DRFGGYCRQD GCSNYIHRST YEWYVSAWGQ GLLVTVSS              168

SEQ ID NO: 8            moltype = AA  length = 110
FEATURE                 Location/Qualifiers
source                  1..110
                        mol_type = protein
                        organism = Bos taurus
SEQUENCE: 8
SYELTQPSSV SGSLGQRVSV TCSGSSSNVG NGYVSWYQLI PGSAPRTIIY GDTSRASGVP  60
ERFSGSRSGN TATLTISSLQ AEDEADFFCA SPDDSSSNAV FGSGTTLTVL             110

SEQ ID NO: 9            moltype = DNA  length = 561
FEATURE                 Location/Qualifiers
source                  1..561
                        mol_type = unassigned DNA
                        organism = Bos taurus
SEQUENCE: 9
atgggatggt catgtatcat ccttttteta gtagcaactg caaccggtgt acattcccag  60
gtgcagctgc gggagtcggg ccccagcctg atgaagccgt cacagaccct ctccctcacc  120
tgcacggtct ctggatcttc attgaacgac aagtctgtag gctgggtccg ccaggctcca  180
gggaaggcgc tgcagtggct cggtagtgtg gacactagtg gaaacacaga ctataaccca  240
ggcctgaaat cccggctcag catcaccaag gacaactcca agagccgaat ctctcttaca  300
gtgactggca tgacaactga agactcggcc acatactact gcattactgc tcaccaaaaa  360
acaaacaaaa aagagtgtcc ggaggattat acttataatc cacgttgccc tcagcagtat  420
ggttggagtg actgtgattg tatgggcgat aggtttgggg gttactgtcg acaggatggt  480
tgtagtaatt atatacatcg tagtacttac gaatggtacg tcagcgcctg ggccaagga   540
ctcctggtca ccgtctcctc a                                            561

SEQ ID NO: 10           moltype = DNA  length = 384
FEATURE                 Location/Qualifiers
source                  1..384
                        mol_type = unassigned DNA
```

```
                         organism = Bos taurus
SEQUENCE: 10
atgggatggt catgtatcat ccttttteta gtagcaactg caaccggtgt acattcctat  60
gagctgactc agccatcatc cgtgtccggg tccctgggcc agagggtctc cgtcacctgc  120
tctggaagca gcagcaatgt tggaaatgga tatgtgagtt ggtaccaact gatcccagga  180
tcggccccca gaacgatcat ctatggtgac accagtcgag cctcgggggt ccccgagcga  240
ttctccggct ccaggtctgg gaacacagcc accctgacca tcagctcgct ccaggctgag  300
gacgaggcgg atttcttctg tgcatctcct gacgatagta gcagtaatgc tgttttcggc  360
agcgggacca cactgaccgt cctg                                         384

SEQ ID NO: 11            moltype = AA  length = 8
FEATURE                  Location/Qualifiers
source                   1..8
                         mol_type = protein
                         organism = Bos taurus
SEQUENCE: 11
GSSLSDKA                                                           8

SEQ ID NO: 12            moltype = AA  length = 7
FEATURE                  Location/Qualifiers
source                   1..7
                         mol_type = protein
                         organism = Bos taurus
SEQUENCE: 12
ISAGGNR                                                            7

SEQ ID NO: 13            moltype = AA  length = 63
FEATURE                  Location/Qualifiers
source                   1..63
                         mol_type = protein
                         organism = Bos taurus
SEQUENCE: 13
GTVHQKTQRK PICPDGYSDD STLRYYSRCS DRDCWRCTGT TYYDTCQCGT YTWIDTHELH  60
VDA                                                                63

SEQ ID NO: 14            moltype = AA  length = 8
FEATURE                  Location/Qualifiers
source                   1..8
                         mol_type = protein
                         organism = Bos taurus
SEQUENCE: 14
SSNVGNGY                                                           8

SEQ ID NO: 15            moltype =   length =
SEQUENCE: 15
000

SEQ ID NO: 16            moltype = AA  length = 11
FEATURE                  Location/Qualifiers
source                   1..11
                         mol_type = protein
                         organism = Bos taurus
SEQUENCE: 16
ASAEDSSSNA V                                                       11

SEQ ID NO: 17            moltype = AA  length = 169
FEATURE                  Location/Qualifiers
source                   1..169
                         mol_type = protein
                         organism = Bos taurus
SEQUENCE: 17
KVQLRESGPS LVKPSQTLSL TCMVSGSSLS DKAVGWVRQA PGKALEWLGI ISAGGNRGYN  60
SGLRSRLTIS KDNSKNEVSL RVRSVTTEDS ATYFCGTVHQ KTQRKPICPD GYSDDSTLRY  120
YSRCSDRDCW RCTGTTYYDT CQCGTYTWID THELHVDAWG QGLLVTVSS              169

SEQ ID NO: 18            moltype = AA  length = 110
FEATURE                  Location/Qualifiers
source                   1..110
                         mol_type = protein
                         organism = Bos taurus
SEQUENCE: 18
QAVLNQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSSNAV FGSGTTLTVL             110

SEQ ID NO: 19            moltype = DNA  length = 564
FEATURE                  Location/Qualifiers
source                   1..564
                         mol_type = unassigned DNA
                         organism = Bos taurus
```

```
SEQUENCE: 19
atgggatggt catgtatcat cctttttcta gtagcaactg caaccggtgt acattccaag  60
gtgcagctgc gggagtcggg ccccagcctg gtgaagccgt cacagaccct ctctctcacc  120
tgcatggtct ctggatcttc attgagcgac aaggctgtag gctgggtccg ccaggctccg  180
gggaaggcgc tggagtggct cggtattatc agcgctggtg gaaacagggg ctataattcg  240
ggcctgaggt cccgactcac tatctccaag gacaactcca agaacgaggt ctctctgaga  300
gtgaggagcg tgacaactga ggactcggcc acatacttct gtggtactgt gcaccagaag  360
acacagcgga aaccaatttg tcctgatggc tatagtgatg atagtactct tcgttactac  420
agtagatgtt ctgatcgtga ttgttggcgt tgtaccggga ctacgtatta tgatacttgt  480
caatgcggta cttatacttg gattgatact cacgaattac acgtcgatgc ctggggccaa  540
ggactcctgg tcaccgtctc ctca                                        564

SEQ ID NO: 20          moltype = DNA  length = 384
FEATURE                Location/Qualifiers
source                 1..384
                       mol_type = unassigned DNA
                       organism = Bos taurus
SEQUENCE: 20
atgggatggt catgtatcat cctttttcta gtagcaactg caaccggtgt acatcaggcc  60
gtcctgaacc agccaagcag cgtctccggg tctctggggc agcgggtctc aatcacctgt  120
agcgggtctt cctccaatgt cggcaacggc tacgtgtctt ggtatcagct gatccctggc  180
agtgccccac gaaccctgat ctacggcgac acatccagag cttctggggt ccccgatcgg  240
ttctcaggga gcagatccgg aaacacagct actctgacca tcagctccct gcaggctgag  300
gacgaagcag attatttctg cgcatctgcc gaggactcta gttcaaatgc cgtgtttgga  360
agcggcacca cactgacagt cctg                                        384

SEQ ID NO: 21          moltype = AA  length = 8
FEATURE                Location/Qualifiers
source                 1..8
                       mol_type = protein
                       organism = Bos taurus
SEQUENCE: 21
GFSLNDKA                                                           8

SEQ ID NO: 22          moltype = AA  length = 7
FEATURE                Location/Qualifiers
source                 1..7
                       mol_type = protein
                       organism = Bos taurus
SEQUENCE: 22
IGTGGNK                                                            7

SEQ ID NO: 23          moltype = AA  length = 63
FEATURE                Location/Qualifiers
source                 1..63
                       mol_type = protein
                       organism = Bos taurus
SEQUENCE: 23
GTVHQRTHRK QNCPGGYSDD NALRYRSRCD DRDCWRCTGT TYYDTCQCAS YFYTDTYEFY  60
VDA                                                                63

SEQ ID NO: 24          moltype = AA  length = 8
FEATURE                Location/Qualifiers
source                 1..8
                       mol_type = protein
                       organism = Bos taurus
SEQUENCE: 24
SSNVGNGY                                                           8

SEQ ID NO: 25          moltype =   length =
SEQUENCE: 25
000

SEQ ID NO: 26          moltype = AA  length = 11
FEATURE                Location/Qualifiers
source                 1..11
                       mol_type = protein
                       organism = Bos taurus
SEQUENCE: 26
ASAEDSSSNA V                                                       11

SEQ ID NO: 27          moltype = AA  length = 169
FEATURE                Location/Qualifiers
source                 1..169
                       mol_type = protein
                       organism = Bos taurus
SEQUENCE: 27
QVQLRESGPS LVKPSQTLSL TCMVSGFSLN DKAVGWVRQA PGKALEWLGS IGTGGNKGYN  60
PGLKSRLSIS KDSSKNQVSL SMSSVTTEDS ATYYCGTVHQ RTHRKQNCPG GYSDDNALRY  120
```

```
RSRCDDRDCW RCTGTTYYDT CQCASYFYTD TYEFYVDAWG QGLLVTVSS            169

SEQ ID NO: 28           moltype = AA  length = 110
FEATURE                 Location/Qualifiers
source                  1..110
                        mol_type = protein
                        organism = Bos taurus
SEQUENCE: 28
QAVLNQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSSNAV FGSGTTLTVL             110

SEQ ID NO: 29           moltype = DNA  length = 564
FEATURE                 Location/Qualifiers
source                  1..564
                        mol_type = unassigned DNA
                        organism = Bos taurus
SEQUENCE: 29
atgggatggt catgtatcat ccttttteta gtagcaactg caaccggtgt acattcccag  60
gtgcagctgc gggagtcggg ccccagcctg gtgaagccgt cacagaccct ctccctcacc  120
tgcatggtct ctggattctc attgaacgac aaggctgtag gctgggtccg ccaggctcca  180
gggaaggcgt tggagtggct cggtagtata ggcactggtg gaaacaaagg ctataaccca  240
ggcctgaaat cccggctcag catctccaag gacagctcca agaaccaagt ctctctgtca  300
atgagcagcg tgacaactga ggactcggcc acatactact gtggtactgt gcaccagagg  360
acacaccgaa aacaaaattg tcctggaggg tatagtgatg ataatgctct tcgttatcgc  420
agtagatgtg atgatcgtga ttgttggcgt tgtactggga ctacgtatta tgatacttgt  480
caatgtgcca gttattttta tactgatact tacgaattct acgtcgatgc ctggggccaa  540
ggactcctgg tcaccgtctc ctca                                        564

SEQ ID NO: 30           moltype = DNA  length = 384
FEATURE                 Location/Qualifiers
source                  1..384
                        mol_type = unassigned DNA
                        organism = Bos taurus
SEQUENCE: 30
atgggatggt catgtatcat ccttttteta gtagcaactg caaccggtgt acatcaggcc  60
gtcctgaacc agccaagcag cgtctccggg tctctggggc agcgggtctc aatcacctgt  120
agcgggtctt cctccaatgt cggcaacggc tacgtgtctt ggtatcagct gatccctggc  180
agtgccccac gaaccctgat ctacggcgac acatccagag cttctggggt ccccgatcgg  240
ttctcaggga gcagatccgg aaacacagct actctgacca tcagctccct gcaggctgag  300
gacgaagcag attatttctg cgcatctgcc gaggactcta gttcaaatgc cgtgtttgga  360
agcggcacca cactgacagt cctg                                        384

SEQ ID NO: 31           moltype = AA  length = 8
FEATURE                 Location/Qualifiers
source                  1..8
                        mol_type = protein
                        organism = Bos taurus
SEQUENCE: 31
GFSLNDEA                                                           8

SEQ ID NO: 32           moltype = AA  length = 7
FEATURE                 Location/Qualifiers
source                  1..7
                        mol_type = protein
                        organism = Bos taurus
SEQUENCE: 32
IDAGGST                                                            7

SEQ ID NO: 33           moltype = AA  length = 63
FEATURE                 Location/Qualifiers
source                  1..63
                        mol_type = protein
                        organism = Bos taurus
SEQUENCE: 33
GTVHQRTQPK QTCPNGYSDD SALRYYSRCS DRDCWRCTGT TYYDTCQCSS YTYIHTYELY  60
VDA                                                                63

SEQ ID NO: 34           moltype = AA  length = 8
FEATURE                 Location/Qualifiers
source                  1..8
                        mol_type = protein
                        organism = Bos taurus
SEQUENCE: 34
SSNVGNGY                                                           8

SEQ ID NO: 35           moltype =   length =
SEQUENCE: 35
000
```

```
SEQ ID NO: 36           moltype = AA  length = 11
FEATURE                 Location/Qualifiers
source                  1..11
                        mol_type = protein
                        organism = Bos taurus
SEQUENCE: 36
ASPEDSSSNA V                                                          11

SEQ ID NO: 37           moltype = AA  length = 169
FEATURE                 Location/Qualifiers
source                  1..169
                        mol_type = protein
                        organism = Bos taurus
SEQUENCE: 37
KVQLRESGPS LVKPSQTLSL TCMVSGFSLN DEAVGWVRQA PGKALEWLGS IDAGGSTGYN  60
PGLKSRLSIS KDNSKNQVSL SVSSVTTEDS ATYYCGTVHQ RTQPKQTCPN GYSDDSALRY  120
YSRCSDRDCW RCTGTTYYDT CQCSSYTYIH TYELYVDAWG QGLLVTVSS              169

SEQ ID NO: 38           moltype = AA  length = 110
FEATURE                 Location/Qualifiers
source                  1..110
                        mol_type = protein
                        organism = Bos taurus
SEQUENCE: 38
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SPEDSSSNAV FGSGTTLTVL             110

SEQ ID NO: 39           moltype = DNA  length = 563
FEATURE                 Location/Qualifiers
source                  1..563
                        mol_type = unassigned DNA
                        organism = Bos taurus
SEQUENCE: 39
tgggatggtc atgtatcatc ctttttctag tagcaactgc aaccggtgta cattccaagg  60
tgcagctgcg ggagtcgggc cccagcctgg tgaagccgtc acagaccctc tccctcacct  120
gcatggtctc tggattctca ttgaacgacg aggctgtagg ctgggtccgc caggctccag  180
ggaaggcgct ggagtggctc ggtagtatag acgctggtgg aagcacaggc tataacccag  240
gcctgaaatc ccgactcagc atctccaagg acaactccaa gaaccaagtt tctctgtcag  300
tgagcagcgt gacaactgag gactcggcca catactactg tggtactgtg caccagagga  360
cacagccaaa acaaacttgt cctaatggct atagtgatga tagtgctctt cgttattaca  420
gtagatgttc tgatcgtgat tgttggcgtt gtactgggac tacgtattat gatacttgtc  480
aatgtagtag ttatacttat attcatactt acgaattata cgtcgatgcc tggggccaag  540
gactcctggt caccgtctcc tca                                          563

SEQ ID NO: 40           moltype = DNA  length = 384
FEATURE                 Location/Qualifiers
source                  1..384
                        mol_type = unassigned DNA
                        organism = Bos taurus
SEQUENCE: 40
atgggatggt catgtatcat ccttttttcta gtagcaactg caaccggtgt acatcaggct  60
gtgctgactc agccatcatc cgtgtccggg tccctgggcc agagggtctc catcacctgc  120
tctggaagca gcagcaatgt tggaaatgga tatgtgagct ggtaccaact gatcccagga  180
tcggccccca gaaccctcat ctatggtgac accagtcgag cctcgggggt ccccgaccga  240
ttctccggct ccaggtctgg gaacacagcc accctgacca tcagctcgct ccaggctgaa  300
gacgaggcag attatttctg tgcatctcct gaggatagta gcagtaatgc tgttttcggc  360
agcgggacca cactgaccgt cctg                                         384

SEQ ID NO: 41           moltype = AA  length = 8
FEATURE                 Location/Qualifiers
source                  1..8
                        mol_type = protein
                        organism = Bos taurus
SEQUENCE: 41
GFSLNDKA                                                              8

SEQ ID NO: 42           moltype = AA  length = 7
FEATURE                 Location/Qualifiers
source                  1..7
                        mol_type = protein
                        organism = Bos taurus
SEQUENCE: 42
IDAGGST                                                               7

SEQ ID NO: 43           moltype = AA  length = 63
FEATURE                 Location/Qualifiers
source                  1..63
                        mol_type = protein
                        organism = Bos taurus
```

```
SEQUENCE: 43
GTVHQRTQPK QTCPNGYSDD SALRYYSRCS DRDCWRCTGT TYYDTCQCSS YTYIHTYELY  60
VDA                                                                63

SEQ ID NO: 44          moltype = AA  length = 8
FEATURE                Location/Qualifiers
source                 1..8
                       mol_type = protein
                       organism = Bos taurus
SEQUENCE: 44
SSNVGNGY                                                           8

SEQ ID NO: 45          moltype =   length =
SEQUENCE: 45
000

SEQ ID NO: 46          moltype = AA  length = 11
FEATURE                Location/Qualifiers
source                 1..11
                       mol_type = protein
                       organism = Bos taurus
SEQUENCE: 46
ASPEDSSSNA V                                                       11

SEQ ID NO: 47          moltype = AA  length = 169
FEATURE                Location/Qualifiers
source                 1..169
                       mol_type = protein
                       organism = Bos taurus
SEQUENCE: 47
QVQLQESGPS LVKPSQTLSL TCMVSGFSLN DKAVGWVRQA PGKALEWLGS IDAGGSTGYN  60
PGLKSRLSIS KDNSKNQVSL SVSSVTTEDS ATYYCGTVHQ RTQPKQTCPN GYSDDSALRY  120
YSRCSDRDCW RCTGTTYYDT CQCSSYTYIH TYELYVDAWG QGLLVTVSS              169

SEQ ID NO: 48          moltype = AA  length = 110
FEATURE                Location/Qualifiers
source                 1..110
                       mol_type = protein
                       organism = Bos taurus
SEQUENCE: 48
QDVLTQPSSV SGSLGQRVSI TCSGSSSNVG NGYVSWYQLI PGSAPRTLIY GDTSRASGVP  60
DRFSGSRSGN TATLTISSLQ AEDEADYFCA SPEDSSSNAV FGSGTTLTVL             110

SEQ ID NO: 49          moltype = DNA  length = 564
FEATURE                Location/Qualifiers
source                 1..564
                       mol_type = unassigned DNA
                       organism = Bos taurus
SEQUENCE: 49
atgggatggt catgtatcat cctttttcta gtagcaactg caaccggtgt acattcccag  60
gtgcagctgc aggagtcggg ccccagcctg gtgaagccgt cacagaccct ctccctcacc  120
tgcatggtct ctggattctc attgaacgac aaggctgtag gctgggtccg ccaggctcca  180
gggaaggcgc tggagtggct cggtagtata gacgctggtg gaagcacagg ctataaccca  240
ggcctgaaat cccgactcag catctccaag gacaactcca agaaccaagt ctctctgtca  300
gtgagcagcg tgacaactga ggactcggcc acatactact gtggtactgt gcaccagagg  360
acacagccaa aacaaacttg tcctaatggc tatagtgatg atagtgctct tcgttattac  420
agtagatgtt ctgatcgtga ttgttggcgt tgtactggga ctacgtatta tgatacttgt  480
caatgtagta gttatactta tattcatact tacgaattat acgtcgatgc ctggggccaa  540
ggactcctgg tcaccgtctc ctca                                         564

SEQ ID NO: 50          moltype = DNA  length = 384
FEATURE                Location/Qualifiers
source                 1..384
                       mol_type = unassigned DNA
                       organism = Bos taurus
SEQUENCE: 50
atgggatggt catgtatcat cctttttcta gtagcaactg caaccggtgt acatcaggat  60
gtgctgactc agccatcatc cgtgtccggg tccctgggcc agagggtctc catcacctgc  120
tctggaagca gcagcaatgt tggaaatgga tatgtgagct ggtaccaact gatcccagga  180
tcggccccca gaaccctcat ctatggtgac accagtcgag cctcgggggt ccccgaccga  240
ttctccggct ccaggtctgg gaacacagcc accctgacca tcagctcgct ccaggctgaa  300
gacgaggcag attatttctg tgcatctcct gaggatagta gcagtaatgc tgttttcggc  360
agcgggacca cactgaccgt cctg                                         384

SEQ ID NO: 51          moltype = AA  length = 8
FEATURE                Location/Qualifiers
source                 1..8
                       mol_type = protein
                       organism = Bos taurus
```

```
SEQUENCE: 51
GFSLNDKA                                                          8

SEQ ID NO: 52           moltype = AA  length = 7
FEATURE                 Location/Qualifiers
source                  1..7
                        mol_type = protein
                        organism = Bos taurus
SEQUENCE: 52
IDAGGST                                                           7

SEQ ID NO: 53           moltype = AA  length = 63
FEATURE                 Location/Qualifiers
source                  1..63
                        mol_type = protein
                        organism = Bos taurus
SEQUENCE: 53
GTVHQRTQPK QTCPNGYSDD SALRYYSRCS DRDCWRCTGT TYYDTCQCSS YTYIHTYELY  60
VDA                                                               63

SEQ ID NO: 54           moltype = AA  length = 8
FEATURE                 Location/Qualifiers
source                  1..8
                        mol_type = protein
                        organism = Bos taurus
SEQUENCE: 54
SSNVGNGY                                                          8

SEQ ID NO: 55           moltype =   length =
SEQUENCE: 55
000

SEQ ID NO: 56           moltype = AA  length = 11
FEATURE                 Location/Qualifiers
source                  1..11
                        mol_type = protein
                        organism = Bos taurus
SEQUENCE: 56
ASPEDSSSNA V                                                      11

SEQ ID NO: 57           moltype = AA  length = 169
FEATURE                 Location/Qualifiers
source                  1..169
                        mol_type = protein
                        organism = Bos taurus
SEQUENCE: 57
QVQLRESGPS LVKPSQTLSL TCMVSGFSLN DKAVGWVRQA PGKALEWLGS IDAGGSTGYN  60
PGLKSRLSIS KDNSKNQVSL SVSSVTTEDS ATYYCGTVHQ RTQPKQTCPN GYSDDSALRY  120
YSRCSDRDCW RCTGTTYYDT CQCSSYTYIH TYELYVDAWG QGLLVTVSS             169

SEQ ID NO: 58           moltype = AA  length = 110
FEATURE                 Location/Qualifiers
source                  1..110
                        mol_type = protein
                        organism = Bos taurus
SEQUENCE: 58
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SPEDSSSNAV FGSGTTLTVL            110

SEQ ID NO: 59           moltype = DNA  length = 564
FEATURE                 Location/Qualifiers
source                  1..564
                        mol_type = unassigned DNA
                        organism = Bos taurus
SEQUENCE: 59
atgggatggt catgtatcat ccttttteta gtagcaactg caaccggtgt acattcccag  60
gtgcagctgc gggagtcggg ccccagcctg gtgaagccgt cacagaccct ctccctcacc  120
tgcatggtct ctggattctc attgaacgac aaggctgtag gctgggtccg ccaggctcca  180
gggaaggcgc tggagtggct cggtagtata gacgctggtg gaagcacagg ctataaccca  240
ggcctgaaat cccgactcag catctccaag gacaactcca agaaccaagt ctctctgtca  300
gtgagcagcg tgacaactga ggactcggcc acatactact gtggtactgt gcaccagagg  360
acacagccaa aacaaacttg tcctaatggc tatagtgatg atagtgctct tcgttattac  420
agtagatgtt ctgatcgtga ttgctggcgt tgtactggga ctacgtatta tgatacttgt  480
caatgtagta gttatactta tattcatact tacgaattat acgtcgatgc ctggggccaa  540
ggactcctgg tcaccgtctc ctca                                        564

SEQ ID NO: 60           moltype = DNA  length = 384
FEATURE                 Location/Qualifiers
source                  1..384
```

```
                         mol_type = unassigned DNA
                         organism = Bos taurus
SEQUENCE: 60
atgggatggt catgtatcat cctttttcta gtagcaactg caaccggtgt acatcaggct  60
gtgctgactc agccatcatc cgtgtccggg tccctgggcc agagggtctc catcacctgc  120
tctggaagca gcagcaatgt tggaaatgga tatgtgagct ggtaccaact gatcccagga  180
tcggcccccca gaaccctcat ctatggtgac accagtcgag cctcgggggt ccccgaccga  240
ttctccggct ccaggtctgg gaacacagcc accctgacca tcagctcgct ccaggctgaa  300
gacgaggcag attatttctg tgcatctcct gaggatagta gcagtaatgc tgttttcggc  360
agcgggacca cactgaccgt cctg                                          384

SEQ ID NO: 61            moltype = AA  length = 8
FEATURE                  Location/Qualifiers
source                   1..8
                         mol_type = protein
                         organism = Bos taurus
SEQUENCE: 61
GFSLSDKA                                                            8

SEQ ID NO: 62            moltype = AA  length = 7
FEATURE                  Location/Qualifiers
source                   1..7
                         mol_type = protein
                         organism = Bos taurus
SEQUENCE: 62
IDTGGNT                                                             7

SEQ ID NO: 63            moltype = AA  length = 62
FEATURE                  Location/Qualifiers
source                   1..62
                         mol_type = protein
                         organism = Bos taurus
SEQUENCE: 63
TTVHQKAYKK VCPDDYSSNP DCVRLYGWSH CDCMRDSFGG WCRADGCSST VEIGPYEWYV  60
NA                                                                  62

SEQ ID NO: 64            moltype = AA  length = 8
FEATURE                  Location/Qualifiers
source                   1..8
                         mol_type = protein
                         organism = Bos taurus
SEQUENCE: 64
SSNVGNGY                                                            8

SEQ ID NO: 65            moltype =   length =
SEQUENCE: 65
000

SEQ ID NO: 66            moltype = AA  length = 11
FEATURE                  Location/Qualifiers
source                   1..11
                         mol_type = protein
                         organism = Bos taurus
SEQUENCE: 66
ASPEDSSSNG V                                                        11

SEQ ID NO: 67            moltype = AA  length = 168
FEATURE                  Location/Qualifiers
source                   1..168
                         mol_type = protein
                         organism = Bos taurus
SEQUENCE: 67
KVQLRESGPS LVKPFETLSL TCTGSGFSLS DKAAGWVRQA PGKAPEWLGS IDTGGNTGYN  60
PGLKYRLSIT KDNSKSQVSL SVSSMTSEDS ATYYCTTVHQ KAYKKVCPDD YSSNPDCVRL  120
YGWSHCDCMR DSFGGWCRAD GCSSTVEIGP YEWYVNAWGQ GLLVTVSS                168

SEQ ID NO: 68            moltype = AA  length = 110
FEATURE                  Location/Qualifiers
source                   1..110
                         mol_type = protein
                         organism = Bos taurus
SEQUENCE: 68
QAVLTQPSSV SGSLGQRVSI TCSGSSSNVG NGYVSWYQLI PGSAPRSLIY GDTSRASGVP  60
DRFSGSRSGN TATLTISSLQ AEDEADYFCA SPEDSSSNGV FGSGTTLTVL              110

SEQ ID NO: 69            moltype = DNA  length = 561
FEATURE                  Location/Qualifiers
source                   1..561
                         mol_type = unassigned DNA
```

```
                        organism = Bos taurus
SEQUENCE: 69
atgggatggt catgtatcat ccttttttcta gtagcaactg caaccggtgt acattccaag  60
gtgcagctgc gggagtcggg ccccagcctg gtgaagccgt ttgagaccct ctccctcacc  120
tgcacgggtt ctggattctc attgagcgac aaggctgcag gctgggtccg ccaggctcca  180
gggaaggcgc cggagtggct tggcagtata gacactggtg gaaacacagg ctataaccca  240
ggcctgaaat accggctgag tatcaccaag gacaactcca agagccaagt ctctctgtca  300
gtgagcagta tgacaagtga ggactcggcc acatactact gtactactgt acaccagaaa  360
gcctacaaaa aagtttgtcc ggatgattat agtagtaatc ccgattgcgt tcggttgtat  420
ggctggagtc actgtgactg tatgagagac agttttgggg gttggtgtcg tgctgatggt  480
tgtagtagta ctgtagagat tgggccttac gaatggtacg tcaatgcctg gggccaagga  540
ctcctggtca ccgtctcctc a                                            561

SEQ ID NO: 70           moltype = DNA  length = 384
FEATURE                 Location/Qualifiers
source                  1..384
                        mol_type = unassigned DNA
                        organism = Bos taurus
SEQUENCE: 70
atgggatggt catgtatcat ccttttttcta gtagcaactg caaccggtgt acatcaggct  60
gtgctgactc agccatcatc cgtgtccggg tccctgggcc agagggtctc catcacctgc  120
tctggaagca gcagcaatgt tggaaatgga tatgtgagtt ggtaccaact gatcccagga  180
tcggcccccca gaagcctcat ctatggtgac actagtcgag cctcgggggt ccccgaccga  240
ttctccggct ccaggtctgg gaacacagcc accctgacca tcagctcgct ccaggctgag  300
gacgaggcag attatttctg tgcatctcct gaggatagta gtagtaatgg tgttttcggc  360
agcgggacca cactgaccgt cctg                                         384

SEQ ID NO: 71           moltype = AA  length = 8
FEATURE                 Location/Qualifiers
source                  1..8
                        mol_type = protein
                        organism = Bos taurus
SEQUENCE: 71
GFSLSDVA                                                           8

SEQ ID NO: 72           moltype = AA  length = 7
FEATURE                 Location/Qualifiers
source                  1..7
                        mol_type = protein
                        organism = Bos taurus
SEQUENCE: 72
IYTSGNT                                                            7

SEQ ID NO: 73           moltype = AA  length = 62
FEATURE                 Location/Qualifiers
source                  1..62
                        mol_type = protein
                        organism = Bos taurus
SEQUENCE: 73
TTVYQKTTKK DCPEYYTYNP DCARRYGWSD CECMADKFGG YCRHDGCATN TVRSTYEWHL  60
DA                                                                 62

SEQ ID NO: 74           moltype = AA  length = 8
FEATURE                 Location/Qualifiers
source                  1..8
                        mol_type = protein
                        organism = Bos taurus
SEQUENCE: 74
SSNVGNGY                                                           8

SEQ ID NO: 75           moltype =   length =
SEQUENCE: 75
000

SEQ ID NO: 76           moltype = AA  length = 11
FEATURE                 Location/Qualifiers
source                  1..11
                        mol_type = protein
                        organism = Bos taurus
SEQUENCE: 76
GSAEDGSGSG V                                                       11

SEQ ID NO: 77           moltype = AA  length = 168
FEATURE                 Location/Qualifiers
source                  1..168
                        mol_type = protein
                        organism = Bos taurus
SEQUENCE: 77
KVQLQESGPS LVKPSQTLSL TCTVSGFSLS DVAVGWVRQA PGKALEWLGT IYTSGNTNVN  60
```

```
PGLKSRLSIT KDNAKSQVSL SVTSLTTDDS ATYYCTTVYQ KTTKKDCPEY YTYNPDCARR  120
YGWSDCECMA DKFGGYCRHD GCATNTVRST YEWHLDAWGQ GLLVTVSS               168

SEQ ID NO: 78           moltype = AA  length = 110
FEATURE                 Location/Qualifiers
source                  1..110
                        mol_type = protein
                        organism = Bos taurus
SEQUENCE: 78
QAVLTQPSSV SGSLGRRVSI TCSGSSSNVG NGYVSWYQVI PGSAPRTLIY GDSNRASGVP  60
DRFSGSRSGN TATLTISSLQ AEDEADYFCG SAEDGSGSGV FGSGTTLTVL             110

SEQ ID NO: 79           moltype = DNA  length = 561
FEATURE                 Location/Qualifiers
source                  1..561
                        mol_type = unassigned DNA
                        organism = Bos taurus
SEQUENCE: 79
atgggatggt catgtatcat ccttttttcta gtagcaactg caaccggtgt acattccaag  60
gtgcagctgc aggagtcggg ccccagcctg gtgaagccgt cacagaccct ctccctcacc  120
tgcacggtct ctggattctc attgagcgac gtggctgtag gctgggtccg ccaggctcca  180
gggaaggcgc tggagtggct cggtacgata tacactagtg gaaacacaaa cgttaaccca  240
ggcctgaaat cccggctcag catcactaag gacaacgcca agagccaagt ctctctatca  300
gtgaccagct tgacaactga cgactcggcc acatactact gtactactgt ataccagaaa  360
acaacgaaaa aagattgtcc ggagtattat acttataatc ccgattgcgc gaggcgctat  420
ggttggagtg actgtgaatg tatggcagat aaatttgggg gttattgtcg tcatgatggt  480
tgtgctacta atacagtccg tagtacttac gaatggcacc tcgatgcctg ggccaagga  540
ctcctggtca ccgtctcctc a                                            561

SEQ ID NO: 80           moltype = DNA  length = 384
FEATURE                 Location/Qualifiers
source                  1..384
                        mol_type = unassigned DNA
                        organism = Bos taurus
SEQUENCE: 80
atgggatggt catgtatcat ccttttttcta gtagcaactg caaccggtgt acatcaggct  60
gtgctgactc aaccatcatc cgtgtccggg tccctgggcc ggagggtctc catcacctgc  120
tctggaagca gcagcaatgt tggaaatgga tatgtgagtt ggtaccaagt gatcccagga  180
tcggcccccca gaaccctcat ctatggtgac agcaatcgag cctcgggggt ccccgaccga  240
ttctccgggt ccaggtctgg gaacacagcc accctgacca tcagctcgct ccaggctgag  300
gacgaggcag attatttctg tggctctgct gaggatggta gcggtagtgg cgttttcggc  360
agcgggacca cactgaccgt cctg                                         384

SEQ ID NO: 81           moltype = AA  length = 8
FEATURE                 Location/Qualifiers
source                  1..8
                        mol_type = protein
                        organism = Bos taurus
SEQUENCE: 81
GFSLSDVA                                                           8

SEQ ID NO: 82           moltype = AA  length = 7
FEATURE                 Location/Qualifiers
source                  1..7
                        mol_type = protein
                        organism = Bos taurus
SEQUENCE: 82
IYTSGNT                                                            7

SEQ ID NO: 83           moltype = AA  length = 62
FEATURE                 Location/Qualifiers
source                  1..62
                        mol_type = protein
                        organism = Bos taurus
SEQUENCE: 83
TTVYQKTTKK DCPEYYTYNP DCARRYGWSD CECMADKFGG YCRHDGCATN TVRSTYEWHL  60
DA                                                                 62

SEQ ID NO: 84           moltype = AA  length = 8
FEATURE                 Location/Qualifiers
source                  1..8
                        mol_type = protein
                        organism = Bos taurus
SEQUENCE: 84
SSNVGNGY                                                           8

SEQ ID NO: 85           moltype =   length =
SEQUENCE: 85
000
```

```
SEQ ID NO: 86           moltype = AA  length = 11
FEATURE                 Location/Qualifiers
source                  1..11
                        mol_type = protein
                        organism = Bos taurus
SEQUENCE: 86
GSAEDGSGSG V                                                        11

SEQ ID NO: 87           moltype = AA  length = 168
FEATURE                 Location/Qualifiers
source                  1..168
                        mol_type = protein
                        organism = Bos taurus
SEQUENCE: 87
QVQLQESGPS LVKPSQTLSL TCTVSGFSLS DVAVGWVRQA PGKALEWLGT IYTSGNTNVN  60
PGLKSRLSIT KDNAKSQVSL SVTSLTTDDS ATYYCTTVYQ KTTKKDCPEY YTYNPDCARR  120
YGWSDCECMA DKFGGYCRHD GCATNTVRST YEWHLDAWGQ GLLVTVSS              168

SEQ ID NO: 88           moltype = AA  length = 110
FEATURE                 Location/Qualifiers
source                  1..110
                        mol_type = protein
                        organism = Bos taurus
SEQUENCE: 88
QAVLTQPSSV SGSLGRRVSI TCSGSSSNVG NGYVSWYQVI PGSAPRTLIY GDSNRASGVP  60
DRFSGSRSGN TATLTISSLQ AEDEADYFCG SAEDGSGSGV FGSGTTLTVL            110

SEQ ID NO: 89           moltype = DNA  length = 561
FEATURE                 Location/Qualifiers
source                  1..561
                        mol_type = unassigned DNA
                        organism = Bos taurus
SEQUENCE: 89
atgggatggt catgtatcat cctttttcta gtagcaactg caaccggtgt acattcccag  60
gtgcagctgc aggagtcggg ccccagcctg gtgaagccgt cacagaccct ctccctcacc  120
tgcacggtct ctggattctc attgagcgac gtggctgtag gctgggtccg ccaggctcca  180
gggaaggcgc tggagtggct cggtacgata tacactagtg gaaacacaaa cgttaaccca  240
ggcctgaaat cccggctcag catcactaag gacaacgcca agagccaagt ctctctatca  300
gtgaccagct tgacaactga cgactcggcc acatactact gtactactgt ataccagaaa  360
acaacgaaaa aagattgtcc ggagtattat acttataatc ccgattgcgc gaggcgctat  420
ggttggagtg actgtgaatg tatggcagat aaatttgggg gttattgtcg tcatgatggt  480
tgtgctacta atacagtccg tagtacttac gaatggcacc tcgatgcctg gggccaagga  540
ctcctggtca ccgtctcctc a                                             561

SEQ ID NO: 90           moltype = DNA  length = 384
FEATURE                 Location/Qualifiers
source                  1..384
                        mol_type = unassigned DNA
                        organism = Bos taurus
SEQUENCE: 90
atgggatggt catgtatcat cctttttcta gtagcaactg caaccggtgt acatcaggct  60
gtgctgactc aaccatcatc cgtgtccggg tccctgggcc ggagggtctc catcacctgc  120
tctggaagca gcagcaatgt tggaaatgga tatgtgagtt ggtaccaagt gatcccagga  180
tcggccccca gaaccctcat ctatggtgac agcaatcgag cctcgggggt ccccgaccga  240
ttctccgggt ccaggtctgg gaacacagcc accctgacca tcagctcgct ccaggctgag  300
gacgaggcag attatttctg tggctctgct gaggatggta gcggtagtgg cgttttcggc  360
agcgggacca cactgaccgt cctg                                          384

SEQ ID NO: 91           moltype = AA  length = 8
FEATURE                 Location/Qualifiers
source                  1..8
                        mol_type = protein
                        organism = Bos taurus
SEQUENCE: 91
GFSLSDKA                                                            8

SEQ ID NO: 92           moltype = AA  length = 7
FEATURE                 Location/Qualifiers
source                  1..7
                        mol_type = protein
                        organism = Bos taurus
SEQUENCE: 92
IDTNRNT                                                             7

SEQ ID NO: 93           moltype = AA  length = 62
FEATURE                 Location/Qualifiers
source                  1..62
                        mol_type = protein
```

```
                         organism = Bos taurus
SEQUENCE: 93
TTVHQKTNEK DCPEYYSYNP DCPRRYGWSN CDCMADKFGG WCRHDGCSDY ADMTTDEWYV  60
DA                                                                 62

SEQ ID NO: 94            moltype = AA  length = 8
FEATURE                  Location/Qualifiers
source                   1..8
                         mol_type = protein
                         organism = Bos taurus
SEQUENCE: 94
SSNVGNGY                                                           8

SEQ ID NO: 95            moltype =   length =
SEQUENCE: 95
000

SEQ ID NO: 96            moltype = AA  length = 11
FEATURE                  Location/Qualifiers
source                   1..11
                         mol_type = protein
                         organism = Bos taurus
SEQUENCE: 96
ASAEDRRSNA I                                                       11

SEQ ID NO: 97            moltype = AA  length = 168
FEATURE                  Location/Qualifiers
source                   1..168
                         mol_type = protein
                         organism = Bos taurus
SEQUENCE: 97
KVQLQESGPS LVKPSQTLSL TCTVSGFSLS DKAVGWVRQA PGKALEWLGT IDTNRNTNYH  60
PGLKSRLSIT KDNSKSRVSL SVSTMTTEDS ATYYCTTVHQ KTNEKDCPEY YSYNPDCPRR  120
YGWSNCDCMA DKFGGWCRHD GCSDYADMTT DEWYVDAWGQ GLLVTVSS               168

SEQ ID NO: 98            moltype = AA  length = 109
FEATURE                  Location/Qualifiers
source                   1..109
                         mol_type = protein
                         organism = Bos taurus
SEQUENCE: 98
DVLTQPSSVS GSLGQRVSIT CSGSSSNVGN GYVSWYQLIS GSAPRTLIYG DTSRASGIPD  60
RFSGSRSGNT ATLTITSLQA EDEADYFCAS AEDRRSNAIF GSGTTLTVL              109

SEQ ID NO: 99            moltype = DNA  length = 561
FEATURE                  Location/Qualifiers
source                   1..561
                         mol_type = unassigned DNA
                         organism = Bos taurus
SEQUENCE: 99
atgggatggt catgtatcat cctttttcta gtagcaactg caaccggtgt acattccaag  60
gtgcagctgc aggagtcggg ccccagcctg gtgaagccgt cacagaccct ctccctcacc  120
tgcacggtct ctggattctc attgagcgac aaggctgtag gctgggtccg ccaggctcca  180
gggaaggcgc tggagtggct cggtacgata gacactaatc gaaacacaaa ctatcaccca  240
ggcctaaaat cccggctcag catcaccaag gacaactcca agagtcgagt ctctctgtcc  300
gtgagcacca tgacaactga ggactcggcc acatactact gtactactgt acaccagaaa  360
acaaacgaaa aagattgtcc ggagtattat agttataacc ccgattgccc taggcggtat  420
ggttggagta actgtgattg tatggcagat aaatttgggg gttggtgtcg tcatgatggt  480
tgtagtgatt atgcagatat gactactgac gaatggtacg tcgatgcctg gggccaagga  540
ctcctggtca ccgtctcctc a                                            561

SEQ ID NO: 100           moltype = DNA  length = 384
FEATURE                  Location/Qualifiers
source                   1..384
                         mol_type = unassigned DNA
                         organism = Bos taurus
SEQUENCE: 100
atgggatggt catgtatcat cctttttcta gtagcaactg caaccggtgt acatcaggat  60
gtgctgactc agccatcatc cgtgtccggg tccctgggcc agagggtctc catcacctgc  120
tctggaagca gcagcaatgt tggaaatgga tatgtgagtt ggtaccaatt gatctcagga  180
tcggccccca gaaccctcat ctatggtgac accagtcgag cctcgggaat ccccgaccga  240
ttctccggct ccaggtctgg gaacacagcc accctgacca tcacctcgct ccaggctgag  300
gacgaggcag attatttctg tgcatctgct gaagataggc gcagtaatgc tattttcggc  360
agcgggacca cactgaccgt cctg                                        384

SEQ ID NO: 101           moltype = AA  length = 62
FEATURE                  Location/Qualifiers
REGION                   1..62
                         note = synthetic construct
```

```
VARIANT               8
                      note = Xaa can be any naturally occurring amino acid
VARIANT               23
                      note = Xaa can be any naturally occurring amino acid
VARIANT               50
                      note = Xaa can be any naturally occurring amino acid
source                1..62
                      mol_type = protein
                      organism = synthetic construct
SEQUENCE: 101
TTVHQKTXKK DCPEYYTYNP DCXRRYGWSD CDCMADKFGG YCRHDGCSTX TVRSTYEWYV  60
DA                                                                 62

SEQ ID NO: 102        moltype = AA  length = 62
FEATURE               Location/Qualifiers
REGION                1..62
                      note = synthetic construct
VARIANT               1
                      note = Xaa can be Thr or Ile
VARIANT               3
                      note = Xaa can be Val or Ala
VARIANT               4
                      note = Xaa can be His or Tyr
VARIANT               7
                      note = Xaa can be Thr or Ala
VARIANT               8
                      note = Xaa can be Asn, Tyr, or Thr
VARIANT               9
                      note = Xaa can be Lys or Glu
VARIANT               11
                      note = Xaa can be Asp, Glu, or Val
VARIANT               14
                      note = Xaa can be Glu or Asp
VARIANT               15
                      note = Xaa can be Tyr or Asp
VARIANT               17
                      note = Xaa can be Thr or Ser
VARIANT               18
                      note = Xaa can be Tyr or Ser
VARIANT               21
                      note = Xaa can be Asp or Arg
VARIANT               23
                      note = Xaa can be Pro, Val, or Ala
VARIANT               24
                      note = Xaa can be Arg or Gln
VARIANT               25
                      note = Xaa can be Arg, Gln, or Leu
VARIANT               30
                      note = Xaa can be Asp, His, or Asn
VARIANT               32
                      note = Xaa can be Asp or Glu
VARIANT               35
                      note = Xaa can be Ala, Gly, or Arg
VARIANT               37
                      note = Xaa can be Lys, Arg, or Ser
VARIANT               41
                      note = Xaa can be Tyr or Trp
VARIANT               44
                      note = Xaa can be His, Gln, or Ala
VARIANT               48
                      note = Xaa can be Ser or Ala
VARIANT               49
                      note = Xaa can be Thr, Asn, Ser, or Asp
VARIANT               50
                      note = Xaa can be Tyr, Thr, or Asn
VARIANT               51
                      note = Xaa can be Val, Thr, Ile, or Ala
VARIANT               52
                      note = Xaa can be Val, His, Glu, or Asp
VARIANT               53
                      note = Xaa can be Arg, Ile, or Met
VARIANT               54
                      note = Xaa can be Ser, Gly, or Thr
VARIANT               55
                      note = Xaa can be Thr, or Pro
VARIANT               56
                      note = Xaa can be Tyr, or Asp
VARIANT               59
                      note = Xaa can be Tyr, or His
```

```
VARIANT                 60
                        note = Xaa can be Val, or Leu
VARIANT                 61
                        note = Xaa can be Asp or Ser
source                  1..62
                        mol_type = protein
                        organism = synthetic construct
SEQUENCE: 102
XTXXQKXXXK XCPXXYXXNP XCXXXYGWSX CXCMXDXFGG XCRXDGCXXX XXXXXXEWXX  60
XA                                                                 62

SEQ ID NO: 103          moltype = AA  length = 110
FEATURE                 Location/Qualifiers
source                  1..110
                        mol_type = protein
                        organism = Bos taurus
SEQUENCE: 103
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSSNAV FGSGTTLTVL             110

SEQ ID NO: 104          moltype = AA  length = 860
FEATURE                 Location/Qualifiers
source                  1..860
                        mol_type = protein
                        organism = Bos taurus
SEQUENCE: 104
MRVMGIQRNC QHLFRWGTMI LGMIIICSAA ENLWVTVYYG VPVWKDAETT LFCASDAKAY  60
ETEKHNVWAT HACVPTDPNP QEIHLENVTE EFNMWKNNMV EQMHTDIISL WDQSLKPCVK  120
LTPLCVTLQC TNVTNNITDD MRGELKNCSF NMTTELRDKK QKVYSLFYRL DVVQINENQG  180
NRSNNSNKEY RLINCNTSAI TQACPKVSFE PIPIHYCAPA GFAILKCKDK KFNGTGPCPS  240
VSTVQCTHGI KPVVSTQLLL NGSLAEEEVM IRSENITNNA KNILVQFNTP VQINCTRPNN  300
NTRKSIRIGP GQAFYATGDI IGDIRQAHCT VSKATWNETL GKVVKQLRKH FGNNTIIRFA  360
NSSGGDLEVT THSFNCGGEF FYCNTSGLFN STWISNTSVQ GSNSTGSNDS ITLPCRIKQI  420
INMWQRIGQA MYAPPIQGVI RCVSNITGLI LTRDGGSTNS TTETFRPGGG DMRDNWRSEL  480
YKYKVVKIEP LGVAPTRAKR RVVGREKRAV GIGAVFLGFL GAAGSTMGAA SMTLTVQARN  540
LLSGIVQQQS NLLRAIEAQQ HLLKLTVWGI KQLQARVLAV ERYLRDQQLL GIWGCSGKLI  600
CTTNVPWNSS WSNRNLSEIW DNMTWLQWDK EISNYTQIIY GLLEESQNQQ EKNEQDLLAL  660
DKWASLWNWF DISNWLWYIK IFIMIVGGLI GLRIVFAVLS VIHRVRQGYS PLSFQTHTPN  720
PRGLDRPERI EEEDGEQDRG RSTRLVSGFL ALAWDDLRSL CLFCYHRLRD FILIAARIVE  780
LLGHSSLKGL RLGWEGLKYL WNLLAYWGRE LKISAINLFD TIAIAVAEWT DRVIEIGQRL  840
CRAFLHIPRR IRQGLERALL                                              860

SEQ ID NO: 105          moltype = AA  length = 860
FEATURE                 Location/Qualifiers
REGION                  1..860
                        note = synthetic construct
source                  1..860
                        mol_type = protein
                        organism = synthetic construct
SEQUENCE: 105
MRVMGIQRNC QHLFRWGTMI LGMIIICSAA ENLWVTVYYG VPVWKDAETT LFCASDAKAY  60
ETEKHNVWAT HACVPTDPNP QEIHLENVTE EFNMWKNNMV EQMHTDIISL WDQSLKPCVK  120
LTPLCVTLQC TNVTNNITDD MRGELKNCSF NMTTELRDKK QKVYSLFYRL DVVQINENQG  180
NRSNNSNKEY RLINCNTSAI TQACPKVSFE PIPIHYCAPA GFAILKCKDK KFNGTGPCPS  240
VSTVQCTHGI KPVVSTQLLL NGSLAEEEVM IRSENITNNA KNILVQFNTP VQINCTRPNN  300
NTRKSIRIGP GQAFYATGDI IGDIRQAHCN VSKATWNETL GKVVKQLRKH FGNNTIIRFA  360
NSSGGDLEVT THSFNCGGEF FYCNTSGLFN STWISNTSVQ GSNSTGSNDS ITLPCRIKQI  420
INMWQRIGQA MYAPPIQGVI RCVSNITGLI LTRDGGSTNS TTETFRPGGG DMRDNWRSEL  480
YKYKVVKIEP LGVAPTRAKR RVVGREKRAV GIGAVFLGFL GAAGSTMGAA SMTLTVQARN  540
LLSGIVQQQS NLLRAIEAQQ HLLKLTVWGI KQLQARVLAV ERYLRDQQLL GIWGCSGKLI  600
CTTNVPWNSS WSNRNLSEIW DNMTWLQWDK EISNYTQIIY GLLEESQNQQ EKNEQDLLAL  660
DKWASLWNWF DISNWLWYIK IFIMIVGGLI GLRIVFAVLS VIHRVRQGYS PLSFQTHTPN  720
PRGLDRPERI EEEDGEQDRG RSTRLVSGFL ALAWDDLRSL CLFCYHRLRD FILIAARIVE  780
LLGHSSLKGL RLGWEGLKYL WNLLAYWGRE LKISAINLFD TIAIAVAEWT DRVIEIGQRL  840
CRAFLHIPRR IRQGLERALL                                              860

SEQ ID NO: 106          moltype = AA  length = 634
FEATURE                 Location/Qualifiers
REGION                  1..634
                        note = synthetic construct
source                  1..634
                        mol_type = protein
                        organism = synthetic construct
SEQUENCE: 106
AENLWVTVYY GVPVWKDAET TLFCASDAKA YETEKHNVWA THACVPTDPN PQEIHLENVT  60
EEFNMWKNNM VEQMHTDIIS LWDQSLKPCV KLTPLCVTLQ CTNVTNNITD DMRGELKNCS  120
FNMTTELRDK KQKVYSLFYR LDVVQINENQ GNRSNNSNKE YRLINCNTSA ITQACPKVSF  180
EPIPIHYCAP AGFAILKCKD KKFNGTGPCP SVSTVQCTHG IKPVVSTQLL LNGSLAEEEV  240
MIRSENITNN AKNILVQFNT PVQINCTRPN NNTRKSIRIG PGQAFYATGD IIGDIRQAHC  300
```

```
NVSKATWNET LGKVVKQLRK HFGNNTIIRF ANSSGGDLEV TTHSFNCGGE FFYCNTSGLF  360
NSTWISNTSV QGSNSTGSND SITLPCRIKQ IINMWQRIGQ AMYAPPIQGV IRCVSNITGL  420
ILTRDGGSTN STTETFRPGG GDMRDNWRSE LYKYKVVKIE PLGVAPTRCK RRVVGRRRRR  480
RAVGIGAVFL GFLGAAGSTM GAASMTLTVQ ARNLLSGIVQ QQSNLLRAPE AQQHLLKLTV  540
WGIKQLQARV LAVERYLRDQ QLLGIWGCSG KLICCTNVPW NSSWSNRNLS EIWDNMTWLQ  600
WDKEISNYTQ IIYGLLEESQ NQQEKNEQDL LALD                             634

SEQ ID NO: 107          moltype = AA  length = 666
FEATURE                 Location/Qualifiers
REGION                  1..666
                        note = synthetic construct
source                  1..666
                        mol_type = protein
                        organism = synthetic construct
SEQUENCE: 107
MDAMKRGLCC VLLLCGAVFV SPSQEIHARF RRAENLWVTV YYGVPVWKDA ETTLFCASDA  60
KAYETEKHNV WATHACVPTD PNPQEIHLEN VTEEFNMWKN NMVEQMHTDI ISLWDQSLKP  120
CVKLTPLCVT LQCTNVTNNI TDDMRGELKN CSFNMTTELR DKKQKVYSLF YRLDVVQINE  180
NQGNRSNNSN KEYRLINCNT SAITQACPKV SFEPIPIHYC APAGFAILKC KDKKFNGTGP  240
CPSVSTVQCT HGIKPVVSTQ LLLNGSLAEE EVMIRSENIT NNAKNILVQF NTPVQINCTR  300
PNNNTRKSIR IGPGQAFYAT GDIIGDIRQA HCNVSKATWN ETLGKVVKQL RKHFGNNTII  360
RFANSSGGDL EVTTHSFNCG GEFFYCNTSG LFNSTWISNT SVQGSNSTGS NDSITLPCRI  420
KQIINMWQRI GQAMYAPPIQ GVIRCVSNIT GLILTRDGGS TNSTTETFRP GGGDMRDNWR  480
SELYKYKVVK IEPLGVAPTR CKRRVVGRRR RRRAVGIGAV FLGFLGAAGS TMGAASMTLT  540
VQARNLLSGI VQQQSNLLRA PEAQQHLLKL TVWGIKQLQA RVLAVERYLR DQQLLGIWGC  600
SGKLICCTNV PWNSSWSNRN LSEIWDNMTW LQWDKEISNY TQIIYGLLEE SQNQQEKNEQ  660
DLLALD                                                            666

SEQ ID NO: 108          moltype = AA  length = 860
FEATURE                 Location/Qualifiers
REGION                  1..860
                        note = synthetic construct
source                  1..860
                        mol_type = protein
                        organism = synthetic construct
SEQUENCE: 108
MRVMGIQRNC QHLFRWGTMI LGMIIICSAA ENLWVTVYYG VPVWKDAETT LFCASDAKAY  60
ETEKHNVWAT HACVPTDPNP QEIHLENVTE EFNMWKNNMV EQMHTDIISL WDQSLKPCVK  120
LTPLCVTLQC TNVTNNITDD MRGELKNCSF NMTTELRDKK QKVYSLFYRL DVVQINENQG  180
NRSNNSNKEY RLINCNTSAI TQACPKVSFE PIPIHYCAPA GFAILKCKDK KFNGTGPCPS  240
VSTVQCTHGI KPVVSTQLLL NGSLAEEEVM IRSENITNNA KNILVQFNTP VQINCTRPNN  300
NTRKSIRIGP GQAFYATGDI IGDIRQAHCN VSKATWNETL GKVVKQLRKH FGNNTIIRFA  360
NSSGGDLEVT THSFNCGGEF FYCNTSGLFN STWISNTSVQ GSNSTGSNDS ITLPCRIKQI  420
INMWQRIGQA MYAPPIQGVI RCVSNITGLI LTRDGGSTNS TTETFRPGGG DMRDNWRSEL  480
YKYKVVKIEP LGVAPTRAKR RVVGREKRAV GIGAVFLGFL GAAGSTMGAA SMTLTVQARN  540
LLSGIVQQQS NLLRAIEAQQ HLLKLTVWGI KQLQARVLAV ERYLRDQQLL GIWGCSGKLI  600
CTTNVPWNSS WSNRNLSEIW DNMTWLQWDK EISNYTQIIY GLLEESQNQQ EKNEQDLLAL  660
DKWASLWNWF DISNWLWYIK IFIMIVGGLI GLRIVFAVLS VIHRVRQGYS PLSFQTHTPN  720
PRGLDRPERI EEEDGEQDRG RSTRLVSGFL ALAWDDLRSL CLFCYHRLRD FILIAARIVE  780
LLGHSSLKGL RLGWEGLKYL WNLLAYWGRE LKISAINLFD TIAIAVAEWT DRVIEIGQRL  840
CRAFLHIPRR IRQGLERALL                                             860

SEQ ID NO: 109          moltype = AA  length = 849
FEATURE                 Location/Qualifiers
source                  1..849
                        mol_type = protein
                        organism = Bos taurus
SEQUENCE: 109
MRVKEKYQHL WRWGWRWGTM LLGMLMICSA TEKLWVTVYY GVPVWKETTT TLFCASDAKA  60
YDTEVHNVWA THACVPTDPN PQEVVLENVT EDFNMWKNNM VEQMQEDVIN LWDQSLKPCV  120
KLTPLCVTLN CKDVNATNTT SSSEGMMERG EIKNCSFNIT KSIRDKVQKE YALFYKLDVV  180
PIDNKNNTKY RLISCNTSVI TQACPKVSFE PIPIHYCAPA GFAILKCNNK TFNGKGQCKN  240
VSTVQCTHGI RPVVSTQLLL NGSLAEEKVV IRSDNFTDNA KTIIVQLNES VKINCTRPSN  300
NTRKSIHIGP GRAFYTTGEI IGDIRQAHCN ISRAQWNNTL KQIVEKLREQ FNNKTIVFTH  360
SSGGDPEIVM HSFNCGGEFF YCNSTQLFNS TWNDTEKSSG TEGNDTIILP CRIKQIINMW  420
QEVGKAMYAP PIKGQIRCSS NITGLLLTRD GGKNESEIEI FRPGGGDMRD NWRSELYKYK  480
VVKIEPLGVA PTKAKRRVVQ REKRAVGIGA LFLGFLGAAG STMGAASMTL TVQARQLLSG  540
IVQQQNNLLR AIEAQQHMLQ LTVWGIKQLQ ARVLAVERYL KDQQLMGIWG CSGKLICTTA  600
VPWNTSWSNK SLDSIWNNMT WMEWEKEIEN YTNTIYTLIE ESQIQQEKNE QELLELDKWA  660
SLWNWFDITK WLWYIKIFIM IVGGLIGLRI VFSVLSIVNR VRQGYSPLSF QTLLPATRGP  720
DRPEGIEEEG GERDRDRSGQ LVNGFLALIW VDLRSLFLFS YHRLRDLLLT VTRIVELLGR  780
RGWEILKYWW NLLQYWSQEL KNSAVSLLNA TAIAVAEGTD RIIEVVQRVY RAILHIPTRI  840
RQGLERALL                                                         849

SEQ ID NO: 110          moltype = AA  length = 856
FEATURE                 Location/Qualifiers
source                  1..856
                        mol_type = protein
                        organism = Bos taurus
```

```
SEQUENCE: 110
MRVKEKYQHL WRWGWRWGTM LLGMLMICSA TEKLWVTVYY GVPVWKEATT TLFCASDAKA  60
YDTEVHNVWA THACVPTDPN PQEVVLVNVT ENFNMWKNDM VEQMHEDIIS LWDQSLKPCV  120
KLTPLCVSLK CTDLKNDTNT NSSSGRMIME KGEIKNCSFN ISTSIRGKVQ KEYAFFYKLD  180
IIPIDNDTTS YKLTSCNTSV ITQACPKVSF EPIPIHYCAP AGFAILKCNN KTFNGTGPCT  240
NVSTVQCTHG IRPVVSTQLL LNGSLAEEEV VIRSVNFTDN AKTIIVQLNT SVEINCTRPN  300
NNTRKRIRIQ RGPGRAFVTI GKIGNMRQAH CNISRAKWNN TLKQIASKLR EQFGNNKTII  360
FKQSSGGDPE IVTHSFNCGG EFFYCNSTQL FNSTWFNSTW STEGSNNTEG SDTITLPCRI  420
KQIINMWQKV GKAMYAPPIS GQIRCSSNIT GLLLTRDGGN SNNESEIFRP GGGDMRDNWR  480
SELYKYKVVK IEPLGVAPTK AKRRVVQREK RAVGIGALFL GFLGAAGSTM GAASMTLTVQ  540
ARQLLSGIVQ QQNNLLRAIE AQQHLLQLTV WGIKQLQARI LAVERYLKDQ QLLGIWGCSG  600
KLICTTAVPW NASWSNKSLE QIWNHTTWME WDREINNYTS LIHSLIEESQ NQQEKNEQEL  660
LELDKWASLW NWFNITNWLW YIKLFIMIVG GLVGLRIVFA VLSIVNRVRQ GYSPLSFQTH  720
LPTPRGPDRP EGIEEEGGER DRDRSIRLVN GSLALIWDDL RSLCLFSYHR LRDLLLIVTR  780
IVELLGRRGW EALKYWWNLL QYWSQELKNS AVSLLNATAI AVAEGTDRVI EVVQGACRAI  840
RHIPRRIRQG LERILL                                                 856

SEQ ID NO: 111          moltype = AA  length = 100
FEATURE                 Location/Qualifiers
source                  1..100
                        mol_type = protein
                        organism = Bos taurus
SEQUENCE: 111
QVQLRESGPS LVKPSQTLSL TCTASGFSLS DKAVGWVRQA PGKALEWLGG IDTGGSTGYN  60
PGLKSRLSIT KDNSKSQVSL SVSSVTTEDS ATYYCTTVHQ                       100

SEQ ID NO: 112          moltype = AA  length = 99
FEATURE                 Location/Qualifiers
source                  1..99
                        mol_type = protein
                        organism = Bos taurus
SEQUENCE: 112
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SAEDSSSNA                        99

SEQ ID NO: 113          moltype = AA  length = 168
FEATURE                 Location/Qualifiers
REGION                  1..168
                        note = synthetic construct
VARIANT                 103
                        note = Xaa can be any naturally occurring amino acid
VARIANT                 118
                        note = Xaa can be any naturally occurring amino acid
VARIANT                 145
                        note = Xaa can be any naturally occurring amino acid
source                  1..168
                        mol_type = protein
                        organism = synthetic construct
SEQUENCE: 113
KVQLQESGPS LVKPSQTLSL TCTVSGFSLS DKAVGWVRQA PGKALEWLGT IDTSGNTNYN  60
PGLKSRLSIT KDNSKSQVSL SVTSMTTEDS ATYYCTTVHQ KTXKKDCPEY YTYNPDCXRR  120
YGWSDCDCMA DKFGGYCRHD GCSTXTVRST YEWYVDAWGQ GLLVTVSS              168

SEQ ID NO: 114          moltype = AA  length = 110
FEATURE                 Location/Qualifiers
REGION                  1..110
                        note = synthetic construct
VARIANT                 92
                        note = Xaa can be any naturally occurring amino acid
source                  1..110
                        mol_type = protein
                        organism = synthetic construct
SEQUENCE: 114
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SXEDSSSNAV FGSGTTLTVL            110

SEQ ID NO: 115          moltype = AA  length = 169
FEATURE                 Location/Qualifiers
REGION                  1..169
                        note = synthetic construct
source                  1..169
                        mol_type = protein
                        organism = synthetic construct
SEQUENCE: 115
QVQLRESGPS LVKPSQTLSL TCMVSGFSLN DKAVGWVRQA PGKALEWLGS IDAGGSTGYN  60
PGLKSRLSIS KDNSKNQVSL SVSSVTTEDS ATYYCGTVHQ RTQPKQTCPN GYSDDSALRY  120
YSRCSDRDCW RCTGTTYYDT CQCSSYTYIH TYELYVDAWG QGLLVTVSS             169

SEQ ID NO: 116          moltype = AA  length = 110
```

```
FEATURE                Location/Qualifiers
REGION                 1..110
                       note = synthetic construct
VARIANT                92
                       note = Xaa can be any naturally occurring amino acid
source                 1..110
                       mol_type = protein
                       organism = synthetic construct
SEQUENCE: 116
QAVLTQPSSV SGSLGQRVSI TCSGSSSNVG NGYVSWYQLI PGSAPRTLIY GDTSRASGVP  60
DRFSGSRSGN TATLTISSLQ AEDEADYFCA SXEDSSSNAV FGSGTTLTVL            110

SEQ ID NO: 117         moltype = AA  length = 169
FEATURE                Location/Qualifiers
REGION                 1..169
                       note = synthetic construct
source                 1..169
                       mol_type = protein
                       organism = synthetic construct
SEQUENCE: 117
QVQLQESGPG LVKPSETLSL TCTVSGYSIS SGYYWGWIRQ PPGKGLEWIG SIYHSGSTYY  60
NPSLKSRVTI SVDTSKNQFS LKLSSVTAAD TAVYYCITAH QKTNKKECPE DYTYNPRCPQ  120
QYGWSDCDCM GDRFGGYCRQ DGCSNYIHRS TYEWYVSAWG QGTLVTVSS             169

SEQ ID NO: 118         moltype = AA  length = 111
FEATURE                Location/Qualifiers
REGION                 1..111
                       note = synthetic construct
source                 1..111
                       mol_type = protein
                       organism = synthetic construct
SEQUENCE: 118
QSVLTQPPSA SGTPGQRVTI SCSGSSSNIG SNTVNWYQQL PGTAPKLLIY SNNQRPSGVP  60
DRFSGSKSGT SASLAISGLQ SEDEADYYCA AWDDSLNGPV VFGGGTKLTV L          111

SEQ ID NO: 119         moltype = AA  length = 169
FEATURE                Location/Qualifiers
REGION                 1..169
                       note = synthetic construct
source                 1..169
                       mol_type = protein
                       organism = synthetic construct
SEQUENCE: 119
QVQLVESGGG VVQPGRSLRL SCAASGFTFS SYGMHWVRQA PGKGLEWVAV ISYDGSNKYY  60
ADSVKGRFTI SRDNSKNTLY LQMNSLRAED TAVYYCITAH QKTNKKECPE DYTYNPRCPQ  120
QYGWSDCDCM GDRFGGYCRQ DGCSNYIHRS TYEWYVSAWG KGTTVTVSS             169

SEQ ID NO: 120         moltype = AA  length = 110
FEATURE                Location/Qualifiers
REGION                 1..110
                       note = synthetic construct
source                 1..110
                       mol_type = protein
                       organism = synthetic construct
SEQUENCE: 120
QSALTQPASV SGSPGQSITI SCNGTSNDVG GYESVSWYQQ HPGKAPKVVI YDVSKRPSGV  60
SNRFSGSKSG NTASLTISGL QAEDEGDYYC KSLTSTRRRV FGTGTKLTVL            110

SEQ ID NO: 121         moltype = AA  length = 64
FEATURE                Location/Qualifiers
source                 1..64
                       mol_type = protein
                       organism = Bos taurus
SEQUENCE: 121
CITAHQKTNK KECPEDYTYN PRCPQQYGWS DCDCMGDRFG GYCRQDGCSN YIHRSTYEWY  60
VSAW                                                              64

SEQ ID NO: 122         moltype = AA  length = 63
FEATURE                Location/Qualifiers
REGION                 1..63
                       note = synthetic construct
VARIANT                6
                       note = Xaa can be Arg or Lys
VARIANT                8
                       note = Xaa can be Gln or His
VARIANT                9
                       note = Xaa can be Pro or Arg
VARIANT                11
                       note = Xaa can be any naturally occurring amino acid
```

```
VARIANT                 12
                        note = Xaa can be Thr, Ile or Asn
VARIANT                 15
                        note = Xaa can be Asn, Asp or Gly
VARIANT                 21
                        note = Xaa can be Ser or Asn
VARIANT                 22
                        note = Xaa can be Ala or Thr
VARIANT                 26
                        note = Xaa can be Tyr or Arg
VARIANT                 30
                        note = Xaa can be Ser or Asp
VARIANT                 49
                        note = Xaa can be Ser, Gly or Ala
VARIANT                 50
                        note = Xaa can be Ser or Thr
VARIANT                 52
                        note = Xaa can be Thr or Phe
VARIANT                 53
                        note = Xaa can be Tyr or Trp
VARIANT                 54
                        note = Xaa can be Ile or Thr
VARIANT                 55
                        note = Xaa can be His or Asp
VARIANT                 57
                        note = Xaa can be Tyr or His
VARIANT                 59
                        note = Xaa can be Leu or Phe
VARIANT                 60
                        note = Xaa can be Tyr or His
source                  1..63
                        mol_type = protein
                        organism = synthetic construct
SEQUENCE: 122
GTVHQXTXXK XXCPXGYSDD XXLRYXSRCX DRDCWRCTGT TYYDTCQCXX YXXXXTXEXX  60
VDA                                                                63

SEQ ID NO: 123          moltype = AA  length = 11
FEATURE                 Location/Qualifiers
source                  1..11
                        mol_type = protein
                        organism = Bos taurus
SEQUENCE: 123
ITAHQKTNKK E                                                       11

SEQ ID NO: 124          moltype = AA  length = 11
FEATURE                 Location/Qualifiers
source                  1..11
                        mol_type = protein
                        organism = Bos taurus
SEQUENCE: 124
TTVHQKAYKK V                                                       11

SEQ ID NO: 125          moltype = AA  length = 11
FEATURE                 Location/Qualifiers
source                  1..11
                        mol_type = protein
                        organism = Bos taurus
SEQUENCE: 125
TTVYQKTTKK D                                                       11

SEQ ID NO: 126          moltype = AA  length = 11
FEATURE                 Location/Qualifiers
source                  1..11
                        mol_type = protein
                        organism = Bos taurus
SEQUENCE: 126
TTVHQKTNEK D                                                       11

SEQ ID NO: 127          moltype = AA  length = 12
FEATURE                 Location/Qualifiers
source                  1..12
                        mol_type = protein
                        organism = Bos taurus
SEQUENCE: 127
GTVHQKTQRK PI                                                      12

SEQ ID NO: 128          moltype = AA  length = 12
FEATURE                 Location/Qualifiers
```

```
source                  1..12
                        mol_type = protein
                        organism = Bos taurus
SEQUENCE: 128
GTVHQRTHRK QN                                                   12

SEQ ID NO: 129          moltype = AA  length = 12
FEATURE                 Location/Qualifiers
source                  1..12
                        mol_type = protein
                        organism = Bos taurus
SEQUENCE: 129
GTVHQRTQPK QT                                                   12

SEQ ID NO: 130          moltype =   length =
SEQUENCE: 130
000

SEQ ID NO: 131          moltype =   length =
SEQUENCE: 131
000

SEQ ID NO: 132          moltype = AA  length = 12
FEATURE                 Location/Qualifiers
REGION                  1..12
                        note = synthetic construct
VARIANT                 6
                        note = Xaa can be Lys or Arg
VARIANT                 8
                        note = Xaa can be Gln or His
VARIANT                 9
                        note = Xaa can be Arg or Pro
VARIANT                 11
                        note = Xaa can be Pro or Gln
VARIANT                 12
                        note = Xaa can be Ile, Asn, or Thr
source                  1..12
                        mol_type = protein
                        organism = synthetic construct
SEQUENCE: 132
GTVHQXTXXK XX                                                   12

SEQ ID NO: 133          moltype = AA  length = 36
FEATURE                 Location/Qualifiers
source                  1..36
                        mol_type = protein
                        organism = Bos taurus
SEQUENCE: 133
CPEDYTYNPR CPQQYGWSDC DCMGDRFGGY CRQDGC                         36

SEQ ID NO: 134          moltype = AA  length = 36
FEATURE                 Location/Qualifiers
source                  1..36
                        mol_type = protein
                        organism = Bos taurus
SEQUENCE: 134
CPDDYSSNPD CVRLYGWSHC DCMRDSFGGW CRADGC                         36

SEQ ID NO: 135          moltype = AA  length = 36
FEATURE                 Location/Qualifiers
source                  1..36
                        mol_type = protein
                        organism = Bos taurus
SEQUENCE: 135
CPEYYTYNPD CARRYGWSDC ECMADKFGGY CRHDGC                         36

SEQ ID NO: 136          moltype = AA  length = 36
FEATURE                 Location/Qualifiers
source                  1..36
                        mol_type = protein
                        organism = Bos taurus
SEQUENCE: 136
CPEYYSYNPD CPRRYGWSNC DCMADKFGGW CRHDGC                         36

SEQ ID NO: 137          moltype = AA  length = 36
FEATURE                 Location/Qualifiers
source                  1..36
                        mol_type = protein
                        organism = Bos taurus
```

```
SEQUENCE: 137
CPDGYSDDST LRYYSRCSDR DCWRCTGTTY YDTCQC                               36

SEQ ID NO: 138          moltype = AA  length = 36
FEATURE                 Location/Qualifiers
source                  1..36
                        mol_type = protein
                        organism = Bos taurus
SEQUENCE: 138
CPGGYSDDNA LRYRSRCDDR DCWRCTGTTY YDTCQC                               36

SEQ ID NO: 139          moltype = AA  length = 36
FEATURE                 Location/Qualifiers
source                  1..36
                        mol_type = protein
                        organism = Bos taurus
SEQUENCE: 139
CPNGYSDDSA LRYYSRCSDR DCWRCTGTTY YDTCQC                               36

SEQ ID NO: 140          moltype = AA  length = 36
FEATURE                 Location/Qualifiers
REGION                  1..36
                        note = synthetic construct
VARIANT                 3
                        note = Xaa can be Glu or Asp
VARIANT                 4
                        note = Xaa can be Asp or Tyr
VARIANT                 6
                        note = Xaa can be Thr or Ser
VARIANT                 7
                        note = Xaa can be Tyr or Ser
VARIANT                 9
                        note = Xaa can be Pro or Arg
VARIANT                 10
                        note = Xaa can be Arg or Asp
VARIANT                 12
                        note = Xaa can be Pro, Val, Glu or Ala
VARIANT                 13
                        note = Xaa can be Gln, Met or Arg
VARIANT                 14
                        note = Xaa can be Gln, Leu, or Arg
VARIANT                 15
                        note = Xaa can be Tyr or Ser
VARIANT                 19
                        note = Xaa can be Asp, His, Tyr, or Asn
VARIANT                 21
                        note = Xaa can be Asp or Glu
VARIANT                 23
                        note = Xaa can be Met, Arg or Leu
VARIANT                 24
                        note = Xaa can be Gly, Arg or Ala
VARIANT                 25
                        note = Xaa can be Asp or Gly
VARIANT                 26
                        note = Xaa can be Arg, Ser, Asn or Lys
VARIANT                 27
                        note = Xaa can be Phe or Val
VARIANT                 30
                        note = Xaa can be Tyr or Trp
VARIANT                 33
                        note = Xaa can be Gln, Ala, or His
VARIANT                 34
                        note = Xaa can be Asp, Glu, or Val
VARIANT                 35
                        note = Xaa can be Gly or Ser
source                  1..36
                        mol_type = protein
                        organism = synthetic construct
SEQUENCE: 140
CPXXYXXNXX CXXXXGWSXC XCXXXXXGGX CRXXXC                               36

SEQ ID NO: 141          moltype = AA  length = 36
FEATURE                 Location/Qualifiers
REGION                  1..36
                        note = synthetic construct
VARIANT                 3
                        note = Xaa can be Glu, Ala or Asp
VARIANT                 4
                        note = Xaa can be Asp, Ala or Tyr
```

```
VARIANT                 6
                        note = Xaa can be Thr, Ala or Ser
VARIANT                 7
                        note = Xaa can be Tyr, Ala or Ser
VARIANT                 9
                        note = Xaa can be Pro, Ala or Arg
VARIANT                 10
                        note = Xaa can be Arg or Asp
VARIANT                 12
                        note = Xaa can be Pro, Val, Glu or Ala
VARIANT                 13
                        note = Xaa can be Gln, Met, Ala or Arg
VARIANT                 14
                        note = Xaa can be Gln, Leu, Ala or Arg
VARIANT                 15
                        note = Xaa can be Tyr or Ser
VARIANT                 19
                        note = Xaa can be Asp, His, Tyr, Ala or Asn
VARIANT                 21
                        note = Xaa can be Asp, Ala or Glu
VARIANT                 23
                        note = Xaa can be Met, Arg, Ala or Leu
VARIANT                 24
                        note = Xaa can be Gly, Arg or Ala
VARIANT                 25
                        note = Xaa can be Asp, Ala or Gly
VARIANT                 26
                        note = Xaa can be Arg, Ser, Asn, Ala or Lys
VARIANT                 27
                        note = Xaa can be Phe or Val
VARIANT                 30
                        note = Xaa can be Tyr, Ala or Trp
VARIANT                 33
                        note = Xaa can be Gln, Ala or His
VARIANT                 34
                        note = Xaa can be Asp, Glu or Val
VARIANT                 35
                        note = Xaa can be Gly, Ala or Ser
source                  1..36
                        mol_type = protein
                        organism = synthetic construct
SEQUENCE: 141
CPXXYXXNXX CXXXXGWSXC XCXXXXXGGX CRXXXC                                  36

SEQ ID NO: 142          moltype = AA  length = 36
FEATURE                 Location/Qualifiers
REGION                  1..36
                        note = synthetic construct
VARIANT                 3
                        note = Xaa can be Asp, Gly or Asn
VARIANT                 9
                        note = Xaa can be Ser or Asn
VARIANT                 10
                        note = Xaa can be Thr or Ala
VARIANT                 14
                        note = Xaa can be Tyr or Arg
VARIANT                 18
                        note = Xaa can be Ser or Asp
source                  1..36
                        mol_type = protein
                        organism = synthetic construct
SEQUENCE: 142
CPXGYSDDXX LRYXSRCXDR DCWRCTGTTY YDTCQC                                  36

SEQ ID NO: 143          moltype = AA  length = 15
FEATURE                 Location/Qualifiers
source                  1..15
                        mol_type = protein
                        organism = Bos taurus
SEQUENCE: 143
SNYIHRSTYE WYVSA                                                         15

SEQ ID NO: 144          moltype = AA  length = 15
FEATURE                 Location/Qualifiers
source                  1..15
                        mol_type = protein
                        organism = Bos taurus
SEQUENCE: 144
SSTVEIGPYE WYVNA                                                         15
```

```
SEQ ID NO: 145          moltype = AA  length = 15
FEATURE                 Location/Qualifiers
source                  1..15
                        mol_type = protein
                        organism = Bos taurus
SEQUENCE: 145
ATNTVRSTYE WHLDA                                                   15

SEQ ID NO: 146          moltype = AA  length = 15
FEATURE                 Location/Qualifiers
source                  1..15
                        mol_type = protein
                        organism = Bos taurus
SEQUENCE: 146
SDYADMTTDE WYVDA                                                   15

SEQ ID NO: 147          moltype = AA  length = 15
FEATURE                 Location/Qualifiers
source                  1..15
                        mol_type = protein
                        organism = Bos taurus
SEQUENCE: 147
GTYTWIDTHE LHVDA                                                   15

SEQ ID NO: 148          moltype = AA  length = 15
FEATURE                 Location/Qualifiers
source                  1..15
                        mol_type = protein
                        organism = Bos taurus
SEQUENCE: 148
ASYFYTDTYE FYVDA                                                   15

SEQ ID NO: 149          moltype = AA  length = 15
FEATURE                 Location/Qualifiers
source                  1..15
                        mol_type = protein
                        organism = Bos taurus
SEQUENCE: 149
SSYTYIHTYE LYVDA                                                   15

SEQ ID NO: 150          moltype =   length =
SEQUENCE: 150
000

SEQ ID NO: 151          moltype =   length =
SEQUENCE: 151
000

SEQ ID NO: 152          moltype = AA  length = 16
FEATURE                 Location/Qualifiers
REGION                  1..16
                        note = synthetic construct
VARIANT                 1
                        note = Xaa can be Gly or Ala
VARIANT                 2
                        note = Xaa can be Thr or Ser
VARIANT                 4
                        note = Xaa can be Thr or Phe
VARIANT                 5
                        note = Xaa can be Trp or Tyr
VARIANT                 6
                        note = Xaa can be Ile or Thr
VARIANT                 7
                        note = Xaa can be Asp or His
VARIANT                 9
                        note = Xaa can be Thr
VARIANT                 11
                        note = Xaa can be His or Tyr
VARIANT                 12
                        note = Xaa can be Leu or Phe
VARIANT                 13
                        note = Xaa can be His or Tyr
source                  1..16
                        mol_type = protein
                        organism = synthetic construct
SEQUENCE: 152
XXYXXXXTXE XXXVDA                                                  16
```

```
SEQ ID NO: 153          moltype = AA  length = 69
FEATURE                 Location/Qualifiers
source                  1..69
                        mol_type = protein
                        organism = Bos taurus
SEQUENCE: 153
CTTVHQSCPD GYSYGYGCGY GYGCSGYDCY GYGGYGGYGG YGYSSYSYSY TYEYYVDAWG  60
QGLLVTVSS                                                          69

SEQ ID NO: 154          moltype = AA  length = 187
FEATURE                 Location/Qualifiers
REGION                  1..187
                        note = synthetic construct
VARIANT                 122
                        note = Xaa can be any naturally occurring amino acid
VARIANT                 137
                        note = Xaa can be any naturally occurring amino acid
VARIANT                 164
                        note = Xaa can be any naturally occurring amino acid
source                  1..187
                        mol_type = protein
                        organism = synthetic construct
SEQUENCE: 154
MGWSCIILFL VATATGVHSK VQLQESGPSL VKPSQTLSLT CTVSGFSLSD KAVGWVRQAP  60
GKALEWLGTI DTSGNTNYNP GLKSRLSITK DNSKSQVSLS VTSMTTEDSA TYYCTTVHQK  120
TXKKDCPEYY TYNPDCXRRY GWSDCDCMAD KFGGYCRHDG CSTXTVRSTY EWYVDAWGQG  180
LLVTVSS                                                            187

SEQ ID NO: 155          moltype = AA  length = 187
FEATURE                 Location/Qualifiers
source                  1..187
                        mol_type = protein
                        organism = Bos taurus
SEQUENCE: 155
MGWSCIILFL VATATGVHSQ VQLRESGPSL MKPSQTLSLT CTVSGSSLND KSVGWVRQAP  60
GKALQWLGSV DTSGNTDYNP GLKSRLSITK DNSKSRISLT VTGMTTEDSA TYYCITAHQK  120
TNKKECPEDY TYNPRCPQQY GWSDCDCMGD RFGGYCRQDG CSNYIHRSTY EWYVSAWGQG  180
LLVTVSS                                                            187

SEQ ID NO: 156          moltype = AA  length = 187
FEATURE                 Location/Qualifiers
source                  1..187
                        mol_type = protein
                        organism = Bos taurus
SEQUENCE: 156
MGWSCIILFL VATATGVHSK VQLRESGPSL VKPFETLSLT CTGSGFSLSD KAAGWVRQAP  60
GKAPEWLGSI DTGGNTGYNP GLKYRLSITK DNSKSQVSLS VSSMTSEDSA TYYCTTVHQK  120
AYKKVCPDDY SSNPDCVRLY GWSHCDCMRD SFGGWCRADG CSSTVEIGPY EWYVNAWGQG  180
LLVTVSS                                                            187

SEQ ID NO: 157          moltype = AA  length = 187
FEATURE                 Location/Qualifiers
source                  1..187
                        mol_type = protein
                        organism = Bos taurus
SEQUENCE: 157
MGWSCIILFL VATATGVHSK VQLQESGPSL VKPSQTLSLT CTVSGFSLSD VAVGWVRQAP  60
GKALEWLGTI YTSGNTNVNP GLKSRLSITK DNAKSQVSLS VTSLTTDDSA TYYCTTVYQK  120
TTKKDCPEYY TYNPDCARRY GWSDCECMAD KFGGYCRHDG CATNTVRSTY EWHLDAWGQG  180
LLVTVSS                                                            187

SEQ ID NO: 158          moltype = AA  length = 187
FEATURE                 Location/Qualifiers
source                  1..187
                        mol_type = protein
                        organism = Bos taurus
SEQUENCE: 158
MGWSCIILFL VATATGVHSQ VQLQESGPSL VKPSQTLSLT CTVSGFSLSD VAVGWVRQAP  60
GKALEWLGTI YTSGNTNVNP GLKSRLSITK DNAKSQVSLS VTSLTTDDSA TYYCTTVYQK  120
TTKKDCPEYY TYNPDCARRY GWSDCECMAD KFGGYCRHDG CATNTVRSTY EWHLDAWGQG  180
LLVTVSS                                                            187

SEQ ID NO: 159          moltype = AA  length = 187
FEATURE                 Location/Qualifiers
source                  1..187
                        mol_type = protein
                        organism = Bos taurus
SEQUENCE: 159
MGWSCIILFL VATATGVHSK VQLQESGPSL VKPSQTLSLT CTVSGFSLSD KAVGWVRQAP  60
```

```
GKALEWLGTI DTNRNTNYHP GLKSRLSITK DNSKSRVSLS VSTMTTEDSA TYYCTTVHQK  120
TNEKDCPEYY SYNPDCPRRY GWSNCDCMAD KFGGWCRHDG CSDYADMTTD EWYVDAWGQG  180
LLVTVSS                                                            187

SEQ ID NO: 160         moltype = AA  length = 188
FEATURE                Location/Qualifiers
REGION                 1..188
                       note = synthetic construct
source                 1..188
                       mol_type = protein
                       organism = synthetic construct
SEQUENCE: 160
MGWSCIILFL VATATGVHSQ VQLRESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                           188

SEQ ID NO: 161         moltype = AA  length = 188
FEATURE                Location/Qualifiers
source                 1..188
                       mol_type = protein
                       organism = Bos taurus
SEQUENCE: 161
MGWSCIILFL VATATGVHSK VQLRESGPSL VKPSQTLSLT CMVSGSSLSD KAVGWVRQAP  60
GKALEWLGII SAGGNRGYNS GLRSRLTISK DNSKNEVSLR VRSVTTEDSA TYFCGTVHQK  120
TQRKPICPDG YSDDSTLRYY SRCSDRDCWR CTGTTYYDTC QCGTYTWIDT HELHVDAWGQ  180
GLLVTVSS                                                           188

SEQ ID NO: 162         moltype = AA  length = 188
FEATURE                Location/Qualifiers
source                 1..188
                       mol_type = protein
                       organism = Bos taurus
SEQUENCE: 162
MGWSCIILFL VATATGVHSQ VQLRESGPSL VKPSQTLSLT CMVSGFSLND KAVGWVRQAP  60
GKALEWLGSI GTGGNKGYNP GLKSRLSISK DSSKNQVSLS MSSVTTEDSA TYYCGTVHQR  120
THRKQNCPGG YSDDNALRYR SRCDDRDCWR CTGTTYYDTC QCASYFYTDT YEFYVDAWGQ  180
GLLVTVSS                                                           188

SEQ ID NO: 163         moltype = AA  length = 188
FEATURE                Location/Qualifiers
source                 1..188
                       mol_type = protein
                       organism = Bos taurus
SEQUENCE: 163
MGWSCIILFL VATATGVHSK VQLRESGPSL VKPSQTLSLT CMVSGFSLND EAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                           188

SEQ ID NO: 164         moltype = AA  length = 188
FEATURE                Location/Qualifiers
source                 1..188
                       mol_type = protein
                       organism = Bos taurus
SEQUENCE: 164
MGWSCIILFL VATATGVHSQ VQLQESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                           188

SEQ ID NO: 165         moltype = AA  length = 188
FEATURE                Location/Qualifiers
source                 1..188
                       mol_type = protein
                       organism = Bos taurus
SEQUENCE: 165
MGWSCIILFL VATATGVHSQ VQLRESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                           188

SEQ ID NO: 166         moltype = AA  length = 128
FEATURE                Location/Qualifiers
REGION                 1..128
                       note = synthetic construct
VARIANT                110
                       note = Xaa can be any naturally occurring amino acid
source                 1..128
```

```
                        mol_type = protein
                        organism = synthetic construct
SEQUENCE: 166
MGWSCIILFL VATATGVHQA VLTQPSSVSG SLGQRVSITC SGSSSNVGNG YVSWYQLIPG  60
SAPRTLIYGD TSRASGVPDR FSGSRSGNTA TLTISSLQAE DEADYFCASX EDSSSNAVFG  120
SGTTLTVL                                                          128

SEQ ID NO: 167          moltype = AA  length = 128
FEATURE                 Location/Qualifiers
source                  1..128
                        mol_type = protein
                        organism = Bos taurus
SEQUENCE: 167
MGWSCIILFL VATATGVHSY ELTQPSSVSG SLGQRVSVTC SGSSSNVGNG YVSWYQLIPG  60
SAPRTIIYGD TSRASGVPER FSGSRSGNTA TLTISSLQAE DEADFFCASP DDSSSNAVFG  120
SGTTLTVL                                                          128

SEQ ID NO: 168          moltype = AA  length = 128
FEATURE                 Location/Qualifiers
source                  1..128
                        mol_type = protein
                        organism = Bos taurus
SEQUENCE: 168
MGWSCIILFL VATATGVHQA VLNQPSSVSG SLGQRVSITC SGSSSNVGNG YVSWYQLIPG  60
SAPRTLIYGD TSRASGVPDR FSGSRSGNTA TLTISSLQAE DEADYFCASA EDSSSNAVFG  120
SGTTLTVL                                                          128

SEQ ID NO: 169          moltype = AA  length = 128
FEATURE                 Location/Qualifiers
source                  1..128
                        mol_type = protein
                        organism = Bos taurus
SEQUENCE: 169
MGWSCIILFL VATATGVHQA VLNQPSSVSG SLGQRVSITC SGSSSNVGNG YVSWYQLIPG  60
SAPRTLIYGD TSRASGVPDR FSGSRSGNTA TLTISSLQAE DEADYFCASA EDSSSNAVFG  120
SGTTLTVL                                                          128

SEQ ID NO: 170          moltype = AA  length = 128
FEATURE                 Location/Qualifiers
source                  1..128
                        mol_type = protein
                        organism = Bos taurus
SEQUENCE: 170
MGWSCIILFL VATATGVHQA VLTQPSSVSG SLGQRVSITC SGSSSNVGNG YVSWYQLIPG  60
SAPRTLIYGD TSRASGVPDR FSGSRSGNTA TLTISSLQAE DEADYFCASP EDSSSNAVFG  120
SGTTLTVL                                                          128

SEQ ID NO: 171          moltype = AA  length = 128
FEATURE                 Location/Qualifiers
source                  1..128
                        mol_type = protein
                        organism = Bos taurus
SEQUENCE: 171
MGWSCIILFL VATATGVHQD VLTQPSSVSG SLGQRVSITC SGSSSNVGNG YVSWYQLIPG  60
SAPRTLIYGD TSRASGVPDR FSGSRSGNTA TLTISSLQAE DEADYFCASP EDSSSNAVFG  120
SGTTLTVL                                                          128

SEQ ID NO: 172          moltype = AA  length = 128
FEATURE                 Location/Qualifiers
source                  1..128
                        mol_type = protein
                        organism = Bos taurus
SEQUENCE: 172
MGWSCIILFL VATATGVHQA VLTQPSSVSG SLGQRVSITC SGSSSNVGNG YVSWYQLIPG  60
SAPRTLIYGD TSRASGVPDR FSGSRSGNTA TLTISSLQAE DEADYFCASP EDSSSNAVFG  120
SGTTLTVL                                                          128

SEQ ID NO: 173          moltype = AA  length = 128
FEATURE                 Location/Qualifiers
source                  1..128
                        mol_type = protein
                        organism = Bos taurus
SEQUENCE: 173
MGWSCIILFL VATATGVHQA VLTQPSSVSG SLGQRVSITC SGSSSNVGNG YVSWYQLIPG  60
SAPRSLIYGD TSRASGVPDR FSGSRSGNTA TLTISSLQAE DEADYFCASP EDSSSNGVFG  120
SGTTLTVL                                                          128

SEQ ID NO: 174          moltype = AA  length = 128
FEATURE                 Location/Qualifiers
```

```
source                  1..128
                        mol_type = protein
                        organism = Bos taurus
SEQUENCE: 174
MGWSCIILFL VATATGVHQA VLTQPSSVSG SLGRRVSITC SGSSSNVGNG YVSWYQVIPG  60
SAPRTLIYGD SNRASGVPDR FSGSRSGNTA TLTISSLQAE DEADYFCGSA EDGSGSGVFG  120
SGTTLTVL                                                          128

SEQ ID NO: 175          moltype = AA  length = 128
FEATURE                 Location/Qualifiers
source                  1..128
                        mol_type = protein
                        organism = Bos taurus
SEQUENCE: 175
MGWSCIILFL VATATGVHQA VLTQPSSVSG SLGRRVSITC SGSSSNVGNG YVSWYQVIPG  60
SAPRTLIYGD SNRASGVPDR FSGSRSGNTA TLTISSLQAE DEADYFCGSA EDGSGSGVFG  120
SGTTLTVL                                                          128

SEQ ID NO: 176          moltype = AA  length = 128
FEATURE                 Location/Qualifiers
source                  1..128
                        mol_type = protein
                        organism = Bos taurus
SEQUENCE: 176
MGWSCIILFL VATATGVHQD VLTQPSSVSG SLGQRVSITC SGSSSNVGNG YVSWYQLISG  60
SAPRTLIYGD TSRASGIPDR FSGSRSGNTA TLTITSLQAE DEADYFCASA EDRRSNAIFG  120
SGTTLTVL                                                          128

SEQ ID NO: 177          moltype = AA  length = 6
FEATURE                 Location/Qualifiers
source                  1..6
                        mol_type = protein
                        organism = Bos taurus
SEQUENCE: 177
CTTVHQ                                                            6

SEQ ID NO: 178          moltype = AA  length = 48
FEATURE                 Location/Qualifiers
source                  1..48
                        mol_type = protein
                        organism = Bos taurus
SEQUENCE: 178
SCPDGYSYGY GCGYGYGCSG YDCYGYGGYG GYGGYGYSSY SYSYTYEY              48

SEQ ID NO: 179          moltype = AA  length = 5
FEATURE                 Location/Qualifiers
source                  1..5
                        mol_type = protein
                        organism = Bos taurus
SEQUENCE: 179
YVDAW                                                             5

SEQ ID NO: 180          moltype = AA  length = 187
FEATURE                 Location/Qualifiers
REGION                  1..187
                        note = synthetic construct
VARIANT                 135
                        note = Xaa can be any naturally occurring amino acid
VARIANT                 139..140
                        note = Xaa can be any naturally occurring amino acid
VARIANT                 153
                        note = Xaa can be any naturally occurring amino acid
VARIANT                 159
                        note = Xaa can be any naturally occurring amino acid
VARIANT                 168
                        note = Xaa can be any naturally occurring amino acid
VARIANT                 172
                        note = Xaa can be any naturally occurring amino acid
source                  1..187
                        mol_type = protein
                        organism = synthetic construct
SEQUENCE: 180
MGWSCIILFL VATATGVHSQ VQLRESGPSL VKPSQTLSLT CTVSGFSLSD KAVGWVRQAP  60
GKALEWLGSI DTGGNTGYNP GLKSRLSITK DNSKSQVSLS VSSVTTEDSA TYYCTTVHQK  120
TQKKTCPDGY SDDSXCRYXX GCSDRDCWRC TGXGYYDTXG CSSYTYIXTY EXYVDAWGQG  180
LLVTVSS                                                           187

SEQ ID NO: 181          moltype = AA  length = 188
FEATURE                 Location/Qualifiers
```

```
source                  1..188
                        mol_type = protein
                        organism = Bos taurus
SEQUENCE: 181
MGWSCIILFL VATATGVHSK VQLRESGPSL VKPSQTLSLT CMVSGFSLND EAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                          188

SEQ ID NO: 182          moltype = AA  length = 188
FEATURE                 Location/Qualifiers
source                  1..188
                        mol_type = protein
                        organism = Bos taurus
SEQUENCE: 182
MGWSCIILFL VATATGVHSQ VQLQESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                          188

SEQ ID NO: 183          moltype = AA  length = 188
FEATURE                 Location/Qualifiers
source                  1..188
                        mol_type = protein
                        organism = Bos taurus
SEQUENCE: 183
MGWSCIILFL VATATGVHSQ VQLRESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQPKQTCPNG YSDDSALRYY SRCSDRDCWR CTGTTYYDTC QCSSYTYIHT YELYVDAWGQ  180
GLLVTVSS                                                          188

SEQ ID NO: 184          moltype = AA  length = 188
FEATURE                 Location/Qualifiers
source                  1..188
                        mol_type = protein
                        organism = Bos taurus
SEQUENCE: 184
MGWSCIILFL VATATGVHSQ VQLRESGPSL VKPSQTLSLT CMVSGFSLND KAVGWVRQAP  60
GKALEWLGSI DAGGSTGYNP GLKSRLSISK DNSKNQVSLS VSSVTTEDSA TYYCGTVHQR  120
TQKKQSCPVG YSDDSALRYY SRCSDRDCWR CTGTTYYDTC QCSSYTYIDT YELYVHAWGQ  180
GLLVTVSS                                                          188

SEQ ID NO: 185          moltype = AA  length = 187
FEATURE                 Location/Qualifiers
source                  1..187
                        mol_type = protein
                        organism = Bos taurus
SEQUENCE: 185
MGWSCIILFL VATATGVHSQ VQLRESGPSL MKPSQTLSLT CTVSGSSLND KSVGWVRQAP  60
GKALQWLGSV DTSGNTDYNP GLKSRLSITK DNSKSRISLT VTGMTTEDSA TYYCITAHQK  120
TNKKECPEDY TYNPRCPQQY GWSDCDCMGD RFGGYCRQDG CSNYIHRSTY EWYVSAWGQG  180
LLVTVSS                                                           187

SEQ ID NO: 186          moltype = AA  length = 188
FEATURE                 Location/Qualifiers
source                  1..188
                        mol_type = protein
                        organism = Bos taurus
SEQUENCE: 186
MGWSCIILFL VATATGVHSK VQLRESGPSL VKPSQTLSLT CMVSGSSLSD KAVGWVRQAP  60
GKALEWLGII SAGGNRGYNS GLRSRLTISK DNSKNEVSLR VRSVTTEDSA TYFCGTVHQK  120
TQRKPICPDG YSDDSTLRYY SRCSDRDCWR CTGTTYYDTC QCGTYTWIDT HELHVDAWGQ  180
GLLVTVSS                                                          188

SEQ ID NO: 187          moltype = AA  length = 188
FEATURE                 Location/Qualifiers
source                  1..188
                        mol_type = protein
                        organism = Bos taurus
SEQUENCE: 187
MGWSCIILFL VATATGVHSQ VQLRESGPSL VKPSQTLSLT CMVSGFSLND KAVGWVRQAP  60
GKALEWLGSI GTGGNKGYNP GLKSRLSISK DSSKNQVSLS MSSVTTEDSA TYYCGTVHQR  120
THRKQNCPGG YSDDNALRYR SRCDDRDCWR CTGTTYYDTC QCASYFYTDT YEFYVDAWGQ  180
GLLVTVSS                                                          188

SEQ ID NO: 188          moltype = AA  length = 188
FEATURE                 Location/Qualifiers
source                  1..188
                        mol_type = protein
```

```
                          organism = Bos taurus
SEQUENCE: 188
MGWSCIILFL VATATGVHSQ VQLRESGPSL VKPSQTLSLT CTVSGFSLTD KAVGWVRQAP  60
GKALEWLGSV DAGGSTGYNS GLRSRLSITK DNSKSQVFLS LSSVSTEDSA TYYCTAVQQK  120
TNGIRSCPDR STWLDGSACV ENCGGYTCCG WGYYGCYGTY GYSTYTYTYT YQNHVDAWGQ  180
GLLVTVSS                                                           188

SEQ ID NO: 189            moltype = AA  length = 188
FEATURE                   Location/Qualifiers
source                    1..188
                          mol_type = protein
                          organism = Bos taurus
SEQUENCE: 189
MGWSCIILFL VATATGVHSQ VQLRESGPSL VKPSQTLSLT CTVSGFSLTD KAVGWVRQTP  60
GKALEWLGSI DTSGTAGYNP GLKSRLSITK DNSKSQVSLS VSSVTTEDSA TYYCVTVHQK  120
TETGRSCPDE HSDLGDDACV ESCGGYPCCG WAWYGCYGTY GRSLYVYTYT YEHHVDAWGQ  180
GLLVTVSS                                                           188

SEQ ID NO: 190            moltype = AA  length = 155
FEATURE                   Location/Qualifiers
source                    1..155
                          mol_type = protein
                          organism = Bos taurus
SEQUENCE: 190
MGWSCIILFL VATATGVHSQ VQLRESGPSL VKPSQTLSLT CTVSEFSLSN DRVAWVRQAP  60
GKALEWLGII CSEGTTGYNP ALKSRLSITK DNSKSQVSLS LSSVTTEDTA KYYCARVDYP  120
NYTVGGYGCY DYGGVQGIGI YVDTWGQGLL VTVSS                             155

SEQ ID NO: 191            moltype = AA  length = 146
FEATURE                   Location/Qualifiers
source                    1..146
                          mol_type = protein
                          organism = Bos taurus
SEQUENCE: 191
MGWSCIILFL VATATGVHSK VQLRESGPSL VKPSQTLSLT CTVSGFSLSS YGVTWIRRAP  60
GKALECLGGV KSDETTGYNP ALKHRLSITK DNSKSQVSLS LRSVTTDDTA TYYCAKGRND  120
GDDPDVCYGG GYIDAWGQGL LVTVSS                                       146

SEQ ID NO: 192            moltype = AA  length = 188
FEATURE                   Location/Qualifiers
source                    1..188
                          mol_type = protein
                          organism = Bos taurus
SEQUENCE: 192
MGWSCIILFL VATATGVHSQ VQLRESGPSL VKPSQTLSLT CTVSGFSLSD KAVGWVRQAP  60
GKALEWLGSM DTGGITGYNP GLKSRLSITK DNSKSQVSLL VSSVTTEDSA AYYCTTVHQN  120
SEKKIGCPDG YSDTYGCCIR YGRGSGDCYG YGDCGSNDGD ACRSKTVTYI YEFHVDAWGQ  180
GLLVTVSS                                                           188

SEQ ID NO: 193            moltype = AA  length = 188
FEATURE                   Location/Qualifiers
source                    1..188
                          mol_type = protein
                          organism = Bos taurus
SEQUENCE: 193
MGWSCIILFL VATATGVHSQ VQLQESGPSL VKPSQTLSLT CTVSGFSLSD KAVGWVRQAP  60
GKALEWLGSI NPRGSTGYNP GLKSRLSITK DNSKSQVSLS VSSVTTEDSA TYYCSTVTQN  120
VLKRSACPDG YSNGDTCGGP WYCGGSDCCE CSGDGGLWGY RGTSYIDTYT YEFWVDAWGQ  180
GLLVTVSS                                                           188

SEQ ID NO: 194            moltype = AA  length = 186
FEATURE                   Location/Qualifiers
source                    1..186
                          mol_type = protein
                          organism = Bos taurus
SEQUENCE: 194
MGWSCIILFL VATATGVHSK VQLRESGPSL VKPSQTLSLT CTVSGFSLSD KVVGWVRQAP  60
GKALEWLGHT DTGGNTGYNP GLKSRLTITK HNSKSQVSLS VSSVTPEDSA TYYCTTVYQK  120
TKKTCPDGYN PGSRCGDAWG CGEHDCYRCH GGNVYCNYAL DSTNFISTSE FSVDAWGQGL  180
LVTVSS                                                             186

SEQ ID NO: 195            moltype = AA  length = 187
FEATURE                   Location/Qualifiers
source                    1..187
                          mol_type = protein
                          organism = Bos taurus
SEQUENCE: 195
MGWSCIILFL VATATGVHSK VQLRESGPSL VKPFETLSLT CTGSGFSLSD KAAGWVRQAP  60
GKAPEWLGSI DTGGNTGYNP GLKYRLSITK DNSKSQVSLS VSSMTSEDSA TYYCTTVHQK  120
```

```
AYKKVCPDDY SSNPDCVRLY GWSHCDCMRD SFGGWCRADG CSSTVEIGPY EWYVNAWGQG  180
LLVTVSS                                                            187

SEQ ID NO: 196          moltype = AA  length = 187
FEATURE                 Location/Qualifiers
source                  1..187
                        mol_type = protein
                        organism = Bos taurus
SEQUENCE: 196
MGWSCIILFL VATATGVHSK VQLQESGPSL VKPSQTLSLT CTVSGFSLSD VAVGWVRQAP  60
GKALEWLGTI YTSGNTNVNP GLKSRLSITK DNAKSQVSLS VTSLTTDDSA TYYCTTVYQK  120
TTKKDCPEYY TYNPDCARRY GWSDCECMAD KFGGYCRHDG CATNTVRSTY EWHLDAWGQG  180
LLVTVSS                                                            187

SEQ ID NO: 197          moltype = AA  length = 187
FEATURE                 Location/Qualifiers
source                  1..187
                        mol_type = protein
                        organism = Bos taurus
SEQUENCE: 197
MGWSCIILFL VATATGVHSQ VQLQESGPSL VKPSQTLSLT CTVSGFSLSD VAVGWVRQAP  60
GKALEWLGTI YTSGNTNVNP GLKSRLSITK DNAKSQVSLS VTSLTTDDSA TYYCTTVYQK  120
TTKKDCPEYY TYNPDCARRY GWSDCECMAD KFGGYCRHDG CATNTVRSTY EWHLDAWGQG  180
LLVTVSS                                                            187

SEQ ID NO: 198          moltype = AA  length = 187
FEATURE                 Location/Qualifiers
source                  1..187
                        mol_type = protein
                        organism = Bos taurus
SEQUENCE: 198
MGWSCIILFL VATATGVHSK VQLQESGPSL VKPSQTLSLT CTVSGFSLSD KAVGWVRQAP  60
GKALEWLGTI DTNRNTNYHP GLKSRLSITK DNSKSRVSLS VSTMTTEDSA TYYCTTVHQK  120
TNEKDCPEYY SYNPDCPRRY GWSNCDCMAD KFGGWCRHDG CSDYADMTTD EWYVDAWGQG  180
LLVTVSS                                                            187

SEQ ID NO: 199          moltype = DNA  length = 22
FEATURE                 Location/Qualifiers
misc_feature            1..22
                        note = synthetic construct
source                  1..22
                        mol_type = other DNA
                        organism = synthetic construct
SEQUENCE: 199
caccatggcc tggtcccctc tg                                          22

SEQ ID NO: 200          moltype = DNA  length = 20
FEATURE                 Location/Qualifiers
misc_feature            1..20
                        note = synthetic construct
source                  1..20
                        mol_type = other DNA
                        organism = synthetic construct
SEQUENCE: 200
gaccccagac tcaccatctc                                             20

SEQ ID NO: 201          moltype = DNA  length = 24
FEATURE                 Location/Qualifiers
misc_feature            1..24
                        note = synthetic construct
source                  1..24
                        mol_type = other DNA
                        organism = synthetic construct
SEQUENCE: 201
agggctgcgg gctcagaagg cagc                                        24

SEQ ID NO: 202          moltype = DNA  length = 21
FEATURE                 Location/Qualifiers
misc_feature            1..21
                        note = synthetic construct
source                  1..21
                        mol_type = other DNA
                        organism = synthetic construct
SEQUENCE: 202
ctgcccctcc tcactctctg c                                           21

SEQ ID NO: 203          moltype = DNA  length = 19
FEATURE                 Location/Qualifiers
misc_feature            1..19
```

```
                         note = synthetic construct
source                   1..19
                         mol_type = other DNA
                         organism = synthetic construct
SEQUENCE: 203
ggaacctttc ctgcagctc                                             19

SEQ ID NO: 204           moltype = DNA  length = 20
FEATURE                  Location/Qualifiers
misc_feature             1..20
                         note = synthetic construct
source                   1..20
                         mol_type = other DNA
                         organism = synthetic construct
SEQUENCE: 204
gcttgcttat ggctcaggtc                                            20

SEQ ID NO: 205           moltype = DNA  length = 21
FEATURE                  Location/Qualifiers
misc_feature             1..21
                         note = synthetic construct
source                   1..21
                         mol_type = other DNA
                         organism = synthetic construct
SEQUENCE: 205
aagtcgctga tgagacacac c                                          21

SEQ ID NO: 206           moltype = DNA  length = 24
FEATURE                  Location/Qualifiers
misc_feature             1..24
                         note = synthetic construct
source                   1..24
                         mol_type = other DNA
                         organism = synthetic construct
SEQUENCE: 206
ccctcctctt tgtgctstca gccc                                       24

SEQ ID NO: 207           moltype = DNA  length = 20
FEATURE                  Location/Qualifiers
misc_feature             1..20
                         note = synthetic construct
source                   1..20
                         mol_type = other DNA
                         organism = synthetic construct
SEQUENCE: 207
gtcaccatgc tgctgagaga                                            20

SEQ ID NO: 208           moltype = DNA  length = 22
FEATURE                  Location/Qualifiers
misc_feature             1..22
                         note = synthetic construct
source                   1..22
                         mol_type = other DNA
                         organism = synthetic construct
SEQUENCE: 208
ctttcggggc tgtggtggag gc                                         22

SEQ ID NO: 209           moltype = DNA  length = 51
FEATURE                  Location/Qualifiers
misc_feature             1..51
                         note = synthetic construct
source                   1..51
                         mol_type = other DNA
                         organism = synthetic construct
SEQUENCE: 209
catccttttt ctagtagcaa ctgcaaccgg ttgaggatga ggcggattat t         51

SEQ ID NO: 210           moltype = DNA  length = 50
FEATURE                  Location/Qualifiers
misc_feature             1..50
                         note = synthetic construct
source                   1..50
                         mol_type = other DNA
                         organism = synthetic construct
SEQUENCE: 210
catccttttt ctagtagcaa ctgcaaccgg tgggtcagaa ggtctccatc           50

SEQ ID NO: 211           moltype = DNA  length = 51
FEATURE                  Location/Qualifiers
```

```
misc_feature          1..51
                      note = synthetic construct
source                1..51
                      mol_type = other DNA
                      organism = synthetic construct
SEQUENCE: 211
catccttttt ctagtagcaa ctgcaaccgg tgattttggg tgtgagctgg t          51

SEQ ID NO: 212        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 212
catccttttt ctagtagcaa ctgcaaccgg tcccccaaaa ccctcatcta t          51

SEQ ID NO: 213        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 213
catccttttt ctagtagcaa ctgcaaccgg tcagcagcaa tgttggaaat g          51

SEQ ID NO: 214        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 214
catccttttt ctagtagcaa ctgcaaccgg tcccccaaaa ccctgatcta t          51

SEQ ID NO: 215        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 215
catccttttt ctagtagcaa ctgcaaccgg tggcggatta tttctgtgca t          51

SEQ ID NO: 216        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 216
catccttttt ctagtagcaa ctgcaaccgg ttctgggaat ctgggacaga c          51

SEQ ID NO: 217        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 217
catccttttt ctagtagcaa ctgcaaccgg tctgccaggg agacgactta g          51

SEQ ID NO: 218        moltype = DNA  length = 51
FEATURE               Location/Qualifiers
misc_feature          1..51
                      note = synthetic construct
source                1..51
                      mol_type = other DNA
                      organism = synthetic construct
SEQUENCE: 218
catccttttt ctagtagcaa ctgcaaccgg tcttcagtgt cagtggcctt g          51

SEQ ID NO: 219        moltype = DNA  length = 51
```

```
FEATURE                 Location/Qualifiers
misc_feature            1..51
                        note = synthetic construct
source                  1..51
                        mol_type = other DNA
                        organism = synthetic construct
SEQUENCE: 219
catccttttt ctagtagcaa ctgcaaccgg tgctccagac cagtgaggaa g          51

SEQ ID NO: 220          moltype = DNA  length = 51
FEATURE                 Location/Qualifiers
misc_feature            1..51
                        note = synthetic construct
source                  1..51
                        mol_type = other DNA
                        organism = synthetic construct
SEQUENCE: 220
catccttttt ctagtagcaa ctgcaaccgg tgtcaccctc acctgtggac t          51

SEQ ID NO: 221          moltype = DNA  length = 51
FEATURE                 Location/Qualifiers
misc_feature            1..51
                        note = synthetic construct
source                  1..51
                        mol_type = other DNA
                        organism = synthetic construct
SEQUENCE: 221
catccttttt ctagtagcaa ctgcaaccgg tagcatcagc cagactcacc t          51

SEQ ID NO: 222          moltype = DNA  length = 51
FEATURE                 Location/Qualifiers
misc_feature            1..51
                        note = synthetic construct
source                  1..51
                        mol_type = other DNA
                        organism = synthetic construct
SEQUENCE: 222
catccttttt ctagtagcaa ctgcaaccgg tgtcaccctc acctgtggac t          51

SEQ ID NO: 223          moltype = DNA  length = 40
FEATURE                 Location/Qualifiers
misc_feature            1..40
                        note = synthetic construct
source                  1..40
                        mol_type = other DNA
                        organism = synthetic construct
SEQUENCE: 223
gttggcttga agctcctcac tcgagggygg gaacagagtg                       40

SEQ ID NO: 224          moltype = DNA  length = 60
FEATURE                 Location/Qualifiers
misc_feature            1..60
                        note = synthetic construct
source                  1..60
                        mol_type = other DNA
                        organism = synthetic construct
SEQUENCE: 224
catccttttt ctagtagcaa ctgcaaccgg tgtacattcc maggtgcagc tgcrggagtc  60

SEQ ID NO: 225          moltype = DNA  length = 58
FEATURE                 Location/Qualifiers
misc_feature            1..58
                        note = synthetic construct
source                  1..58
                        mol_type = other DNA
                        organism = synthetic construct
SEQUENCE: 225
ggaagaccga tgggcccttg gtcgacgctg aggagacggt gaccaggagt ccttggcc    58

SEQ ID NO: 226          moltype = AA  length = 127
FEATURE                 Location/Qualifiers
REGION                  1..127
                        note = synthetic construct
source                  1..127
                        mol_type = protein
                        organism = synthetic construct
SEQUENCE: 226
MGWSCIILFL VATATGVHQA VLNQPSSVSG SLGQRVSITC SGSSSNVGNG YVSWYQLIPG  60
SAPRTLIYGD TSRASGVPDR FSGSRSGNTA TLTISSLQAE DEADYFCASA EDSSSNAVFG  120
```

```
SGTTLTV                                                          127

SEQ ID NO: 227          moltype = AA  length = 62
FEATURE                 Location/Qualifiers
source                  1..62
                        mol_type = protein
                        organism = Bos taurus
SEQUENCE: 227
TTVYQKTTKK DCPEYYTYNP DCARRYGWSD CDCMADKFGG SCRLDGCATN TVRSTYEWHL  60
DA                                                                 62

SEQ ID NO: 228          moltype = AA  length = 62
FEATURE                 Location/Qualifiers
source                  1..62
                        mol_type = protein
                        organism = Bos taurus
SEQUENCE: 228
TTVYQKTTKK DCPEYYTYNR DCERRYGWSD CECRADNVGG HCRHEGCATN TVRSTYEWHL  60
DA                                                                 62

SEQ ID NO: 229          moltype = AA  length = 62
FEATURE                 Location/Qualifiers
source                  1..62
                        mol_type = protein
                        organism = Bos taurus
SEQUENCE: 229
TTVYLKTTKQ DCPEYYTYNP DCARRYGWSD CECMADKFGG YCRHDGCATN TVRSTDEWHL  60
DA                                                                 62

SEQ ID NO: 230          moltype = AA  length = 62
FEATURE                 Location/Qualifiers
source                  1..62
                        mol_type = protein
                        organism = Bos taurus
SEQUENCE: 230
TTVYLKTTKQ DCPEYYTYNP DCARRYGWRD CECLADKVGG YCRHVGCANN TVRSTDEWHL  60
DA                                                                 62

SEQ ID NO: 231          moltype = AA  length = 62
FEATURE                 Location/Qualifiers
source                  1..62
                        mol_type = protein
                        organism = Bos taurus
SEQUENCE: 231
TTVYLKTTKQ DCPEYYTYNP DCARRYGWSD CECMADKVGG ECRHDGCATN TVRSNDEWHL  60
DA                                                                 62

SEQ ID NO: 232          moltype = AA  length = 62
FEATURE                 Location/Qualifiers
source                  1..62
                        mol_type = protein
                        organism = Bos taurus
SEQUENCE: 232
TTVYQKTTKK DCPEYYTYNP DCARRSGWSD CECMADKFGG YCRHDGCATN TVRSTYEWHL  60
DA                                                                 62

SEQ ID NO: 233          moltype = AA  length = 62
FEATURE                 Location/Qualifiers
source                  1..62
                        mol_type = protein
                        organism = Bos taurus
SEQUENCE: 233
TTVYLKTTKQ DCPEYYTYNP DCARRYGWSD CECMADKFGG YCRHDGCATN PVRSTDEWHL  60
DA                                                                 62

SEQ ID NO: 234          moltype = AA  length = 62
FEATURE                 Location/Qualifiers
source                  1..62
                        mol_type = protein
                        organism = Bos taurus
SEQUENCE: 234
TTVYLKTTKQ DCPEYYTYNP DCARRYGWSD CECMADKFGG YCRHDGCATN TVRSTDGFHL  60
DA                                                                 62

SEQ ID NO: 235          moltype = AA  length = 62
FEATURE                 Location/Qualifiers
source                  1..62
                        mol_type = protein
                        organism = Bos taurus
```

```
SEQUENCE: 235
TTVYQKTTKQ DCPEYYTYNP DCARRYGWSD CECMADKFGG YCRHDGCATN TVRSTYEWHL  60
DA                                                                62

SEQ ID NO: 236          moltype = AA  length = 62
FEATURE                 Location/Qualifiers
source                  1..62
                        mol_type = protein
                        organism = Bos taurus
SEQUENCE: 236
TTVYLKTTKQ DCPEYYTYNP DRARRSGWSD CECMADKFGG YCRHDGCATN TVRSTDEWHL  60
DA                                                                62

SEQ ID NO: 237          moltype = AA  length = 62
FEATURE                 Location/Qualifiers
source                  1..62
                        mol_type = protein
                        organism = Bos taurus
SEQUENCE: 237
TTVYQKTTKQ DCPEYYTYNP DCARRYGWSD CECMADKFGG YCRHEGFATH TVRSPYEWHL  60
HA                                                                62

SEQ ID NO: 238          moltype = AA  length = 62
FEATURE                 Location/Qualifiers
source                  1..62
                        mol_type = protein
                        organism = Bos taurus
SEQUENCE: 238
TTVYQKTTKK DCPEYYTYNP DCAMRYGWSY CECMAGKFWG YWCHESCATN TVRSTYEGPR  60
DA                                                                62

SEQ ID NO: 239          moltype = AA  length = 64
FEATURE                 Location/Qualifiers
source                  1..64
                        mol_type = protein
                        organism = Bos taurus
SEQUENCE: 239
CTTVYQKTTK KDCPEYYTYN PDCARRYGWS DCDCMADKFG GSCRLDGCAT NTVRSTYEWH  60
LDAW                                                              64

SEQ ID NO: 240          moltype = AA  length = 64
FEATURE                 Location/Qualifiers
source                  1..64
                        mol_type = protein
                        organism = Bos taurus
SEQUENCE: 240
CTTVYQKTTK KDCPEYYTYN RDCERRYGWS DCECRADNVG GHCRHEGCAT NTVRSTYEWH  60
LDAW                                                              64

SEQ ID NO: 241          moltype = AA  length = 64
FEATURE                 Location/Qualifiers
source                  1..64
                        mol_type = protein
                        organism = Bos taurus
SEQUENCE: 241
CTTVYLKTTK QDCPEYYTYN PDCARRYGWS DCECMADKFG GYCRHDGCAT NTVRSTDEWH  60
LDAW                                                              64

SEQ ID NO: 242          moltype = AA  length = 64
FEATURE                 Location/Qualifiers
source                  1..64
                        mol_type = protein
                        organism = Bos taurus
SEQUENCE: 242
CTTVYLKTTK QDCPEYYTYN PDCARRYGWR DCECLADKVG GYCRHVGCAN NTVRSTDEWH  60
LDAW                                                              64

SEQ ID NO: 243          moltype = AA  length = 64
FEATURE                 Location/Qualifiers
source                  1..64
                        mol_type = protein
                        organism = Bos taurus
SEQUENCE: 243
CTTVYLKTTK QDCPEYYTYN PDCARRYGWS DCECMADKVG GECRHDGCAT NTVRSNDEWH  60
LDAW                                                              64

SEQ ID NO: 244          moltype = AA  length = 64
FEATURE                 Location/Qualifiers
source                  1..64
```

```
                        mol_type = protein
                        organism = Bos taurus
SEQUENCE: 244
CTTVYQKTTK KDCPEYYTYN PDCARRSGWS DCECMADKFG GYCRHDGCAT NTVRSTYEWH  60
LDAW                                                               64

SEQ ID NO: 245          moltype = AA  length = 64
FEATURE                 Location/Qualifiers
source                  1..64
                        mol_type = protein
                        organism = Bos taurus
SEQUENCE: 245
CTTVYLKTTK QDCPEYYTYN PDCARRYGWS DCECMADKFG GYCRHDGCAT NPVRSTDEWH  60
LDAW                                                               64

SEQ ID NO: 246          moltype = AA  length = 64
FEATURE                 Location/Qualifiers
source                  1..64
                        mol_type = protein
                        organism = Bos taurus
SEQUENCE: 246
CTTVYLKTTK QDCPEYYTYN PDCARRYGWS DCECMADKFG GYCRHDGCAT NTVRSTDGFH  60
LDAW                                                               64

SEQ ID NO: 247          moltype = AA  length = 64
FEATURE                 Location/Qualifiers
source                  1..64
                        mol_type = protein
                        organism = Bos taurus
SEQUENCE: 247
CTTVYQKTTK QDCPEYYTYN PDCARRYGWS DCECMADKFG GYCRHDGCAT NTVRSTYEWH  60
LDAW                                                               64

SEQ ID NO: 248          moltype = AA  length = 64
FEATURE                 Location/Qualifiers
source                  1..64
                        mol_type = protein
                        organism = Bos taurus
SEQUENCE: 248
CTTVYLKTTK QDCPEYYTYN PDRARRSGWS DCECMADKFG GYCRHDGCAT NTVRSTDEWH  60
LDAW                                                               64

SEQ ID NO: 249          moltype = AA  length = 64
FEATURE                 Location/Qualifiers
source                  1..64
                        mol_type = protein
                        organism = Bos taurus
SEQUENCE: 249
CTTVYQKTTK QDCPEYYTYN PDCARRYGWS DCECMADKFG GYCRHEGFAT HTVRSPYEWH  60
LHAW                                                               64

SEQ ID NO: 250          moltype = AA  length = 64
FEATURE                 Location/Qualifiers
source                  1..64
                        mol_type = protein
                        organism = Bos taurus
SEQUENCE: 250
CTTVYQKTTK KDCPEYYTYN PDCAMRYGWS YCECMAGKFW GYWCHESCAT NTVRSTYEGP  60
RDAW                                                               64

SEQ ID NO: 251          moltype = AA  length = 11
FEATURE                 Location/Qualifiers
source                  1..11
                        mol_type = protein
                        organism = Bos taurus
SEQUENCE: 251
TTVYLKTTKQ D                                                       11

SEQ ID NO: 252          moltype = AA  length = 11
FEATURE                 Location/Qualifiers
source                  1..11
                        mol_type = protein
                        organism = Bos taurus
SEQUENCE: 252
TTVYQKTTKQ D                                                       11

SEQ ID NO: 253          moltype = AA  length = 36
FEATURE                 Location/Qualifiers
source                  1..36
```

```
                        mol_type = protein
                        organism = Bos taurus
SEQUENCE: 253
CPEYYTYNPD CARRYGWSDC DCMADKFGGS CRLDGC                          36

SEQ ID NO: 254          moltype = AA  length = 36
FEATURE                 Location/Qualifiers
source                  1..36
                        mol_type = protein
                        organism = Bos taurus
SEQUENCE: 254
CPEYYTYNRD CERRYGWSDC ECRADNVGGH CRHEGC                          36

SEQ ID NO: 255          moltype = AA  length = 36
FEATURE                 Location/Qualifiers
source                  1..36
                        mol_type = protein
                        organism = Bos taurus
SEQUENCE: 255
CPEYYTYNPD CARRYGWRDC ECLADKVGGY CRHVGC                          36

SEQ ID NO: 256          moltype = AA  length = 36
FEATURE                 Location/Qualifiers
source                  1..36
                        mol_type = protein
                        organism = Bos taurus
SEQUENCE: 256
CPEYYTYNPD CARRYGWSDC ECMADKVGGE CRHDGC                          36

SEQ ID NO: 257          moltype = AA  length = 36
FEATURE                 Location/Qualifiers
source                  1..36
                        mol_type = protein
                        organism = Bos taurus
SEQUENCE: 257
CPEYYTYNPD CARRSGWSDC ECMADKFGGY CRHDGC                          36

SEQ ID NO: 258          moltype = AA  length = 36
FEATURE                 Location/Qualifiers
source                  1..36
                        mol_type = protein
                        organism = Bos taurus
SEQUENCE: 258
CPEYYTYNPD RARRSGWSDC ECMADKFGGY CRHDGC                          36

SEQ ID NO: 259          moltype = AA  length = 36
FEATURE                 Location/Qualifiers
source                  1..36
                        mol_type = protein
                        organism = Bos taurus
SEQUENCE: 259
CPEYYTYNPD CARRYGWSDC ECMADKFGGY CRHEGF                          36

SEQ ID NO: 260          moltype = AA  length = 36
FEATURE                 Location/Qualifiers
source                  1..36
                        mol_type = protein
                        organism = Bos taurus
SEQUENCE: 260
CPEYYTYNPD CAMRYGWSYC ECMAGKFWGY WCHESC                          36

SEQ ID NO: 261          moltype = AA  length = 15
FEATURE                 Location/Qualifiers
source                  1..15
                        mol_type = protein
                        organism = Bos taurus
SEQUENCE: 261
ATNTVRSTDE WHLDA                                                 15

SEQ ID NO: 262          moltype = AA  length = 15
FEATURE                 Location/Qualifiers
source                  1..15
                        mol_type = protein
                        organism = Bos taurus
SEQUENCE: 262
ANNTVRSTDE WHLDA                                                 15

SEQ ID NO: 263          moltype = AA  length = 15
FEATURE                 Location/Qualifiers
```

```
source                  1..15
                        mol_type = protein
                        organism = Bos taurus
SEQUENCE: 263
ATNTVRSNDE WHLDA                                                            15

SEQ ID NO: 264          moltype = AA  length = 15
FEATURE                 Location/Qualifiers
source                  1..15
                        mol_type = protein
                        organism = Bos taurus
SEQUENCE: 264
ATNPVRSTDE WHLDA                                                            15

SEQ ID NO: 265          moltype = AA  length = 15
FEATURE                 Location/Qualifiers
source                  1..15
                        mol_type = protein
                        organism = Bos taurus
SEQUENCE: 265
ATNTVRSTDG FHLDA                                                            15

SEQ ID NO: 266          moltype = AA  length = 15
FEATURE                 Location/Qualifiers
source                  1..15
                        mol_type = protein
                        organism = Bos taurus
SEQUENCE: 266
ATHTVRSPYE WHLHA                                                            15

SEQ ID NO: 267          moltype = AA  length = 15
FEATURE                 Location/Qualifiers
source                  1..15
                        mol_type = protein
                        organism = Bos taurus
SEQUENCE: 267
ATNTVRSTYE GPRDA                                                            15

SEQ ID NO: 268          moltype = AA  length = 62
FEATURE                 Location/Qualifiers
REGION                  1..62
                        note = synthetic construct
VARIANT                 1
                        note = Xaa can be Ile or Thr
VARIANT                 3
                        note = Xaa can be Ala or Val
VARIANT                 4
                        note = Xaa can be His or Tyr
VARIANT                 5
                        note = Xaa can be Gln or Leu
VARIANT                 7
                        note = Xaa can be Thr or Ala
VARIANT                 8
                        note = Xaa can be Asn, Tyr or Thr
VARIANT                 9
                        note = Xaa can be Lys or Glu
VARIANT                 11
                        note = Xaa can be Glu, Val or Asp
VARIANT                 14
                        note = Xaa can be Glu or Asp
VARIANT                 15
                        note = Xaa can be Asp or Tyr
VARIANT                 17
                        note = Xaa can be Thr or Ser
VARIANT                 18
                        note = Xaa can be Tyr or Ser
VARIANT                 20
                        note = Xaa can be Pro or Arg
VARIANT                 21
                        note = Xaa can be Arg or Asp
VARIANT                 23
                        note = Xaa can be Pro, Val, Glu or Ala
VARIANT                 24
                        note = Xaa can be Gln, Met or Arg
VARIANT                 25
                        note = Xaa can be Gln, Leu or Arg
VARIANT                 26
                        note = Xaa can be Tyr or Ser
VARIANT                 30
```

```
                        note = Xaa can be Asp, His, Tyr or Asn
VARIANT                 32
                        note = Xaa can be Asp or Glu
VARIANT                 34
                        note = Xaa can be Met, Arg or Leu
VARIANT                 35
                        note = Xaa can be Gly, Arg or Ala
VARIANT                 36
                        note = Xaa can be Asp or Gly
VARIANT                 37
                        note = Xaa can be Arg, Ser, Asn or Lys
VARIANT                 38
                        note = Xaa can be Phe or Val
VARIANT                 41
                        note = Xaa can be Tyr or Trp
VARIANT                 44
                        note = Xaa can be Gln, Ala or His
VARIANT                 45
                        note = Xaa can be Asp, Glu or Val
VARIANT                 46
                        note = Xaa can be Gly or Ser
VARIANT                 48
                        note = Xaa can be Ser or Ala
VARIANT                 49
                        note = Xaa can be Asn, Ser, Thr or Asp
VARIANT                 50
                        note = Xaa can be Tyr, Thr, His or Asn
VARIANT                 51
                        note = Xaa can be Ile, Val, Thr, Pro or Ala
VARIANT                 52
                        note = Xaa can be His, Glu, Val or Asp
VARIANT                 53
                        note = Xaa can be Arg, Ile or Met
VARIANT                 54
                        note = Xaa can be Ser, Gly or Thr
VARIANT                 55
                        note = Xaa can be Thr, Asn or Pro
VARIANT                 56
                        note = Xaa can be Tyr or Asp
VARIANT                 59
                        note = Xaa can be Tyr or His
VARIANT                 60
                        note = Xaa can be Val or Leu
VARIANT                 61
                        note = Xaa can be Ser, Asn, His or Asp
source                  1..62
                        mol_type = protein
                        organism = synthetic construct
SEQUENCE: 268
XTXXXKXXXK XCPXXYXXNX XCXXXXGWSX CXCXXXXXGG XCRXXXCXXX XXXXXXEWXX  60
XA                                                                 62

SEQ ID NO: 269          moltype = AA  length = 62
FEATURE                 Location/Qualifiers
REGION                  1..62
                        note = synthetic construct
VARIANT                 1
                        note = Xaa can be Ile, Ala or Thr
VARIANT                 3
                        note = Xaa can be Ala or Val
VARIANT                 4
                        note = Xaa can be His, Ala or Tyr
VARIANT                 5
                        note = Xaa can be Gln, Ala or Leu
VARIANT                 7
                        note = Xaa can be Thr or Ala
VARIANT                 8
                        note = Xaa can be Asn, Tyr, Ala or Thr
VARIANT                 9
                        note = Xaa can be Ala or Glu
VARIANT                 11
                        note = Xaa can be Glu, Val, Ala or Asp
VARIANT                 14
                        note = Xaa can be Glu, Ala or Asp
VARIANT                 15
                        note = Xaa can be Asp, Ala or Tyr
VARIANT                 17
                        note = Xaa can be Thr, Ala or Ser
VARIANT                 18
```

-continued

```
                      note = Xaa can be Tyr, Ala or Ser
VARIANT               20
                      note = Xaa can be Pro, Ala or Arg
VARIANT               21
                      note = Xaa can be Arg or Asp
VARIANT               23
                      note = Xaa can be Pro, Val, Glu or Ala
VARIANT               24
                      note = Xaa can be Gln, Met, Ala or Arg
VARIANT               25
                      note = Xaa can be Gln, Leu, Ala or Arg
VARIANT               26
                      note = Xaa can be Tyr or Ser
VARIANT               30
                      note = Xaa can be Asp, His, Tyr, Ala or Asn
VARIANT               32
                      note = Xaa can be any naturally occurring amino acid
VARIANT               34
                      note = Xaa can be Met, Arg, Ala or Leu
VARIANT               35
                      note = Xaa can be Gly, Arg or Ala
VARIANT               36
                      note = Xaa can be Asp, Ala or Gly
VARIANT               37
                      note = Xaa can be Arg, Ser, Asn, Ala or Lys
VARIANT               38
                      note = Xaa can be Phe or Val
VARIANT               41
                      note = Xaa can be Tyr, Ala or Trp
VARIANT               44
                      note = Xaa can be Gln, Ala or His
VARIANT               45
                      note = Xaa can be Asp, Glu or Val
VARIANT               46
                      note = Xaa can be Gly, Ala or Ser
VARIANT               48
                      note = Xaa can be Ser or Ala
VARIANT               49
                      note = Xaa can be Asn, Ser, Thr, Ala or Asp
VARIANT               50
                      note = Xaa can be Tyr, Thr, His, Ala or Asn
VARIANT               51
                      note = Xaa can be Ile, Val, Thr, Pro or Ala
VARIANT               52
                      note = Xaa can be His, Glu, Val, Ala or Asp
VARIANT               53
                      note = Xaa can be Arg, Ile, Ala or Met
VARIANT               54
                      note = Xaa can be Ser, Gly, Ala or Thr
VARIANT               55
                      note = Xaa can be Thr, Asn, Ala or Pro
VARIANT               56
                      note = Xaa can be Tyr, Ala or Asp
VARIANT               59
                      note = Xaa can be Tyr, Ala or His
VARIANT               60
                      note = Xaa can be Val, Ala or Leu
VARIANT               61
                      note = Xaa can be Ser, Asn, His, Ala or Asp
source                1..62
                      mol_type = protein
                      organism = synthetic construct
SEQUENCE: 269
XTXXXKXXXK XCPXXYXXNX XCXXXXGWSX CXCXXXXXGG XCRXXXCXXX XXXXXXEWXX  60
XA                                                                 62
```

What is claimed is:

1. An isolated monoclonal antibody that specifically binds to Env and comprises a VH CDR1, VH CDR2, VH CDR3, VL CDR1, VL CDR2, and VL CDR3 comprising the amino acid sequence of (a) SEQ ID NO: 1-4, GDT and SEQ ID NO: 6, respectively;

(b) SEQ ID NO: 11-14, GDT and SEQ ID NO: 16, respectively;

(c) SEQ ID NO: 21-24, GDT and SEQ ID NO: 26, respectively;

(d) SEQ ID NO: 31-34, GDT and SEQ ID NO: 36, respectively;

(e) SEQ ID NO: 41-44, GDT and SEQ ID NO: 46, respectively;

(f) SEQ ID NO: 51-54, GDT and SEQ ID NO: 56, respectively;

(g) SEQ ID NO: 61-64, GDT and SEQ ID NO: 66, respectively;

(h) SEQ ID NO: 71-74, GDS and SEQ ID NO: 76, respectively;

(i) SEQ ID NO: 81-84, GDS and SEQ ID NO: 86, respectively; or (j) SEQ ID NO: 91-94, GDT and SEQ ID NO: 96, respectively.

2. The isolated monoclonal antibody of claim 1, wherein the antibody is a recombinant antibody, a chimeric antibody, a humanized antibody, an antibody fragment, a bispecific antibody, or a trispecific antibody.

3. The isolated monoclonal antibody of claim 1, wherein the VH CDR1, VH CDR2, VH CDR3, VL CDR1, VL CDR2, and VL CDR3 comprises the amino acid sequence of SEQ ID NO: 61-64, GDT and SEQ ID NO: 66, respectively.

4. The isolated monoclonal antibody of claim 1, comprising a heavy chain variable region (VH) and a light chain variable region (VL) wherein the VH and VL comprises an amino acid sequence that is at least about 90% identical to (a) SEQ ID NO: 7 and 8, respectively;

(b) SEQ ID NO: 17 and 18, respectively;

(c) SEQ ID NO: 27 and 28, respectively;

(d) SEQ ID NO: 37 and 38, respectively;

(e) SEQ ID NO: 47 and 48, respectively;

(f) SEQ ID NO: 57 and 58, respectively;

(g) SEQ ID NO: 67 and 68, respectively;

(h) SEQ ID NO: 77 and 78, respectively;

(i) SEQ ID NO: 87 and 88, respectively; or (j) SEQ ID NO: 97 and 98, respectively.

5. The isolated monoclonal antibody of claim 4, wherein the VH and VL comprises an amino acid sequence that is at least about 90% identical to SEQ ID NO: 67 and 68, respectively.

6. An isolated polynucleotide encoding the monoclonal antibody of claim 1.

7. A recombinant virus comprising the polynucleotide of claim 6.

8. A method of producing an antibody that binds to HIV comprising culturing a host cell comprising the polynucleotide of claim 6 so that the polynucleotide is expressed and the antibody is produced.

9. A method of neutralizing an HIV virus comprising contacting the virus with a sufficient amount of the antibody of claim 1.

10. A method for passively immunizing a subject comprising administering to the subject in need thereof an effective amount of the antibody of claim 1.

11. A method of treating HIV/AIDS comprising administering to a subject in need thereof a therapeutically sufficient amount of the antibody of claim 1.

12. The method of claim 11, further comprising administering at least one additional therapeutic agent.

13. A method of neutralizing an HIV virus comprising contacting the virus with a sufficient amount of the antibody of claim 4.

14. A method for passively immunizing a subject comprising administering to the subject in need thereof an effective amount of the antibody of claim 4.

15. A method of treating HIV/AIDS comprising administering to a subject in need thereof a therapeutically sufficient amount of the antibody of claim 4.

16. A method of neutralizing an HIV virus comprising contacting the virus with a sufficient amount of the antibody of claim 5.

17. A method for passively immunizing a subject comprising administering to the subject in need thereof an effective amount of the antibody of claim 5.

18. A method of treating HIV/AIDS comprising administering to a subject in need thereof a therapeutically sufficient amount of the antibody of claim 5.

* * * * *